US011008397B2

(12) United States Patent
Lafleur et al.

(10) Patent No.: US 11,008,397 B2
(45) Date of Patent: *May 18, 2021

(54) DE NOVO BINDING DOMAIN CONTAINING POLYPEPTIDES AND USES THEREOF

(71) Applicants: SUBDOMAIN, LLC, Washington, DC (US); ARCELLX, INC., Germantown, MD (US)

(72) Inventors: David William Lafleur, Washington, DC (US); David M. Hilbert, Germantown, MD (US)

(73) Assignees: Subdomain, LLC, Washington, DC (US); Arcellx, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/817,755

(22) Filed: Mar. 13, 2020

(65) Prior Publication Data

US 2020/0223934 A1 Jul. 16, 2020

Related U.S. Application Data

(63) Continuation of application No. 15/564,325, filed as application No. PCT/US2016/025868 on Apr. 4, 2016, now Pat. No. 10,662,248.

(60) Provisional application No. 62/143,772, filed on Apr. 6, 2015.

(51) Int. Cl.
| | |
|---|---|
| C07K 16/28 | (2006.01) |
| A61K 39/00 | (2006.01) |
| C07K 14/705 | (2006.01) |
| C07K 16/10 | (2006.01) |
| C07K 14/435 | (2006.01) |
| G01N 33/574 | (2006.01) |
| A61K 38/17 | (2006.01) |
| A61K 9/00 | (2006.01) |
| A61K 38/00 | (2006.01) |
| A61P 35/00 | (2006.01) |
| C40B 40/10 | (2006.01) |

(52) U.S. Cl.
CPC ........ *C07K 16/2878* (2013.01); *A61K 9/0019* (2013.01); *A61K 38/1774* (2013.01); *A61K 39/00111* (2018.08); *A61K 39/001104* (2018.08); *A61K 39/001112* (2018.08); *A61K 39/001113* (2018.08); *A61K 39/001124* (2018.08); *A61K 39/001129* (2018.08); *A61K 39/001168* (2018.08); *A61K 39/001171* (2018.08); *A61K 39/001186* (2018.08); *A61K 39/001188* (2018.08); *A61K 39/001195* (2018.08); *C07K 14/435* (2013.01); *C07K 14/70575* (2013.01); *C07K 16/1027* (2013.01); *G01N 33/57484* (2013.01); *A61K 38/00* (2013.01); *A61K 38/1764* (2013.01); *A61K 39/0011* (2013.01); *A61P 35/00* (2018.01); *C07K 2317/24* (2013.01); *C07K 2317/31* (2013.01); *C07K 2318/20* (2013.01); *C07K 2319/00* (2013.01); *C07K 2319/035* (2013.01); *C07K 2319/21* (2013.01); *C07K 2319/41* (2013.01); *C07K 2319/43* (2013.01); *C40B 40/10* (2013.01); *G01N 2333/70596* (2013.01)

(58) Field of Classification Search
CPC combination set(s) only.
See application file for complete search history.

(56) References Cited

U.S. PATENT DOCUMENTS

| | | | |
|---|---|---|---|
| 6,534,528 B1 | 3/2003 | Nilsson et al. | |
| 6,534,628 B1 | 3/2003 | Nilsson et al. | |
| 7,314,974 B2 | 1/2008 | Cao et al. | |
| 8,268,756 B2 | 9/2012 | Logtenberg et al. | |
| 9,045,545 B1 | 6/2015 | Clube | |
| 9,902,758 B2 | 2/2018 | Shin et al. | |
| 10,647,775 B2 * | 5/2020 | Lafleur | A61K 39/001168 |
| 10,662,248 B2 * | 5/2020 | Lafleur | A61K 39/001168 |
| 2012/0195882 A1 | 8/2012 | Doms et al. | |
| 2013/0158232 A1 | 6/2013 | Timmerman et al. | |
| 2013/0190221 A1 | 7/2013 | Burrows et al. | |
| 2016/0311878 A1 * | 10/2016 | Shin | C07K 14/4702 |
| 2018/0209983 A1 | 7/2018 | Lafleur et al. | |
| 2018/0251521 A1 | 9/2018 | Lafleur et al. | |

(Continued)

FOREIGN PATENT DOCUMENTS

| | | |
|---|---|---|
| WO | WO 2007/019376 | 2/2007 |
| WO | WO 2010/124829 | 11/2010 |

(Continued)

OTHER PUBLICATIONS

U.S. Appl. No. 15/564,430, filed Oct. 5, 2017, U.S. Pat. No. 2018/0209983, Jul. 26, 2018.
U.S. Appl. No. 15/564,319, filed Oct. 4, 2017, U.S. Pat No 2018/0251563, Sep. 6, 2018.
U.S. Appl. No. 16/751,730, filed Jan. 24, 2020, unpublished.
International Search Report for PCT/US2016/026054, filed on Apr. 5, 2016; dated Sep. 21, 2016.
Written Opinion of the International Searching Authority for PCT/US2016/026054, filed on Apr. 5, 2016; dated Sep. 21, 2016.
Walsh et al. "Solution structure and dynamics of a de novo designed three-helix bundle protein," Proceedings of the National Academy of Sciences, vol. 96, No. 10, pp. 5480-5491, May 11, 1999.

(Continued)

*Primary Examiner* — Daniel E Kolker
*Assistant Examiner* — James L Rogers
(74) *Attorney, Agent, or Firm* — Nixon & Vanderhye P.C.

(57) ABSTRACT

Provided herein are de novo binding domain containing polypeptides (DBDpp) that specifically bind a target of interest. Nucleic acids encoding the DBDpp, and vectors and host cells containing the nucleic acids are also provided. Libraries of DBDpp, methods of producing and screening such libraries and the DBDpp identified from such libraries and screens are also encompassed. Methods of making and using the DBDpp are additionally provided. Such uses include, without limitation, affinity purification, and diagnostic and therapeutic applications.

28 Claims, 48 Drawing Sheets

Specification includes a Sequence Listing.

(56) References Cited

U.S. PATENT DOCUMENTS

| | | |
|---|---|---|
| 2018/0251563 A1 | 9/2018 | Lafleur et al. |
| 2020/0362046 A1 | 11/2020 | Lafleur et al. |
| 2021/0002381 A1* | 1/2021 | Lafleur |

FOREIGN PATENT DOCUMENTS

| | | |
|---|---|---|
| WO | WO 2014/138805 | 9/2014 |
| WO | WO 20160154621 | 9/2016 |
| WO | WO 2016/164305 | 10/2016 |
| WO | WO 2016164308 | 10/2016 |
| WO | WO 2016164369 | 10/2016 |
| WO | WO2019099433 | 5/2019 |
| WO | WO 2019099440 | 5/2019 |

OTHER PUBLICATIONS

International Search Report for PCT/US2016/025880, filed on Apr. 4, 2016; dated Jul. 26, 2016.
Written Opinion of the International Searching Authority for PCT/US2016/026054, filed on Apr. 4, 2016; dated Jul. 26, 2016.
Unknown; Lipoprotein, UniProtKB database accession No. F2UEQ6, accessed at https://www.uniprot.org/uniprot/F2UEQ6 on May 20, 2019.
Unknown; Cytoplasmic dynein 2 heavy chain 1, UniProtKB database accession No. Q9SMH5, secondary accession No. Q9ZSS7, accessed at https://www.uniprot.org/uniprot/Q9SMH5 on May 20, 2019.
Unknown; Coiled-coil domain-containing protein 70, UniProtKB database accession No. T2MC19, accessed at https://www.uniprot.org/uniprot/T2MC19 on May 20, 2019.
Unknown; Protein-disulfide isomerase, UniProtKB database accession No. S9SHI3, accessed at https://www.uniprot.org/uniprot/S9SHI3 on May 20, 2019.
Lafleur et al., "Monoclonal antibody therapeutics with up to five specificities: Functional enhancement through fusion of target-specific peptides" MABS vol. 5. No. 2 pp. 208-218, Mar. 1, 2013.
Per-Ake Nygren "Alternative binding proteins: Affibody binding proteins developed from a small three-helix bundle scaffold : Affibody binding proteins" FEBS Journal vol. 275. No. 11 pp. 2668-2676, Apr. 24, 2008.
Andreas Pluckthun "Designed Ankyrin Repeat Proteins (DARPins): Binding Proteins for Research. Diagnostics. And Therapy" Annual Review of Pharmacology and Toxicology vol. 55 No. 1 pp. 489-511, Jan. 6, 2015.
International Search Report for PCT/US2016/025868, filed on Apr. 4, 2016; dated Sep. 2, 2016.
Written Opinion of the International Searching Authority for PCT/US2016/025868, filed on Apr. 4, 2016; dated Sep. 2, 2016.
Walker et al., "Targeting high-risk pediatric solid tumors with CART cells directed against ALK (anaplastic lymphoma kinase, CD246);" J Immunother. Cancer, 2(Suppl 3):P40 (2014).
Mardiros et al. "T cells expressing CD123-specific chimeric antigen receptors exhibit specific cytolytic effector functions and antitumor effects against human acute myeloid leukemia" Blood 122(18). 3138-48 (2013).
Noad et al., "Virus-like particles as immunogens" Trends in Microbiology vol. 11. No. 9 pp. 438-444, Sep. 1, 2003.
Office Action dated Jul. 25, 2019 for U.S. Appl. No. 15/564,430, filed Oct. 5, 2017.
Office Action dated Jul. 17, 2019 for U.S. Appl. No. 15/564,319, inventors: Lafleur et al., filed Oct. 4, 2017.
Final Office Action dated Dec. 26, 2019 for U.S. Appl. No. 15/564,319, inventors: Lafleur et al., filed Oct. 4, 2017.
Attwood, "The babel of bioinformatics," Science 290(5491):471-473 (2000).
Baker et al., "Protein Structure Prediction and Structural Genomics," Science, 294: 93-96 (2001).
Pakula et al., "Genetic analysis of protein stability and function," Annu. Rev. Genet., 23: 289-310 (1989).
Gilbreth et al., "Structural insights for engineering binding proteins based on non-antibody scaffolds," Current opinion in structural biology, 22:413-420 (2012).
Ngo et al., "Computational Complexity, Protein Structure Prediction, and the Levinthal Paradox," The Protein Folding Problem and Tertiary Structure Prediction, pp. 433 and 492-495 (1994).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. of Cell Bio., 111:2129-2138 (1990).
Lazar et al., "Transforming Growth Factor x; Mutation of Aspartic Acid 47 and Leucine 48 Results in Different Biological Activities," Molecular and Cellular Biology, 8(3):1247-1252 (1988).
Bowie et al., "Deciphering the Message in Protein Sequences: Tolerance to Amino Acid Substitutions," Science, 247:1306-1310 (1990).
Traxlmayr, et al., "Directed evolution of proteins for increased stability and expression using yeast display," Archives of Biochemistry Biophysics, 526:74-180 (2012).
Park et al., "Limitations of yeast surface display in engineering proteins of high thermostability," Protein Engineering, Design & Selection, 19(5:211-217 (2006).
Cangelosi et al., "A de novodesigned metalloenzyme for the hydration of $CO_2$," Angew Chem. Int. Ed Engl., 53(30)7900-7903 (2014).
Chakraborty et al., "Realization of a Designed Three-Helix Bundle Capable of Binding Heavy Metals in a Tris (Cysteine) Environment," Angew Chem. Int. Ed Engl., 50(9):2049-2053 (2011).
Mouratou et al., "Artificial Affinity Proteins as Ligands of Immunoglobulins," Biomolecules, 5:60-75 (2015).
Löfblom et al., "Affibody molecules: Engineered proteins for therapeutic, diagnostic and biotechnological applications," FEBS Letters; 584:2670-2680 (2010).
Ronnmark et al., "Human Immunoglobulin A (IgA)-specific ligands from combinatorial engineering of protein A," Eur. J. Biochem., 269:2647-2655 (2002).
Kuchar et al., "Human interleukin-23 receptor antagonists derived from an albumin-binding domain scaffold inhibit IL-23-dependent ex vivo expansion of IL-17-producing T-cells," 82:975-989 (2013).
Heiko et al., "Short term culture of breast tissues to study the activity of the anticancer drug taxol in an intact tumor environment," BMC Cancer 2006, 6: 86, pp. 1-11 (Year:2006).
Unpublished U.S. Appl. No. 16/751,730, inventor: Lafleur, David William, filed Jan. 24, 2020.
Unpublished U.S. Appl. No. 16/824,809, inventor: Lafleur et al., filed Mar. 20, 2020.
Unpublished U.S. Appl. No. 16/763,776, inventor: Hilbert et al., filed May 13, 2020.
Unpublished U.S. Appl. No. 16/763,784, inventor: Hilbert et al., filed May 13, 2020.
International Search Report and Written Opinion of the International Searching Authority for PCT/US2018/060902, filed on Nov. 14, 2018; dated Mar. 27, 2019.
International Search Report and Written Opinion of the International Searching Authority for PCT/US2018/060887, filed on Nov. 14, 2018; dated Apr. 1, 2019.
Hey et al., "Artificial, non-antibody binding proteins for pharmaceutical and industrial applications." TRENDS Biotechnol. 23(10): 514-522 (2005).

\* cited by examiner

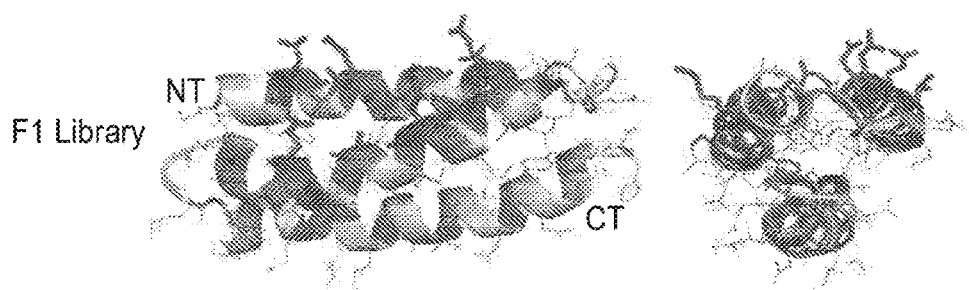
*FIG. 2A*  *FIG. 2B*
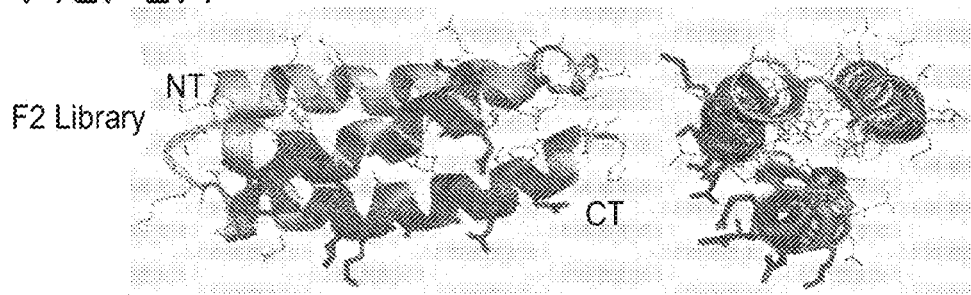
*FIG. 2C*  *FIG. 2D*
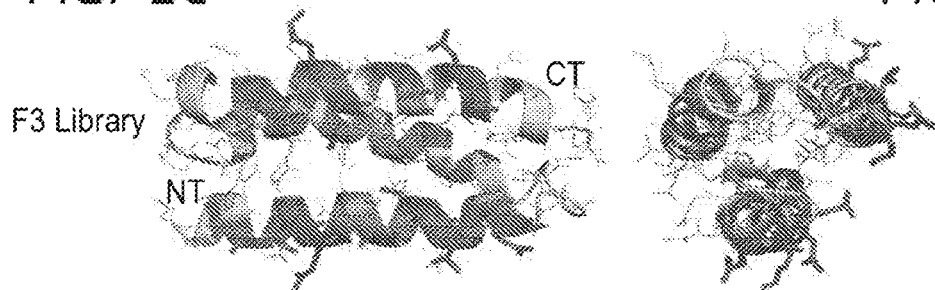
*FIG. 2E*  *FIG. 2F*
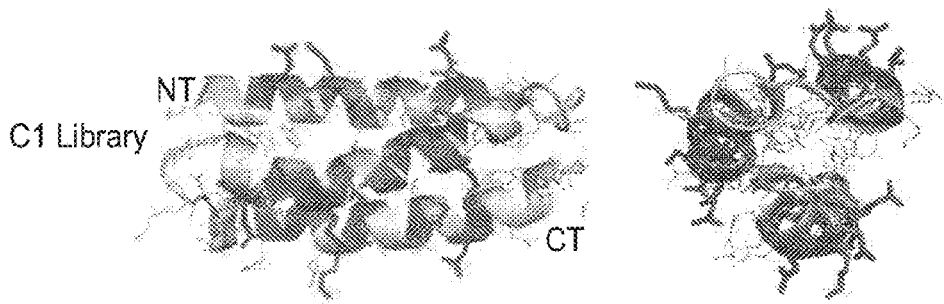
*FIG. 2G*  *FIG. 2H*
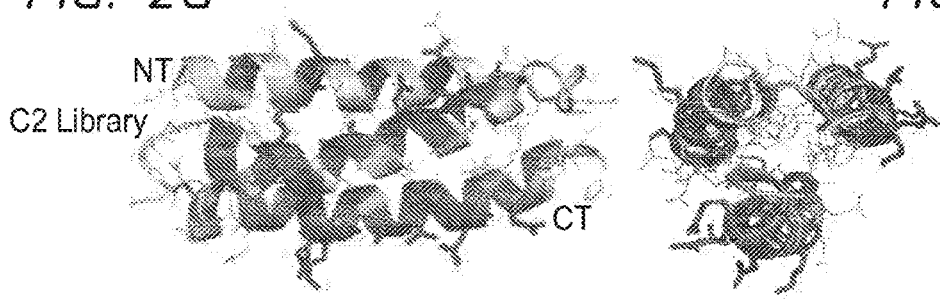
*FIG. 2I*  *FIG. 2J*

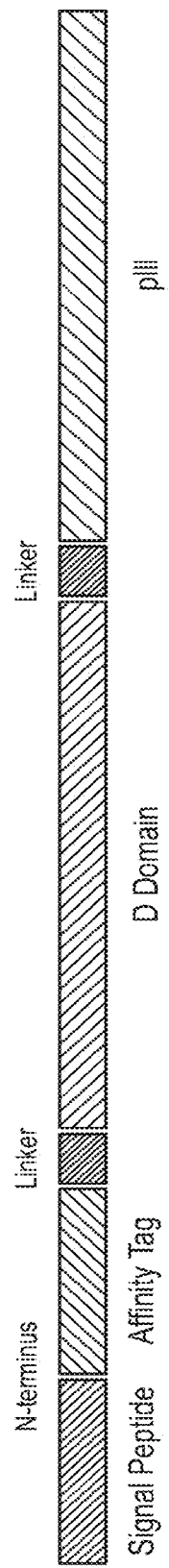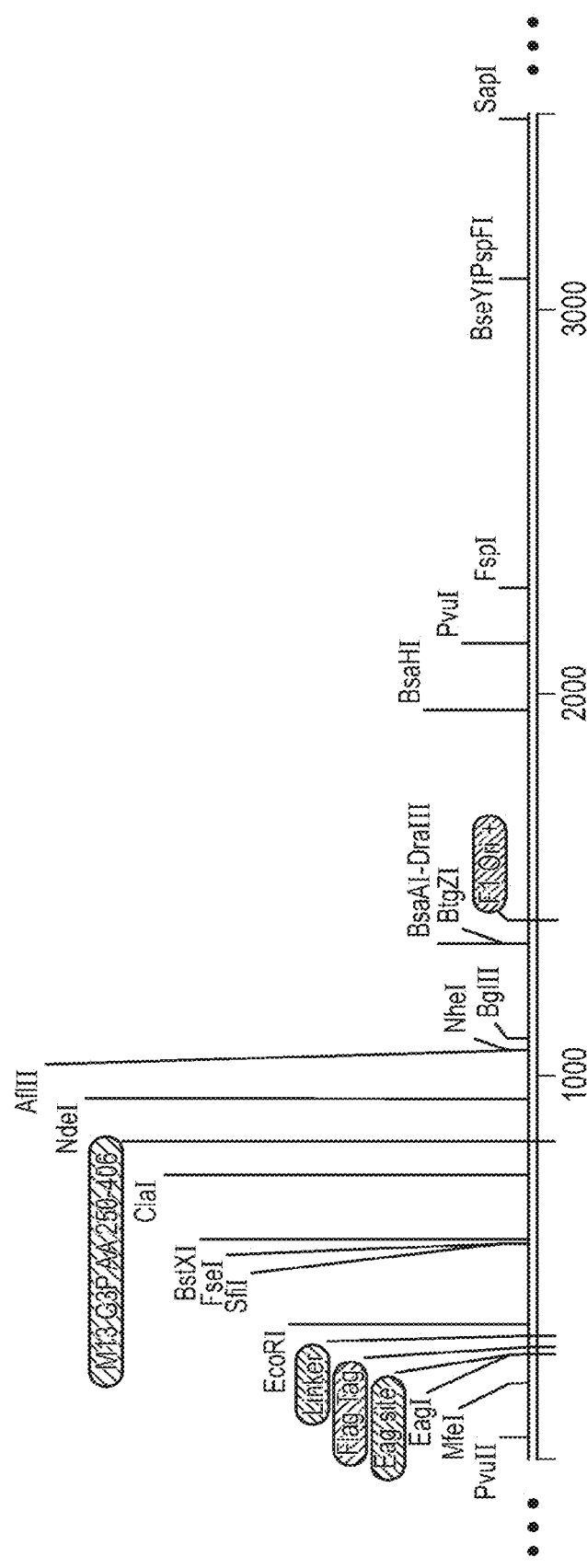
FIG. 3A
FIG. 3B

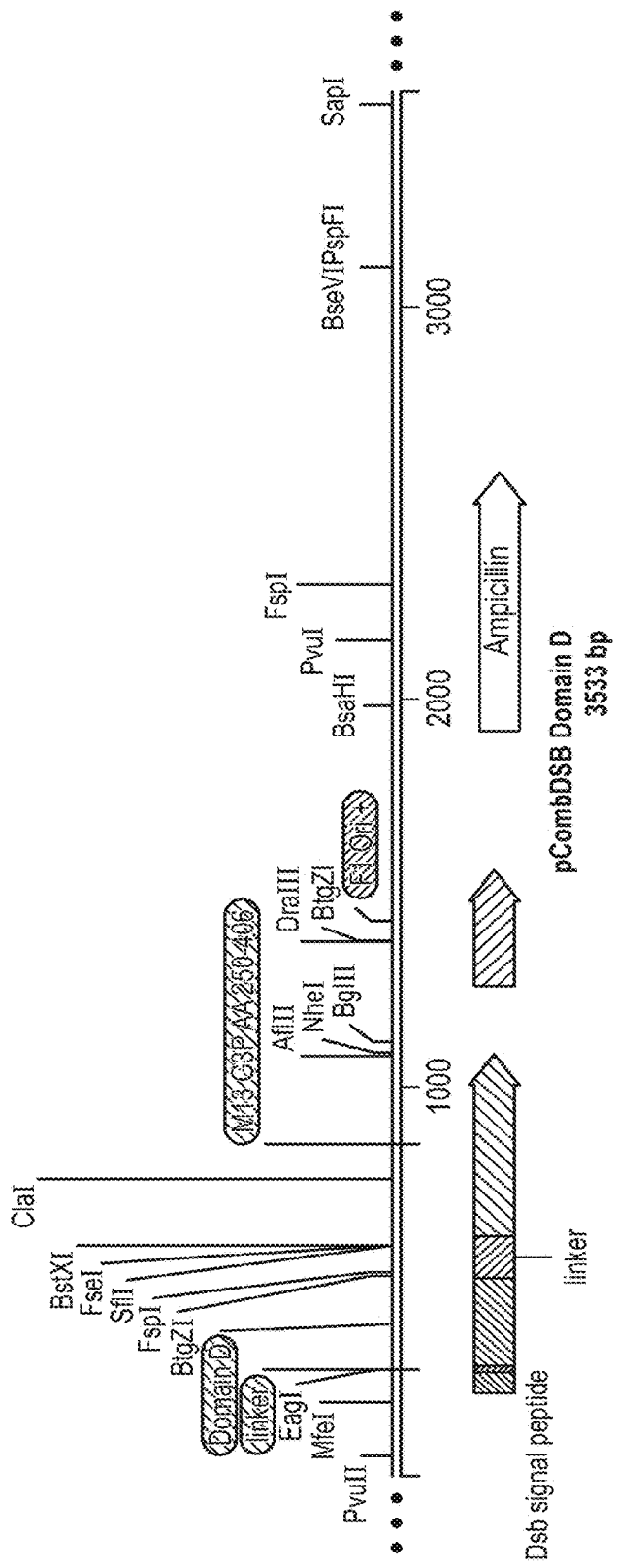
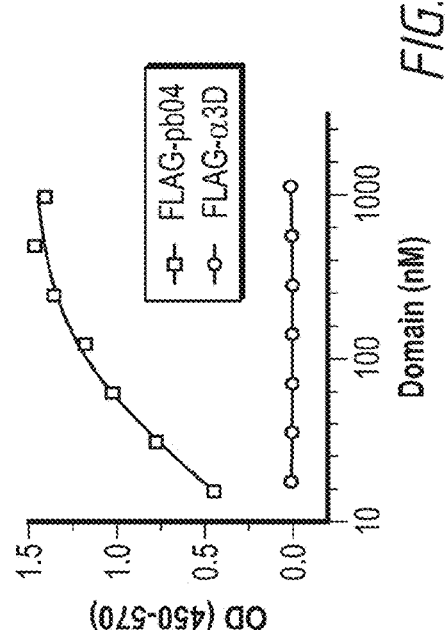
FIG. 3C
FIG. 3D

Parental cg06

FIG. 28A cg06
One epitope removed

FIG. 28B cg06
Two epitopes removed

FIG. 28C cg06
Three epitopes removeded

DE NOVO BINDING DOMAIN CONTAINING POLYPEPTIDES AND USES THEREOF

CROSS-REFERENCE TO RELATED CASES

This application is a continuation of U.S. application Ser. No. 15/564,325, 371(c) date Oct. 4, 2017, which is a U.S. National Phase of PCT Application No. PCT/US2016/025868, filed Apr. 4, 2016, which claims priority to U.S. Provisional Application Ser. No. 62/143,772, filed Apr. 6, 2015, the entirety of each of which is incorporated by reference herein. All references, patents and patent applications referred to herein are herein incorporated by reference in their entireties.

REFERENCE TO SEQUENCE LISTING

The present application is being filed accompanied by a Sequence Listing in electronic format. The Sequence Listing is provided as a file entitled 6666_0048_Sequence_Listing.txt, created Mar. 12, 2020, and which is 147 kilobytes in size. The information in the Sequence Listing is incorporated herein by reference in its entirety.

BACKGROUND

Antibody-based reagents have accelerated the pace of biological research and development. Antibody compositions represent one of the most important and successful classes of therapeutic and diagnostic agents utilized in the pharmaceutical industry. However, cost, time and efficacy have motivated the development of alternative affinity reagents.

A variety of non-antibody binding formats have emerged for applications historically served by antibodies. While many successes have been reported for unstructured, linear peptides, more robust results have been achieved by imposing a structural constraint on the peptide sequence—typically through the introduction of a disulfide bond. This constraint affords higher affinity and greater specificity through the more favorable thermodynamics of fixed-shape complementarity and surface presentations of residues (e.g., hydrophobic amino acids) that might otherwise be buried and therefore not target-facing (Ladner, Trends in Biotech. 13(10):426-430, 1995). Conversely, formats that contain disulfide bonds are typically prone to improper pairing of cysteines, either intra-domain or inter-domain, that can lead to lower expression, product yield and product quality.

Structure found in protein subdomains has provided another source of structural constraint. Structures such as fibronectin type III repeats (adnectins), z-proteins (affibodies), knottins, lipocalins (anticalins) and ankyrin repeats (DARPins) have been developed with antibody-like affinities against a variety of different targets (Hey et al., Trends in Biotech. 23(10):514-422, 2005). These domains typically contain two features that are analogous to the frameworks and complementarity determining regions (CDRs) found in antibody variable domains: a structural scaffold that imparts high thermodynamic stability and residues or loops that form the basis of the display library's variability.

SUMMARY

In general, there remains a substantial unmet need for new target-binding agents and compositions, and particularly for such agents containing alternative binding scaffolds (e.g., non-antibody scaffolds). In several embodiments, agents of particular interest may be characterized by, for example, substantially reduced production costs and/or comparable or superior reagent, diagnostic and/or therapeutic properties as compared to antibodies. The present disclosure provides such desirable agents in several embodiments. For example, in several embodiments, the present disclosure provides certain polypeptide agents that are characterized by high target binding affinity and by a non-antibody structural scaffold. Alternatively or additionally, in several embodiments, target-binding agents, such as the polypeptides disclosed herein, for example resulting from the production methods disclosed herein have advantages including, for example, highly target-specific binding. In some embodiments, this can advantageously be used to target therapeutics (e.g., immune cells) to particular cells (e.g., diseased cells), thereby reducing or eliminating off-target effects. In some embodiments, the agents provided herein, such as the target-specific polypeptides, can be used as protein therapeutics to bind cells or soluble factors involved in disease. In some embodiments, the provided agents can be used to purify targets (e.g., proteins or other targets) with a high degree of specificity, which may, for example, result in higher purity and/or reduced downstream processing to purify a target.

Several embodiments of the inventions disclosed herein relate to agents that specifically bind targets of interest, such as the de novo binding domain (DBD) containing polypeptides (DBDpp) disclosed herein. Nucleic acids encoding the DBDpp and vectors and host cells containing the nucleic acids are also provided, as are DBDpp libraries and methods for producing and screening such libraries and the DBDpp identified from such libraries and/or screens. DBDpp including DBDpp fusion proteins are also provided, as are methods of making and using the DBDpp. Non-limiting examples of such uses include, but are not limited to, affinity purification, target analysis, diagnostic and/or therapeutic applications.

In several embodiments, there is provided a binding agent that binds with a high degree of specificity to a target of interest. In several embodiments the binding agent is a non-antibody agent. In several embodiments, the binding agent is a polypeptide. In several embodiments, there are provided polypeptides for binding a target of interest that have a sequence that differs, at least at one position, from the sequence of SEQ ID NO:1. In several such embodiments, the agent (e.g., a polypeptide) exhibits specific binding to the target of interest, that binding being greater than the binding of a polypeptide according to SEQ ID NO:1 to the target of interest. In several embodiments, there is provided a polypeptide for binding a target of interest, the polypeptide comprising an amino acid sequence comprising MGSWX$_5$EFX$_8$X$_9$RLX$_{12}$AIX$_{15}$X$_{16}$RLX$_{19}$ALGGSEAELA AFEKEIAAFESELQAYKGKGNPEVEX$_{55}$LRX$_{58}$X$_{59}$ AAX$_{62}$IRX$_{65}$X$_{66}$LQAYRHN (SEQ ID NO:4), wherein the sequence differs in sequence from the sequence of SEQ ID NO:1 (e.g., by modifications to the amino acid sequence of SEQ ID NO:1). In several embodiments, the polypeptide specifically binds a target of interest (such as a cancer marker or other distinctive marker related to a target of interest), and the specific binding of the polypeptide to the target of interest is greater than binding of a polypeptide according to SEQ ID NO:1 to the target of interest. In several embodiments, the polypeptide does not contain the sequence of SEQ ID NO:50.

In several embodiments, the polypeptide has a sequence that differs from SEQ ID NO:1 because certain selected amino acid positions have been modified. In some embodiments, the modifications comprise substitutions. In several embodiments, the substitutions are conservative substitutions, while in some embodiments, the substitutions are non-conservative substitutions. In still additional embodiments, combinations of conservative and non-conservative substitutions are used. In some embodiments, the substitutions do not include substitution with a cysteine (e.g., no cysteines are added to the sequence). In some embodiments, wherein the substitutions do not include substitution with a proline (e.g., no prolines are added to the sequence). In some embodiments, neither cysteine nor proline is substituted into the sequence of the polypeptide.

Various targets of interest can be bound by the agents disclosed herein. For example, in several embodiments, the target of interest specifically bound by the polypeptide is a cancer antigen. In some embodiments, the cancer antigen specifically bound by polypeptide is PD-L1. In several such embodiments, target-binding polypeptide comprises or consists essentially of an amino acid sequence selected from the group consisting of SEQ ID NO:38, SEQ ID NO:39, SEQ ID NO:40, SEQ ID NO:41, SEQ ID NO:42, SEQ ID NO: 43, SEQ ID and NO:44. In some embodiments, the cancer antigen specifically bound by polypeptide is CD137. In some such embodiment, the polypeptide comprises or consists essentially of an amino acid sequence selected from the group consisting of SEQ ID NO: 12, SEQ ID NO: 13, SEQ ID NO:14, SEQ ID NO:15, SEQ ID NO:16, SEQ ID NO: 17, SEQ ID NO:18, and SEQ ID NO:19. In some embodiments, the cancer antigen specifically bound by polypeptide is CD123. In some such embodiments, the polypeptide comprises or consists essentially of an amino acid sequence selected from SEQ ID NOS: 92-127. In some embodiments, a combination of cancer antigens is targeted, for example by coupling or otherwise combining various target-binding polypeptides. In some embodiments, two, three, four or more different cancer antigens are targeted. In some embodiments, multiple target-binding polypeptides are used to enhance the ability and/or capacity to bind a single target (e.g., dimers, trimers, etc.)

Additionally provided for in several embodiments is a method for transforming a reference polypeptide into a polypeptide having specific binding for a target of interest, the method comprising modifying a plurality of amino acid residues from a reference polypeptide to generate a plurality of candidate binding polypeptides, packaging the plurality of candidate binding polypeptides in a plurality of vectors to generate a candidate library, and screening the candidate library for candidate binding polypeptides that exhibit specific binding to the target of interest. In several embodiments, the reference polypeptide comprises a variant of a non-naturally occurring polypeptide and comprises three anti-parallel alpha helices joined by linker peptides. In several embodiments the amino acid residues to be modified are solvent accessible or solvent inaccessible amino acids. In several embodiments, a greater degree of solvent accessible amino acids are modified, while in some embodiments a greater degree of solvent inaccessible amino acids are modified. In some embodiments, the modification comprises amino acid substitutions. As discussed above, the substitutions can comprise conservative amino acid substitutions, non-conservative amino acid substitutions, and/or combinations thereof. Optionally, in several embodiments, the substitution does not comprise substitution in of a cysteine, does not comprise substitution in of a proline, and in some cases does not comprise substitution in of a cysteine or a proline.

In several embodiments, the method further comprises identifying potentially immunogenic amino acid residues in the candidate binding polypeptides and modifying at least one of the potentially immunogenic amino acid residues (e.g., to reduce the potential immunogenicity of the resultant polypeptides that bind a target of interest). In several embodiments, the modification to reduce immunogenicity comprises an amino acid substitution (e.g., conservative and/or non-conservative substitutions).

In several embodiments, there is provided a de novo binding domain polypeptide (DBDpp) that comprises or consists essentially of three anti-parallel alpha helices, the DBDpp being a variant of a synthetic polypeptide, wherein the DBDpp immunospecifically binds to a protein that is at least 95% identical to CD123. In several embodiments, the DBDpp has a dissociation constant (KD) between about $10^{-4}$M and about $10^{-12}$M. In some embodiments, the target to which the DBDpp immunospecifically binds comprises amino acids 19-305 of CD123 (SEQ ID NO: 187). There is also provided herein a DBDpp having an amino acid sequence MGSWX$_5$EFX$_8$X$_9$RLX$_{12}$AIX$_{15}$X$_{16}$RLX$_{19}$ALGGSEAEL AAFEKEIAAFESELQAYKGKGNPEVEX$_{55}$LRX$_{58}$X$_{59}$ AAX$_{62}$IRX$_{65}$X$_{66}$LQAYRHN (SEQ ID NO:4), and wherein X$_n$ is a natural or non-natural amino acid. Moreover, there is also provided for a DBDpp having an amino acid sequence at least 85% identical to the amino acid sequence of any one of SEQ ID NO:60-SEQ ID NO: 136. Still further embodiments provide for a fusion protein that binds to CD123 (or other target of interest disclosed herein) and further comprises one or more additional DBDpp exhibiting binding specificity for a tumor target.

In several embodiments, the target-binding agent (e.g., a polypeptide with specificity for a target of interest) is labeled. Depending on the embodiment, various labels can be used, including but not limited to an enzymatic label, a fluorescent label, a luminescent label, and a bioluminescent label. In some embodiments, the label is a biotin moiety. In several embodiments, a streptavidin moiety can be used. In some embodiments, a His-tag, FLAG-tag or other tag is used. In some embodiments, the label is luciferase, green fluorescent protein, red fluorescent protein, or other similar agent.

In several embodiments, the target-binding agent (e.g., a polypeptide) is conjugated to a therapeutic or cytotoxic agent (e.g., chemotherapeutic agent, radiotherapeutic agent, etc.). Depending on the embodiment, the target-binding agent may optionally comprise a pharmaceutically acceptable carrier.

In several embodiments, there are provided kits comprising any of the target-binding agents disclosed herein (e.g., a therapeutic kit, a diagnostic kit, a kit for research use, etc.).

Several embodiments also provide for isolated nucleic acid molecules encoding the any of the target-binding polypeptides disclosed herein. Still additional embodiments provide for a vector (e.g., a plasmid, viral vector, or non-viral vector) containing the isolated nucleic acid molecule. Several such embodiments may also include standard components for expression of protein encoded by the nucleic acid (e.g., promoters, packaging components, etc.). For example, in several embodiments, the vector further comprises an additional nucleotide sequence which regulates the expression of the polypeptide encoded by the nucleic acid molecule. In several embodiments, the additional nucleic acid sequence is an inducible promoter.

Further provided for in several embodiments are host cells that comprise the nucleic acid molecules encoding the any of the target-binding polypeptides disclosed herein. In several embodiments such embodiments, the host cell (e.g., a cell line) is engineered to express the target-binding polypeptides disclosed herein. In some embodiments, the expression of the target-binding polypeptides by the host cells allows production and isolation of the target-binding polypeptides.

In some embodiments, the expression results in the target-binding polypeptides expressed on the surface and/or integral to the membrane of the cells.

Also provided for herein are de novo binding domain polypeptides (DBDpp) that compete with the polypeptides disclosed herein for binding to CD123 (or other targets of interest). In several embodiments, there are also provided polypeptides that compete with those disclosed herein for binding to other targets of interest, including CD123, PD-L1, CD19, CD22, and the like (or other targets disclosed herein). Competitors that are provided for include full or partial agonists, full or partial antagonists, and the like. Those agents that compete for binding to a target of interest (either to the same epitope, an overlapping epitope, or a non-overlapping epitope that leads to steric or other hindrances to the agent binding a target of interest) can be identified by competitive binding assays.

Also provided for herein are polypeptides (either alone or expressed by a cell) that bind to a tumor. In several embodiments, the binding is based on the polypeptide having been generated and identified as having specific binding for one or more markers expressed by the tumor. The tumor, depending on the embodiment, may be a suspension tumor or a solid tumor.

Several embodiments, also provide for a chimeric antigen receptor (CAR), wherein the CAR includes a targeting domain, a transmembrane domain, and an intracellular signaling domain. In several embodiments, the targeting domain is made up of, at least in part, a target-binding polypeptide as disclosed herein. In several embodiments, the intracellular signaling domain is selected from the group consisting of a human CD3 zeta domain, 41BB domain, a CD28 domain and any combination thereof. Depending on the embodiment, the costimulatory signaling region comprises the intracellular domain of a costimulatory molecule selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof. In several embodiments, the CAR comprises a fusion protein that includes an additional target-binding polypeptide. Also provided for are isolated nucleic acid sequences encoding CARs that include the target-binding polypeptides as part (or all) of the targeting region.

Further provided for herein are cells comprising a nucleic acid sequence encoding a CAR, wherein the CAR comprises an antigen binding domain made up of, at least in part, a polypeptide that binds a target of interest, a transmembrane domain, and a signaling domain. In several embodiments, the polypeptide binds specifically to a tumor antigen (and thus functions to deliver the cell expressing the CAR to the tumor. In several embodiments, the tumor antigen is associated with a hematologic malignancy. In additional embodiments, tumor antigen is associated with a solid tumor. Both solid and hematologic tumors can be simultaneously targeted in some embodiments. In several embodiments, the tumor antigen is selected from the group consisting of CD137, PD-L1, CD123, CTLA4, CD47, KIR, DR5, TIM3, PD1, EGFR, TCR, CD19, CD20, CD22, ROR 1, mesothelin, CD33/IL3Ra, cMet, PSMA, Glycolipid F77, EGFRvIII, GD2, NY-ESO-1, MAGE A3, and combinations thereof. Depending on the embodiment, the cell expressing the CAR can be a T cell or a natural killer (NK) cell. In several embodiments, the cell (whether T cell, NK cell or other cell type) exhibits an anti-tumor immunity when the polypeptide binds to its corresponding tumor antigen.

Still additional embodiments provide for amino acids having the sequence of SEQ ID 4, wherein $X_n$ is not cysteine or proline.

Also provided for in several embodiments are mammalian cells that generate membrane-bound virus-like particles (VLPs), wherein the mammalian cell is engineered to express a fusion protein comprising a de novo binding domain polypeptide (DBDpp) fused to a chimeric antigen receptor (CAR), the fusion protein being expressed on the generated VLPs (e.g., as transmembrane proteins). Depending on the embodiments, the VLPs produced by the mammalian cells are suitable for use as immunogens for antibody generation. In some such embodiments, the antibodies are directed against the de novo binding domain polypeptide (DBDpp) (e.g., the antibodies bind to the DBDpp and can be used to detect the DBDpp, isolate the DBDpp, etc.

The target-binding polypeptides disclosed herein are also useful in a therapeutic context, e.g., for treatment and/or diagnosis of a disease, such as a cancer (e.g., a solid or hematologic malignancy). Thus, there are provided, in several embodiments methods of treating a subject having cancer, comprising administering to the subject an immune cell comprising a chimeric antigen receptor (CAR), wherein the CAR comprises a target binding domain, wherein the target binding domain comprises a polypeptide having an amino acid sequence comprising: MGSWX$_5$EFX$_8$X$_9$RLX$_{12}$AIX$_{15}$X$_{16}$RLX$_{19}$ALGGSEAELA AFEKEIAAFESELQAYKGKGNPEVEX$_{55}$LRX$_{58}$X$_{59}$ AAX$_{62}$IRX$_{65}$X$_{66}$LQAYRHN (SEQ ID NO:4), a transmembrane domain, and an intracellular domain (comprising a signaling domain). Upon administration to a subject having cancer, the target binding domain specifically binds to a target of interest expressed by a cancer cell, and the binding of the target of interest induces the immune cell to generate cytotoxic signals that result in cytotoxic effects on the cancer cell, thereby treating the cancer. In several embodiments, the polypeptide has a sequence that differs from SEQ ID NO:1 (e.g., the polypeptide is generated by modifying the amino acid sequence of SEQ ID NO:1). As a result of the differing sequence, the polypeptide's specific binding to the target of interest is greater than binding of a polypeptide according to SEQ ID NO:1 to the target of interest.

Depending on the embodiment, the immune cell can be a T cell. In some embodiments, the immune cell is a NK cell. Other immune cells, and/or combinations of different immune cell types can optionally be used. In some embodiments, combinations of cell types (e.g., NK cells and T cells) are advantageous because they act synergistically to treat a cancer. When combinations are used, the various cell types can target the same or different (or overlapping) tumor antigens.

In several embodiments wherein T cells are used, the binding of the target of interest stimulates the T cell to initiate intracellular signaling, produce cytokines, and degranulate, leading to the cytotoxic effects on the cancer cell. Additionally, in several embodiments, the T cell proliferates in response to binding the target of interest. Advantageously, however, the activity of the T cell does not result in the T cells exhibiting a phenotype associated with T cell exhaustion. In several embodiments where T cells are used, the transmembrane domain of the CAR comprises 41BB or CD28, and the cytoplasmic domain comprises an alpha, beta, or zeta chain of the T cell receptor.

In several embodiments where NK cells are used, the transmembrane domain comprises CD28, and the cytoplasmic domain comprises a zeta chain of the T cell receptor.

In several embodiments, the CAR-containing immune cells are designed to bind to a target of interest expressed by the cancer cell, such as a tumor antigen selected from the group consisting of CD137, PD-L1, CD123, CTLA4, CD47, KIR, DR5, TIM3, PD1, EGFR, TCR, CD19, CD20, CD22, ROR 1, mesothelin, CD33/1L3Ra, cMet, PSMA, Glycolipid F77, EGFRvIII, GD2, NY-ESO-1, MAGE A3, and combinations thereof.

In several embodiments, the CAR further comprises a second polypeptide having an amino acid of SEQ ID NO:4, the polypeptide being able to specifically bind a second target of interest expressed by a cancer cell, and wherein the second polypeptide's specific binding the second target of interest is greater than binding of a polypeptide according to SEQ ID NO:1 to the second target of interest. In several embodiments, the generation of the polypeptide that makes up at least a portion of the targeting domain of the CAR does not include substituting a cysteine or a proline into SEQ ID NO: 1.

In several embodiments, the administration of the immune cells with a CAR is intravenous, though other routes, such as intra-arterial, intramuscular, local, or other acceptable route can be used for a given treatment scenario.

There are also provided, in several embodiments, methods of treating a subject having cancer, comprising administering to the subject an immune cell comprising a chimeric antigen receptor (CAR), wherein the CAR comprises a target binding domain, wherein the target binding domain comprises a polypeptide having an amino acid sequence selected from of SEQ ID NO:2, SEQ ID NO:3, SEQ ID NO:4, SEQ ID NO:5, and SEQ ID NO:6, wherein no cysteine or proline residues are substituted into any of SEQ ID NO:2, SEQ ID NO:3, SEQ ID NO:4, SEQ ID NO:5, and SEQ ID NO:6, wherein the polypeptide specifically binds a target of interest expressed by a cancer cell, and wherein the polypeptide's specific binding to the target of interest is greater than binding of a polypeptide according to SEQ ID NO:1 to the target of interest, a transmembrane domain, and an intracellular domain, wherein the intracellular domain comprises a signaling domain, wherein, upon administration to a subject having cancer, the target binding domain specifically binds to the target of interest expressed by a cancer cell, and wherein the binding of the target of interest induces the immune cell to generate cytotoxic signals that result in cytotoxic effects on the cancer cell, thereby treating the cancer. As discussed above, depending on the embodiment, the immune cell can be a T cell, a NK cell, or other type of immune cell (or combinations of various types). In one embodiment, the transmembrane domain comprises 41BB or CD28, wherein the cytoplasmic domain comprises an alpha, beta, or zeta chain of the T cell receptor, and wherein the immune cell is a T cell. In some such embodiments, upon binding the target of interest, the T cell is stimulated to initiate intracellular signaling, produce cytokines, proliferates and degranulates, leading to the cytotoxic effects on the cancer cell, without the T cells exhibiting a phenotype associated with T cell exhaustion.

Further embodiments provide for a method of treating a subject having cancer, the method comprising intravenously administering to the subject an immune cell comprising a chimeric antigen receptor (CAR) expressed on a T cell, wherein the CAR comprises a target binding domain comprising a polypeptide having an amino acid sequence comprising, the polypeptide having an amino acid sequence of SEQ ID NO:2, SEQ ID NO:3, SEQ ID NO:4, SEQ ID NO:5, or SEQ ID NO:6, however, no cysteine or proline residues are substituted into any of SEQ ID NO:2, SEQ ID NO:3, SEQ ID NO:4, SEQ ID NO:5, or SEQ ID NO:6, the polypeptide capable of specifically binding a target of interest expressed by a cancer cell with a binding to the target of interest that is greater than binding of a polypeptide according to SEQ ID NO:1 to the target of interest, a transmembrane domain selected from 41BB and CD28, and an intracellular domain, wherein the intracellular domain comprises a signaling domain selected from an alpha, beta, or zeta chain of the T cell receptor, wherein, upon administration to a subject having cancer, the target binding domain specifically binds to the target of interest expressed by a cancer cell, and wherein the binding of the target of interest induces the T cell to generate cytotoxic signals that result in cytotoxic effects on the cancer cell. In several embodiments, the cytotoxic effects result from degranulation of the T cells. Advantageously, in several embodiments, the activation and cytotoxic activity of the T cells is not associated with the T cells exhibiting a phenotype associated with T cell exhaustion. In several embodiments, the CAR optionally further comprises a second target binding domain comprising a second polypeptide having a different target than the target binding domain. In still further embodiments, additional targeting domains can optionally be included to enhance binding capacity to a marker, or impart binding specificity to other markers.

Additionally provided for in several embodiments, is the use of an immune cell comprising a chimeric antigen receptor (CAR) for the treatment of cancer, wherein the CAR comprises a target binding domain comprising a polypeptide having an amino acid sequence comprising, the polypeptide having an amino acid sequence selected from the group consisting of SEQ ID NO:2, SEQ ID NO:3, SEQ ID NO:4, SEQ ID NO:5, and SEQ ID NO:6, wherein no cysteine or proline residues are substituted into any of SEQ ID NO:2, SEQ ID NO:3, SEQ ID NO:4, SEQ ID NO:5, and SEQ ID NO:6, wherein the polypeptide specifically binds a target of interest expressed by a cancer cell, and wherein the polypeptide's specific binding to the target of interest is greater than binding of a polypeptide according to SEQ ID NO:1 to the target of interest, a transmembrane domain selected from 41BB and CD28, and an intracellular domain, wherein the intracellular domain comprises a signaling domain selected from an alpha, beta, or zeta chain of the T cell receptor, wherein, upon administration to a subject having cancer, the target binding domain specifically binds to the target of interest expressed by a cancer cell, and wherein the binding of the target of interest induces the immune cell to generate cytotoxic signals that result in cytotoxic effects on the cancer cell. Depending on the embodiment the immune cells can be a T cell or a natural killer (NK) cell.

In addition to binding domain compositions, methods for generating, screening and using same, there are also provided methods for purifying targets of interest. Thus, provided for herein, in several embodiments, is a method for purifying a target of interest comprising contacting a sample comprising a target of interest with a composition comprising a polypeptide agent attached to a solid support, wherein the polypeptide agent has an amino acid sequence comprising MGSWX$_5$EFX$_8$X$_9$RLX$_{12}$AIX$_{15}$X$_{16}$RLX$_{19}$ALGGSEAEL AAFEKEIAAFESELQAYKGKGNPEVEX$_{55}$LRX$_{58}$X$_{59}$ AAX$_{62}$IRX$_{65}$X$_{66}$LQAYRHN (SEQ ID NO:4), wherein the polypeptide has an amino acid sequence that differs from SEQ ID NO:1, wherein the polypeptide specifically binds the target of interest, wherein the polypeptide's specific binding to the target of interest is greater than binding of a polypeptide according to SEQ ID NO:1 to the target of interest, the contacting performed under conditions that permit binding of the composition to the target of interest, and removing a portion of the sample that is not bound to the composition. In several embodiments the method further comprises dissociating the composition from the target of interest and recovering the target of interest. In several embodiments, the target of interest can be eluted from the composition, thereby purifying (wholly or partially) the target of interest.

Depending on the embodiment, the solid support may be a bead, a glass slide, a chip, a gelatin, or an agarose. Combinations of supports may be used in certain embodiments. In several embodiments, the polypeptide agent is coupled to the solid support through non-covalent association, while in other embodiments, the polypeptide agent is coupled to the solid support through covalent bonding. Depending on the embodiment, the supports, and the target of interest, combinations of covalent and non-covalent association can also be used.

In several embodiments, the polypeptide agent of the composition further comprises a peptide tag, wherein the peptide tag comprises a hexahistidine moiety or a FLAG tag. In some embodiments, the polypeptide agent of the composition further comprises a streptavidin moiety. Other types of tags, e.g., enzymes, colorimetric, bioluminescent and/or fluorescent tags can be used, depending on the embodiment.

In some embodiments, the solid support comprises a bead, and the composition is suitable for use in affinity chromatography to purify the target of interest.

In several embodiments, a nucleic acid molecule encoding the polypeptide is packaged in an expression vector that is used to transduce a cell line to cause the cell line to express the polypeptide. Such embodiments, allow for production of the polypeptide in larger scale for use in protein purification.

Also provided for in several embodiments is a method for purifying a target of interest comprising contacting a sample comprising a target of interest with a composition comprising a virus-like particle coupled to a solid support, wherein the virus-like particle expresses a polypeptide as a membrane protein, the polypeptide having an amino acid sequence selected from the group consisting of SEQ ID NO:2, SEQ ID NO:3, SEQ ID NO:4, SEQ ID NO:5, and SEQ ID NO:6, wherein the polypeptide has an amino acid sequence that differs from SEQ ID NO:1, wherein the polypeptide specifically binds the target of interest, wherein the polypeptide's specific binding to the target of interest is greater than binding of a polypeptide according to SEQ ID NO:1 to the target of interest; and the contacting performed under conditions that permit binding of the composition to the target of interest; and removing a portion of the sample that is not bound to the composition. In several embodiments, wherein no cysteine or proline residues are substituted into any of SEQ ID NO:2, SEQ ID NO:3, SEQ ID NO:4, SEQ ID NO:5, and SEQ ID NO:6 when generating the polypeptide.

In several embodiments, the solid support comprises one or more of a bead, a glass slide, a chip, a gelatin, or an agarose. In several embodiments, the polypeptide of the composition further comprises a peptide tag, wherein the peptide tag comprises a hexahistidine moiety or a FLAG tag. As discussed herein, other types of tags may be used in additional embodiments.

In some embodiments, the portion of the sample that is not bound to the composition is discarded. In some embodiments, the portion of the sample that is not bound to the composition is contacted with the composition a second time to capture additional target of interest, thereby improving the overall yield of the purification.

In several embodiments, the method further comprises contacting the portion of the sample that is not bound to the composition with an antibody directed against the polypeptide of the composition, the antibody being generated from membrane bound virus-like particles (VLP) expressing the polypeptide released from a mammalian cell is engineered to express a fusion protein comprising the polypeptide fused to a chimeric antigen receptor (CAR), the fusion protein being expressed on the generated VLPs, wherein the antibodies are suitable for use in an assay to detect residual polypeptides detached from the solid support.

Not only are there provided methods for purifying a target (e.g., removing the target from a larger sample), but several embodiments provide for a method for removing one or more contaminants from a sample comprising a target of interest, the method comprising contacting a sample comprising a target of interest with a composition comprising a virus-like particle coupled to a solid support, wherein the virus-like particle expresses a polypeptide as a membrane protein, the polypeptide having an amino acid sequence selected from the group consisting of SEQ ID NO:2, SEQ ID NO:3, SEQ ID NO:4, SEQ ID NO:5, and SEQ ID NO:6, wherein no cysteine or proline residues are substituted into any of SEQ ID NO:2, SEQ ID NO:3, SEQ ID NO:4, SEQ ID NO:5, and SEQ ID NO:6, wherein the polypeptide has an amino acid sequence that differs from SEQ ID NO:1, wherein the polypeptide specifically binds one or more contaminants to be removed from a sample comprising the target of interest, wherein the polypeptide's specific binding to one or more contaminants is greater than binding of a polypeptide according to SEQ ID NO:1 to the one or more contaminants; the contacting performed under conditions that permit binding of the composition to the one or more contaminants; and collecting a portion of the sample that is not bound to the composition. As discussed above, in several embodiments, the polypeptide of the composition further comprises a tag, such as a peptide tag. In several embodiments, the peptide tag comprises a hexahistindine moiety or a FLAG tag. Depending on the embodiments, the solid support may comprise a bead, a glass slide, a chip, a gelatin, or an agarose and the virus-like particles are coupled to the solid support through non-covalent association. In some embodiments, the portion of the sample that collected is contacted with the composition a second time to remove additional contaminants from the sample.

Also provided for herein are compositions for use in protein purification. In several embodiments, there is provided an affinity resin comprising a polypeptide agent having an amino acid sequence comprising a sequence selected from the group consisting of: MGSW$X_5X_6$FK$X_9X_{10}$LA$X_{13}$IK$X_{16}X_{17}$LEALGGSEAEL A$X_{30}$FE$X_{33}X_{34}$IA$X_{37}$FE$X_{40}X_{41}$LQ$X_{44}$YKG KGNPE-VEALRKEAAAIRDELQAYRHN (SEQ ID NO:2), MGSWAEFKQRLAAIKTRLEALGGSEAELAAF$X_{32}X_{33}$ EI$X_{36}$AF$X_{39}X_{40}$EL$X_{43}$AYKGKGNPEVE AL$X_{57}X_{58}$EA$X_{61}$AI$X_{64}X_{65}$EL$X_{68}$AYRHN (SEQ ID NO:3), MGSW$X_5$EF$X_8X_9$RL$X_{12}$AI$X_{15}X_{16}$RL$X_{19}$ALGGSEAELA AFEKEIAAFESELQAYKGKGNPEVE$X_{55}$LR$X_{58}X_{59}$ AA$X_{62}$IR$X_{65}X_{66}$LQAYRHN (SEQ ID NO:4), MGSW$X_5X_6$FK$X_9X_{10}$LA$X_{13}$IK$X_{16}X_{17}$LEALGGSEAEL AAF$X_{32}X_{33}$EI$X_{36}$AF$X_{39}X_{40}$EL$X_{43}$AYKGK GNPEVE$X_{55}$LR$X_{58}X_{59}$AA$X_{62}$IR$X_{65}X_{66}$LQAY RHN (SEQ ID NO:5), MGSWX$_5$EFX$_8$X$_9$RLX$_{12}$AIX$_{15}$X$_{16}$RLX$_{19}$ALGGSEAEL AX$_{30}$FEX$_{33}$X$_{34}$IAX$_{37}$FEX$_{40}$X$_{41}$LQX$_{44}$YKG KGNPEVEALX$_{57}$X$_{58}$EAX$_{61}$AIX$_{64}$X$_{65}$ELX$_{68}$AYRHN (SEQ ID NO:6), MGSWX$_5$X$_6$FKX$_9$X$_{10}$LAX$_{13}$IKX$_{16}$X$_{17}$LEALZ$_1$EAEL AX$_{28}$FEX$_{31}$X$_{32}$IAX$_{35}$FEX$_{38}$X$_{39}$LQX$_{42}$YZ$_2$NPE VEALRKEAAAIRDELQAYRHN (SEQ ID NO:7), MGSWAEFKQRLAAIKTRLEALZ$_1$EAELAAFX$_{30}$X$_{31}$ EIX$_{34}$AFX$_{37}$X$_{38}$ELX$_{41}$AYZ$_2$NPEVEALX$_{52}$X$_{53}$EAX$_{56}$ AIX$_{59}$X$_{60}$ELX$_{63}$AYRHN (SEQ ID NO:8), MGSWX$_5$EFX$_8$X$_9$RLX$_{12}$AIX$_{15}$X$_{16}$RLX$_{19}$ALZ$_1$EAELAA FEKEIAAFESELQAYZ$_2$NPEVEX$_{50}$LRX$_{53}$X$_{54}$AAX$_{57}$ IRX$_{60}$X$_{61}$LQAYRHN (SEQ ID NO:9), MGSWX$_5$X$_6$FKX$_9$X$_{10}$LAX$_{13}$IKX$_{16}$X$_{17}$LEALZ$_1$EAELAA FX$_{30}$X$_{31}$EIX$_{34}$AFX$_{37}$X$_{38}$ELX$_{41}$AYZ$_2$NPEV EX$_{50}$LRX$_{53}$X$_{54}$AAX$_{57}$IRX$_{60}$X$_{61}$LQAYRHN (SEQ ID NO:10) and MGSWX$_5$EFX$_8$X$_9$RLX$_{12}$MX$_{15}$X$_{16}$RLX$_{19}$ALZ$_1$EAE LAX$_{28}$FEX$_{31}$X$_{32}$IAX$_{35}$FEX$_{38}$X$_{39}$LQX$_{42}$YZ$_2$NPEVEA LX$_{52}$X$_{53}$E AX$_{56}$AIX$_{59}$X$_{60}$ELX$_{63}$AYRHN (SEQ ID NO:11), as well as combinations thereof, and wherein the amino acid sequence is not SEQ ID NO:1.

In any of the sequences listed above, any of the X positions (e.g., "X$_n$") can be a natural or non-natural amino acid; wherein each X$_n$ is the same or different natural or non-natural amino acid. Additionally, in several embodiments, Z$_1$ and/or Z$_2$ can comprise between about 2 to about 30 natural or non-natural amino acids.

In several embodiments, the polypeptide agent has an amino acid sequence that differs from SEQ ID NO:1 by an amino acid substitution at one or more residues. Depending on the embodiments the amino acid substitution at one or more residues can comprise a conservative substitution, or a non-conservative substitution. Combinations of conservative and non-conservative substitutions may also be use, in several embodiments. Additionally, in several embodiments, the amino acid substitution at one or more residues comprises a substitution at a solvent accessible residue. In some embodiments, the amino acid substitution at one or more residues comprises a substitution at a solvent inaccessible residue. In some embodiments, substitutions (whether conservative or non-conservative) can optionally be made at both solvent accessible and solvent inaccessible residues. In several embodiments, the polypeptide agent has an amino acid sequence that differs from SEQ ID NO:1 by an amino acid deletion at one or more residues.

In several embodiments, there is provided a method of making an affinity resin comprising attaching to a solid support a polypeptide agent having an amino acid sequence comprising a sequence selected from the group consisting of: MGSWX$_5$X$_6$FKX$_9$X$_{10}$LAX$_{13}$IKX$_{16}$X$_{17}$LEALGGSEAEL AX$_{30}$FEX$_{33}$X$_{34}$IAX$_{37}$FEX$_{40}$X$_{41}$LQX$_{44}$YKG KGNPEVEALRKEAAAIRDELQAYRHN (SEQ ID NO:2), MGSWAEFKQRLAAIKTRLEALGGSEAELAAFX$_{32}$X$_{33}$ EIX$_{36}$AFX$_{39}$X$_{40}$ELX$_{43}$AYKGKGNPEVE ALX$_{57}$X$_{58}$EAX$_{61}$AIX$_{64}$X$_{65}$ELX$_{68}$AYRHN (SEQ ID NO:3), MGSWX$_5$EFX$_8$X$_9$RLX$_{12}$AIX$_{15}$X$_{16}$RLX$_{19}$ALGGSEAEL AAFEKEIAAFESELQAYKGKGNPEVEX$_{55}$LRX$_{58}$X$_{59}$ AAX$_{62}$IRX$_{65}$X$_{66}$LQAYRHN (SEQ ID NO:4), MGSWX$_5$X$_6$FKX$_9$X$_{10}$LAX$_{13}$IKX$_{16}$X$_{17}$LEALGGSEAEL AAFX$_{32}$X$_{33}$EIX$_{36}$AFX$_{39}$X$_{40}$ELX$_{43}$AYKGK GNPEVEX$_{55}$LRX$_{58}$X$_{59}$AAX$_{62}$IRX$_{65}$X$_{66}$LQAYRHN (SEQ ID NO:5), MGSWX$_5$EFX$_8$X$_9$RLX$_{12}$AIX$_{15}$X$_{16}$RLX$_{19}$ALGGSEAEL AX$_{30}$FEX$_{33}$X$_{34}$IAX$_{37}$FEX$_{40}$X$_{41}$LQX$_{44}$YKG KGNPEVEALX$_{57}$X$_{58}$EAX$_{61}$AIX$_{64}$X$_{65}$ELX$_{68}$AYRHN (SEQ ID NO:6), MGSWX$_5$X$_6$FKX$_9$X$_{10}$LAX$_{13}$IKX$_{16}$X$_{17}$LEALZ$_1$EAEL AX$_{28}$FEX$_{31}$X$_{32}$IAX$_{35}$FEX$_{38}$X$_{39}$LQX$_{42}$YZ$_2$NPE VEALRKEAAAIRDELQAYRHN (SEQ ID NO:7), MGSWAEFKQRLAAIKTRLEALZ$_1$EAELAAFX$_{30}$X$_{31}$ EIX$_{34}$AFX$_{37}$X$_{38}$ELX$_{41}$AYZ$_2$NPEVEALX$_{52}$X$_{53}$EAX$_{56}$ AIX$_{59}$X$_{60}$ELX$_{63}$AYRHN (SEQ ID NO:8), MGSWX$_5$EFX$_8$X$_9$RLX$_{12}$AIX$_{15}$X$_{16}$RLX$_{19}$ALZ$_1$EAELAA FEKEIAAFESELQAYZ$_2$NPEVEX$_{50}$LRX$_{53}$X$_{54}$AAX$_{57}$ IRX$_{60}$X$_{61}$LQAYRHN (SEQ ID NO:9), MGSWX$_5$X$_6$FKX$_9$X$_{10}$LAX$_{13}$IKX$_{16}$X$_{17}$LEALZ$_1$EAELAA FX$_{30}$X$_{31}$EIX$_{34}$AFX$_{37}$X$_{38}$ELX$_{41}$AYZ$_2$NPEV EX$_{50}$LRX$_{53}$X$_{54}$AAX$_{57}$IRX$_{60}$X$_{61}$LQAYRHN (SEQ ID NO:10) and MGSWX$_5$EFX$_8$X$_9$RLX$_{12}$MX$_{15}$X$_{16}$RLX$_{19}$ALZ$_1$EAE LAX$_{28}$FEX$_{31}$X$_{32}$IAX$_{35}$FEX$_{38}$X$_{39}$LQX$_{42}$YZ$_2$NPEVEA LX$_{52}$X$_{53}$E AX$_{56}$AIX$_{59}$X$_{60}$ELX$_{63}$AYRHN (SEQ ID NO:11), and combinations thereof, wherein the amino acid sequence is not SEQ ID NO:1. In several embodiments, the X positions of the sequences (e.g., "X$_n$") can comprise a natural or non-natural amino acid; wherein each X$_n$ is the same or different natural or non-natural amino acid; and/or wherein Z$_1$ and/or Z$_2$ is 2 to 30 natural or non-natural amino acids. In several embodiments, the polypeptide agent is attached to the solid support by covalent bonding, by non-covalent association, or combinations thereof. In several embodiments, the solid support comprises one or more of a bead, glass slide, chip, gelatin, or agarose.

Further provided for protein purification, in several embodiments, is a composition comprising a solid support coupled to a polypeptide agent having an amino acid sequence comprising a sequence selected from the group consisting of MGSWX$_5$X$_6$FKX$_9$X$_{10}$LAX$_{13}$IKX$_{16}$X$_{17}$LEALGGSEAEL AX$_{30}$FEX$_{33}$X$_{34}$IAX$_{37}$FEX$_{40}$X$_{41}$LQX$_{44}$YKG KGNPEVEALRKEAAAIRDELQAYRHN (SEQ ID NO:2), MGSWAEFKQRLAAIKTRLEALGGSEAELAAFX$_{32}$X$_{33}$ EIX$_{36}$AFX$_{39}$X$_{40}$ELX$_{43}$AYKGKGNPEVE ALX$_{57}$X$_{58}$EAX$_{61}$AIX$_{64}$X$_{65}$ELX$_{68}$AYRHN (SEQ ID NO:3), MGSWX$_5$EFX$_8$X$_9$RLX$_{12}$AIX$_{15}$X$_{16}$RLX$_{19}$ALGGSEAELA AFEKEIAAFESELQAYKGKGNPEVEX$_{55}$LRX$_{58}$X$_{59}$ AAX$_{62}$IRX$_{65}$X$_{66}$LQAYRHN (SEQ ID NO:4), MGSWX$_5$X$_6$FKX$_9$X$_{10}$LAX$_{13}$IKX$_{16}$X$_{17}$LEALGGSEAEL AAFX$_{32}$X$_{33}$EIX$_{36}$AFX$_{39}$X$_{40}$ELX$_{43}$AYKGK GNPEVEX$_{55}$LRX$_{58}$X$_{59}$AAX$_{62}$IRX$_{65}$X$_{66}$LQAYRHN (SEQ ID NO:5), MGSWX$_5$EFX$_8$X$_9$RLX$_{12}$AIX$_{15}$X$_{16}$RLX$_{19}$ALGGSEAEL AX$_{30}$FEX$_{33}$X$_{34}$IAX$_{37}$FEX$_{40}$X$_{41}$LQX$_{44}$YKG KGNPEVEALX$_{57}$X$_{58}$EAX$_{61}$AIX$_{64}$X$_{65}$ELX$_{68}$AYRHN (SEQ ID NO:6), MGSWX$_5$X$_6$FKX$_9$X$_{10}$LAX$_{13}$IKX$_{16}$X$_{17}$LEALZ$_1$EAEL AX$_{28}$FEX$_{31}$X$_{32}$IAX$_{35}$FEX$_{38}$X$_{39}$LQX$_{42}$YZ$_2$NPE VEALRKEAAAIRDELQAYRHN (SEQ ID NO:7), MGSWAEFKQRLAAIKTRLEALZ$_1$EAELAAFX$_{30}$X$_{31}$ EIX$_{34}$AFX$_{37}$X$_{38}$ELX$_{41}$AYZ$_2$NPEVEALX$_{52}$X$_{53}$EAX$_{56}$ AIX$_{59}$X$_{60}$ELX$_{63}$AYRHN (SEQ ID NO:8), MGSWX$_5$EFX$_8$X$_9$RLX$_{12}$AIX$_{15}$X$_{16}$RLX$_{19}$ALZ$_1$EAELAA FEKEIAAFESELQAYZ$_2$NPEVEX$_{50}$LRX$_{53}$X$_{54}$AAX$_{57}$ IRX$_{60}$X$_{61}$LQAYRHN (SEQ ID NO:9), MGSWX$_5$X$_6$FKX$_9$X$_{10}$LAX$_{13}$IKX$_{16}$X$_{17}$LEALZ$_1$EAELA AFX$_{30}$X$_{31}$EIX$_{34}$AFX$_{37}$X$_{38}$ELX$_{41}$AYZ$_2$NPEV EX$_{50}$LRX$_{53}$X$_{54}$AAX$_{57}$IRX$_{60}$X$_{61}$LQAYRHN (SEQ ID NO:10) and MGSWX$_5$EFX$_8$X$_9$RLX$_{12}$MX$_{15}$X$_{16}$RLX$_{19}$ALZ$_1$EAEL AX$_{28}$FEX$_{31}$X$_{32}$IAX$_{35}$FEX$_{38}$X$_{39}$LQX$_{42}$YZ$_2$NPEVEA L$X_{52}X_{53}$E A$X_{56}$AI$X_{59}X_{60}$EL$X_{63}$AYRHN (SEQ ID NO:11), and combinations thereof, wherein the amino acid sequence is not SEQ ID NO:1. In several embodiments, $X_n$ is a natural or non-natural amino acid; wherein each $X_n$ is the same or different natural or non-natural amino acid; and/or $Z_1$ and/or $Z_2$ is 2 to 30 natural or non-natural amino acids. In several embodiments, the polypeptide agent has an amino acid sequence that differs from SEQ ID NO:1 by an amino acid substitution at one or more residues.

Depending on the embodiment, the amino acid substitution at one or more residues may comprise a conservative substitution or may comprise a non-conservative substitution. Combinations of conservative and non-conservative substitutions may also be used, in certain embodiments. In several embodiments, the amino acid substitution at one or more residues comprises a substitution at a solvent accessible residue. In several embodiments, the amino acid substitution at one or more residues comprises a substitution at a solvent inaccessible residue. Some embodiments employ substitutions at both solvent accessible and inaccessible residues. In several embodiments, the polypeptide agent has an amino acid sequence that differs from SEQ ID NO:1 by an amino acid deletion at one or more residues. Depending on the embodiments, the solid support may comprise one or more of a bead, glass slide, chip, gelatin, or agarose.

In several embodiments, the polypeptides disclosed herein can be used in protein analytics, such as function as detectable agents or tags. As such, there is provided herein, in several embodiments, a composition comprising a polypeptide agent conjugated to a detectable agent and/or tag, wherein the polypeptide agent has an amino acid sequence comprising a sequence selected from the group consisting of:

MGSW$X_5X_6$FK$X_9X_{10}$LA$X_{13}$IK$X_{16}X_{17}$LEALGGSEAEL A$X_{30}$FE$X_{33}X_{34}$IA$X_{37}$FE$X_{40}X_{41}$LQ$X_{44}$YKG KGNPEVEALRKEAAAIRDELQAYRHN (SEQ ID NO:2),

MGSWAEFKQRLAAIKTRLEALGGSEAELAAF$X_{32}X_{33}$ EI$X_{36}$AF$X_{39}X_{40}$EL$X_{43}$AYKGKGNPEVE AL$X_{57}X_{58}$EA$X_{61}$AI$X_{64}X_{65}$EL$X_{68}$AYRHN (SEQ ID NO:3),

MGSW$X_5$EF$X_8X_9$RL$X_{12}$AI$X_{15}X_{16}$RL$X_{19}$ALGGSEAEL AAFEKEIAAFESELQAYKGKGNPEVE$X_{55}$LR$X_{58}X_{59}$ AA$X_{62}$IR$X_{65}X_{66}$LQAYRHN (SEQ ID NO:4),

MGSW$X_5X_6$FK$X_9X_{10}$LA$X_{13}$IK$X_{16}X_{17}$LEALGGSEAEL AAF$X_{32}X_{33}$EI$X_{36}$AF$X_{39}X_{40}$EL$X_{43}$AYKGK GNPEVE$X_{55}$LR$X_{58}X_{59}$AA$X_{62}$IR$X_{65}X_{66}$LQAYRHN (SEQ ID NO:5),

MGSW$X_5$EF$X_8X_9$RL$X_{12}$AI$X_{15}X_{16}$RL$X_{19}$ALGGSEAEL A$X_{30}$FE$X_{33}X_{34}$IA$X_{37}$FE$X_{40}X_{41}$LQ$X_{44}$YKG KGNPEVEAL$X_{57}X_{58}$EA$X_{61}$AI$X_{64}X_{65}$EL$X_{68}$AYRHN (SEQ ID NO:6),

MGSW$X_5X_6$FK$X_9X_{10}$LA$X_{13}$IK$X_{16}X_{17}$LEAL$Z_1$EAEL A$X_{28}$FE$X_{31}X_{32}$IA$X_{35}$FE$X_{38}X_{39}$LQ$X_{42}$Y$Z_2$NPE VEALRKEAAAIRDELQAYRHN (SEQ ID NO:7),

MGSWAEFKQRLAAIKTRLEAL$Z_1$EAELAAF$X_{30}X_{31}$ EI$X_{34}$AF$X_{37}X_{38}$EL$X_{41}$AY$Z_2$NPEVEAL$X_{52}X_{53}$EA$X_{56}$ AI$X_{59}X_{60}$EL$X_{63}$AYRHN (SEQ ID NO:8),

MGSW$X_5$EF$X_8X_9$RL$X_{12}$AI$X_{15}X_{16}$RL$X_{19}$AL$Z_1$EAELAA FEKEIAAFESELQAY$Z_2$NPEVE$X_{50}$LR$X_{53}X_{54}$AA$X_{57}$ IR$X_{60}X_{61}$LQAYRHN (SEQ ID NO:9),

MGSW$X_5X_6$FK$X_9X_{10}$LA$X_{13}$IK$X_{16}X_{17}$LEAL$Z_1$EAELA AF$X_{30}X_{31}$EI$X_{34}$AF$X_{37}X_{38}$EL$X_{41}$AY$Z_2$NPEV E$X_{50}$LR$X_{53}X_{54}$AA$X_{57}$IR$X_{60}X_{61}$LQAYRHN (SEQ ID NO:10) and MGSW$X_5$EF$X_8X_9$RL$X_{12}$AI$X_{15}X_{16}$RL$X_{19}$AL$Z_1$EAEL A$X_{28}$FE$X_{31}X_{32}$IA$X_{35}$FE$X_{38}X_{39}$LQ$X_{42}$Y$Z_2$NPEVEA L$X_{52}X_{53}$E A$X_{56}$AI$X_{59}X_{60}$EL$X_{63}$AYRHN (SEQ ID NO:11), and combinations thereof, wherein the amino acid sequence is not SEQ ID NO:1. In several embodiments, $X_n$ is a natural or non-natural amino acid; wherein each $X_n$ is the same or different natural or non-natural amino acid; and/or wherein $Z_1$ and/or Z2 is 2 to 30 natural or non-natural amino acids.

In several embodiments, the detectable agent comprises a chromogen. In several embodiments, the detectable agent comprises a fluorescent dye. In several embodiments, the detectable agent comprises a radionuclide. In such embodiments, the detectable agent is quantifiable.

In several embodiments of the composition, the polypeptide agent is conjugated to a chromatography bead, resin, glass slide, chip, gelatin, or agarose. In several embodiments, the tag comprises polyhistidyl tag, a myc tag, or a FLAG tag. Combinations of tags may also be used in several embodiments. In several embodiments, the polypeptide agent is conjugated to a detectable agent or tag by covalent binding. In several embodiments of the composition, the polypeptide agent is a fusion protein. In several embodiments, the polypeptide agent is multimeric.

De novo binding domain (DBD) containing polypeptides (DBDpp) that specifically bind targets of interest are provided, as are nucleic acids encoding the provided DBDpp, vectors containing the nucleic acids and host cells containing the nucleic acids and vectors. DBDpp libraries, methods for producing and screening such libraries and the DBDpp identified from such libraries and screens are also provided. DBDpp such as DBDpp fusion proteins, are also provided as are methods of making and using the DBDpp. Such uses include, but are not limited to, affinity purification, and diagnostic and therapeutic applications.

In one embodiment, a DBDpp is provided whose amino acid sequence differs (e.g., due to amino acid modifications) from that of a reference scaffold having the sequence of SEQ ID NO: 1. The reference scaffold is a variant of a non-naturally occurring and targetless (e.g., to Applicant's knowledge, no target is presently known) antiparallel three helical bundle reference polypeptide originally engineered as an exercise in protein folding (see, Walsh et al., PNAS 96:5486-5491 (1999) incorporated by reference herein in its entirety). It has been discovered, and is disclosed herein in several embodiments, that polypeptides containing modifications of the targetless reference scaffold having the amino acid sequence of SEQ ID NO:1 are able to specifically bind targets of interest. While not wishing to be bound by theory, it is believed that in designing the DBD, the structural constraints of surface-exposed residues (that can be modified) confer the ability of the surface exposed residues to specifically bind a target of interest.

In one embodiment, a DBDpp agent comprises a polypeptide whose amino acid sequence shows homology with SEQ ID NO:1 but differs from SEQ ID NO:1 by modification of one or more amino acids. According to several embodiments, the target-binding agents (e.g., the DBDpp) provided herein specifically bind to a target of interest (such as a marker associated with cancer or a tumor, such as CD123, CD137, PD-L1, CD19, CD22, NY-ESO, MAGE A3, as non-limiting embodiments). In several embodiments, a provided target-binding agent (e.g., a DBDpp) comprises a total of 5 to 25, 5 to 30, 5 to 35, 5 to 40, 5 to 45, 5 to 50, 5 to 55, or 5 to 60 amino acid residues that have been modified as compared to SEQ ID NO:1; and wherein the agent specifically binds a target of interest. In another embodiment, 5 to 25, 5 to 30, 5 to 35, 5 to 40, 5 to 45, 5 to 50, 5 to 55, or 5 to 60 of the modified amino acid residues are substitutions. In another embodiment, 5 to 25, 5 to 30, 5 to 35, 5 to 40, 5 to 45, or 5 to 50 of the modified amino acid residues are conservative substitutions. In another embodiment, 5 to 25, 5 to 30, 5 to 35, 5 to 40, 5 to 45, or 5 to 50 of the modified amino acid residues are non-conservative substitutions. In a further embodiment, 5 to 15, 5 to 20, 5 to 25, 5 to 30, 5 to 35, 5 to 40, or 5 to 45 of the amino acid residue modifications are conservative substitutions and 5 to 15, 5 to 20, 5 to 25, 5 to 30, 5 to 35, 5 to 40, or 5 to 45 of the amino acid residue modifications are non-conservative substitutions. In additional embodiments, 1 to 25, 1 to 30, 1 to 35, 5 to 40, 5 to 45, 5 to 50, 5 to 55, or 5 to 60 of the substitutions are at amino acid residues of SEQ ID NO:1 selected from the group consisting of: M1, G2, S3, W4, A5, E6, K8, Q9, R10, A12, A13, K15, T16, R17, E19, A20, L21, G22, G23, S24, E25, A26, E27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 of the substitutions are at amino acid residues of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In an optional further embodiment, the DBDpp optionally further comprises an amino acid sequence wherein 1 to 5, 1 to 10, 1 to 15, 5 to 10 or 5 to 15 of the residues corresponding to the solvent inaccessible residues of the amino acid sequence of SEQ ID NO:1 are substituted and wherein the DBDpp specifically binds a target of interest. In several embodiments, the DBDpp comprise an amino acid sequence wherein about 1 to about 5, about 1 to about 10, about 1 to about 15, about 5 to about 10, about 5 to about 15 (or more) of the residues that correspond to the solvent accessible or the solvent inaccessible residues of the amino acid sequence of SEQ ID NO:1 are substituted. In several embodiments, the substitution of both accessible and inaccessible residues confers a greater degree of target specificity as compared to substitution of only accessible or only inaccessible residues. In a further optional embodiment, the substituted residues corresponding to a solvent inaccessible residue of SEQ ID NO:1 are selected from the group consisting of: F7, L11, I14, L18, L28, F31, I35, F38, L42, V53, L56, A60, I63, and L67, and Y70. In an additional embodiment, L21 and Y45 are also included in the group of substituted, solvent inaccessible residues. In an additional embodiment, the DBDpp is a fusion protein (e.g., the DBDpp is fused, conjugated, or otherwise associated with another molecule, directly or indirectly, such as a therapeutic or diagnostic agent). In one embodiment, the DBDpp is attached to a solid support. In a further embodiment, the solid support is selected from the group consisting of: a bead, a glass slide, a chip, a gelatin, and an agarose. In an additional embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a tumor-specific antigen (TSA), a cancer-specific antigen (CSA), and a protein containing a peptide tag. In another embodiment, the DBDpp specifically binds a target disclosed herein. Nucleic acids encoding the DBDpp and vectors containing the nucleic acids are also provided. Host cells (including viral particles) containing the nucleic acids and vectors are also provided. In some embodiments, the host cell displays the DBDpp on its surface. In additional embodiments, the host cell is a prokaryote or a eukaryote that display the DBDpp on its surface. In a further embodiment, the host cell is a phage that displays the DBDpp on its surface. In a further embodiment, the host cell is a human immune cell that expresses a DBDpp fusion protein on its surface. Libraries comprising a plurality of DBDpp are also provided.

In one embodiment, a DBDpp comprises an amino acid sequence selected from the group consisting of: (a) MGSWX$_5$EFX$_8$X$_9$RLX$_{12}$AIX$_{15}$X$_{16}$RLX$_{19}$ALGGSEAEL AAFEKEIA AFESELQAYKGKGNPEVEX$_{55}$LRX$_{58}$X$_{59}$AAX$_{62}$IRX$_{65}$ X$_{66}$LQAYRHN (SEQ ID NO:4), wherein X$_5$, X$_8$, X$_9$, X$_{12}$, X$_{15}$, X$_{16}$, X$_{19}$, X$_{55}$, X$_{58}$, X$_{59}$, X$_{62}$, X$_{65}$, and/or X$_{66}$, is a natural and/or non-natural amino acid residue; (b) MGSWX$_5$X$_6$FKX$_9$X$_{10}$LAX$_{13}$IKX$_{16}$X$_{17}$LEALGGSEAEL AX$_{30}$FEX$_{33}$X$_{34}$IAX$_{37}$FEX$_{40}$X$_{41}$LQX$_{44}$YKGKGNPEVEA LRKEAAAIRDELQAYRHN (SEQ ID NO:2), wherein X$_5$, X$_6$, X$_9$, X$_{10}$, X$_{13}$, X$_{16}$, X$_{17}$, X$_{30}$, X$_{33}$, X$_{34}$, X$_{37}$, X$_{40}$, X$_{41}$, and/or X$_{44}$, is a natural and/or non-natural amino acid residue; (c) MGSWAEFKQRLAAIKTRLEALGGSEAE-LAA FX$_{32}$X$_{33}$EIX$_{36}$AFX$_{39}$X$_{40}$ELX$_{43}$AYKGKGNPEVEALX$_{57}$ X$_{58}$EAX$_{61}$AIX$_{64}$X$_{65}$ELX$_{68}$AYRHN (SEQ ID NO:3), wherein X$_{32}$, X$_{33}$, X$_{36}$, X$_{39}$, X$_{40}$, X$_{43}$, X$_{57}$, X$_{58}$, X$_{61}$, X$_{64}$, X$_{65}$, and/or X$_{68}$, is a natural and/or non-natural amino acid residue, and; (d) MGSWX$_5$X$_6$FKX$_9$X$_{10}$LAX$_{13}$IKX$_{16}$X$_{17}$LEALGGSEAEL AAFX$_{32}$X$_{33}$EIX$_{36}$AFX$_{39}$X$_{40}$ELX$_{43}$AYKGKGNPEVEX$_{55}$ LRX$_{58}$X$_{59}$AA X$_{62}$IRX$_{65}$X$_{66}$LQAYRHN (SEQ ID NO:5), wherein X$_5$, X$_6$, X$_9$, X$_{10}$, X$_{13}$, X$_{16}$, X$_{17}$, X$_{32}$, X$_{33}$, X$_{36}$, X$_{39}$, X$_{40}$, X$_{43}$, X$_{55}$, X$_{58}$, X$_{59}$, X$_{62}$, X$_{65}$, and/or X$_{66}$, is a natural and/or non-natural amino acid residue; and (e) MGSWX$_5$EFX$_8$X$_9$RLX$_{12}$AIX$_{15}$X$_{16}$RLX$_{19}$ALGGSEAEL AX$_{30}$FEX$_{33}$X$_{34}$IAX$_{37}$FEX$_{40}$X$_{41}$LQX$_{44}$YKGKGNPEVEA LX$_{57}$X$_{58}$EAX$_{61}$AIX$_{64}$X$_{65}$ELX$_{68}$AYRHN (SEQ ID NO:6), wherein X$_5$, X$_8$, X$_9$, X$_{12}$, X$_{15}$, X$_{16}$, X$_{19}$, X$_{30}$, X$_{33}$, X$_{34}$, X$_{37}$, X$_{40}$, X$_{41}$, X$_{44}$, X$_{57}$, X$_{58}$, X$_{61}$, X$_{64}$, X$_{65}$, and/or X$_{68}$, is a natural and/or non-natural amino acid residue; and wherein the DBDpp specifically binds a target of interest. In several embodiments, a DBDpp comprises, consists of, or consists essentially of an amino acid sequence selected from the group consisting of SEQ ID NO:2, SEQ ID NO:3, SEQ ID NO:4, and SEQ ID NO:5. In an additional embodiment, X$_n$ is a natural amino acid residue. In a further embodiment, $X_n$ is a natural amino acid residue other than cysteine or proline. In still additional embodiments, $X_n$ is a deletion of an amino acid (e.g., optionally a null position in the sequence). In an additional embodiment, the DBDpp is a fusion protein. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell (e.g., B-cell, T-cell, killer T-cell, helper T-cell, regulatory T-cell, antigen presenting cell, natural killer cell, and the like) that expresses one or more DBDpp fusion proteins on its surface. In one embodiment, the DBDpp is attached to a solid support. In a further embodiment, the solid support is selected from the group consisting of: a bead, a glass slide, other glass or plastic-based materials (e.g., a filter or filter device), a filtration material (e.g., glass fiber, steel wool, polyethersulfone, etc.), a chip, a gelatin, and an agarose, and combinations thereof.

Also provided is an isolated DBDpp that comprises an amino acid sequence selected from the group consisting of:
(a) MGSWX$_5$EFX$_8$X$_9$RLX$_{12}$AIX$_{15}$X$_{16}$RLX$_{19}$ALZ$_1$EAELAAF EKEIAAFESELQAYZ$_2$NPEVEX$_{50}$LRX$_{53}$X$_{54}$AAX$_{57}$ IRX$_{60}$X$_{61}$LQAYRHN (SEQ ID NO:9), wherein X$_5$, X$_8$, X$_9$, X$_{12}$, X$_{15}$, X$_{16}$, X$_{19}$, X$_{50}$, X$_{53}$, X$_{54}$, X$_{57}$, X$_{60}$, and/or X$_{61}$, is a natural and/or non-natural amino acid residue, and Z$_1$ and/or Z$_2$ is 2 to 30 natural and/or non-natural amino acid residues;
(b) MGSWX$_5$X$_6$FKX$_9$X$_{10}$LAX$_{13}$IKX$_{16}$X$_{17}$LEALZ$_1$EAEL AX$_{28}$FEX$_{31}$X$_{32}$IAX$_{35}$FEX$_{38}$X$_{39}$LQX$_{42}$YZ$_2$NPEVEALR KEAAAIRDELQAYRHN (SEQ ID NO:7), wherein X$_5$, X$_6$, X$_9$, X$_{10}$, X$_{13}$, X$_{16}$, X$_{17}$, X$_{28}$, X$_{31}$, X$_{32}$, X$_{35}$, X$_{38}$, X$_{39}$, and/or X$_{42}$, is a natural and/or non-natural amino acid residue, and Z$_1$ and/or Z$_2$ is 2 to 30 natural and/or non-natural amino acid residues;
(c) MGSWAEFKQRLAAIKTRLEALZ$_1$EAELAAFX$_{30}$X$_{31}$ EIX$_{34}$AFX$_{37}$X$_{38}$ELX$_{41}$AYZ$_2$NPEVEALX$_{52}$X$_{53}$EAX$_{56}$ AIX$_{59}$X$_{60}$ELX$_{63}$AYRHN (SEQ ID NO:8), wherein X$_{30}$, X$_{31}$, X$_{34}$, X$_{37}$, X$_{38}$, X$_{41}$, X$_{52}$, X$_{53}$, X$_{56}$, X$_{59}$, X$_{60}$, and/or X$_{63}$, is a natural and/or non-natural amino acid residue, and Z$_1$ and/or Z$_2$ is 2 to 30 natural and/or non-natural amino acid residues;
(d) MGSWX$_5$X$_6$FKX$_9$X$_{10}$LAX$_{13}$IKX$_{16}$X$_{17}$LEALZ$_1$EAELA AFX$_{30}$X$_{31}$EIX$_{34}$AFX$_{37}$X$_{38}$ELX$_{41}$AYZ$_2$NPEVEX$_{50}$ LRX$_{53}$X$_{54}$AAX$_{57}$IRX$_{60}$X$_{61}$LQAYRHN (SEQ ID NO:10), wherein X$_5$, X$_6$, X$_9$, X$_{10}$, X$_{13}$, X$_{16}$, X$_{17}$, X$_{30}$, X$_{31}$, X$_{34}$, X$_{37}$, X$_{38}$, X$_{41}$, X$_{50}$, X$_{53}$, X$_{54}$, X$_{57}$, X$_{60}$, and/or X$_{61}$, is a natural and/or non-natural amino acid residue, and Z$_1$ and/or Z$_2$ is 2 to 30 natural and/or non-natural amino acid residues; and (e)
MGSWX$_5$EFX$_8$X$_9$RLX$_{12}$AIX$_{15}$X$_{16}$RLX$_{19}$ALZ$_1$EAE LAX$_{28}$FEX$_{31}$X$_{32}$IAX$_{35}$FEX$_{38}$X$_{39}$LQX$_{42}$YZ$_2$NPEVEAL X$_{52}$X$_{53}$EAX$_{56}$AIX$_{59}$X$_{60}$ELX$_{63}$AYRHN (SEQ ID NO:11), wherein X$_5$, X$_8$, X$_9$, X$_{12}$, X$_{15}$, X$_{16}$, X$_{19}$, X$_{28}$, X$_{31}$, X$_{32}$, X$_{35}$, X$_{38}$, X$_{39}$, X$_{42}$, X$_{52}$, X$_{53}$, X$_{56}$, X$_{59}$, X$_{60}$, and/or X$_{63}$, is a natural and/or non-natural amino acid residue, and Z$_1$ and/or Z$_2$ is 2 to 30 natural and/or non-natural amino acid residues; and wherein the DBDpp specifically binds a target of interest. In several embodiments, a DBDpp comprises, consists of, or consists essentially of an amino acid sequence selected from the group consisting of SEQ ID NO:7, SEQ ID NO:8, SEQ ID NO:9, and SEQ ID NO:10, and SEQ ID NO:11. In an additional embodiment, X$_n$ is a natural amino acid residue. In a further embodiment, X$_n$ is a natural amino acid residue other than cysteine or proline. In still additional embodiments, X$_n$ is a deletion of an amino acid (e.g., optionally a null position in the sequence). In still additional embodiments, Z$_1$ and/or Z$_2$ are deletions of amino acids (e.g., optionally null positions in the sequence). In an additional embodiment, the DBDpp is a fusion protein. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells, including viral particles, containing the nucleic acids are also provided. In some embodiments, the host cell displays the DBDpp on its surface. In a further embodiment, the host cell is a phage that displays the DBDpp on its surface. In additional embodiments, the host cell is a prokaryote or a eukaryote that display the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

Nucleic acids encoding a DBDpp such as a DBDpp fusion protein are also provided. Additionally provided are vectors containing nucleic acids encoding DBDpp (e.g., DBDpp fusion proteins) and host cells containing the nucleic acids and vectors. In some embodiments, the host cell is a viral particle, or a bacterial, yeast, fungal, or plant cell. In a particular embodiment, the host cell is a mammalian cell. In another embodiment, the mammalian cell is an immune cell. In a further embodiment, the host cell is a human immune cell. In some embodiments, the host cell displays the DBDpp as a fusion protein on the cell surface. In a further embodiment, the host cell is a human immune cell that displays a DBDpp on the cell surface. Additionally provided herein are vector libraries comprising nucleic acids encoding a plurality of DBDpp.

Also provided is a library containing a plurality of DBDpp. In one embodiment, the DBDpp library comprises a plurality of DBDpp containing a different amino acid sequences and that comprise the amino acid sequence of SEQ ID NO:1 wherein a total of 5 to 25, 5 to 30, 5 to 35, 5 to 40, 5 to 45, 5 to 50, 5 to 55, or 5 to 60 amino acid residues (including any number between those listed) have been modified; and wherein the DBDpp specifically binds a target of interest. In another embodiment, 5 to 25, 5 to 30, 5 to 35, 5 to 40, 5 to 45, 5 to 50, 5 to 55, or 5 to 60 (including any number between those listed) of the modified amino acid residues are substitutions. In another embodiment, 5 to 25, 5 to 30, 5 to 35, 5 to 40, 5 to 45, or 5 to 50 (including any number between those listed) of the modified amino acid residues are conservative substitutions. In another embodiment, 5 to 25, 5 to 30, 5 to 35, 5 to 40, 5 to 45, or 5 to 50 (including any number between those listed) of the modified amino acid residues are non-conservative substitutions. In a further embodiment, 5 to 15, 5 to 20, 5 to 25, 5 to 30, 5 to 35, 5 to 40, or 5 to 45 (including any number between those listed) of the amino acid residue modifications are conservative substitutions and 5 to 15, 5 to 20, 5 to 25, 5 to 30, 5 to 35, 5 to 40, or 5 to 45 (including any number between those listed) of the amino acid residue modifications are non-conservative substitutions. In additional embodiments, 5 to 25, 5 to 30, 5 to 35, 5 to 40, 5 to 45, 5 to 50, 5 to 55, or 5 to 60 (including any number between those listed) of the substitutions are at one or more amino acid residues of SEQ ID NO:1 selected from the group consisting of: M1, G2, S3, W4, A5, E6, K8, Q9, R10, A12, A13, K15, T16, R17, E19, A20, L21, G22, G23, S24, E25, A26, K27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 (including any number between those listed) of the substitutions are at one or more of amino acid residues of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In another embodiment, the library comprises at least 2, 3, 4, 5, 10, 25, 50, 75, 100, 250, 500, or 1000 (including any range between those numbers listed, such as 2-10, 5-25, 50-100, 250-1000, etc.) different DBDpp that specifically binding different targets (or DBDpp that have differential specificity for a given target). In a further embodiment, the different targets bound by DBDpp in the library are selected from the group consisting of: a nucleic acid, an oligosaccharide, a peptide, a protein, a cell surface antigen, and a small organic molecule. In a further embodiment, the library comprises at least 2, 3, 4, 5, 10, 25, 50, 75, 100, 250, 500, or 1000 (including any range between those numbers listed, such as 2-10, 5-25, 50-100, 250-1000, etc.) different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises at least 2, 3, 4, 5, 10, 25, 50, 75, 100, 250, 500, or 1000 (including any range between those numbers listed, such as 2-10, 5-25, 50-100, 250-1000, etc.) different DBDpp that specifically bind a target disclosed herein. In an additional embodiment, the library is a vector library or a host cell library. In an additional embodiment, the vector library is a library of host cells. In another embodiment, the host cell library comprises a plurality of host cells that display the DBDpp on their surface. In a further embodiment, the host cells are phage that display the DBDpp on their surface. In some embodiments, the vector library comprises: (a) nucleic acids encoding 3 DBDpp that specifically bind to different targets; (b) nucleic acids encoding 3 DBDpp having different sequences that specifically bind to the same target; (c) nucleic acids encoding 3 DBDpp having different sequences that specifically bind to the same epitope of a target; (d) nucleic acids encoding 3 DBDpp having different sequences that specifically bind to different epitopes of a target; (e) nucleic acids encoding 3 DBDpp having different sequences that compete for binding to the same target; or (f) 3 different nucleic acid sequences encoding the same DBDpp sequence. Host cells containing the vectors are also provided.

Also provided is a vector library comprising a plurality of different nucleic acid sequences encoding DBDpp, that comprise the amino acid sequence of SEQ ID NO:1 wherein a total of 1 to 5, 5 to 25, 5 to 30, 5 to 35, 5 to 40, 5 to 45, 5 to 50, 5 to 55, or 5 to 60 amino acid residues have been modified (or any number in between those listed); and wherein the DBDpp specifically binds a target of interest. In another embodiment, 1 to 5, 5 to 25, 5 to 30, 5 to 35, 5 to 40, 5 to 45, 5 to 50, 5 to 55, or 5 to 60 of the modified amino acid residues (or any number in between those listed) encoded by the nucleic acids sequences are substitutions. In another embodiment, 1 to 5, 5 to 25, 5 to 30, 5 to 35, 5 to 40, 5 to 45, or 5 to 50 of the modified amino acid residues (or any number in between those listed) are conservative substitutions. In another embodiment, 1 to 5, 5 to 25, 5 to 30, 5 to 35, 5 to 40, 5 to 45, or 5 to 50 of the encoded modified amino acid residues (or any number in between those listed) are non-conservative substitutions. In a further embodiment, 1 to 5, 5 to 15, 5 to 20, 5 to 25, 5 to 30, 5 to 35, 5 to 40, or 5 to 45 of the encoded amino acid residue modifications (or any number in between those listed) are conservative substitutions and 1 to 5, 5 to 15, 5 to 20, 5 to 25, 5 to 30, 5 to 35, 5 to 40, or 5 to 45 of the encoded amino acid residue modifications (or any number in between those listed) are non-conservative substitutions. In additional embodiments, 1 to 5, 5 to 25, 5 to 30, 5 to 35, 5 to 40, 5 to 45, 5 to 50, 5 to 55, or 5 to 60 of the encoded substitutions (or any number in between those listed) are at amino acid residues of SEQ ID NO:1 selected from the group consisting of one or more of: M1, G2, S3, W4, A5, E6, K8, Q9, R10, A12, A13, K15, T16, R17, E19, A20, L21, G22, G23, S24, E25, A26, E27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 of the encoded substitutions (or any number in between those listed) are at amino acid residues of SEQ ID NO:1 selected from the group consisting of one or more of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In a further embodiment, the nucleic acids optionally encode a DBDpp that further comprises an amino acid sequence wherein 1 to 5, 5 to 15, 5 to 20, 5 to 25, 5 to 30, 5 to 35, 5 to 40, or 5 to 45 (or any number in between those listed) of the residues corresponding to the solvent inaccessible residues of the amino acid sequence of SEQ ID NO:1 are substituted and wherein the DBDpp specifically binds a target of interest. In another embodiment, the library comprises nucleic acids encoding at least 2, 3, 4, 5, 10, 25, 50, 75, 100, 250, 500, or 1000 different DBDpp that specifically bind different targets (or have varied affinity for the same target). In a further embodiment, the different targets bound by DBDpp in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, the vector library is contained in host cells (e.g., viral particles). In another embodiment, the library comprises a plurality of host cells that display the DBDpp on their surface. In a further embodiment, the host cells are phage that display the DBDpp on their surface. In some embodiments, the vector library comprises: (a) nucleic acids encoding 3 DBDpp that specifically bind to different targets; (b) nucleic acids encoding 3 DBDpp having different sequences that specifically bind to the same target; (c) nucleic acids encoding 3 DBDpp having different sequences that specifically bind to the same epitope of a target; (d) nucleic acids encoding 3 DBDpp having different sequences that specifically bind to different epitopes of a target; (e) nucleic acids encoding 3 DBDpp having different sequences that compete for binding to the same target; or (f) 3 different nucleic acid sequences encoding the same DBDpp sequence. Host cells containing the vectors are also provided.

In one embodiment, a vector library comprises a plurality of different nucleic acids encoding DBDpp, wherein the encoded DBDpp comprises an amino acid sequence selected from the group consisting of: (a) MGSWX$_5$EFX$_8$X$_9$RLX$_{12}$AIX$_{15}$X$_{16}$RLX$_{19}$ALGGSEAELA AFEKEIAAFESELQAYKGKGNPEVEX$_{55}$LRX$_{58}$X$_{59}$ AAX$_{62}$IRX$_{65}$X$_{66}$LQAYRHN (SEQ ID NO:4), wherein X$_5$, X$_8$, X$_9$, X$_{12}$, X$_{15}$, X$_{16}$, X$_{19}$, X$_{55}$, X$_{58}$, X$_{59}$, X$_{62}$, X$_{65}$, and/or X$_{66}$, is a natural and/or non-natural amino acid residue; (b) MGSWX$_5$X$_6$FKX$_9$X$_{10}$LAX$_{13}$IKX$_{16}$X$_{17}$LEALGG SEAELAX$_{30}$FEX$_{33}$X$_{34}$IAX$_{37}$FEX$_{40}$X$_{41}$LQX$_{44}$YKGKGN PEVEALRKEAAAIRDELQAYRHN (SEQ ID NO:2), wherein X$_5$, X$_6$, X$_9$, X$_{10}$, X$_{13}$, X$_{16}$, X$_{17}$, X$_{30}$, X$_{33}$, X$_{34}$, X$_{37}$, X$_{40}$, X$_{41}$, and/or X$_{44}$, is a natural and/or non-natural amino acid residue; (c) MGSWAEFKQRLAAIKTRLEA LGGSEAELAAFX$_{32}$X$_{33}$EIX$_{36}$AFX$_{39}$X$_{40}$ELX$_{43}$AYKGK GNPEVEALX$_{57}$X$_{58}$EAX$_{61}$AIX$_{64}$X$_{65}$ELX$_{68}$AYRHN (SEQ ID NO:3), wherein X$_{32}$, X$_{33}$, X$_{36}$, X$_{39}$, X$_{40}$, X$_{43}$, X$_{57}$, X$_{58}$, X$_{61}$, X$_{64}$, X$_{65}$, and/or X$_{68}$, is a natural and/or non-natural amino acid residue, and; (d) MGSWX$_5$X$_6$FKX$_9$X$_{10}$LAX$_{13}$IKX$_{16}$X$_{17}$LEALGGSEAEL AAFX$_{32}$X$_{33}$EIX$_{36}$AFX$_{39}$X$_{40}$ELX$_{43}$AYKGKGNPEVE X$_{55}$LRX$_{58}$X$_{59}$AAX$_{62}$IRX$_{65}$X$_{66}$LQAYRHN (SEQ ID NO:5), wherein X$_5$, X$_6$, X$_9$, X$_{10}$, X$_{13}$, X$_{16}$, X$_{17}$, X$_{32}$, X$_{33}$, X$_{36}$, X$_{39}$, X$_{40}$, X$_{43}$, X$_{55}$, X$_{58}$, X$_{59}$, X$_{62}$, X$_{65}$, and/or X$_{66}$, is a natural and/or non-natural amino acid residue; and (e) MGSWX$_5$EFX$_8$X$_9$RLX$_{12}$AIX$_{15}$X$_{16}$RLX$_{19}$ALGGSEAEL AX$_{30}$FEX$_{33}$X$_{34}$IAX$_{37}$FEX$_{40}$X$_{41}$LQX$_{44}$YKGKGNPEVE ALX$_{57}$X$_{58}$EAX$_{61}$AIX$_{64}$X$_{65}$ELX$_{68}$AYRHN (SEQ ID NO:6), wherein X$_5$, X$_8$, X$_9$, X$_{12}$, X$_{15}$, X$_{16}$, X$_{19}$, X$_{30}$, X$_{33}$, X$_{34}$, X$_{37}$, X$_{40}$, X$_{41}$, X$_{44}$, X$_{57}$, X$_{58}$, X$_{61}$, X$_{64}$, X$_{65}$, and/or X$_{68}$, is a natural and/or non-natural amino acid residue; and wherein the DBDpp specifically binds a target of interest. In an additional embodiment, X$_n$ is a natural amino acid residue. In a further embodiment, X$_n$ is a natural amino acid residue other than cysteine or proline. In still additional embodiments, X$_n$ is a deletion of an amino acid (e.g., optionally a null position in the sequence). In an additional embodiment, a plurality of the vectors in the library encode a DBDpp fusion protein. In another embodiment, the library comprises nucleic acids encoding at least 2, 3, 4, 5, 10, 25, 50, 75, 100, 250, 500, or 1000 different DBDpp that specifically bind different targets. In a further embodiment, the different targets bound by DBDpp encoded by the nucleic acids in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, a plurality of the vectors of the vector library are contained in host cells (e.g., viral particles such as phage), E. coli, yeast, and mammalian cells. In another embodiment, the host cells display DBDpp on their surface. In a further embodiment, the host cells are phage that display DBDpp on their surface. In some embodiments, the vector library comprises: (a) nucleic acids encoding 3 DBDpp that specifically bind to different targets; (b) nucleic acids encoding 3 DBDpp having different sequences that specifically bind to the same target; (c) nucleic acids encoding 3 DBDpp having different sequences that specifically bind to the same epitope of a target; (d) nucleic acids encoding 3 DBDpp having different sequences that specifically bind to different epitopes of a target; (e) nucleic acids encoding 3 DBDpp having different sequences that compete for binding to the same target; or (f) 3 different nucleic acid sequences encoding the same DBDpp sequence. Host cells containing the vectors are also provided.

In one embodiment, a vector library comprises a plurality of nucleic acids encoding DBDpp comprising an amino acid sequence selected from the group consisting of: (a) MGSWX$_5$EFX$_8$X$_9$RLX$_{12}$AIX$_{15}$X$_{16}$RLX$_{19}$ALZ$_1$EAELAA FEKEIAAFESELQAYZ$_2$NPEVE X$_{50}$LRX$_{53}$X$_{54}$AAX$_{57}$IRX$_{60}$X$_{61}$LQAYRHN (SEQ ID NO:9), wherein X$_5$, X$_8$, X$_9$, X$_{12}$, X$_{15}$, X$_{16}$, X$_{19}$, X$_{50}$, X$_{53}$, X$_{54}$, X$_{57}$, X$_{60}$, and/or X$_{61}$, is a natural and/or non-natural amino acid residue, and Z$_1$ and Z$_2$ is 2 to 30 natural and/or non-natural amino acid residues; (b) MGSWX$_5$X$_6$FKX$_9$X$_{10}$LA X$_{13}$IKX$_{16}$X$_{17}$LEALZ$_1$EAELAX$_{28}$FEX$_{31}$X$_{32}$IAX$_{35}$FEX$_{38}$ X$_{39}$LQX$_{42}$YZ$_2$NPEVEALRKEAAA IRDELQAYRHN (SEQ ID NO:7), wherein X$_5$, X$_6$, X$_9$, X$_{10}$, X$_{13}$, X$_{16}$, X$_{17}$, X$_{28}$, X$_{31}$, X$_{32}$, X$_{35}$, X$_{38}$, X$_{39}$, and/or X$_{42}$, is a natural and/or non-natural amino acid residue, and Z$_1$ and Z$_2$ is 2 to 30 natural and/or non-natural amino acid residues; (c) MGSWAEFKQRLAAIKTRLEALZ$_1$EAEL AAFX$_{30}$X$_{31}$EIX$_{34}$AFX$_{37}$X$_{38}$ELX$_{41}$AYZ$_2$NPEVEALX$_{52}$ X$_{53}$EAX$_{56}$AIX$_{59}$X$_{60}$ELX$_{63}$AYRHN (SEQ ID NO:8), wherein X$_{30}$, X$_{31}$, X$_{34}$, X$_{37}$, X$_{38}$, X$_{41}$, X$_{52}$, X$_{53}$, X$_{56}$, X$_{59}$, X$_{60}$, and/or X$_{63}$, is a natural and/or non-natural amino acid residue, and Z$_1$ and Z$_2$ is 2 to 30 natural and/or non-natural amino acid residues; (d) MGSWX$_5$X$_6$FKX$_9$X$_{10}$LAX$_{13}$IKX$_{16}$X$_{17}$LEALZ$_1$EAELAA FX$_{30}$X$_{31}$EIX$_{34}$AFX$_{37}$X$_{38}$ELX$_{41}$AYZ$_2$NPEVEX$_{50}$LRX$_{53}$ X$_{54}$AAX$_{57}$IRX$_{60}$X$_{61}$LQAYRHN (SEQ ID NO:10), wherein X$_5$, X$_6$, X$_9$, X$_{10}$, X$_{13}$, X$_{16}$, X$_{17}$, X$_{30}$, X$_{31}$, X$_{34}$, X$_{37}$, X$_{38}$, X$_{41}$, X$_{50}$, X$_{53}$, X$_{54}$, X$_{57}$, X$_{60}$, and/or X$_{61}$, is a natural and/or non-natural amino acid residue, and Z$_1$ and Z$_2$ is 2 to 30 natural and/or non-natural amino acid residues; and (e) MGSWX$_5$EFX$_8$X$_9$RLX$_{12}$AIX$_{15}$X$_{16}$RL X$_{19}$ALZ$_1$EAELAX$_{28}$FEX$_{31}$X$_{32}$IAX$_{35}$FEX$_{38}$X$_{39}$LQX$_{42}$ YZ$_2$NPEVEALX$_{52}$X$_{53}$EAX$_{56}$AIX$_{59}$X$_{60}$ELX$_{63}$AYRHN (SEQ ID NO:11), wherein X$_5$, X$_8$, X$_9$, X$_{12}$, X$_{15}$, X$_{16}$, X$_{19}$, X$_{28}$, X$_{31}$, X$_{32}$, X$_{35}$, X$_{38}$, X$_{39}$, X$_{42}$, X$_{52}$, X$_{53}$, X$_{56}$, X$_{59}$, X$_{60}$, and/or X$_{63}$, is a natural and/or non-natural amino acid residue, and Z$_1$ and Z$_2$ is 2 to 30 natural and/or non-natural amino acid residues; and wherein the DBDpp specifically binds a target of interest. In an additional embodiment, X$_n$ is a natural amino acid residue. In a further embodiment, X$_n$ is a natural amino acid residue other than cysteine or proline. In still additional embodiments, X$_n$ is a deletion of an amino acid (e.g., optionally a null position in the sequence). In an additional embodiment, a plurality of the vectors in the library encode a DBDpp fusion protein. In another embodiment, the library comprises nucleic acids encoding at least 2, 3, 4, 5, 10, 25, 50, 75, 100, 250, 500, or 1000 different DBDpp that specifically bind different targets. In a further embodiment, the different targets bound by DBDpp encoded by the nucleic acids in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, a plurality of the vectors of the vector library are contained in host cells. [In another embodiment, the host cells (e.g., viral particles) display DBDpp on their surface. In a further embodiment, the host cells are phage that display DBDpp on their surface. In some embodiments, the host cells are mammalian cells. In some embodiments, the vector library comprises: (a) nucleic acids encoding 3 DBDpp that specifically bind to different targets; (b) nucleic acids encoding 3 DBDpp having different sequences that specifically bind to the same target; (c) nucleic acids encoding 3 DBDpp having different sequences that specifically bind to the same epitope of a target; (d) nucleic acids encoding 3 DBDpp having different sequences that specifically bind to different epitopes of a target; (e) nucleic acids encoding 3 DBDpp having different sequences that compete for binding to the same target; or (f) 3 different nucleic acid sequences encoding the same DBDpp sequence. Host cells containing the vectors are also provided.

The DBDpp according to several embodiments provided herein possess activities that include but are not limited to target binding, the ability to bind, link, and/or otherwise associate with a target of interest (e.g., a purification target, a therapeutic target, a diagnostic target, a peptide tag, and a serum protein such as human serum albumin (HSA) or an immunoglobulin) in vitro or in vivo and the ability to serve as a reactive site for linking or associating proteins such as DBDpp fusion proteins with additional moieties (e.g., a solid support), and/or other modifications. The DBDpp provided herein can also possess additional desirable properties and/or functionalities useful in manufacturing, purification, formulation and biological, diagnostic, and therapeutic applications.

In some embodiments, a DBDpp is used to bind, detect, quantitate, remove, and/or purify a target of interest in a sample containing the target.

One non-limiting embodiment provides a method for detecting a target of interest in a sample, comprising: (a) contacting the sample with a DBDpp that specifically binds the target, under conditions suitable for specific binding of the DBDpp to the target, to form a target/DBDpp complex, and (b) detecting the presence of the complex and/or captured target. In one embodiment, the DBDpp is immobilized on a solid support.

Also provided is a method for quantifying a target of interest in a sample containing the target, comprising: (a) contacting the sample with a DBDpp that specifically binds the target and that is immobilized on a solid support, under conditions suitable for specific binding of the DBDpp to the target, to form a target/DBDpp complex and (b) detecting the presence of the target/DBDpp complex and/or captured target, wherein quantitative detection of the product indicates, or is otherwise able to be correlated with, the quantity of the target in the sample.

Some embodiments provide methods for purifying a target of interest from a sample containing the target that comprises: (a) contacting a sample containing a target of interest with a DBDpp that specifically binds the target, under conditions suitable for specific binding of the DBDpp to the target, and (b) recovering the bound target. In some embodiments, the target is recovered by elution. In one embodiment, the DBDpp is immobilized on a solid support. In a further embodiment, the elution of the bound target is monitored by ultra violet light absorption, or other visualization or chemical-based detection technique. In some embodiments, methods are provided to remove an undesired target of interest from a sample and wherein the bound undesired target is discarded directly or is eluted (or otherwise collected or separated) and then discarded.

An additional embodiment provides a method of screening a library of DBDpp for a DBDpp that specifically binds a target of interest, that comprises: (a) obtaining a plurality of host cells (e.g., viral particles, phage, bacteria, and/or mammalian cells) displaying a library of DBDpp on their surface; (b) contacting the plurality of host cells with a target of interest under conditions suitable for specific binding of the target to a DBDpp; and (c) determining the binding of the target to the DBDpp. In one embodiment, the host cells are phage that display the DBDpp on their surface.

Methods of using DBDpp in diagnostic and therapeutic applications are also provided, in several embodiments. One embodiment provides a method of treating a disease or disorder comprising administering a therapeutically effective amount of a DBDpp (e.g., a DBDpp fusion protein) that specifically binds a therapeutic target of interest to a subject in need thereof. In some embodiments, the disease or disorder is cancer, a disease or disorder of the immune system, or an infection. Methods of treating a disease or disorder that comprises co-administering an additional therapeutic agent along with a DBDpp are also provided.

Additionally provided are methods for treating or preventing cancer comprising administering a DBDpp-CAR T lymphocyte to a patient (e.g., predisposed to or having a cancer) that expresses a tumor antigen on the surface of target cells, and wherein the DBDpp specifically binds the antigen.

Certain methods summarized above and set forth in further detail below describe certain actions taken by a practitioner; however, it should be understood that they can also include the instruction of those actions by another party. Thus, actions such as "administering a T cell comprising a target specific binding polypeptide-CAR" include "instructing the administration of a T cell comprising a target specific binding polypeptide-CAR."

BRIEF DESCRIPTION OF THE DRAWINGS

FIGS. 2A-J. Schematic representation of different homology models of DBDpp based off the reference scaffold of SEQ ID NO:1. The residues targeted for modification in the Face libraries (F1, F2, and F3) and Combined libraries (C1 and C2) of DBDpp are darkly shaded. Longitudinal and transverse perspective views of the F1 library are shown in FIG. 2A and FIG. 2B respectively. Longitudinal and transverse perspective views of the F2 library are shown in FIG. 2C and FIG. 2D respectively. Longitudinal and transverse perspective views of the F3 library are shown in FIG. 2E and FIG. 2F respectively. Longitudinal and transverse perspective views of the C1 library are shown in FIG. 2G and FIG. 2H respectively. Longitudinal and transverse perspective views of the C2 library are shown in FIG. 2I and FIG. 2J respectively. N-terminus (NT) and C-terminus (CT) for each model are indicated.

FIGS. 3A-D. FIG. 3A. Schematic depiction of phage display construct for use in accordance with several embodiments disclosed herein. FIG. 3B. Depicts a linear vector map for the pComb phagemid vector used to generate the libraries disclosed herein. The libraries were created through Kunkel mutagenesis, utilizing oligos containing NNK or trimer codons. DBDpp variant peptide sequences were expressed in-frame, between the FLAG peptide tag sequence and M13 gene pIII. The DBDpp were expressed as an N-terminal pIII gene fusion, under the control of a DsbA signal peptide. FIG. 3C. Depicts a linear vector map for the pComb phagemid vector used to generate DBDpp libraries described in the examples. DBDpp were expressed in-frame, between the DsbA signal peptide and M13 gene pIII. The modified pComb phagemid vector is the same as that depicted in FIG. 3B, but absent the FLAG peptide tag sequence, which is in accordance with certain embodiments disclosed herein (wherein the FLAG tag is optionally removed or replaced with another variety of tag). FIG. 3D depicts data from a comparative binding assay. N-terminal FLAG tag fusions were expressed and purified from E. coli cultures. ELISA-based binding assessment demonstrated that purified FLAG-pb04 (targets PD-L1) binds in a dose dependent manner to PD-L1-Fc coated microtiter wells, whereas FLAG-α3D (the reference sequence of SEQ ID 49, with an N-terminal FLAG tag) exhibits no change in binding.

FIG. 5A. Depicts a schematic representation of DBDpp-CAR fusion proteins according to several embodiments disclosed herein. Six different DBDpp-CAR formats are presented, by way of example, and are intended to be illustrative and not limiting. Extracellular DBDpp domains may be specific for a single target (e.g. DBDpp "A") or more than one target or epitope (e.g. DBDpp "A" and DBDpp "B"). Non-limiting examples of transmembrane (TM) domains are shown, as are non-limiting examples of intracellular domains derived from CD3, CD28 and 41BB. Domains are optionally linked via peptide linkers (shown in shading). FIG. 5B. Depicts a further schematic of a membrane bound (e.g., extracellular) DBDpp-CAR fusion. FIG. 5C. Depicts a schematic of a soluble DBDpp.

FIG. 9 depicts HPLC purification of a DBDpp produced according to several embodiments disclosed herein.

FIG. 10 depicts SDS-PAGE analysis of purified DBDpp produced according to several embodiments disclosed herein. Lane 1 is a molecular weight marker, Lane 2 correspond to a purified DBDpp of SEQ ID NO: 58, and lanes 3-9 correspond to purified DBDpp of SEQ ID NOS: 51-57, respectively.

FIG. 11 depicts a deconvoluted electrospray ionisation mass spectrometry (ESI-MS) spectrum of SEQ ID NO. 54.

FIGS. 12A-12P depict data related to the binding of CD137-targeting DBDpp to CD137 that was immobilized on a solid surface. FIGS. 12A, 12C, 12E, 12G, 12I, 12K, 12M, and 12O are sensorgrams for DBDpps of SEQ ID NOS: 51 (12A), 52 (12C), 53 (12E), 54 (12G), 55 (12I), 56 (12K), 57 (12M) and 58 (12O). FIGS. 12B, 12D, 12F, 12H, 12J, 12L, 12N, and 12P depict the corresponding steady state binding data for DBDpps of SEQ ID 51 (12B), 52 (12D), 53 (12F), 54 (12H), 55 (12J), 56 (12L), 57 (12N) and 58 (12P).

FIG. 13 depicts chromatographic data for the purification of CD137 protein from Chinese Hamster Ovary (CHO) cell supernatant.

FIG. 14A depicts a Coomassie stained gel loaded with purified fractions from DBDpp purification columns. Lane 1 is a molecular weight marker. Lane 2 is IMAC-purified CD137 protein, and Lanes 3-8 are eluates from columns with various DBDpp according to several embodiments herein. FIG. 14B is a western blot analysis with corresponding samples to those shown in FIG. 14A.

FIG. 15A depicts assessment of DR5 scFv binding to PD-L1PD-L1-Fc coated microplate wells after exposure to various elevated temperatures. FIG. 15B depicts data showing a correlation between increased temperature and reduced PDL1 binding by a PD-L1PD-L1-directed scFv. FIG. 15C shows a DBDpp, according to one embodiment disclosed herein (pb04 DBDpp), retained PD-L1PD-L1 binding affinity after being exposed to increasing temperatures, up to 100° C. FIG. 15D shows an additional DBDpp (pb06 DBDpp) that also demonstrates thermal stability and can bind PD-L1PD-L1 after being exposed to temperatures up to 100° C.

FIG. 16A depicts data related to the ability of DBDpp to bind targets across species. In particular, FIG. 16A demonstrates that a soluble DBDpp directed against PD-L1 can bind to human PD-L1 (upper trace) as well as cynomolgus PD-L1 (lower trace) with similar binding affinities. FIG. 16B depicts flow cytometry data confirming that when expressed in a T cell, specifically a chimeric antigen receptor T cell, the T cell can recognize and bind to both human and cynomolgus PD-L1.

FIG. 17 depicts data related to the DBDpp-CAR expression and CD-123-Fc binding of various candidate DBDpp-CAR HEK-293T cells.

FIG. 18 depicts data related to the expression and ability of DBDpp-CAR Jurkat cells to function through an intracellular signaling pathway.

FIG. 19A shows data related to the production of interferon gamma (IFNγ) by T cells expressing DBDpp-CARs that target CD123. FIG. 19B depicts similar data measuring the production of interleukin 2 (IL2) by CD123-targeting DBDpp-CAR T cells.

FIG. 20A shows data related to the production of interferon gamma (IFNγ) by T cells expressing DBDpp-CARs that target PD-L1. FIG. 20B depicts similar data measuring the production of interleukin 2 (IL2) by PD-L1-targeting DBDpp-CAR T cells.

FIG. 21 depicts data related to the proliferation of CD123-targeting DBDpp-CAR T cells as compared to control and CD123-targeting scFv.

FIG. 22 depicts data related to the proliferation of PD-L1-targeting DBDpp-CAR T cells as compared to mock conditions.

FIG. 23A depicts expression of three exhaustion markers (LAG-3, PD-1, and TIM3) on T cells expressing various DBDpp-CARs at similar levels of the expression of those markers on scFv. FIG. 23B shows flow cytometry data depicting similar exhaustion marker expression on DBDpp-CAR T cells (expressing CD123 targeting cg06 DBDpp) as compared to a CAR T cell expressing CD123-specific scFv (32716).

FIG. 24A depicts CD107a production (as a marker of degranulation of the DBDpp-CAR T cells) when CD123-targeting DBDpp-CAR T cells are cultured alone. FIG. 24B shows CD107a production when DBDpp-CAR T cells are co-cultured with CD123 negative K562 tumor cells. FIG. 24C shows CD107a when CD123-targeting DBDpp-CAR T cells are co-cultured with CD123 positive BDCM cells. FIG. 24D depicts data from experimental replicates of co-culture of CD123-targeting DBDpp-CAR T with CD123 positive BDCM cells.

FIG. 25A shows CD107a expression (as a marker of degranulation of the DBDpp-CAR T cells) when PD-L1-targeting DBDpp-CAR T cells are cultured alone, e.g., unactivated. FIG. 25B shows the measurement of CD107a when DBDpp-CAR T cells are co-cultured with PD-L1 negative K562 tumor cells. FIG. 25C shows increased CD107a when PD-L1-targeting DBDpp-CAR T cells are co-cultured with PD-L1 positive SUDHL1 cells. FIG. 25D depicts data from experimental replicates of co-culture of PD-L1-targeting DBDpp-CAR T with PD-L1 positive SUDHL1 cells.

FIG. 26A shows data related CD123 targeting DBDpp-CAR T cells kill percentage of K562 tumor cells that are negative for CD123. FIG. 26B shows kill percentages when the CD123 targeting DBDpp-CAR T cells are co-cultured with CD123 positive BDCM cells. The data from FIGS. 26A and 26B were generated using T cells from a first donor blood sample. FIGS. 26C and 26D show similar data from T cells collected from a second donor.

FIG. 27A shows data related to PD-L1 targeting DBDpp-CAR T cells kill percentage of K562 tumor cells that are negative for PD-L1. The CAR T cells expressing the various PD-L1 targeting DBDpp exhibited kill rates lower than mock controls. Similar data is shown in FIGS. 27C and 27E for two additional donors. FIG. 27B shows elevated kill percentages when the PD-L1 targeting DBDpp-CAR T cells are co-cultured with PD-L1 positive SUDHL1 cells. Similar data is shown in FIGS. 27D and 27F for two additional donors.

FIGS. 28A-28D. DBDpp having reduced immunogenicity potential. Because the DBDpp as disclosed herein are synthetic, an analysis was performed to identify potentially immunogenic epitopes. A three-dimensional model of a DBDpp (cg06) is shown in FIG. 28A. FIG. 28B depicts cg06 with one (of three) of the potentially immunogenic epitopes modified to be less potentially immunogenic. FIG. 28C depicts cg06 with two (of three) of the potentially immunogenic epitopes modified. FIG. 28D depicts cg06 with all three of the potentially immunogenic epitopes modified.

FIG. 29A depicts data related to CAR T cells expressing variants of CD123 targeting DBDpp (cg06). Even with all three potentially immunogenic epitopes removed from the DBDpp sequence, the variants retain the ability mediate signal transduction (activating Jurkat cells engineered to express luciferase) after binding to CD123 positive BDCM target cells (unmodified cg06 designated with arrow). FIG. 29B shows similar efficacy when modified variants bound to CD123 positive KG-1a cells (unmodified cg06 designated with arrow).

FIG. 30A depicts flow cytometry data for expression of CD123 on K562 cells, KG1a cells, BDCM cells, SUDHL cells, or H460 cells. FIG. 30B depicts flow cytometry data for expression of PD-L1 on the same cells lines.

FIG. 31A shows the percentage of T cells expressing CD123 targeting DBDpp-CARs. FIG. 31B shows the percentage of T cells expressing PD-L1 targeting DBDpp-CARs. FIG. 31C shows the percentage of T cells expressing bi-specific CD123-PD-L1 targeting DBDpp-CARs (expressed with cg06 DBDpp distal to the T cell membrane versus the pb04 DBDpp). FIG. 31D shows the percentage of T cells expressing bi-specific PD-L1-CD123 targeting DBDpp-CARs (expressed with pb04 DBDpp distal to the T cell membrane versus the cg06 DBDpp). FIG. 31E depicts data related to the increased intracellular signaling of bispecific DBDpp.

FIG. 32 demonstrates one embodiment of a competitive binding assay that can be used to identify DBDpp that display shared epitope binding even though the DBDpp tested have different primary amino acid sequences.

DETAILED DESCRIPTION

Figure 1A:
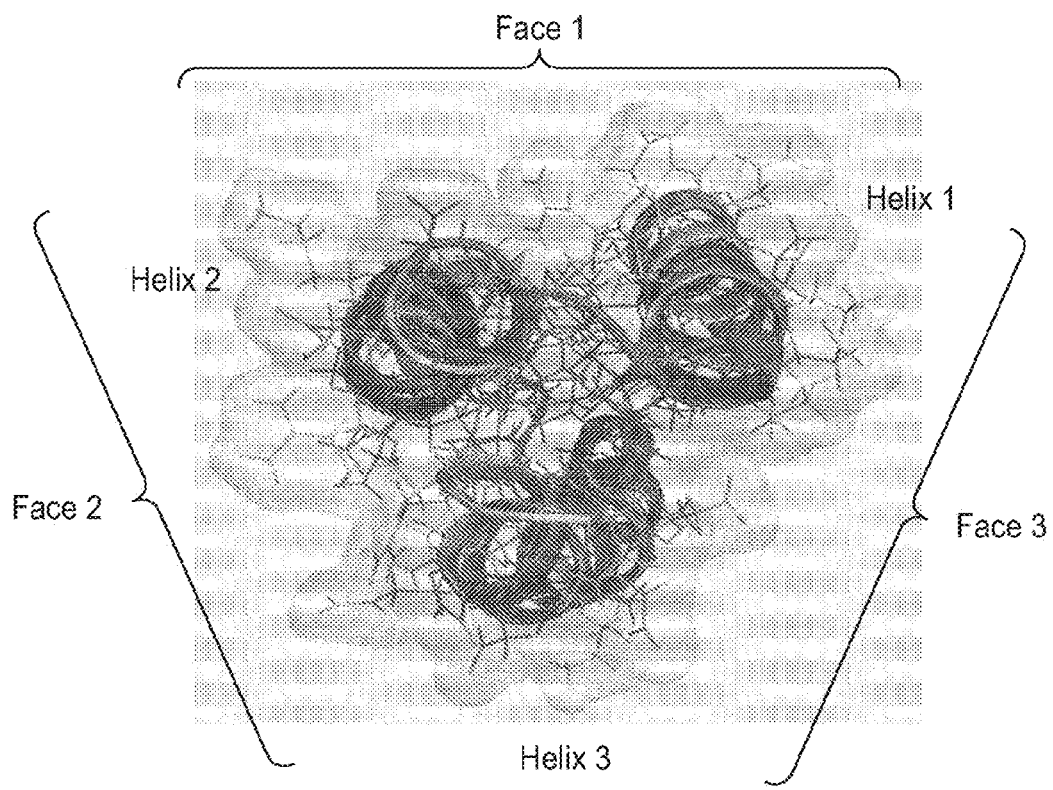
FIGS. 1A-B. Schematic depicting SEQ ID NO:1 derived homology model of DBDpp. Transverse view illustrating the helices and three faces of domain (FIG. 1A). Longitudinal view illustrating position of residue E19, N-terminus (NT) and C-terminus (CT) (FIG. 1B).

The section headings used herein are for organizational purposes only and are not to be construed as in any way limiting of the subject matter described.

Definition of Terms

It is understood that wherever embodiments are described herein with the language "comprising" otherwise analogous embodiments described in terms of "consisting of" and/or "consisting essentially of" are also provided. However, when used in the claims as transitional phrases, each should be interpreted separately and in the appropriate legal and factual context (e.g., "comprising" is considered more of an open-ended phrase while "consisting of" is more exclusive and "consisting essentially of" achieves a middle ground).

As used herein, the singular form "a", "an", and "the" includes plural references unless indicated otherwise.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The terms "protein" and "polypeptide" are used interchangeably herein to refer to a biological polymer comprising units derived from amino acids linked via peptide bonds; a protein can be composed of two or more polypeptide chains.

The terms "antibody" or "immunoglobulin," as used interchangeably herein, include whole antibodies and antibody fragments including any functional domain of an antibody such as an antigen-binding fragment or single chains thereof, an effector domain, salvage receptor binding epitope, or portion thereof. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, C1. The VH and VL regions can be further subdivided into regions of hypervariablity, termed Complementarity Determining Regions (CDRs), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Non-limiting types of antibodies of the present disclosure include typical antibodies, scFvs, and combinations thereof where, for example, a DBDpp is covalently linked (e.g., via peptide bonds or via a chemical linker) to the N-terminus of either the heavy chain and/or the light chain of a typical whole (full-length) antibody, or intercalated in the H chain and/or the L chain of a whole antibody.

The term "antibody fragment" refers to a portion of an intact antibody and refers to any functional domain of an antibody such as an antigen-binding fragment or single chains thereof, an effector domain or a portion thereof, and a salvage receptor binding epitope or a portion thereof. Examples of antibody fragments include, but are not limited to, Fab, Fab', F(ab')2, and Fv fragments, linear antibodies, single chain antibodies, and multi-specific antibodies formed from antibody fragments. "Antibody fragment" as used herein comprises an antigen-binding site or epitope binding site. In one embodiment, the DBDpp fusion protein comprises an effector domain or portion thereof. In one embodiment, the DBDpp fusion protein comprises a salvage receptor binding epitope, or portion thereof.

As used herein, the term, "Fc region" or simply "Fc" is understood to mean the carboxyl-terminal portion of an immunoglobulin chain constant region, preferably an immunoglobulin heavy chain constant region, or a portion thereof. For example, an immunoglobulin Fc region may comprise (1) a CH1 domain, a CH2 domain, and a CH3 domain, (2) a CH1 domain and a CH2 domain, (3) a CH1 domain and a CH3 domain, 4) a CH2 domain and a CH3 domain, or (5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087, and 5,726,044, each of which is incorporated by reference herein, in their entirety. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM. Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole, J. Immunol. 159:3613 (1997)).

"Antibody-dependent cell-mediated cytotoxicity" or "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis (or other cytotoxic effects) of the target cell. To assess ADCC activity of a molecule of interest, any in vitro ADCC assay known in the art can be used, such as that described in U.S. Pat. No. 5,500,362 or 5,821,337. Useful effector cells for such assays include, but are not limited to, peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. PNAS 95:652-656 (1998).

The terms "single chain variable fragment(s)," or "scFv" antibodies as used herein refer to forms of antibodies (e.g., antibody fragments) comprising the variable regions of only the heavy and light chains, connected by a linker peptide. In one embodiment, a DBDpp fusion protein comprises a DBDpp and a scFv.

The term "linker" refers to a peptide or other chemical linkage located between a DBDpp and another polypeptide of a DBDpp fusion protein. Suitable linkers for coupling the two or more linked DBDpp will be clear to the persons skilled in the art and non-limiting examples are described herein.

The term "operably linked," as used herein, indicates that two molecules are attached so as to each retain at least some level of functional activity that each molecule had alone (assuming that each molecule had a function activity). In embodiments when one molecule was without functional activity, it is operably lined with another molecule if the other molecule retains at least some level of its functional activity. Operably linked can also refer to linkage of two non-function molecules. Two molecules can be "operably linked" whether they are attached directly or indirectly (e.g., via a linker).

The terms "specifically binds" or "having selective affinity for" mean that a binding agent such as a DBDpp reacts or associates more frequently, more rapidly, with greater duration, with greater affinity, or with some combination of the above to the epitope, protein, or target molecule than with alternative substances, including proteins unrelated to the target epitope. Because of the sequence identity between homologous proteins in different species, specific binding can, in several embodiments, include a binding agent that recognizes a protein or target in more than one species. Likewise, because of homology within certain regions of polypeptide sequences of different proteins, specific binding can include a binding agent that recognizes more than one protein or target. It is understood that, in certain embodiments, a binding agent that specifically binds a first target may or may not specifically bind a second target. As such, "specific binding" does not necessarily require (although it can include) exclusive binding, e.g., binding to a single target. Thus, a binding agent may, in certain embodiments, specifically bind more than one target. In certain embodiments, multiple targets may be bound by the same antigen-binding site on the binding agent.

"Target" refers to any molecule or combination of molecules that can be bound by a DBDpp such as a DBDpp fusion protein, or other component of the DBDpp fusion protein such as an antibody or antibody variable domain fragment.

The terms "epitope" and "antigenic determinant" are used interchangeably herein and refer to that portion of any molecule (e.g., a target of interest) capable of being recognized and specifically bound by a particular binding agent (e.g., an DBDpp or antibody). When the recognized molecule is a polypeptide, epitopes can be formed from contiguous amino acids and noncontiguous amino acids and/or other chemically active surface groups of molecules (such as carbohydrates) juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3 amino acids, and more usually, at least 5 or 8-10 amino acids in a unique spatial conformation.

A "peptide tag" as used herein refers to a peptide sequence that is part of or attached (for instance through genetic engineering) to another protein, to provide a function to the resultant fusion. Peptide tags are usually relatively short in comparison to a protein to which they are fused; by way of example, peptide tags are, in several embodiments, four or more amino acids in length, such as, 5, 6, 7, 8, 9, 10, 15, 20, or 25 or more amino acids. In some embodiments, the DBDpp is a fusion protein that contains a peptide tag. In other embodiments, the DBDpp specifically binds a peptide tag. Numerous peptide tags that have uses as provided herein are known in the art. Examples of peptide tags that may be a component of a DBDpp fusion protein or a target bound by a DBDpp (e.g., a DBDpp fusion protein). Examples of peptide tags that may be a component of a DBDpp fusion protein or a target bound by a DBDpp (e.g., a DBDpp fusion protein) include but are not limited to HA (hemagglutinin), c-myc, the Herpes Simplex virus glycoprotein D (gD), T7, GST, GFP, MBP, Strep-tags, His-tags, Myc-tags, TAP-tags and FLAG® tag (Eastman Kodak, Rochester, N.Y.) Likewise, antibodies to the tag epitope allow detection and localization of the fusion protein in, for example, affinity purification, Western blots, ELISA assays, and immunostaining of cells.

The term "naturally occurring" when used in connection with biological materials such as a nucleic acid molecules, polypeptides, and host cells, refers to those which are found in nature and not modified by a human being. Conversely, "non-natural" or "synthetic" when used in connection with biological materials refers to those which are not found in nature and have been modified by a human being.

As used herein "modifications" with respect to the sequence of reference scaffold SEQ ID NO:1 (or with respect to other sequences) includes substitutions, deletions insertions and/or additions of the sequence of the corresponding amino acid position of SEQ ID NO:1 (or with respect to the corresponding position of the other sequence).

A "substitution" with respect to the sequence of reference scaffold SEQ ID NO:1 (or with respect to other sequences) refers to a replacement of a particular amino acid residue with a different amino acid residue at a corresponding amino acid position of SEQ ID NO:1 (or with respect to the corresponding position of the other sequence).

A "conservative" amino acid substitution is one in which one amino acid residue is replaced with another amino acid residue having a similar side chain. Families of amino acid residues having similar side chains have been defined in the art, including basic side chains (e.g., lysine (K), arginine (R), histidine (H)), acidic side chains (e.g., aspartic acid (D), glutamic acid (E)), uncharged polar side chains (e.g., glycine (G), asparagine (N), glutamine (Q), serine (S), threonine (T), tyrosine (Y), cysteine (C)), nonpolar side chains (e.g., alanine (A), valine (V), leucine (L), isoleucine (I), proline (P), phenylalanine (F), methionine (M), tryptophan (W), beta-branched side chains (e.g., threonine (T), valine (V), isoleucine (I)) and aromatic side chains (e.g., tyrosine (Y), phenylalanine (F), tryptophan (W), histidine (H)). For example, substitution of a phenylalanine for a tyrosine is a conservative substitution. In one embodiment, conservative substitutions in the sequences of the DBDpp result in the specific binding of the DBDpp containing the substitution to the target of interest to which it binds. In one embodiment, conservative substitutions in the sequences of the DBDpp do not abrogate the binding of the DBDpp containing the substitution to the target of interest to which it binds. Methods of identifying nucleotide and amino acid conservative substitutions and non-conservative substitutions which confer, alter or maintain selective binding affinity are known in the art (see, e.g., Brummell, Biochem. 32:1180-1187 (1993); Kobayashi, Protein Eng. 12(10):879-884 (1999); and Burks, PNAS 94:412-417 (1997)).

A "non-conservative" amino acid substitution is one in which one amino acid residue is replaced with another amino acid residue having a dissimilar side chain. In one embodiment, non-conservative substitutions in the sequences of the DBDpp result in the specific binding of the DBDpp containing the substitution to the target of interest to which it binds. In one embodiment, non-conservative substitutions in the sequences of the DBDpp do not abrogate the binding of the DBDpp containing the substitution to the target of interest to which it binds.

"Non natural amino acids," "amino acid analogs" and "non-standard amino acid residues" are used interchangeably herein. Non-natural amino acids that can be substituted in a DBDpp as provided herein are known in the art. In one embodiment the non-natural amino acid is 4-hydroxyproline which can be substituted for proline; 5-hydroxylysine which can be substituted for lysine; 3-methylhistidine which can be substituted for histidine; homoserine which can be substituted for serine; and ornithine which can be substituted for lysine. Additional examples of non-natural amino acids that can be substituted in a DBDpp include, but are not limited to molecules such as: D-isomers of the common amino acids, 2,4-diaminobutyric acid, alpha-amino isobutyric acid, A-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, lanthionine, dehydroalanine, γ-aminobutyric acid, selenocysteine and pyrrolysine fluoro-amino acids, designer amino acids such as beta-methyl amino acids, C alpha-methyl amino acids, and N alpha-methyl amino acids, or combinations of non-natural amino acids. Still additional non-natural amino acids can include 4-amino butyric acid, 4-amino-3-hydroxy-5-phenylpentanoic acid, 4-amino-3-hydroxy-6-methylheptanoic acid, 2-thienyl alanine, and/or D-isomers of amino acids. As discussed herein, in several embodiments non-natural amino acids or amino acid analogs can include deletion of one or more amino acids from a sequence.

The terms "polynucleotide" and "nucleic acid," used interchangeably herein, refer to a polymeric form of nucleotides of any length, either ribonucleotides or deoxyribonucleotides. These terms include, but are not limited to, DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

The term "naked DNA" as used herein refers to DNA (e.g., histone free DNA) encoding a protein such as a DBDpp (e.g., a CAR) is a DNA cloned in a suitable expression vector in proper orientation for expression (e.g., a plasmid). Viral vectors which may be used include but are not limited to SIN lentiviral vectors, retroviral vectors, foamy virus vectors, adenovirus vectors, adeno-associated virus (AAV) vectors, hybrid vectors and/or plasmid transposons (for example sleeping beauty transposon system) or integrase based vector systems. Other vectors that can be used in connection with making and using DBDpp are described herein or otherwise known in the art.

The terms "vector", "cloning vector" and "expression vector" as used herein refer to the vehicle by which a nucleic acid sequence (e.g., a DBDpp coding sequence) can be maintained or amplified in a host cell (e.g., cloning vector) or introduced into a host cell, so as to transform the host and promote expression (e.g., transcription and translation) of the introduced sequence. Vectors include plasmids, phages, viruses, etc.

A "host cell" includes an individual cell or cell culture which can be or has been a recipient of nucleic acids encoding a DBDpp. Host cells includes but are not limited to viral particles, phagemids, bacteria, yeast plant, animal, and mammalian cells. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo, in vitro, or ex vivo with nucleic acids encoding a DBDpp. In some examples, the host cell is capable of expressing and displaying DBDpp on its surface, such as for example, in phage display. "Expression" includes transcription and/or translation.

A "library" of DBDpp refers to a plurality of unique DBDpp, and optionally including multiple DBDpp that bind to the same target, but with varied binding sites and/or specificities.

A "vector library" of DBDpp refers to a plurality of unique nucleic acids encoding DBDpp (as above, optionally including nucleic acids encoding DBDpp that bind to the same target, but with varied binding sites and/or specificities).

As used herein, the terms "solid support," "support," "matrices," and "resins" are used interchangeably and refer to, without limitation, any column (or column material), bead, test tube, microtiter dish, solid particle (for example, agarose or sepharose), microchip (for example, silicon, silicon-glass, or gold chip), or membrane (e.g., biologic or filter membrane) to which a DBDpp, antibody, or other protein may be attached (e.g., coupled, linked, or adhered), either directly or indirectly (for example, through other binding partner intermediates such as other antibodies or Protein A), or in which a DBDpp or antibody may be embedded (for example, through a receptor or channel). Reagents and techniques for attaching polypeptides to solid supports (e.g., matrices, resins, plastic, etc.) are well known in the art. Suitable solid supports include, but are not limited to, a chromatographic resin or matrix (e.g., SEPHAROSE-4 FF agarose beads), the wall or floor of a well in a plastic microtiter dish, a silica based biochip, polyacrylamide, agarose, silica, nitrocellulose, paper, plastic, nylon, metal, and combinations thereof. DBDpp and other compositions may be attached on a support material by a non-covalent association or by covalent bonding, using reagents and techniques known in the art. In one embodiment, the DBDpp is coupled to a chromatography material using a linker.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a human without the production of therapeutically prohibitive undesirable physiological effects such as nausea, dizziness, gastric upset and the like.

"Modulate," means adjustment or regulation of amplitude, frequency, degree, or activity. In another related aspect, such modulation may be positively modulated (e.g., an increase in frequency, degree, or activity) or negatively modulated (e.g., a decrease in frequency, degree, or activity). In several embodiments, modulation in a positive or negative direction is referenced as compared to the cell, tissue, or organ function prior to administration of a therapeutic. In additional embodiments, modulation in a positive or negative direction is referenced with respect to a normal, healthy cell, tissue or organ.

An "effective amount" of a DBDpp such as a DBDpp fusion protein as provided herein is an amount sufficient to carry out a specifically stated purpose such as to bring about an observable change in the level of one or more biological activities related to the target to which the DBDpp (e.g., a DBDpp fusion protein) binds. In certain embodiments, the change increases the level of target activity. In other embodiments, the change decreases the level of target activity. An "effective amount" can be determined empirically and in a routine manner, in relation to the stated purpose. The term "therapeutically effective amount" refers to an amount of a DBDpp such as a DBDpp fusion protein, or other therapeutic agent effective to "treat" (e.g., reduce symptoms of) a disease or disorder in a subject (mammal). A "prophylactically effective amount" refers to an amount effective, at dosages and for periods of time necessary, to achieve the desired prophylactic result.

"Patient," "subject," "animal" and "mammal" are used interchangeably and refer to mammals such as human patients and non-human primates, as well as experimental animals such as rabbits, rats, and mice, and other animals. Animals include all vertebrates, e.g., mammals and non-mammals, such as chickens, amphibians, and reptiles. "Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. In a particular embodiment, the patient is a human. The term does not denote a particular age or sex. Thus, adult and newborn subjects, as well as embryos and fetuses, whether male or female, are intended to be included within the scope of this term.

The terms "treat," "treatment," and "treating," as used herein refer to both therapeutic treatment and prophylactic or preventative measures, wherein the object is to prevent or slow down (lessen or delay) the symptoms, complications, or biochemical indicia of a disease, condition, or disorder, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease, condition, or disorder targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Treatment can be with a DBDpp fusion protein alone or in combination with an additional therapeutic agent.

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. "Tumor," as used herein refers to all neoplastic cell growth and proliferation, whether malignant or benign, and all pre-cancerous and cancerous cells and tissues. A "cancerous tumor," or "malignant cell" is understood as a cell having specific structural properties, lacking differentiation and being capable of invasion and metastasis. Cancers that can be treated using DBDpp fusion proteins provided herein include without limitation, breast, lung, brain, bone, liver, kidney, colon, head and neck, ovarian, hematopoietic (e.g., leukemia), and prostate cancer. Other types of cancer and tumors that may be treated using DBDpp-containing antibodies are described herein or otherwise known in the art.

The terms tumor antigen or cancer antigen are used interchangeably herein. Tumor and cancer antigens may be tumor-specific antigen (TSA), cancer-specific antigens (CSA) tumor-associated antigen (TAA) or cancer-associated antigens (CAA). A TSA is an antigen that is unique to tumor cells and does not occur on other cells in the body. A TAA is an antigen that is found on both tumor and some normal cells. Because of the dynamic nature of tumors, in some instances, tumor cells may express unique antigens at certain stages, and at others also express antigens that are also expressed on non-tumor cells. Thus, inclusion of a certain marker as a TAA does not preclude it being considered a TSA. Examples of TAAs and TSAs that may be specifically bound by a DBDpp include but are not limited to: CD19, CD20, CD22, ROR 1, mesothelin, CD33/1L3Ra, cMet, PSMA, Glycolipid F77, EGFRvIII, GD2, NY-ESO-1TCR, MAGE A3 TCR MARTI, gp100 (Pmel 17), tyrosinase, TRP1, TRP2, MAGE1, MAGE3, BAGE, GAGE1, GAGE2, pi5, CEA; p53, Ras, HER-2/neu; BCR-ABL, E2A-PRL, H4-RET, 1GH-IGK, MYL-RAR; EBVA, HPV antigens E6 and E7, TSP-180, MAGE4, MAGE5, MAGE6, RAGE, NY-ESO, p185erbB2, p180erbB3, nm-23H1, PSA, CA19-9, CA72-4, CAM 17.1, NuMa, K-ras, beta-Catenin, CDK4, Mum-1, p15, p16, 43-9F, 5T4(791Tgp72) alpha-fetoprotem, beta-HCG, BCA225, BTAA, CA125, CA 15-3\CA 27.29\BCAA, CA195, CA242, CA50, CAM43, CD68\I, CO-029, FGF5, G250, Ga733VEpCAM, HTgp-175, M344, MA50, MG7-Ag, MOV 18, NB/70K, NY-CO-1, RCAS1, SDCCAG16, TA90\Mac-2, TAAL6, TAG72, TLP, and TPS.

The term "target cell" as used herein refers to cells which are involved in a disease and can be targeted by DBDpp containing compositions. Other target cells include any cell in a subject (e.g., a human or animal) that can be targeted by DBDpp of the invention. The target cell can be a cell expressing or overexpressing a target specifically bound by a DBDpp fusion protein.

The term "effector cells" are leukocytes which express one or more FcRs and perform effector functions. Preferably, the cells express at least Fc(RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred in certain embodiments. The effector cells can be isolated from native source thereof, e.g., from blood or PBMCs as described herein or otherwise known in the art. In a specific embodiment, the effector cells are human effector cells.

The term "effector function" refers to the specialized immune function of a differentiated cell. Effector function of a T-cell, for example, may be cytolytic activity or helper activity including the secretion of cytokines.

The terms "T-cell" and "T-lymphocyte" are interchangeable and used synonymously herein. Examples include but are not limited to naive T cells, central memory T cells, effector memory T cells or combinations thereof.

The term "immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells.

The term "immune response" as used herein refers to immunities including but not limited to innate immunity, humoral immunity, cellular immunity, immunity, inflammatory response, acquired (adaptive) immunity, autoimmunity and/or overactive immunity.

The term "transduction" as used herein refers to the introduction of a foreign nucleic acid into a cell using a viral vector. "Transfection" as used herein refers to the introduction of a foreign nucleic acid into a cell using recombinant DNA technology. The term "transformation" means the introduction of a "foreign" (e.g., extrinsic, extracellular, or otherwise non-endogenous) nucleic acid (DNA or RNA) sequence to a host cell, so that the host cell will express the introduced nucleic acid to produce a desired substance, such as a protein or enzyme coded by the introduced coding sequence. The introduced nucleic acid sequence can also be called a "cloned" or "foreign" gene or sequence, can include regulatory or control sequences, such as start, stop, promoter, signal, secretion, or other sequences used by a cell's genetic machinery. The nucleic acid sequence can include nonfunctional sequences or sequences with no known function. A host cell that receives and expresses introduced nucleic acid (e.g., DNA or RNA) has been "transformed" and is a "transformant" or a "clone." The DNA or RNA introduced to a host cell can come from any source, including cells of the same genus or species as the host cell, or cells of a different genus or species or may be non-naturally occurring.

"Cell surface receptor" refers to molecules and complexes of molecules capable of receiving a signal and the transmission of such a signal across the plasma membrane of a cell. An example of a cell surface receptor provided herein is an activated integrin receptor, for example, an activated αvβ3 integrin receptor on a metastatic cell. As used herein, "cell surface receptor" also includes a molecule expressed on a cell surface that contains a DBDpp capable of binding a target of interest. The term "receptor" denotes a cell-associated protein that binds to, or otherwise interacts with, a molecule (e.g., a ligand) and mediates the effect of the ligand on the cell. In several embodiments, the molecule that interacts with a receptor is a bioactive molecule. Membrane-bound cell-surface receptors are characterized by a multidomain structure comprising an extracellular ligand-binding domain, a membrane spanning domain, and an intracellular effector domain that is typically involved in signal transduction.

"Chimeric antigen receptor" or "CAR" or "CARs" as used herein refers to engineered receptors, which graft an antigen or target specificity onto cells (for example T cells such as naive T cells, central memory T cells, effector memory T cells, NK cells, NKT cells or combination thereof). CARs are also known as artificial T-cell receptors, chimeric T-cell receptors or chimeric immunoreceptors.

De Novo Binding Domain Polypeptides

The terms "de novo binding domain" and DBD are used interchangeably herein to describe a target binding sequence sharing certain sequence and certain structural features of the reference scaffold sequence: MGSWAEFKQRLAAI-KTRLEALGGSEAELAAFEKEIAAF-ESELQAYKGKGNPEVEALRKEAA AIRDELQAYRHN (SEQ ID NO:1). The terms DBDpp and DBD polypeptides include singular (i.e., a DBD polypeptide) and plural (i.e., DBD polypeptides) references unless otherwise indicated explicitly or by context. A DBDpp is polypeptide that can specifically (non-randomly) bind to a target molecule.

It has been discovered, and is disclosed herein in several embodiments, that a non-naturally occurring and targetless (Applicant has no knowledge of a target that can be bound) antiparallel three-helical bundle having the amino acid sequence of SEQ ID NO:1 can be used as a reference scaffold platform for producing de novo binding domain (DBD) containing polypeptides (DBDpp) that bind to a target of interest and for creating libraries of DBDpp which can be screened for DBDpp having desired functional and/or biological activities. Accordingly, in some aspects, the disclosure relates to the use of DBDpp, in methods of producing DBDpp having desired properties such as the ability to bind a target of interest; methods of producing libraries of DBDpp; the libraries of DBDpp produced by such methods; methods for screening such libraries of DBDpp for desired biological activities; and the DBDpp identified from such libraries.

Unless otherwise indicated, the practice of the disclosed compositions and methods employs standard techniques of molecular biology (including recombinant techniques, tissue culture, and cell transformation), microbiology, cell biology, biochemistry and immunology, which are within the skill of the art. Such techniques are typically performed according to the manufacturer's specifications or as commonly accomplished using or routinely modifying known procedures such as, those set forth in Sambrook et al. (Molecular Cloning: A Laboratory Manual. Cold Spring Harbor Laboratory Press, Cold Spring Harbor, N.Y. (1989)); PCR Technology: Principles and Applications for DNA Amplification (ed. H. A. Erlich, Freeman Press, NY, N.Y., 1992); Oligonucleotide Synthesis (Gait, ed., 1984); Animal Cell Culture (Freshney, ed., 1987); Handbook of Experimental Immunology (Weir et al., eds.; Gene Transfer Vectors for Mammalian Cells (Miller, ed., 1987); Current Protocols in Molecular Biology (Ausubel., ed., 1987); PCR Protocols: A Guide to Methods and Applications (Innis, ed., Academic Press, San Diego, Calif., 1990); Mattila, et al., Nucleic Acids Res. 19:967 (1991); Eckert, et al., PCR Methods and Applications 1:17 (1991); PCR (McPherson, ed., IRL Press, Oxford); PCR: The Polymerase Chain Reaction, (Mullis, ed., 1994); Harlow, Antibodies: A Laboratory Manual, (Cold Spring Harbor Laboratory Press, 2nd ed. 1988) and Kontermann, ed., "The Antibody Engineering Lab Manual" (Springer Verlag, Heidelberg/New York, 2000); Current Protocols in Immunology (Coligan, ed., 1991); The Immunoassay Handbook (Wild, ed., Stockton Press NY, 1994); and Methods of Immunological Analysis (Masseyeff., ed., Weinheim: VCH Verlags gesellschaft mbH, 1993); and Gennaro, et al. 2000, Remington: the Science and Practice of Pharmacy, 20th Ed. Lipincott Williams and Wilkins: Baltimore, Md., or as described herein. Unless specific definitions are provided, the nomenclature utilized in connection with, and the laboratory procedures and techniques of analytical chemistry, synthetic organic chemistry, and medicinal and pharmaceutical chemistry described herein, are those known and used in the art. Additionally, standard techniques can be used for chemical syntheses, chemical analyses, recombinant production, purification, pharmaceutical preparation, formulation, delivery, and treatment of patients.

In one embodiment, the DBDpp is not derived from a natural cellular ligand of public record (as of the filing of U.S. Provisional Application Ser. No. 62/143,772, filed Apr. 6, 2015 and according to the Applicant's knowledge). In another embodiment, the DBDpp is not derived from an immunoglobulin-derived antigen binding domain, or another antibody domain such as a constant region, a variable region, a complementarity determining region (CDR), a framework region, an Fc domain, or a hinge region. In another embodiment, the DBDpp does not contain three CDRs. In another embodiment, the DBDpp does not contain CDR1 and CDR2. In yet another embodiment, the DBDpp does not contain CDR1. In yet another embodiment, the DBDpp does not contain CDR2. In another embodiment, the DBDpp in not derived from protein A. In another embodiment the DBDpp is not derived from a natural bacterial receptor. In another embodiment the DBDpp is not derived from fibronectin. In another embodiment the DBDpp is not derived from fibronectin type III domain. In yet another embodiment, the DBDpp is not derived from a knottin protein. In yet another embodiment, the DBDpp is not derived from a lipocalin. In yet another embodiment, the DBDpp is not derived from an affibody.

Sequence Characteristics

As indicated above, the reference scaffold polypeptide of SEQ ID NO:1 contains three anti-parallel alpha helices and is a variant of a non-naturally occurring and targetless polypeptide sequence originally engineered as an exercise in protein folding. Provided herein are DBDpp containing certain modifications of amino acid residues in the sequence of reference scaffold polypeptide of SEQ ID NO:1 that confer the ability of the DBDpp to bind a target of interest and the use of the DBDpp as a target binding and targeting agent.

In one embodiment, an individual DBDpp has a length of about 65 to 150 amino acids, about 65 to 125 amino acids, about 65 to 100 amino acids, about 65 to 90 amino acids, about 65 to 80 amino acids, about 65 to 70 amino acids. It is also contemplated in some embodiments, that a DBDpp has a length of about 75 to 150 amino acids, about 75 to 125 amino acids, about 75 to 100 amino acids, about 75 to 90 amino acids, about 75 to 80 amino acids. DBDpp can be naked or conjugated to other molecules, including but not limited to, toxins and radioisotopes. In still additional embodiments, longer DBDpp are employed, for example DBDpp ranging in length from about 150 to about 160 amino acids, about 160 to about 170 amino acids, about 170 to about 180 amino acids, about 180 to about 190 amino acids, about 190 to about 200 amino acids, or any length between those listed (including endpoints).

For known binding proteins, the specific residues that constitute the binding region of the molecule either have been (or theoretically can be) experimentally determined. Natural binding proteins (e.g. antibodies or protein A) have identifiable residues that promote the binding to their known targets. However, unlike natural ligands and binding proteins, the designed protein α3d (SEQ ID NO: 49) or the reference scaffold sequence of SEQ ID NO:1 are not known to specifically bind to another protein (e.g., a target). Therefore endogenous binding residues cannot be utilized as a guide to engineer novel binding specificity. In the construction of DBDpp that bind to targets, residues were considered for mutation (e.g., randomization within the library) if they were surface exposed—exhibiting significant solvent accessibility. The relative accessibility of a residue within the domain (area D) as compared to the isolated state (area I) is represented as a percent value (% A). Amino residues of SEQ ID NO:1 that have % A values less than about 10% to 11% (e.g., residues corresponding to F7, L11, I14, L18, L21, S24, L28, F31, I35, F38, L42, Y45, G49, V53, L56, A60, I63, and L67, of SEQ ID NO:1), are believed to be inaccessible to the exterior solvent and are considered to be interior core residues of the SEQ ID NO:1 structure. Conversely, amino acid residues of SEQ ID NO:1 with % A values that are greater than about 10% to 11% are believed to occupy positions that have greater potential for interaction a target of interest. Binding surfaces of proteins are typically composed of several amino residues that are either adjacent, or in close proximity, to each other in three-dimensional space. Therefore, a secondary consideration in the construction of libraries, according to several embodiments herein, was the relative proximity of these selected residues within the predicted secondary and tertiary structure of the DBDpp.

Protein secondary structure such as alpha helices can change depending on environmental variables such as temperature, matrix or buffer composition and concentration. The alpha helical secondary structures of the reference polypeptide sequence of SEQ ID NO:1 are predicted to be composed of residues G2-A20 for helix 1, residues L28-A44 for helix 2, and residues E52-Y70 for helix 3. In additional embodiments, the alpha helical secondary structures of the reference polypeptide sequence of SEQ ID NO:1 are predicted to be composed of residues W4-L21 for helix 1, residues E25-Y45 for helix 2, and residues P51-Y70 for helix 3. The amino acid positions of the reference scaffold corresponding to alpha helical residues with low solvent accessibility are: F7, L11, I14, L18, L21, L28, F31, I35, F38, L42, Y45, V53, L56, A60, I63 and L67 of SEQ ID NO: 1. The amino acid positions of the reference scaffold corresponding to solvent accessible, alpha helical residues are: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70 of SEQ ID NO:1. The amino acid positions of the reference scaffold corresponding to the non-alpha helical residues are as follows: M1, G22, G23, S24, E25, A26, E27, K46, G47, K48, G49, N50, P51, R71, H72, and N73 of SEQ ID NO:1.

In one embodiment, DBDpp are defined as target-binding polypeptides composed of SEQ ID NO:1 with one or more amino acid substitutions. In one embodiment, a sequence alignment of the DBDpp with SEQ ID NO:1 would reveal a sequence identity greater than 90%. In other embodiments, a sequence alignment of the DBDpp with SEQ ID NO:1 would reveal a sequence identity greater than 80%. In other embodiments, a sequence alignment of the DBDpp with SEQ ID NO:1 would reveal a sequence identity greater than 70%. In other embodiments, a sequence alignment of the DBDpp with SEQ ID NO:1 would reveal a sequence identity greater than 60%. In other embodiments, a sequence alignment of the DBDpp with SEQ ID NO:1 would reveal a sequence identity greater than 50%.

In some embodiments, DBDpp residues with % A values that are less than 10% would remain constant, or be substituted with a conserved amino acid change. In particular embodiments, the solvent accessible (i.e., % A greater than 10) residue DBDpp has an amino acid sequence that are modified subject to mutagenesis would be located within regions of the polypeptide associated with alpha-helical secondary structure. The alpha helical positions of the sequence of SEQ ID NO:1 having solvent inaccessible residues correspond to F7, L11, I14, L18, L21, L28, F31, I35, F38, L42, Y45, V53, L56, A60, I63, and L67, of SEQ ID NO:1. Amino acid substitutions in these positions are preferably conservative in nature and can include unconventional or non-natural amino acids. In some embodiments, the selection of natural amino acid substitutions includes L, I, V, A and F (and W, Y, M). In some DBDpp, the solvent inaccessible residues of a DBD contained in a DBDpp is greater than 60%, 70%, 80%, or 90%, or is 100% identical to the corresponding residues in SEQ ID NO:1. F7, L11, I14, L18, L21, L28, F31, I35, F38, L42, Y45, V53, L56, A60, I63, and L67, of SEQ ID NO:1.

In one embodiment, a DBDpp comprises an amino acid sequence of SEQ ID NO:1 wherein a total of 5 to 25, 5 to 30, 5 to 35, 5 to 40, 5 to 45, 5 to 50, 5 to 55, or 5 to 60 amino acid residues have been modified; and wherein the DBDpp specifically binds a target of interest. In another embodiment, 5 to 25, 5 to 30, 5 to 35, 5 to 40, 5 to 45, 5 to 50, 5 to 55, or 5 to 60 of the modified amino acid residues are substitutions. In another embodiment, 5 to 25, 5 to 30, 5 to 35, 5 to 40, 5 to 45, or 5 to 50 of the modified amino acid residues are conservative substitutions. In another embodiment, 5 to 25, 5 to 30, 5 to 35, 5 to 40, 5 to 45, or 5 to 50 of the modified amino acid residues are non-conservative substitutions. In a further embodiment, 5 to 15, 5 to 20, 5 to 25, 5 to 30, 5 to 35, 5 to 40, or 5 to 45 of the amino acid residue modifications are conservative substitutions and 5 to 15, 5 to 20, 5 to 25, 5 to 30, 5 to 35, 5 to 40, or 5 to 45 of the amino acid residue modifications are non-conservative substitutions. In additional embodiments, 1 to 25, 1 to 30, 1 to 35, 5 to 40, 5 to 45, 5 to 50, 5 to 55, or 5 to 60 of the substitutions are at amino acid residues of SEQ ID NO:1 selected from the group consisting of: M1, G2, S3, W4, A5, E6, K8, Q9, R10, A12, A13, K15, T16, R17, E19, A20, L21, G22, G23, S24, E25, A26, E27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In additional embodiments, 1 to 25, 1 to 30, 1 to 35, 5 to 40, 5 to 45, 5 to 50, 5 to 55, or 5 to 60 of the substitutions are at amino acid residues of SEQ ID NO:1 selected from the group consisting of: M1, G2, S3, W4, A5, E6, K8, Q9, R10, A12, A13, K15, T16, R17, E19, A20, G22, G23, S24, E25, A26, E27, A29, A30, E32, K33, E34, A36, A37, E39, S40, E41, Q43, A44, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 of the substitutions are at amino acid residues of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In an optional further embodiment, the DBDpp optionally further comprises an amino acid sequence wherein 1 to 5, 1 to 10, 1 to 15, 5 to 10 or 5 to 15 of the residues corresponding to the solvent inaccessible residues of the amino acid sequence of SEQ ID NO:1 are substituted and wherein the DBDpp specifically binds a target of interest. In a further optional embodiment, the substituted residues corresponding to a solvent inaccessible residue of SEQ ID NO:1 are selected from the group consisting of: F7, L11, I14, L18, L28, F31, I35, F38, L42, V53, L56, A60, I63, and L67, and Y70. In some embodiments, the substituted residues corresponding to a solvent inaccessible residue of SEQ ID NO:1 are selected from the group consisting of: F7, L11, I14, L18, L21, L28, F31, I35, F38, L42, Y45, V53, L56, A60, I63, and L67, and Y70. In an additional embodiment, the DBDpp is a fusion protein. In one embodiment, the DBDpp is attached to a solid support. In a further embodiment, the solid support is selected from the group consisting of: a bead, a glass slide, a chip, a gelatin, and an agarose. In an additional embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In another embodiment, the DBDpp specifically binds a target disclosed herein. Nucleic acids encoding the DBDpp and vectors containing the nucleic acids are also provided. Host cells (including viral particles) containing the nucleic acids and vectors are also provided. In some embodiments, the host cell displays the DBDpp on its surface. In additional embodiments, the host cell is a prokaryote or a eukaryote that display the DBDpp on its surface. In a further embodiment, the host cell is a phage that displays the DBDpp on its surface. In a further embodiment, the host cell is a human immune cell that expresses a DBDpp fusion protein on its surface. Libraries comprising a plurality of DBDpp are also provided.

In one embodiment, an isolated DBDpp comprises an amino acid sequence variation of SEQ ID NO:1 wherein 5 to 15, 5 to 20, 5 to 25, 5 to 30, 5 to 35, 5 to 40 solvent accessible amino acid residues of SEQ ID NO:1 are substituted, and wherein 1 to 5, 1 to 10, 1 to 15, 5 to 10 or 5 to 15 solvent inaccessible residues of SEQ ID NO:1 are optionally substituted by a conservative amino acid substitution, and wherein the DBDpp specifically binds a target of interest. In some embodiments, the substituted solvent accessible amino acid residues of SEQ ID NO:1 have a % A of greater than 10. In some embodiments, the substituted solvent inaccessible amino acid residues of SEQ ID NO:1 have a % A of less than 10. In one embodiment, the substituted solvent accessible amino acid residues of SEQ ID NO:1 are selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In some embodiments, at least 3, 5, 6, 7, 8, 9, 10, 15, 20, 25, 30, or 35 of the solvent accessible acid residues are substituted. In some embodiments, at least 3, 5, 6, 7, 8, 9, 10, 15, 20, 25, or 30 of the solvent accessible acid residues of SEQ ID NO:1 are substituted with conservative amino acid residue substitutions. In some embodiments, at least 3, 5, 6, 7, 8, 9, 10, 15, 20, 25, or 30 of the solvent accessible acid residues of SEQ ID NO:1 are substituted with non-conservative amino acid residue substitutions. In some embodiments, the amino acid substitutions do not contain proline. In some embodiments, the amino acid substitutions do not contain cysteine or proline. In some embodiments, the amino acid residue substitutions include no more than one cysteine. In some embodiments, 1 to 5, 1 to 10, 5 to 15, 5 to 20, 5 to 25, 5 to 30, or 5 to 35 of the solvent accessible acid residues are substituted. In some embodiments, 5 to 41, 10 to 41, 15 to 41, 20 to 41, 25 to 41, 30 to 41, or 35 to 41 of the solvent accessible acid residues are substituted. In some embodiments, 5 to 35 of the solvent accessible acid residues are substituted with conservative substitutions and 5 to 35 of the solvent accessible acid residues are substituted with non-conservative substitutions, or 5 to 25 of the solvent accessible acid residues are substituted with conservative substitutions and 5 to 25 of the solvent accessible acid residues are substituted with non-conservative substitutions. In an optional further embodiment, the DBDpp optionally further comprises an amino acid sequence wherein 1 to 5, 1 to 10, 1 to 15, 5 to 10 or 5 to 15 of the residues corresponding to the solvent inaccessible residues of the amino acid sequence of SEQ ID NO:1 are substituted and wherein the DBDpp specifically binds a target of interest. In a further optional embodiment, the substituted residues corresponding to a solvent inaccessible residue of SEQ ID NO:1 are selected from the group consisting of: F7, L11, I14, L18, L28, F31, I35, F38, L42, V53, L56, A60, I63, and L67, and Y70. In a further optional embodiment, the substituted residues corresponding to a solvent inaccessible residue of SEQ ID NO:1 are selected from the group consisting of: F7, L11, I14, L18, L21, L28, F31, I35, F38, L42, Y45, V53, L56, A60, I63, and L67, and Y70. In an additional embodiment, the DBDpp is a fusion protein. In one embodiment, the DBDpp is attached to a solid support. In a further embodiment, the solid support is selected from the group consisting of: a bead, a glass slide, a chip, a gelatin, and an agarose. In an additional embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In another embodiment, the DBDpp specifically binds a target disclosed herein. Nucleic acids encoding the DBDpp and vectors containing the nucleic acids are also provided. Host cells (including viral particles) containing the nucleic acids and vectors are also provided. In some embodiments, the host cell displays the DBDpp on its surface. In additional embodiments, the host cell is a prokaryote or a eukaryote that display the DBDpp on its surface. In a further embodiment, the host cell is a phage that displays the DBDpp on its surface. In a further embodiment, the host cell is a human immune cell that expresses a DBDpp fusion protein on its surface. Libraries comprising a plurality of DBDpp are also provided.

The term "loop" refers to sequences in the DBD corresponding to the loop located between, for example, helix 1 and helix 2 of reference scaffold SEQ ID NO:1 (e.g., positions 22-24 of SEQ ID NOS:2-6, and $Z_1$ of SEQ ID NOS:7-11) and/or the loop located between helix 2 and helix 3 of reference scaffold SEQ ID NO:1 e.g., positions 46-48 of SEQ ID NOS:2-6, and $Z_2$ of SEQ ID NOS:7-11). In particular embodiments, one or both of the $Z_1$ and $Z_2$ loops are amino acid sequences consisting of 2 to 5, 2 to 10, 2 to 15, 2 to 20, 2 to 25 or 2 to 30 amino acid residues (including endpoints and any number in between those listed). In some embodiments, one or both of the $Z_1$ and $Z_2$ loops are amino acid sequences consisting of 1, 2, 3, 4, 5, 5, 7, 8, 9, 10, 11, 12, 13, 14, 15, 16, 17, 18, 19 20, or more than 20 amino acid residues (including endpoints and any number in between those listed). In a further embodiment, at least 50%, 60%, 70%, 80%, 90%, or 95% of the amino acid residues of the $Z_1$ and/or $Z_2$ loop are glycine or serine. In additional embodiments, at least 50%, 60%, 70%, 80%, 90%, or 95% of the amino acid residues of the $Z_1$ and/or $Z_2$ loop are selected from the group consisting of glycine, serine, threonine, alanine, proline, histidine, asparagine, aspartic acid, glutamine, glutamic acid, lysine and arginine. In one embodiment the $Z_1$ loop has the amino acid sequence GGS. In one embodiment the $Z_2$ loop has the amino acid sequence KGKG.

In one embodiment, a DBDpp comprises an amino acid sequence of MGSWX$_5$X$_6$FK X$_9$X$_{10}$LAX 13IKX$_{16}$X$_{17}$LEALGGSEAELAX$_{30}$FEX$_{33}$X$_{34}$IAX$_{37}$FEX$_{40}$X$_{41}$LQX$_{44}$YKGKGNPE VEALRKEAAAIRDELQAYRHN (SEQ ID NO:2), wherein X$_5$, X$_6$, X$_9$, X$_{10}$, X$_{13}$, X$_{16}$, X$_{17}$, X$_{30}$, X$_{33}$, X$_{34}$, X$_{37}$, X$_{40}$, X$_{41}$, and X$_{44}$, is a natural and/or non-natural amino acid residue, and wherein the DBDpp specifically binds a target of interest. In an additional embodiment, X$_n$ is a natural amino acid residue. In a further embodiment, X$_n$ is a natural amino acid residue other than cysteine or proline. In a particular embodiment, the DBDpp does not contain the amino acid sequence LAAIKTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

In one embodiment, the DBDpp comprises an amino acid sequence of MGSWAEFK QRLAAIKTRLEALGGSEAELAAFX32X$_{33}$EIX$_{36}$AFX$_{39}$X$_{40}$ELX$_{43}$AYKGKGNPEVEALX$_{57}$X$_{58}$EAX$_{61}$AIX$_{64}$X$_{65}$ELX$_{68}$AYRHN (SEQ ID NO:3), wherein X$_{32}$, X$_{33}$, X$_{36}$, X$_{39}$, X$_{40}$, X$_{43}$, X$_{57}$, X$_{58}$, X$_{61}$, X$_{64}$, X$_{65}$, and X$_{68}$, is a natural and/or non-natural amino acid residue, and wherein the DBDpp specifically binds a target of interest. In an additional embodiment, $X_n$ is a natural amino acid residue. In a further embodiment, $X_n$ is a natural amino acid residue other than cysteine or proline. In a particular embodiment, the DBDpp does not contain the amino acid sequence LAAI-KTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

In one embodiment, the DBDpp comprises an amino acid sequence of MGSWXSE FX$_8$X$_9$RLX$_{12}$AIX$_{15}$X$_{16}$RLX$_{19}$ALGGSEAELAAFEKEIA AFESELQAYKGKGNPEVEX$_{55}$LRX$_{58}$X$_{59}$AAX$_{62}$IRX$_{65}$ X$_{66}$LQAYRHN (SEQ ID NO:4), wherein X$_5$, X$_8$, X$_9$, X$_{12}$, X$_{15}$, X$_{16}$, X$_{19}$, X$_{55}$, X$_{58}$, X$_{59}$, X$_{62}$, X$_{65}$, and X$_{66}$ is a natural and/or non-natural amino acid residue, and wherein the DBDpp specifically binds a target of interest. In an additional embodiment, $X_n$ is a natural amino acid residue. In a further embodiment, $X_n$ is a natural amino acid residue other than cysteine or proline. In a particular embodiment, the DBDpp does not contain the amino acid sequence LAAI-KTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

In one embodiment, the DBDpp comprises an amino acid sequence of MGSWXSX$_6$F KX$_9$X$_{10}$LAX$_{13}$IKX$_{16}$X$_{17}$LEALGGSEAELAAFX$_{32}$X$_{33}$ EIX$_{36}$AFX$_{39}$X$_{40}$ELX$_{43}$AYKGKGNPEVEX$_{55}$L RX$_{58}$X$_{59}$AAX$_{62}$IRX$_{65}$X$_{66}$LQAYRHN (SEQ ID NO:5), wherein X$_5$, X$_6$, X$_9$, X$_{10}$, X$_{13}$, X$_{16}$, X$_{17}$, X$_{32}$, X$_{33}$, X$_{36}$, X$_{39}$, X$_{40}$, X$_{43}$, X$_{55}$, X$_{58}$, X$_{59}$, X$_{62}$, X$_{65}$, and X$_{66}$, is a natural and/or non-natural amino acid residue, and wherein the DBDpp specifically binds a target of interest. In an additional embodiment, $X_n$ is a natural amino acid residue. In a further embodiment, $X_n$ is a natural amino acid residue other than cysteine or proline. In a particular embodiment, the DBDpp does not contain the amino acid sequence LAAI-KTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

In one embodiment, the DBDpp comprises an amino acid sequence of MGSWXSE FX$_8$X$_9$RLX$_{12}$AIX$_{15}$X$_{16}$RLX$_{19}$ALGGSEAELAX$_{30}$FEX$_{33}$ X$_{34}$IAX$_{37}$FEX$_{40}$X$_{41}$LQX$_{44}$YKGKGNPEVEA LX$_{57}$X$_{58}$EAX$_{61}$AIX$_{64}$X$_{65}$ELX$_{68}$AYRHN (SEQ ID NO:6), wherein X$_5$, X$_8$, X$_9$, X$_{12}$, X$_{15}$, X$_{16}$, X$_{19}$, X$_{30}$, X$_{33}$, X$_{34}$, X$_{37}$, X$_{40}$, X$_{41}$, X$_{44}$, X$_{57}$, X$_{58}$, X$_{61}$, X$_{64}$, X$_{65}$, and X$_{68}$, is a natural and/or non-natural amino acid residue, and wherein the DBDpp specifically binds a target of interest. In an additional embodiment, X$_n$ is a natural amino acid residue. In a further embodiment, X$_n$ is a natural amino acid residue other than cysteine or proline. In a particular embodiment, the DBDpp does not contain the amino acid sequence LAAIKTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

Also provided is an isolated DBDpp that comprises an amino acid sequence of: MGSWX$_5$X$_6$FKX$_9$X$_{10}$LAX$_{13}$IKX$_{16}$X$_{17}$LEALZ$_1$EAEL AX$_{28}$FEX$_{31}$X$_{32}$IAX$_{35}$FEX$_{38}$X$_{39}$LQX$_{42}$YZ$_2$NPE VEALRKEAAAIRDELQAYRHN (SEQ ID NO:7), wherein X$_5$, X$_6$, X$_9$, X$_{10}$, X$_{13}$, X$_{16}$, X$_{17}$, X$_{28}$, X$_{31}$, X$_{32}$, X$_{35}$, X$_{38}$, X$_{39}$, and X$_{42}$, is a natural and/or non-natural amino acid residue, wherein Z$_1$ and Z$_2$ are 2 to 30 natural and/or non-natural amino acid residues, and wherein the DBDpp specifically binds a target of interest. In an additional embodiment, X$_n$ is a natural amino acid residue. In a further embodiment, X$_n$ is a natural amino acid residue other than cysteine or proline. In a particular embodiment, the DBDpp does not contain the amino acid sequence LAAIKTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

Also provided is an isolated DBDpp that comprises an amino acid sequence of: MGSWAEFKQRLAAIKTRLEALZ$_1$EAELAAFX$_{30}$X$_{31}$ EIX$_{34}$AFX$_{37}$X$_{38}$ELX$_{41}$AYZ$_2$NPEVE ALX$_{52}$X$_{53}$EAX$_{56}$AIX$_{59}$X$_{60}$ELX$_{63}$AYRHN (SEQ ID NO:8), wherein X$_{30}$, X$_{31}$, X$_{34}$, X$_{37}$, X$_{38}$, X$_{41}$, X$_{52}$, X$_{53}$, X$_{56}$, X$_{59}$, X$_{60}$, and X$_{63}$, is a natural and/or non-natural amino acid residue, wherein Z$_1$ and Z$_2$ are 2 to 30 natural and/or non-natural amino acid residues, and wherein the DBDpp specifically binds a target of interest. In an additional embodiment, X$_n$ is a natural amino acid residue. In a further embodiment, X$_n$ is a natural amino acid residue other than cysteine or proline. In a particular embodiment, the DBDpp does not contain the amino acid sequence LAAIKTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

Also provided is an isolated DBDpp that comprises an amino acid sequence MGSW X$_5$X$_6$FKX$_9$X$_{10}$LAX$_{13}$IKX$_{16}$X$_{17}$LEALZ$_1$EAELAAFX$_{30}$ X$_{31}$EIX$_{34}$AFX$_{37}$X$_{38}$ELX$_{41}$AYZ$_2$NPEV EX$_{50}$LRX$_{53}$X$_{54}$AAX$_{57}$IRX$_{60}$X$_{61}$LQAYRHN (SEQ ID NO:10), wherein X$_5$, X$_6$, X$_9$, X$_{10}$, X$_{13}$, X$_{16}$, X$_{17}$, X$_{30}$, X$_{31}$, X$_{34}$, X$_{37}$, X$_{38}$, X$_{41}$, X$_{50}$, X$_{53}$, X$_{54}$, X$_{57}$, X$_{60}$, and X$_{61}$ is a natural and/or non-natural amino acid residue, wherein Z$_1$ and Z$_2$ are 2 to 30 natural and/or non-natural amino acid residues, and wherein the DBDpp specifically binds a target of interest. In an additional embodiment, X$_n$ is a natural amino acid residue. In a further embodiment, X$_n$ is a natural amino acid residue other than cysteine or proline. In a particular embodiment, the DBDpp does not contain the amino acid sequence LAAIKTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

Also provided is an isolated DBDpp that comprises an amino acid sequence of MGSWX$_5$EFX$_8$X$_9$RLX$_{12}$AIX$_{15}$X$_{16}$RLX$_{19}$ALZ$_1$EAEL AX$_{28}$FEX$_{31}$X$_{32}$IAX$_{35}$FEX$_{38}$X$_{39}$LQX$_{42}$YZ$_2$NPE VEAL X$_{52}$X$_{53}$EAX$_{56}$AIX$_{59}$X$_{60}$ELX$_{63}$AYRHN (SEQ ID NO:11), wherein X$_5$, X$_8$, X$_9$, X$_{12}$, X$_{15}$, X$_{16}$, X$_{19}$, X$_{28}$, X$_{31}$, X$_{32}$, X$_{35}$, X$_{38}$, X$_{39}$, X$_{42}$, X$_{52}$, X$_{53}$, X$_{56}$, X$_{59}$, X$_{60}$, and X$_{63}$, is a natural and/or non-natural amino acid residue, wherein Z$_1$ and Z$_2$ are 2 to 30 natural and/or non-natural amino acid residues, and wherein the DBDpp specifically binds a target of interest. In an additional embodiment, X$_n$ is a natural amino acid residue. In a further embodiment, X$_n$ is a natural amino acid residue other than cysteine or proline. In a particular embodiment, the DBDpp does not contain the amino acid sequence LAAIKTRLQ (SEQ ID NO:50). In an additional embodiment, the DBDpp is a fusion protein. In some embodiments, at least 1, 2, 3, 4, 5, 6, 7, 8, 9, or 10 of the substituted amino acid residues of SEQ ID NO:1 are substituted with conservative amino acid residue substitutions. In some embodiments, at least 1, 2, 3, 4, 5, 6, 7, 8, 9, or 10 of the above amino acid residues of SEQ ID NO:1 are substituted with non-conservative amino acid residue substitutions. In some embodiments, the amino acid substitutions do not contain proline. In some embodiments, the amino acid substitutions do not contain cysteine. In some embodiments, neither proline nor cysteine is included in the amino acid substitutions. In some embodiments, the amino acid residue substitutions include no more than one cysteine. In some embodiments, 1 to 12 of the solvent accessible acid residues are substituted with conservative substitutions and 1 to 12 of the solvent accessible acid residues are substituted with non-conservative substitutions, or 5 to 12 of the solvent accessible acid residues are substituted with conservative substitutions and 5 to 12 of the solvent accessible amino acid residues are substituted with non-conservative substitutions. In another embodiment, the DBDpp specifically binds a target of interest selected from the group consisting of: a nucleic acid, an oligosaccharide, a peptide, a protein, a cell surface antigen, and a small organic molecule. In a further embodiment, the DBDpp specifically binds a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. In an additional embodiment, a library containing a plurality of DBDpp is provided. Nucleic acids encoding the DBDpp and vectors containing the nucleic acids are also provided. Host cells (including viral particles) containing the nucleic acids and vectors are also provided. In some embodiments, the host cell is a prokaryote or a eukaryote that display the DBDpp on its surface. In some embodiments, the host cell displays the DBDpp on its surface. In a further embodiment, the host cell is a phage that displays the DBDpp on its surface. In a further embodiment, the host cell is a human immune cell that expresses a DBDpp fusion protein on its surface. In one embodiment, the DBDpp is attached to a solid support. In a further embodiment, the solid support is selected from the group consisting of: a bead, a glass slide, a chip, a gelatin, and an agarose.

In some embodiments, the DBDpp comprises a substitution at a corresponding position in the sequence of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In additional embodiments, the DBDpp comprises substitutions of at least 1, 5, 10, 15, 20, or 30 of the above positions in the sequence of SEQ ID NO:1. These substitutions can be conservative, non-conservative, or a mix of conservative and non-conservative substitutions. In some embodiments, the substitutions do not include the addition of a proline or cysteine. In some embodiments, the substitutions include no more than a single cysteine. In some DBDpp, these residues may be greater than 90% identical to SEQ ID NO:1. In other DBDpp, these residues may be greater than 80% identical to SEQ ID NO:1. In other DBDpp, these residues may be greater than 70% identical to SEQ ID NO:1. In other DBDpp, these residues may be greater than 60% identical to SEQ ID NO:1. In other DBDpp, these residues may be greater than 50% identical to SEQ ID NO:1. In other DBDpp, these residues may be greater than 40% identical to SEQ ID NO:1. In other DBDpp, these residues may be greater than 30% identical to SEQ ID NO:1. In other DBDpp, these residues are greater than 20% identical to SEQ ID NO:1. In other DBDpp, these residues are greater than 10% identical to SEQ ID NO:1.

In some embodiments, the DBDpp comprises a substitution at a position in the sequence of SEQ ID NO:1 selected from the group consisting of: M1, L21, G22, G23, S24, E25, A26, E27, Y45, K46, G47, K48, G49, N50, P51, R71, H72, and N73.

Additionally provided herein are DBDpp in which amino acid residues have been deleted from the amino terminus, the carboxy terminus or both the amino and carboxy termini of the corresponding sequence of SEQ ID NO: 1. In some embodiments the DBDpp contains a sequence with 1, 2, 3, 4, 5, 6, 7, 8, 9, 10, 11, or 12 amino acid residues deleted from the amino terminus of the DBDpp sequence corresponding to the sequence of SEQ ID NO: 1. In some embodiments the DBDpp contains a sequence with 1, 2, 3, 4, 5, 6, 7, 8, 9, 10, 11, or 12 amino acid residues deleted from the carboxy terminus of the DBDpp sequence corresponding to the sequence of SEQ ID NO:1. In some embodiments the DBDpp contains a sequence with 1, 2, 3, 4, 5, 6, 7, 8, 9, 10, 11, 11, or 12 amino acid residues deleted from the amino terminus of the corresponding sequence of SEQ ID NO:1 and a sequence with 1, 2, 3, 4, 5, 6, 7, 8, 9, 10, 11, or 12 amino acid residues deleted from the carboxy terminus corresponding to the sequence of SEQ ID NO:1. In additional embodiments, the DBDpp contains a sequence with 1-5, 1-10, or 1 to 15 amino acid residues deleted from the carboxy terminus of the sequence corresponding to SEQ ID NO: 1. In some embodiments the DBDpp contains a sequence with 1-5, 1-10, or 1 to 15 amino acid residues deleted from the amino terminus of the sequence corresponding to the SEQ ID NO:1 and a sequence with 1-5, 1-10, or 1 to 15 amino acid residues deleted from the carboxy terminus of the sequence corresponding to SEQ ID NO:1.

In some embodiments, the DBDpp contains a sequence that differs from the corresponding sequence in reference SEQ ID NO:1 in 2 or more categories of sequence modifications (i.e., substitutions, deletions, insertions, and additions). For example DBDpp may include combinations of amino acid deletions, insertions and substitutions compared to the corresponding sequence in the reference polypeptide sequence. In some embodiments the DBDpp contains 1, 2, 3, 4, 5, 6, 7, 8, 9, 10, or more than 10 amino acid deletions within the sequence reference sequence shown in SEQ ID NO:1. In some embodiments the DBDpp contains 1, 2, 3, 4, 5, 6, 7, 8, 9, 10, or more than 10 amino acid insertions within the reference sequence shown in SEQ ID NO:1.

DBDpp Bind to Targets of Interest

According to some embodiments, DBDpp can bind to a target of interest, and in several embodiments, have no discernable impact on the function of the target. Alternatively, in several embodiments, DBDpp can bind to a target of interest and completely or partially inhibit, antagonize, agonize, block, increase, stimulate or interfere with the biological activity of that target. Binding can be identified as agonistic or antagonistic and determined using or routinely modifying assays, bioassays, and/or animal models known in the art for evaluating such activity.

A DBDpp agonist refers to a DBDpp that in some way increases or enhances the biological activity of the DBDpp target or has biological activity comparable to a known agonist of the DBDpp target. In another embodiment, the DBDpp is an antagonist of the target it binds. A DBDpp antagonist refers to a DBDpp that completely or partially blocks or in some way interferes with the biological activity of the DBDpp target protein or has biological activity comparable to a known antagonist or inhibitor of the DBDpp target protein.

Expressions like "binding affinity for a target", "binding to a target" and the like refer to a property of a polypeptide which may be directly measured through the determination of the affinity constants, e.g., the amount of DBDpp that associates and dissociates at a given antigen concentration. Different methods can be used to characterize the molecular interaction, such as, but not limited to, competition analysis, equilibrium analysis and microcalorimetric analysis, and real-time interaction analysis based on surface plasmon resonance interaction (for example using a Biacore® instrument). These methods are well-known to the skilled person and are described, for example, in Neri D et al. (1996) Tibtech 14:465-470 and Jansson M et al. (1997) J Biol Chem 272:8189-8197.

Affinity requirements for a given DBDpp binding event are contingent on a variety of factors including, but not limited to: the composition and complexity of the binding matrix, the valency and density of both the DBDpp and target molecules, and the functional application of the DBDpp. In one embodiment, DBDpp bind a target of interest with a dissociation constant (KD) of less than or equal to $5 \times 10^{-3}$ M, $10^{-3}$ M, $5 \times 10$ M, $10^{-4}$ M, $5 \times 10^{-5}$ M, or $10^{-5}$ M. In an additional embodiment, a DBDpp binds a target of interest with a KD of less than or equal to $5 \times 10^{-6}$ M, $10^{-6}$ M, $5 \times 10^{-7}$ M, $10^{-7}$ M, $5 \times 10^{-8}$ M, or $10^{-8}$ M. In additional embodiments, a DBDpp binds a target of interest with a KD less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In several embodiments, the DBDpp generated by the methods disclosed herein have a dissociation constant selected from the group consisting of between $10^{-4}$ M and $10^{-5}$ M, between $10^{-5}$ M and $10^{-6}$ M, between $10^{-6}$ M and $10^{-7}$ M, between $10^{-7}$ M and $10^{-8}$ M, between $10^{-8}$ M and $10^{-9}$ M, between $10^{-9}$ M and $10^{-10}$ M, between $10^{-10}$ M and $10^{-11}$ M and between $10^{-11}$ M and $10^{-12}$ M.

In one embodiment a DBDpp binds a target of interest in active form. In one embodiment a DBDpp reversibly binds a target of interest in active form and also releases the bound target in active form. In one embodiment a DBDpp binds a target of interest in the native form. In specific embodiments, DBDpp bind targets of interest with off-rates or $K_{off}$ of greater than or equal to $10^{-10}$ sec$^{-1}$, $5 \times 10^{-9}$ sec$^{-1}$, $10^{-9}$ sec$^{-1}$, $5 \times 10^{-8}$ sec$^{-1}$, $10^{-8}$ sec$^{-1}$, $5 \times 10^{-7}$ sec$^{-1}$, $10^{-7}$ sec$^{-1}$, $5 \times 10^{-6}$ sec$^{-1}$, $10^{-6}$ sec$^{-1}$, $5 \times 10^{-5}$ sec$^{-1}$, $10^{-5}$ sec$^{-1}$, $5 \times 10^{-4}$ sec$^{-1}$, $10^{-4}$ sec$^{-1}$, $5 \times 10^{-3}$ sec$^{-1}$, $10^{-3}$ sec$^{-1}$, $5 \times 10^{-2}$ sec$^{-1}$, $10^{-2}$ sec$^{-1}$, $5 \times 10^{-1}$ sec$^{-1}$, or $10^{-1}$ sec$^{-1}$.

Binding experiments to determine KD and off-rates can be performed in a number of conditions including, but not limited to, [pH 6.0, 0.01% Tween 20], [pH 6.0, 0.1% gelatin], [pH5.0, 0.01% Tween 20], [pH9.0, 0.1% Tween 20], [pH6.0, 15% ethylene glycol, 0.01% Tween 20], [pH5.0, 15% ethylene glycol, 0.01% Tween 20], and [pH9.0, 15% ethylene glycol, 0.01% Tween 20]. The buffers in which to make these solutions can readily be determined by one of skill in the art, and depend largely on the desired pH of the final solution. Low pH solutions (<pH 5.5) can be made, for example, in citrate buffer, glycine-HCl buffer, or in succinic acid buffer. High pH solutions can be made, for example, in Tris-HCl, phosphate buffers, or sodium bicarbonate buffers. A number of conditions may be used to determine KD and off-rates for the purpose of determining, for example, optimal pH and/or salt concentrations.

In one embodiment, a DBDpp specifically binds a target of interest with a $K_{Off}$ ranging from 0.1 to $10^{-7}$ sec$^{-1}$, $10^{-2}$ to $10^{-7}$ sec$^{-1}$, or $0.5 \times 10^{-2}$ to $10^{-7}$ sec$^{-1}$. In a specific embodiment, a DBDpp (e.g., a DBDpp fusion protein) binds a target of interest with an off rate ($K_{Off}$) of less than $5 \times 10^{-2}$ sec$^{-1}$, $10^{-2}$ sec$^{-1}$, $5 \times 10^{-3}$ sec$^{-1}$, or $10^{-3}$ sec$^{-1}$. In an additional embodiment, a DBDpp, binds a target of interest with an off rate ($K_{Off}$) of less than $5 \times 10^{-4}$ sec$^{-1}$, $10^{-4}$ sec$^{-1}$, $5 \times 10^{-5}$ sec$^{-1}$, or $10^{-5}$ sec$^{-1}$, $10^{-5}$ sec$^{-1}$, $5 \times 10^{-6}$ sec$^{-1}$, $10^{-6}$ sec$^{-1}$, $5 \times 10^{-7}$ sec$^{-1}$, or $10^{-7}$ sec$^{-1}$.

In one embodiment, a DBDpp specifically binds a target of interest with a $K_{On}$ ranging from $10^3$ to $10^7$ M$^{-1}$ sec-1, $10^3$ to $10^6$ M$^{-1}$ sec-1, or $10^3$ to $10^5$ M$^{-1}$ sec-1. In other specific embodiments, a DBDpp (e.g., a DBDpp fusion protein) binds the target of interest its target of interest with an on rate ($K_{On}$) of greater than $10^3$ M$^{-1}$ sec$^{-1}$, $5 \times 10^3$ M$^{-1}$ sec$^{-1}$, $10^4$ M$^{-1}$ sec$^{-1}$, or $5 \times 10^4$ M$^{-1}$ sec$^{-1}$. In an additional embodiment, a DBDpp, binds a target of interest with a $K_{On}$ of greater than $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$, or $10^7$ M$^{-1}$ sec$^{-1}$.

DBDpp Targets of Interest

The target of interest specifically bound by a DBDpp can be any molecule for which it is desirable for a DBDpp to bind. For example, the targets specifically bound by DBDpp can be any target of purification, manufacturing, formulation, therapeutic, diagnostic, or prognostic relevance or value. A number of exemplary targets are provided herein, by way of example, and are intended to be illustrative and not limiting. The target of interest can be naturally occurring or synthetic. The target of interest can be an extracellular component or an intracellular component, a soluble factor (e.g., an enzyme, hormone, cytokine, and growth factor, toxin, venom, pollutant, etc.), or a transmembrane protein (e.g., a cell surface receptor). In one embodiment, the target of interest specifically bound by a DBDpp is itself a DBDpp having a different sequence.

In one embodiment, a DBDpp fusion protein specifically binds a target of interest on the surface of a target cell. In a further embodiment, the DBDpp fusion protein specifically binds a cell surface receptor. In one embodiment, a DBDpp fusion protein specifically binds a target of interest that is a member of a family selected from: a growth factor receptor, a tyrosine kinase receptor, a TNF family receptor, a G-protein-coupled receptor, and a chemokine receptor. In some embodiments, the DBDpp fusion protein binds multiple members of the same family (e.g., the TNF receptors TRAILR1 and TRAILR2). In some embodiments, the DBDpp fusion protein binds members from different families. Thus, for example, in some embodiments, a DBDpp fusion protein can bind to a growth factor receptor and a TNF receptor or a G-protein-coupled receptor and a chemokine receptor.

In one embodiment, a DBDpp specifically binds a serum protein or a therapeutic protein, such as an antibody or antibody fragment. In some embodiments, a target of interest bound by a DBDpp (e.g., a DBDpp fusion protein) is a human protein. In one embodiment, a DBDpp (e.g., a DBDpp fusion protein) binds a human protein target of interest and its monkey (e.g., cynomolgous monkey), mouse, rabbit, hamster and/or a rabbit ortholog.

In one embodiment a DBDpp specifically binds a target of interest that is a serum protein. In one embodiment, embodiment a DBDpp specifically binds a serum protein selected from: serum albumin (e.g., human serum albumin (HSA)), thyroxin-binding protein, transferrin, fibrinogen, and an immunoglobulin (e.g., IgG, IgE and IgM). Without being bound by theory, the binding of a DBDpp to a carrier protein is believed to confer upon the DBDpp (or a fusion thereof) an improved pharmacodynamic profile that includes, but is not limited to, improved tumor targeting, tumor penetration, diffusion within the tumor, and enhanced therapeutic activity compared to the DBDpp fusion protein in which the carrier protein binding sequence is missing (see, e.g., WO 01/45746, the contents of which are herein incorporated by reference in its entirety).

In one embodiment the target of interest specifically bound by a DBDpp is a disease-related antigen. The antigen can be an antigen characteristic of a cancer, and/or of a particular cell type (e.g., a hyperproliferative cell), and/or of a pathogen (e.g., a bacterial cell (e.g., tuberculosis, smallpox, and anthrax), a virus (e.g., HIV), a parasite (e.g., malaria and leishmaniosis), a fungal infection, a mold, a mycoplasm, a prion antigen, or an antigen associated with a disorder of the immune system.

In an additional embodiment, the target of interest bound by a DBDpp (e.g., a DBDpp fusion protein) is a bacterial antigen, a viral antigen, a fungal antigen, a mycoplasm antigen, a prion antigen, or a parasite antigen (e.g., one infecting a mammal). In one embodiment, the target of a DBDpp is anthrax, hepatitis b, rabies, Nipah virus, west Nile virus, a meningitis virus, or CMV. In an additional embodiment, a DBDpp specifically binds a pathogen.

In one embodiment, a DBDpp specifically binds a cancer target. In another embodiment, a DBDpp specifically binds a TSA or TAA. In some embodiments the DBDpp specifically binds a target selected from the group consisting of PTGER4, ITGA4, CD37, CD52, CD62L (L-selectin), CXCR4, CD69, EVI2B (CD361), SLC39A8, MICB, LRRC70, CLELC2B, HMHA1, LST1, and CMTM6 (CK-LFSF6).

In one embodiment, a DBDpp specifically binds CD19 (B-CLL, B-ALL, leukemia, lymphoma, BNHL/CLL, ALL post-HCST, B lymphoid malignancies, B lineage malignancies), CD20 (mantle cell lymphoma/indolent B-NHL), PMSA (prostate cancer), CEA (breast cancer, colorectal cancer), Her2/neu (lung cancer, osteosarcoma, glioblastoma), kappa light chain (B-NHL and B-CLL).

In one embodiment, a DBDpp specifically binds a target selected from the group consisting of CD47, CTLA4, DR5, KIR, LAGS, OX40, PD-L1 and TIM3.

In one embodiment, a DBDpp specifically binds a target of interest is selected from the group consisting of: PDGFRA, PDGFRB, PDGFA, PDGFB, PDGFCC, PDGFC, PDGFD, VEGFR1, VEGFR2, VEGFR3, VEGFC, VEGFD, neuropilin 2 (NRP2), betacellulin, PLGF, RET (rearranged during transfection), TIE1, TIE2 (TEK), CA125, CD3, CD4, CD7, CD10, CD13, CD19, CD22, CD25, CD30, CD32, CD32b, CD33, CD38, FRSF5 (CD40), CD44 (e.g., CD44v6), CD47, CD49e (integrin alpha 5), CD52, CD54 (ICAM), CD55, CD64, CD74, CD80, CD90, CD117 (cKit), CD133, CD200, (prominin 1), CD147, CD166, CD200, ESA, SHH, DHH, IHH, patched 1 (PTCH1), smoothened (SMO), WNT1, WNT2B, WNT3A, WNT4. WNT4A, WNT5A, WNT5B, WNT7B, WNT8A, WNT10A, WNT10B, WNT16B, LKP5, LRP5, LRP6, FZD1, FZD2, FZD4, FZD5, FZD6, FZD7, FZD8, Notch, Notch1, Notch3, Notch4, DLL4, Jagged, Jagged1, Jagged2, Jagged3, TNFSF1 (TNFb, LTa), TNFRSF1A (TNFR1, p55, p60), TNFRSF1B (TNFR2), TNFSF6 (Fas Ligand), TNFRSF6 (Fas, CD95), TNFRSF6B (DcR3), TNFSF4 (OX40 Ligand), TNFSF5 (CD40 Ligand), TNFSF7 (CD27 Ligand, CD70), TNFRSF7 (CD27), TNFSF8 (CD30 Ligand), TNFSF9 (41BB Ligand), TNFRSF8 (CD30), TNFSF11 (RANKL), TNFRSF10A (TRAILR1, DR4), TNFRSF10B (TRAILR2, DR5), TNFRSF4 (OX40), TNFRSF11A (RANK), TNFSF12 (TWEAK), TNFRSF12 (TWEAKR), TNFSF13 (APRIL), TNFSF13B (BLYS), TNFRSF13B (TACI), TNFRSF13C (BAFFR), TNFSF15 (TL1A), TNFRSF17 (BCMA), TNFRSF19L (KELT), TNFRSF19 (TROY), TNFRSF21 (DR6), TNFRSF25 (DR3), ANG1 (ANGPT1), ANG2 (ANGPT2), ANG3 (ANGPTL1), ANG4 (ANGPT4), TIE2, IL1 alpha, IL1 beta, ILIRI, 1L1R2, IL2 IL2R, IL5, IL5R, IL6, IL6R, 1L8, 1L8R, IL10, IL10R, IL12, IL12R, IL13, IL13R, IL15, IL15R, IL18, IL18R, IL19, IL19R, IL21, IL21R, IL23, IL23R, mif, XAG1, XAG3, REGIV, FGF1, FGF2, FGF3, FGF4, FGFR1, FGFR2, FGFR3, ALK, ALK1, ALK7, ALCAM, Artemin, Axl, TGFb, TGFb2, TGFb3, TGFBR1, IGFIIR, BMP2, BMP5, BMP6, BMPRI, GDF3, GDF8, GDF9, N-cadherin, E-cadherin, VE-cadherin, EPCAM (EGP2), NCAM, LI CAM (GDI 71), ganglioside GM2, ganglioside GD2, calcitonin, PSGR, DCC, CDCP1, CXCR2, CXCR7, CCR3, CCR4, CCR5, CCR7, CCR10, CXCR4, CXCL1, CXCL5, CXCL6, CXCL8, CXCL12, CCL2, CCL3, CCL4, CCL5, CCL11, Claudin1, Claudin2, Claudin3, Claudin4, TMEFF2, neuregulin, MCSF, CSF, CSFR (fms), GCSF, GCSFR, BCAM, HPV, hCG, SR1F, PSA, FOLR2 (folate receptor beta), BRCA1, BRCA2, HLA-DR, ABCC3, ABCB5, HM 1.24, LFA1, LYNX, S100A8, S100A9, SCF, Von Willebrand factor, Lewis Y6 receptor, Lewis Y, CA G250 (CA9), CRYPTO, VLA5, CTLA4, HLA-DR, MUCl, MUC 8, mucin CanAg, ganglioside GD3, EGFL7, PDGFRa, IL21, IGF1, IGF2, HGF, PSMA, SLAMF7, carcinoembryonic antigen (CEA), FAP, integrin avb3, integrin α5β activin B1 alpha, leukotriene B4 receptor (LTB4R), neurotensin NT receptor (NTR), 5T4 oncofetal antigen, Tenascin C, MMP, MMP2, MMP7, MMP9, MMP12, MMP14, MMP26, cathepsin G, cathepsin H, cathepsin L, SULF1, SULF2, MET, UP A, MHCL MN (CA9), TAG-72, TM4SF1, Heparanase (HPSE), syndecan (SDC1), Ephrin B2, Ephrin B4, T neuropilin 1 (NRP1), TEM1, mesothelin, TGFbeta 1, TGFBRII, FcRn, phosphatidlyserine, folate receptor alpha (FOLR1), and relaxin2. The above targets and those otherwise described herein are intended to be illustrative and not limiting.

In one embodiment, a DBDpp (e.g., a DBDpp fusion protein) specifically binds a target of interest selected from: VEGF, VEGFA, VEGFR1, VEGFR2, IGF1R, integrin, cMet, EGFR, ErbB2 (Her2), CD20, nerve growth factor (NGR), hepatocyte growth factor receptor, ErbB3 (Her3), ErbB4, prostate specific membrane antigen.

In one embodiment, a target of interest specifically bound by a DBDpp (e.g., a DBDpp fusion protein) is an antigen associated with an autoimmune disorder, inflammatory or other disorder of the immune system or is associated with regulating an immune response.

In one embodiment, a DBDpp specifically binds a target of interest that is an immunoinhibitory target. In another embodiment, a DBDpp specifically binds an immunoinhibitory target, selected from: IL1, IL1b, IL1Ra, IL5, IL6, IL6R, CD26L, CD28, CD80, FcRn, or FcGamma RIIB In another embodiment, a DBDpp specifically binds an immunostimulatory target selected from: CD25, CD28, CTLA4, PD1, B7-H1 (PD-L1), B7-H4, IL10, TGFbeta, TNFSF4 (OX40 Ligand), TNFRSF4 (OX40), TNFSF5 (CD40 Ligand), TNFRSF5 (CD40), TNFSF9 (41BB Ligand), TNFRSF9 (41BB, CD137), TNFSF14 (LIGHT, HVEM Ligand), TNFRSF14 (HVEM), TNFSF15 (TL1A), TNFRSF25 (DR3), TNFSF18 (GITR Ligand), and TNFRSF18 (GITR).

In an additional embodiment, a DBDpp specifically binds a target of interest selected from: IL1Rb, IL2, IL3, IL4, IL7, IL11, IL15, IL16, IL17, IL17A, IL17F, IL18, IL19, IL25, IL32, IL33, interferon beta, SCF, BCA1/CXCL13, CXCL1, CXCL2, CXCL6, CXCL13, CXCL16, C3AR, C5AR, CXCR1, CXCR2, CCR1, CCR3, CCR7, CCR8, CCR9, CCR10, ChemR23, CCL3, CCL5, CCL11, CCL13, CCL17, CCL18, CCL19, CCL20, CCL21, CCL22, CCL24, CCL25, CCL26, CCL27, MPL, GP130, TLR2, TLR3, TLR4, TLR5, TLR7, TLR8, TLR9, TREM1, TREM2, oncostatin M, lymphotoxin alpha (LTa), integrin beta 7 subunit, CD49a (integrin alpha 1), integrin a5b3, MIF, ESM1, WIF1, cathepsin B, cathepsin D, cathepsin K, cathepsin S, TNFSF2 (TNFa), TNFSF3 (LTb), TNFRSF3 (LTBR), TNFSF6 (Fas Ligand), TNFRSF6 (Fas, CD95), TNFRSF6B (DcR3), TNFSF8 (CD30 Ligand), TNFRSF8 (CD30), TNFSF11 (RANKL), TNFRSF11A (RANK), TNFRSF16 (NGFR), TNFRSF19L (RELT), TNFRSF19 (TROY), TNFRSF21 (DR6), CD14, CD23 CD36, CD36L, CD39, CD52, CD91, CD137, CD153, CD164, CD200, CD200R, BTLA, B7-1 (CD80), B7-2 (CD86), B7h, B7-DC (PDL2), ICOS, ICOSL, MHC, CD, B7-H2, B7-H3, B7x, SLAM, KIM-1, SLAMF2, SLAMF3, SLAMF4, SLAMF5, SLAMF6, and SLAMF7, TNFSF1A (TNF-alpha), TNFRSF1A (TNFR1, p55, p60), TNFRSF1B (TNFR2), TNFSF7 (CD27 Ligand, CD70), TNFRSF7 (CD27), TNFSF13B (BLYS), TNFSF13 (APRIL), TNFRSF13B (TACI), TNFRSF13C (BAFFR), TNFRSF17 (BCMA), TNFSF12 (TWEAK), TNFRSF12 (TWEAKR), TNFRSF5 (CD40), IL1, IL1b, IL1R, IL2R, IL4-Ra, IL5, IL5R, IL6, IL6R, IL9, IL12, IL13, IL14, IL15, IL15R, IL17f, IL17R, IL17Rb, IL17RC, IL20, IL21, IL22RA, IL23, IL23R, IL31, TSLP, TSLPR, interferon alpha, interferon gamma, B7RP1, cKit, GMCSF, GMCSFR, CTLA4, CD2, CD3, CD4, CD11a, CD18, CD20, CD22, CD30, CD40, CD86, CXCR3, CXCR4, CCR2, CCR4, CCR5, CCR8, CCL2, CXCL10, P1GF, alpha4 integrin subunit, A4B7 integrin, C5, RhD, IgE, and Rh.

In another embodiment, a DBDpp specifically binds a target of interest selected from: amyloid beta (Abeta), beta amyloid, complement factor D, PLP, ROBO4, ROBO, GDNF, NGF, LINGO, myostatin, oxidized LDL, gpIIB, gpIIIa, PCSK9, Factor VIII, integrin a2bB3, AOC3, mesothelin, DKK1, osteopontin, cathepsin K, TNFRSF19L (RELT), TNFRSF19 (TROY), and sclerostin.

In one embodiment, a DBDpp specifically binds a target of interest selected from the group consisting of: CD137, CD47, CTLA4, DR5, KIR, PD-L1, PD1 and TIM3.

In one embodiment a DBDpp specifically binds CD137. In a further embodiment, a DBDpp specifically binds CD137 and comprises an amino acid sequence selected from: (a) MGSWVEFGHRLWAIDQRLYALGGSEAEL-AAFEKEIAAFESELQAYKGKGNPEVEK LRQRAAFIR-FRLQAYRHN (SEQ ID NO:12), (b) MGSWVEFANRL-WAIDQRLFALGGS EAELAAFEKEIAAFESELQAYKGKGNPE-VEHLRDQAAFIRHKLQAYRHN (SEQ ID NO:13), (c) MGSWYEFRHRLWAIDQRLYALGGSEAELAAFEKE-IAAFESELQAYKGK GNPEVEGLREAAAFIRAKLQAY-RHN (SEQ ID NO:14), (d) MGSWYEFSMRLWAIDQ RLYALGGSEAELAAFEKEIAAFESELQAYKGKGNPE-VEALRAKAAYIRWKLQAYRHN (SEQ ID NO:15), (e) MGSWFEFNHRLWAINERLYALGGSEAELAAFEKE-IAA FESELQAYKGKGNPEVERLRSMAAFIRYKLQAY-RHN (SEQ ID NO:16), (f) MGSWY EFGHRLWAIDQR-LYALGGSEAELAAFEKEIAAFESELQAYKGKGNPEV EYLRETAA HIRTRLQAYRHN (SEQ ID NO:17), (g) MGSWYEFHYRLHAIDQRLYALGGSEAELAA FEKE-IAAFESELQAYKGKGNPEVEELRIKAAFIRDRLQAY-RHN (SEQ ID NO:18), and (h) MGSWAEFKQRLAAI-KTRLEALGGSEAELAAFLGEIWAFEMELAAYKGKG NPEV EALGREAAAIRMELQAYRHN (SEQ ID NO:19). Other DBDpp and polypeptides that completely or partially (e.g., overlap with an epitope) bind to the same epitope of CD137 as an above DBDpp are provided. Additionally, DBDpp and polypeptides that completely or partially compete with an above DBDpp for binding to CD137 are also provided. Nucleic acids encoding the DBDpp are also provided, as are vectors containing the nucleic acids and host cells containing the nucleic acids and vectors.

In one embodiment a DBDpp specifically binds CD47. In a further embodiment, a DBDpp specifically binds CD47 and comprises an amino acid sequence selected from (a) MGSWYEFDLRLHAIYDRLVALGGSEAELAAFEKE-IAAFESELQAYKGKGNPEVEIL RDNAAYIRQMLQAY-RHN (SEQ ID NO:20), (b) MGSWVEFANRLWAIDQRL-FALGGS EAELAAFEKEIAAFESELQAYKGKGNPE-VEHLRDQAAFIRHKLQAYRHN (SEQ ID NO:21), (c) MGSWTEFTYRLSAIEWRLWALGGSEAELAWFEQKI-AFFEDFLQYYKGK GNPEVEALKHEAGAILNELMAY-RHN (SEQ ID NO:22), (d) MGSWAEFDHRLHAIRE RLHALGGSEAELAAFEKEIAAFESELQAYKGKGNPE-VEILRGNAAYIRALLQAYRHN (SEQ ID NO:23), and (e) MGSWTEFVGRLAAIEFRLWALGGSEAELAWFEA-HIAFFE DYLQWYKGKGNPEVEALREEAGAIMEEL-KAYRHN (SEQ ID NO:24). Other DBDpp and polypeptides that completely or partially bind to the same epitope of CD47 as an above DBDpp are provided. Additionally, DBDpp and polypeptides that completely or partially compete with an above DBDpp for binding to CD47 are also provided. Nucleic acids encoding the DBDpp are also provided, as are vectors containing the nucleic acids and host cells containing the nucleic acids and vectors.

In one embodiment a DBDpp specifically binds CTLA4. In a further embodiment, a DBDpp specifically binds CTLA4 and comprises an amino acid sequence of MGSWH EFHDRLQAIHERLYALGGSEAELAAFEKEIAAF-ESELQAYKGKGNPEVESLRIAAAHI RQVLQAYRHN (SEQ ID NO:25). Other DBDpp and polypeptides that completely or partially bind to the same epitope of CTLA4 as the above DBDpp are provided. Additionally, DBDpp and polypeptides that completely or partially compete with the above DBDpp for binding to CTLA4 are also provided. Nucleic acids encoding the DBDpp are also provided, as are vectors containing the nucleic acids and host cells containing the nucleic acids and vectors.

In one embodiment, a DBDpp specifically binds DR5. In a further embodiment, a DBDpp specifically binds DR5 and comprises an amino acid sequence selected from (a) MG SWNYFKDHLAWIKNSLEALGGSEAELAHFETAIASFERQLQEYKGKGNPEVEALRK EAAAIRDELQAYRHN (SEQ ID NO:26), (b) MGSWLYFKEHLAHIKAWLEALGGS EAELAHFELAIADFEYHLQEYKGKGNPEVEALRKEAAAIRDELQAYRHN (SEQ ID NO:27), (c) MGSWTEFTYRLSAIEWRLWALGGSEAELAWFEQKIAFFEDFLQYYKGK GNPEVEALKHEAGAILNELMAYRHN (SEQ ID NO:28), (d) MGSWFYFKQHLAWIKSYLEALGGSEAELAHFERAIAAFEQHLQMYKGKGNPEVEALRKEAAAIRDELQAYRHN (SEQ ID NO:29), (e) MGSWHYFKDHLAEIKGLLEALGGSEAELAHFEMAIAD FEHNLQYYKGKGNPEVEALRKEAAAIRDELQAYRHN (SEQ ID NO:30), (f) MGSWH YFKGHLAEIKNHLEALGGSEAELAHFERAIAAFERSLQWYKGKGNPEVEALRKEAA AIRDELQAYRHN (SEQ ID NO:31), (g) MGSWIYFKEHLAYIKKELEALGGSEAE LAHFESAIAVFESTLQYYKGKGNPEVEALRKEAAAIRDELQAYRHN (SEQ ID NO:32), (h) MGSWTYFKEHLAEIKYMLEALGGSEAELAHFEVAIADFEKMLQYYK GKGNPEVEALRKEAAAIRDELQAYRHN (SEQ ID NO:33), and (i) MGSWWLFKDHL AEIKTALEALGGSEAELAHFEMAIAAFEKQLQYYKGKGNPEVEALRKEAAAIRDEL QAYRHN (SEQ ID NO:34). Other DBDpp and polypeptides that completely or partially bind to the same epitope of DR5 as an above DBDpp are provided. Additionally, DBDpp and polypeptides that completely or partially compete with an above DBDpp for binding to DR5 are also provided. Nucleic acids encoding the DBDpp are also provided, as are vectors containing the nucleic acids and host cells containing the nucleic acids and vectors.

In one embodiment, a DBDpp specifically binds KIR. In a further embodiment, a DBDpp specifically binds KIR and comprises an amino acid sequence selected from (a) MG SWSEFYNRLDAIESRLLALGGSEAELALFEIQIARFEKVLQAYKGKGNPEVEALR GEARAIFAELYAYRHN (SEQ ID NO:35), (b) MGSWYEFYNRLYAIEIRLYALGGSEA ELAAFEKIAAFESELQAYKGKGNPEVERLRVRAAKIRVILQAYRHN (SEQ ID NO:36), and (c) MGSWLWFKIFLAEIKYFLEALGGSEAELAAFDFEIHAFHVELFAYKG KGNPEVEVLREVAAEIRWDLQAYRHN (SEQ ID NO:37). Other DBDpp and polypeptides that completely or partially bind to the same epitope of KIR as an above DBDpp are provided. Additionally, DBDpp and polypeptides that completely or partially compete with an above DBDpp for binding to KIR are also provided. Nucleic acids encoding the DBDpp are also provided, as are vectors containing the nucleic acids and host cells containing the nucleic acids and vectors.

In one embodiment, a DBDpp specifically binds PD-L1. In a further embodiment, a DBDpp specifically binds PD-L1 and comprises an amino acid sequence selected from (a) MGSWTEFQSRLDAIHSRLRALGGSEAELAAFEKEIAAFESELQAYKGKGNPEVELLR DDAAFIRHFLQAYRHN (SEQ ID NO:38), (b) MGSWQEFDDRLNAIKARLQALGGSEA ELAAFEKEIAAFESELQAYKGKGNPEVEDLRDDAAFIRRFLQAYRHN (SEQ ID NO:39), (c) MGSWYEFQNRLHAIHERLNALGGSEAELAAFEKEIAAFESELQAYKGK GNPEVELLRDDAAFIRHFLQAYRHN (SEQ ID NO:40), (d) MGSWFEFQDRLTAINER LSALGGSEAELAAFEKEIAAFESELQAYKGKGNPEVETLRSDAAFIRRFLQAYRHN (SEQ ID NO:41), (e) MGSWYEFESRLDAIHERLHALGGSEAELAAFEKEIAAFESE LQAYKGKGNPEVENLRGDAAFIRHFLQAYRHN (SEQ ID NO:42), (f) MGSWYEFNHR LDAISKRLNALGGSEAELAAFEKEIAAFESELQAYKGKGNPEVEELRGDAAFIRHFL QAYRHN (SEQ ID NO:43), and (g) MGSWFEFENRLHAIVHRLGALGGSEAELAAFE KEIAAFESELQAYKGKGNPEVETLRADAAFIRHYLQAYRHN (SEQ ID NO:44). Other DBDpp and polypeptides that completely or partially bind to the same epitope of PD-L1 as an above DBDpp are provided. Additionally, DBDpp and polypeptides that completely or partially compete with a DBDpp for binding to PD-L1 are also provided. Nucleic acids encoding the DBDpp are also provided, as are vectors containing the nucleic acids and host cells containing the nucleic acids and vectors.

In one embodiment, a DBDpp specifically binds PD1. In a further embodiment, a DBDpp specifically binds PD1 and comprises an amino acid sequence selected from (a) MGSWTIFKEWLAFIKTDLEALGGSEAELAFFEGWIASFEMELQKYKGKGNPEVEAL RKEAAAIRDELQAYRHN (SEQ ID NO:46), (b) MGSWVMFKWLLADIKSHLEALGG SEAELAFFEGFIAAFETHLQVYKGKGNPEVEALRKEAAAIRDELQAYRHN (SEQ ID NO:47), and (c) MGSWYAFKDYLADIKGWLEALGGSEAELAFFEIFIARFELELQAY KGKGNPEVEALRKEAAAIRDELQAYRHN (SEQ ID NO:48). Other DBDpp and polypeptides that completely or partially bind to the same epitope of PD1 as an above DBDpp are provided. Additionally, DBDpp and polypeptides that completely or partially compete with an above DBDpp for binding to PD1 are also provided. Nucleic acids encoding the DBDpp are also provided, as are vectors containing the nucleic acids and host cells containing the nucleic acids and vectors.

In one embodiment, a DBDpp specifically binds TIM3. In a further embodiment, a DBDpp specifically binds TIM3 and comprises an amino acid sequence of MGSWHEFHD RLQAIHERLYALGGSEAELAAFEKEIAAFESELQAYKGKGNPEVESLRIAAAHIRQV LQAYRHN (SEQ ID NO:45). Other DBDpp and polypeptides that completely or partially bind to the same epitope of TIM3 as the above DBDpp are provided. Additionally, DBDpp and polypeptides that completely or partially compete with the DBDpp for binding to TIM3 are also provided. Nucleic acids encoding the DBDpp are also provided, as are vectors containing the nucleic acids and host cells containing the nucleic acids and vectors.

In another embodiment, the DBDpp binds a peptide tag present on a target of interest. Such peptide tags provide a useful means by which to purify, detect and/or attach targets of interest containing the peptide tags. In one embodiment, a DBDpp specifically binds a peptide tag selected from the group: a hexahistidyl (His6) tag, a myc tag or a FLAG tag. Other peptide tags are described herein or otherwise known in the art.

In another embodiment, the target to which DBDpp binds is the subject of purification from a mixture of contaminants. In one embodiment the target may be a natural or recombinantly expressed protein that requires selective isolation from a cell lysate or cell culture supernatant.

DBDpp Fusion Proteins

A "fusion polypeptide," "fusion protein," "chimeric polypeptide," "chimeric protein," "chimeric antigen" is a polypeptide comprised of at least two polypeptides and optionally a linker to operatively link the two polypeptides into one continuous polypeptide produced, e.g., by recombinant processes. The two polypeptides may be operably attached directly or indirectly.

A "DBDpp fusion protein" comprises at least one DBDpp that specifically binds a target of interest. In one embodiment, the DBDpp fusion proteins comprise more than one DBDpp, wherein the two or more DBDpp have the same or different specificities. In additional embodiments, the DBDpp fusion protein is comprised of a tandem repeat of the same or different DBDpp that allow a DBDpp fusion protein to bind multiple targets and/or repeating epitopes or different epitopes on the same target. In additional embodiments, a DBDpp fusion protein comprises a DBDpp and a polypeptide sequence containing an additional domain. In some embodiments, the DBDpp fusion protein comprises a DBDpp and a member selected from: an antibody, an antibody fragment (e.g., an antigen binding domain or portion thereof (e.g., an ScFv), an effector domain or portion thereof, an FcRn binding domain or portion thereof, and an Fc or a portion thereof), a serum protein (e.g., albumin or a portion thereof), a cytokine, a growth factor, a hormone, an imaging agent, a labeling agent, and a peptide tag. In some embodiments, the DBDpp fusion protein comprises an Fc domain of an immunoglobulin (e.g., a human Fc domain) or a portion thereof. In further embodiments, the Fc domain is a variant human Fc domain.

The DBDpp provided herein include DBDpp fusion proteins. A DBDpp and any polypeptide of interest can be operably linked to form a DBDpp fusion protein. Thus, in some embodiments, the DBDpp is incorporated into a larger, multi-domain molecular complex (e.g., a monomeric or multimeric DBDpp fusion protein) and in so doing, imparts the functional attributes of the incorporated DBDpp to the resultant fusion protein. In some embodiments, DBDpp fusion proteins comprise a DBDpp and a polypeptide sequence from an antibody, an antibody fragment, a serum protein (e.g., human serum albumin) or serum protein fragment, or a cell surface receptor, an alpha chain of a T cell receptor (TCR), a beta chain of a T cell receptor, cytokine, growth factor, hormone, or enzyme, or fragment thereof. Incorporation of DBD into multidomain and/or multifunctional complexes can routinely be achieved by way of recombinant fusion to another polypeptide, binding to another chemical moiety, and covalent chemical linkage to another polypeptide (or other desirable chemical compound) using techniques known in the art. DBDpp fusion proteins can additionally contain other optional components such as linkers and other components described herein.

DBDpp Multimers

Figure 5A:
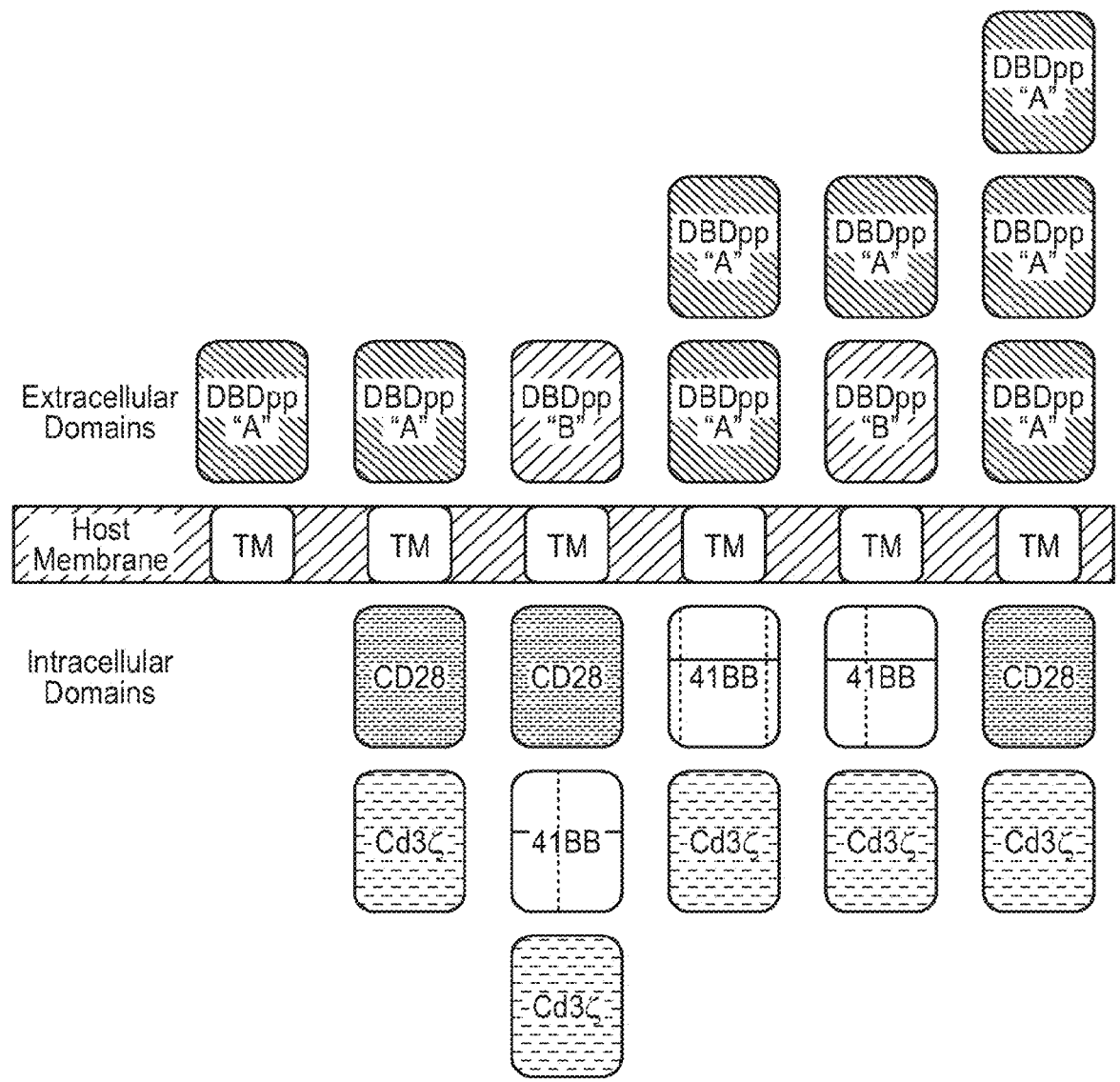
FIGS. 5A-5C.

In some embodiments, the DBDpp fusion protein contains one DBDpp. In some embodiments, the DBDpp fusion protein comprises at least 2, 3, 4, or 5, or more than 5 DBDpp. In some embodiments, the DBDpp fusion protein contains 1-3, 1-4, 1-5, or more than 5 different DBDpp. In some embodiments, the DBDpp fusion protein contains at least 2, 3, 4, or 5, or more than 5 different DBDpp. Thus, a DBDpp fusion protein can be a monomeric DBDpp (i.e., containing one DBDpp) or multimeric DBDpp (i.e., containing more than one DBDpp in tandem optionally operably connected by a linker). Non-limiting embodiments of such multimeric DBDpp are shown in FIG. 5A. In several embodiments, the use of multimeric DBDpp provides enhanced (e.g., synergistic) target binding. In additional embodiments, multimeric DBDpp allows targeting of more than one target using a single DBDpp construct (e.g., bi-, tri-specific, etc.).

The multimeric DBDpp fusion protein can be a DBDpp homo-multimeric (i.e., containing more than one of the same DBDpp in tandem optionally connected by linker(s) (e.g., homodimers, homotrimers, homotetramers etc.) or DBDpp hetero-multimeric (i.e., containing two or more DBDpp in which there are at least two different DBDpp protein. The number of monomeric DBDpp included within a multimeric composition may vary, depending on the embodiment, and may be defined, at least in part, by the expression system in which the DBDpp is produced. In several embodiments, however, the fusion proteins may comprises multimers of about 5 to about 10 DBDpp subunits, about 10 to about 15 subunits, about 15 to about 20 subunits, about 20 to about 25 subunits, or about 25 to about 30 subunits (including numbers in between those listed as well as endpoints). Moreover, multiple tandem components of a DBDpp fusion protein can contain the same or different DBDpp. In some DBDpp fusions, the DBDpp are present as a monomer, or in homo-multimers or heteromers such as, homodimers or heterodimers, homotrimers or heterotrimers, homotetramers or heterotetramers.

In one embodiment, two or more DBDpp are operably fused to form a DBDpp fusion protein. In one embodiment, the fusion partner of a DBDpp is an identical DBDpp. The linkage of two or more identical DBDpp results in a multivalent molecule that provides distinct advantages (e.g., increased binding avidity, target clustering and receptor activation) over monomeric compositions. In another embodiment the fusion partner of a DBDpp is a non-identical DBDpp. The linkage of two or more non-identical DBDpp results in a multivalent and multi-specific molecule that has the potential to bind more than one target antigen, either independently or simultaneously.

A DBDpp fusion protein can be "monospecific" or "multi-specific." A DBDpp fusion protein that is "multi-specific" (e.g., bispecific, trispecific or of greater multi-specificity) recognizes and binds to two or more different epitopes present on one or more different molecules (e.g., proteins, solid support structures, etc.).

In one embodiment, a multi-specific DBDpp fusion protein contains at least two DBDpp that bind to at least two different epitopes on a single target of interest. In additional embodiments, a multi-specific DBDpp fusion protein comprises at least one DBDpp that specifically binds one epitope on a target of interest and at least one other domain or sequence conferring function (e.g., an antibody fragment or domain such as an scFv) that specifically binds to a different epitope on the same target of interest. In one embodiment, a multi-specific DBDpp fusion protein comprises at least one DBDpp that specifically binds to an epitope on a target of interest and at least one domain or sequence conferring function e.g., an antibody fragment or domain (e.g., scFv), that specifically binds to an epitope on a different target of interest. In other embodiments, a DBDpp fusion protein comprises at least one DBDpp and at least one other DBDpp or domain sequence conferring function, e.g., an antibody fragment or domain, that specifically binds to a solid support.

In a further embodiment, the multimeric DBDpp fusion comprising 2 or more DBDpp are in turn fused with other heterologous proteins (or their subdomains) and in so doing, impart the multivalent and multi-specific properties to the fusion partner. Examples of fusion partners of a DBDpp includes but is not limited to, antibodies, antibody subdomains (e.g., scFv or Fc domains), serum albumin, serum albumin subdomains, cell surface receptors, an alpha chain of a T cell receptor (TCR), a beta chain of a T cell receptor, cell surface receptor subdomains, peptides, peptide tags (e.g., FLAG or myc), fibronectin type III repeats, z-domains, elastin-like polypeptides. The number and location of DBDpp and their respective positions within the fusion protein can vary. For example, DBDpp(s) can be located at one or all termini of a fusion partner and/or interspersed within heterologous subunits within the DBDpp fusion partner.

In one embodiment, the DBDpp fusion is bispecific and specifically binds to two different targets expressed on the surface of two different cell types. In one embodiment the bispecific DBDpp fusion protein specifically binds to a cancer cell target and an immune effector cell target. In one embodiment the bispecific DBDpp fusion protein specifically binds a target expressed on a cancer cell (e.g. CD19) and a target expressed on the surface of a T lymphocyte (e.g., CD3).

DBDpp as Fusions to Antibodies and Antibody Fragments

In one embodiment, a DBDpp fusion protein comprises a whole antibody or an antibody fragment or domain (e.g., an IgG1 antibody, IgG3 antibody, antibody variable region, CDR3, ScFv, Fc, FcRn binding domain, and other antibody domains). DBDpp and DBDpp fusion proteins can be operably linked to one another and/or to one or more termini of an antibody, antibody chain, antibody fragment or antibody domain.

The antibody component of a DBDpp fusion protein can be any suitable whole immunoglobulin or antibody fragment (e.g., an antigen binding domain and/or effector domain) or a fragment thereof. In one embodiment, the DBDpp-antibody fusion protein retains the structural and functional properties of a traditional monoclonal antibody. Thus, in some embodiments, the DBDpp-antibody fusion protein retains the epitope binding properties, but advantageously also incorporate, via the DBDpp fusion, one or more additional target-binding specificities. Antibodies that can be used in the DBDpp fusions include, but are not limited to, monoclonal, multi-specific, human, humanized, primatized, and chimeric antibodies. Immunoglobulin or antibody molecules provided herein can be of any type (e.g., IgG, IgE, IgM, IgD, IgA, and IgY), class (e.g., IgG1, IgG2, IgG3, IgG4, IgA1 and IgA2) or subclass of immunoglobulin molecule. In specific embodiments, the antibodies are Fc optimized antibodies. Antibodies can be from or derived from any animal origin including birds and mammals or generated synthetically. The antibody component of the DBDpp-antibody fusion protein can be naturally derived or the result of recombinant engineering (e.g., phage display, xenomouse, and synthetic). In certain embodiments, the antibody component of the antibody-DBDpp fusion enhances half-life, and increase or decrease antibody dependent cellular cytotoxicity (ADCC), and/or complement dependent cytotoxicity (CDC) activity. In some embodiments, the antibodies are human, murine, donkey, rabbit, goat, guinea pig, camel, llama, horse, or chicken antibodies. In specific embodiments, the antibodies are human.

In one embodiment, a DBDpp is operably linked to an antibody fragment or subdomain (e.g., ScFv, diabody, EP 404,097; WO 93/111161; WO 2014/028776; and Holliger et al., PNAS 90:6444-6448 (1993), each of which are herein incorporated by reference in its entirety). The antibody fragment or subdomain can be any fragment or domain of an antibody. See for example, WO 04/058820, WO 99/42077 and WO 05/017148, each of which is herein incorporated by reference in its entirety. For example, a DBDpp fusion protein can contain an antibody effector domain or derivative of an antibody effector domain that confers one or more effector functions to the DBDpp and/or confers upon the DBDpp fusion protein the ability to bind to one or more Fc receptors. In some embodiments, a DBDpp-antibody fusion protein contains an antigen-binding fragment of an antibody or a fragment thereof. In additional embodiments, a DBDpp-antibody fusion protein contains an immunoglobulin effector domain that comprises one or more CH2 and or CH3 domains of an antibody having effector function provided by the CH2 and CH3 domains. Other sequences in the DBDpp fusion that provide an effector function and that are encompassed by the invention will be clear to those skilled in the art and can routinely be chosen and designed into a DBDpp fusion protein encompassed herein on the basis of the desired effector function(s).

In one embodiment, the antibody component of an antibody-DBDpp fusion provided herein has been modified to increase antibody dependent cellular cytotoxicity (ADCC) (see, e.g., Bruhns et al., Blood 113:3716-3725 (2009); Shields et al., J. Biol. Chem. 276:6591-6604 (2001); Lazar et al., PNAS 103:4005-4010 (2006); Stavenhagen et al., Cancer Res., 67:8882-8890 (2007); Horton et al., Cancer Res. 68:8049-8057 (2008); Zalevsky et al., Blood 113:3735-3743 (2009); Bruckheimer, Neoplasia 11:509-517 (2009); WO2006/0201 14; Strohl, Curr. Op. Biotechnol. 20:685-691 (2009); and WO2004/074455, each of which is herein incorporated by reference in its entirety). Examples of Fc sequence engineering modifications contained in the antibody component of the DBDpp-antibody fusion proteins that increases ADCC include one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues in the Fc region is that of the EU index of Kabat et al. (Kabat et al., Sequences of proteins of Immunological Interest, 1991 Fifth edition).

In one embodiment, the DBDpp fusion contains a whole antibody or an antibody fragment that is an antigen-binding fragment. In a further embodiment, the antibody or antibody fragment binds a disease-related antigen. In one embodiment the DBDpp fusion protein comprises an antibody or an antibody fragment that specifically binds a cancer antigen. In another embodiment, the DBDpp fusion protein comprises an antibody or an antibody fragment that specifically binds a particular pathogen (e.g., a bacterial cell (e.g., tuberculosis, smallpox, anthrax)), a virus (e.g., HIV), a parasite (e.g., malaria, leishmaniosis), a fungal infection, a mold, a mycoplasm, a prion antigen, In another embodiment, the DBDpp fusion protein comprises an antibody or an antibody fragment that specifically binds a particular pathogen (e.g., a bacterial cell (e.g., tuberculosis, smallpox, anthrax)), a virus (e.g., HIV), a parasite (e.g., malaria, leishmaniosis), a fungal infection, a mold, a mycoplasm, or a prion antigen. In another embodiment, the DBDpp fusion protein comprises an antibody or an antibody fragment that specifically binds an antigen associated with a disease or disorder of the immune system.

In preferred embodiments, the DBDpp fusion protein containing an antibody fragment or domain retains activities of the parent antibody. Thus, in certain embodiments, the DBDpp fusion protein containing an antibody fragment or domain is capable of inducing complement dependent cytotoxicity. In certain embodiments, the DBDpp fusion protein containing an antibody fragment or domain is capable of inducing antibody dependent cell mediated cytotoxicity (ADCC).

Accordingly, in some embodiments, the DBDpp fusion protein comprises an antibody fragment that confers upon the DBDpp fusion protein a biological or biochemical characteristic of an immunoglobulin. In some embodiments, the antibody fragment confers a characteristic selected from: the ability to non-covalently dimerize, the ability to localize at the site of a tumor, and an increased serum half-life when compared to the DBDpp fusion protein in which said one or more DBDpp have been deleted. In certain embodiments, the DBDpp fusion protein is at least as stable as the corresponding antibody without the attached DBDpp. In certain embodiments, the DBDpp fusion protein is more stable than the corresponding antibody without the attached DBDpp. DBDpp fusion protein stability can be measured using established methods, including, for example, ELISA techniques. In some embodiments, the DBDpp fusion protein is stable in whole blood (in vivo or ex vivo) at 37° C. for at least about 10 hours, at least about 15 hours, at least about 20 hours, at least about 24 hours, at least about 25 hours, at least about 30 hours, at least about 35 hours, at least about 40 hours, at least about 45 hours, at least about 48 hours, at least about 50 hours, at least about 55 hours, at least about 60 hours, at least about 65 hours, at least about 70 hours, at least about 72 hours, at least about 75 hours, at least about 80 hours, at least about 85 hours, at least about 90 hours, at least about 95 hours, or at least about 100 hours (including any time between those listed). In one embodiment, a DBDpp fusion contains an immunoglobulin effector domain or half-life influencing domain that corresponds to an immunoglobulin domain or fragment in which at least a fraction of one or more of the constant region domains has been altered so as to provide desired biochemical characteristics such as reduced or increased effector functions, the ability to non-covalently dimerize, increased ability to localize at the site of a tumor, reduced serum half-life, or increased serum half-life when compared with an immunoglobulin fragment having the corresponding unaltered immunoglobulin sequence. These alterations of the constant region domains can be amino acid substitutions, insertions, or deletions.

In one embodiment, a DBDpp fusion protein comprises an amino acid sequence of an immunoglobulin effector domain or a derivative of an immunoglobulin effector domain that confers antibody dependent cellular cytotoxicity (ADCC) to the DBDpp fusion protein. In additional embodiments, a DBDpp fusion protein comprises a sequence of an immunoglobulin effector domain that has been modified to increase ADCC (see, e.g., Bruhns, Blood 113:3716-3725 (2009); Shields, J. Biol. Chem. 276:6591-6604 (2001); Lazar, PNAS 103:4005-4010 (2006); Stavenhagen, Cancer Res. 67:8882-8890 (2007); Horton, Cancer Res. 68:8049-8057 (2008); Zalevsky, Blood 113:3735-3743 (2009); Bruckheimer, Neoplasia 11:509-517 (2009); WO 06/020114; Strohl, Curr. Op. Biotechnol. 20:685-691 (2009); and WO 04/074455, the contents of each of which is herein incorporated by reference in its entirety). Examples of immunoglobulin fragment engineering modifications contained in an amino acid sequence in a DBDpp fusion protein that increases ADCC include immunoglobulin effector domain sequences having one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues in the Fc region is that of the EU index of Kabat et al. (Kabat et al., Sequences of proteins of Immunological Interest, 1991 Fifth edition, herein incorporated by reference).

In other embodiments, a DBDpp fusion protein comprises a sequence of an immunoglobulin effector domain that has been modified to decrease ADCC (see, e.g., Idusogie et al., J. Immunol. 166:2571-2575 (2001); Sazinsky et al., PNAS 105:20167-20172 (2008); Davis et al., J. Rheumatol. 34:2204-2210 (2007); Bolt et al., Eur. J. Immunol. 23:403-411 (1993); Alegre et al., Transplantation 57:1537-1543 (1994); Xu et al., Cell Immunol. 200:16-26 (2000); Cole et al., Transplantation 68:563-571 (1999); Hutchins et al., PNAS 92:11980-11984 (1995); Reddy et al., J. Immunol. 164:1925-1933 (2000); WO 97/11971; WO 07/106585; US 2007/0148167A1; McEarchern et al., Blood 109:1185-1192 (2007); Strohl, Curr. Op. Biotechnol. 20:685-691 (2009); and Kumagai et al., J. Clin. Pharmacol. 47:1489-1497 (2007), the contents of each of which is herein incorporated by reference in its entirety). Examples of immunoglobulin fragment sequence engineering modifications contained in an amino acid sequence in a DBDpp fusion protein that decreases ADCC include immunoglobulin effector domain sequences having one or more modifications corresponding to: IgG1-K326W, E333S; IgG2-E333S; IgG1-N297A; IgG1-L234A, L235A; IgG2-V234A, G237A; IgG4-L235A, G237A, E318A; IgG4-S228P, L236E; IgG2-118-260; IgG4-261-447; IgG2-H268Q, V309L, A330S, A331S; IgG1-C220S, C226S, C229S, P238S; IgG1-C226S, C229S, E233P, L234V, L235A; or IgG1-L234F, L235E, P331S; wherein the numbering of the residues is that of the EU index of Kabat et al. (Kabat et al., Sequences of Proteins of Immunological Interest, 1991 Fifth edition, herein incorporated by reference).

In additional embodiments, a DBDpp fusion protein comprises an amino acid sequence of an immunoglobulin effector domain, or a derivative of an immunoglobulin effector domain, that confers antibody-dependent cell phagocytosis (ADCP) to the DBDpp fusion protein. In additional embodiments, a DBDpp fusion protein comprises a sequence of an immunoglobulin effector domain that has been modified to increase antibody-dependent cell phagocytosis (ADCP); (see, e.g., Shields et al., J. Biol. Chem. 276:6591-6604 (2001); Lazar et al., PNAS 103:4005-4010 (2006); Stavenhagen et al., Cancer Res., 67:8882-8890 (2007); Richards et al., Mol. Cancer Ther. 7:2517-2527 (2008); Horton et al., Cancer Res. 68:8049-8057 (2008), Zalevsky et al., Blood 113:3735-3743 (2009); Bruckheimer et al., Neoplasia 11:509-517 (2009); WO 06/020114; Strohl, Curr. Op. Biotechnol. 20:685-691 (2009); and WO 04/074455, the contents of each of which is herein incorporated by reference in its entirety. Examples of immunoglobulin fragment engineering modifications contained in an amino acid sequence in a DBDpp fusion protein that increases ADCP include immunoglobulin effector domain sequences having one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; IgG1-F243L, R292P, Y300L, V305I, P396L; and IgG1-G236A, S239D, I332E; wherein the numbering of the residues is that of the EU index of Kabat et al. (Kabat et al., Sequences of proteins of Immunological Interest, 1991 Fifth edition, herein incorporated by reference).

In other embodiments, a DBDpp fusion protein comprises a sequence of an immunoglobulin effector domain that has been modified to decrease ADCP (see, e.g., Sazinsky et al., PNAS 105:20167-20172 (2008); Davis et al., J. Rheumatol. 34:2204-2210 (2007); Bolt et al., Eur. J. Immunol. 23:403-411 (1993); Alegre et al., Transplantation 57:1537-1543 (1994); Xu et al., Cell Immunol. 200:16-20 (2000); Cole et al., Transplantation 68:563-571 (1999); Hutchins et al., PNAS 92:11980-11984 (1995); Reddy et al., J. Immunol. 164:1925-1933 (2000); WO 97/11971; WO 07/106585; US 2007/0148167A1; McEarchern et al., Blood 109:1185-1192 (2007); Strohl, Curr. Op. Biotechnol. 20:685-691 (2009); and Kumagai et al., J. Clin. Pharmacol. 47:1489-1497 (2007), the contents of each of which is herein incorporated by reference in its entirety). By way of example, DBDpp fusion proteins can contain an antibody fragment or domain that contains one or more of the following modifications that decrease ADCC: IgG1-N297A; IgG1-L234A, L235A; IgG2-V234A, G237A; IgG4-L235A, G237A, E318A; IgG4-S228P, L236E; IgG2 EU sequence 118-260; IgG4-EU sequence 261-447; IgG2-H268Q, V309L, A330S, A331S; IgG1-C220S, C226S, C229S, P238S; IgG1-C226S, C229S, E233P, L234V, L235A; and IgG1-L234F, L235E, P331S; wherein the numbering of the residues is that of the EU index of Kabat et al. (Kabat et al., Sequences of proteins of Immunological Interest, 1991 Fifth edition, herein incorporated by reference).

In additional embodiments, a DBDpp fusion protein comprises an amino acid sequence of an immunoglobulin effector domain, or a derivative of an immunoglobulin effector domain, that confers complement-dependent cytotoxicity (CDC) to the DBDpp fusion protein. In additional embodiments, a DBDpp fusion protein comprises a sequence of an immunoglobulin effector domain that has been modified to increase complement-dependent cytotoxicity (CDC) (see, e.g., Idusogie et al., J. Immunol. 166:2571-2575 (2001); Strohl, Curr. Op. Biotechnol. 20:685-691 (2009); and Natsume et al., Cancer Res. 68:3863-3872 (2008), the contents of each of which is herein incorporated by reference in its entirety). By way of example, DBDpp fusion proteins can contain an antibody fragment or domain that contains one or more of the following modifications that increase CDC: IgG1-K326A, E333A; IgG1-K326W, E333S, IgG2-E333S; wherein the numbering of the residues is that of the EU index of Kabat et al. (Kabat et al., Sequences of proteins of Immunological Interest, 1991 Fifth edition, herein incorporated by reference).

In additional embodiments, a DBDpp fusion protein comprises an amino acid sequence of an immunoglobulin effector domain, or a derivative of an immunoglobulin effector domain, that confers the ability to bind FcgammaRIIb receptor to the DBDpp fusion. In additional embodiments, a DBDpp fusion protein comprises a sequence of an immunoglobulin effector domain that has been modified to increase inhibitory binding to FcgammaRIIb receptor (see, e.g., Chu et al., Mol. Immunol. 45:3926-3933 (2008)). An example of an immunoglobulin fragment engineering modification contained in an amino acid sequence in a DBDpp fusion protein that increases binding to inhibitory FcgammaRIIb receptor is IgG1-S267E, L328F.

In other embodiments, a DBDpp fusion protein comprises a sequence of an immunoglobulin effector domain that has been modified to decrease CDC (see, e.g., WO 97/11971; WO 07/106585; US 2007/0148167A1; McEarchern et al., Blood 109:1185-1192 (2007); Hayden-Ledbetter et al., Clin. Cancer 15:2739-2746 (2009); Lazar et al., PNAS 103:4005-4010 (2006); Bruckheimer et al., Neoplasia 11:509-517 (2009); Strohl, Curr. Op. Biotechnol. 20:685-691 (2009); and Sazinsky et al., PNAS 105:20167-20172 (2008); the contents of each of which is herein incorporated by reference in its entirety). By way of example, DBDpp fusion proteins can contain an antibody fragment or domain that contains one or more of the following modifications that decrease CDC: IgG1-S239D, A330L, 1332E; IgG2-118-260; IgG4-261-447; IgG2-H268Q, V309L, A330S, A331S; IgG1-C226S, C229S, E233P, L234V, L235A; IgG1-L234F, L235E, P331S; and IgG1-C226S, P230S; wherein the numbering of the residues is that of the EU index of Kabat et al. (Kabat et al., Sequences of proteins of Immunological Interest, 1991 Fifth edition, herein incorporated by reference).

The half-life of an IgG is mediated by its pH-dependent binding to the neonatal receptor FcRn. In certain embodiments a DBDpp fusion protein comprises an amino acid sequence of an immunoglobulin effector domain, or a derivative of an immunoglobulin effector domain, that confers the ability to bind neonatal receptor FcRn to the to the DBDpp fusion. In certain embodiments a DBDpp fusion protein comprises a sequence of an immunoglobulin FcRn binding domain that has been modified to enhance binding to FcRn (see, e.g., Petkova et al., Int. Immunol. 18:1759-1769 (2006); Dall'Acqua et al., J. Immunol.169:5171-5180 (2002); Oganesyan et al., Mol. Immunol. 46:1750-1755 (2009); Dall'Acqua et al., J. Biol. Chem. 281:23514-23524 (2006), Hinton et al., J. Immunol. 176:346-356 (2006); Datta-Mannan et al., Drug Metab. Dispos. 35:86-94 (2007); Datta-Mannan et al., J. Biol. Chem. 282:1709-1717 (2007); WO 06/130834; Strohl, Curr. Op. Biotechnol. 20:685-691 (2009); and Yeung et al., J. Immunol. 182:7663-7671 (2009) the contents of each of which is herein incorporated by reference in its entirety).

In additional embodiments, a DBDpp fusion protein comprises a sequence of an immunoglobulin effector domain that has been modified to have a selective affinity for FcRn at pH 6.0, but not pH 7.4. By way of example, DBDpp fusion proteins can contain an antibody fragment or domain that contains one or more of the following modifications that increase half-life: IgG1-M252Y, S254T, T256E; IgG1-T250Q, M428L; IgG1-H433K, N434Y; IgG1-N434A; and IgG1-T307A, E380A, N434A; wherein the numbering of the residues is that of the EU index of Kabat et al. (Kabat et al., Sequences of Proteins of Immunological Interest, 1991 Fifth edition, herein incorporated by reference).

In other embodiments a DBDpp fusion protein comprises a sequence of an immunoglobulin effector domain that has been modified to decrease binding to FcRn (see, e.g., Petkova et al., Int. Immunol. 18:1759-1769 (2006); Datta-Mannan et al., Drug Metab. Dispos. 35:86-94 (2007); Datta-Mannan et al., J. Biol. Chem. 282:1709-1717 (2007); Strohl, Curr. Op. Biotechnol. 20:685-691 (2009) and Vaccaro et al., Nat. Biotechnol. 23:1283-1288 (2005), the contents of each of which is herein incorporated by reference in its entirety). By way of example, DBDpp fusion proteins can contain an antibody fragment or domain that contains one or more of the following modifications that decrease half-life: IgG1-M252Y, S254T, T256E; H433K, N434F, 436H; IgG1-I253A; and IgG1-P2571, N434H and D376V, N434H; wherein the numbering of the residues is that of the EU index of Kabat et al. (Kabat et al., Sequences of proteins of Immunological Interest, 1991 Fifth edition, herein incorporated by reference).

According to another embodiment, DBDpp fusion protein comprises an amino acid sequence corresponding to a immunoglobulin effector domain that has been modified to contain at least one substitution in its sequence corresponding to the Fc region (e.g., FC gamma) position selected from the group consisting of: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 and 439, wherein the numbering of the residues in the Fc region is according to the EU numbering system; of Kabat et al. (Kabat et al., Sequences of proteins of Immunological Interest, 1991 Fifth edition, herein incorporated by reference). In a specific embodiment, the DBDpp fusion protein comprises a sequence of an immunoglobulin effector domain derivative wherein at least one residue corresponding to position 434 is a residue selected from the group consisting of: A, W, Y, F and H. According to another embodiment, the DBDpp fusion protein comprises a sequence of an immunoglobulin effector fragment derivative having the following respective substitutions S298A/E333A/K334A. In an additional embodiment, the DBDpp fusion protein comprises an immunoglobulin effector domain derivative having a substitution corresponding to K322A. In another embodiment, the DBDpp fusion protein comprises a sequence of an immunoglobulin effector domain derivative having one or any combination of the following substitutions K246H, H268D, E283L, S324G, S239D and I332E. According to yet another embodiment, a DBDpp fusion protein comprises a sequence of an immunoglobulin effector domain derivative having substitutions corresponding to D265A/N297A.

In certain embodiments, a DBDpp fusion protein comprises a sequence of an immunoglobulin effector domain that has been glycoengineered or mutated to increase effector function using techniques known in the art. For example, the inactivation (through point mutations or other means) of a constant region domain sequence contained in a DBDpp may reduce Fc receptor binding of the circulating DBDpp fusion protein thereby increasing tumor localization. In other cases it may be that constant region modifications consistent with certain embodiments of the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well know immunological techniques without undue experimentation.

In certain embodiments an immune effector cell comprises a cell surface receptor for an immunoglobulin or other peptide binding molecule, such as a receptor for an immunoglobulin constant region and including the class of receptors commonly referred to as "Fc receptors" ("FcR"s). A number of FcRs have been structurally and/or functionally characterized and are known in the art, including FcR having specific abilities to interact with a restricted subset of immunoglobulin heavy chain isotypes, or that interact with Fc domains with varying affinities, and/or which may be expressed on restricted subsets of immune effector cells under certain conditions (e.g., Kijimoto-Ochichai et al., Cell Mol. Life. Sci. 59:648 (2002); Davis et al., Curr. Top. Microbiol. Immunol. 266:85 (2002); Pawankar, Curr. Opin. Allerg. Clin. Immunol. 1:3 (2001); Radaev et al., Mol. Immunol. 38:1073 (2002); Wurzburg et al., Mol. Immunol. 38:1063 (2002); Sulica et al., Int. Rev. Immunol. 20:371 (2001); Underhill et al., Ann. Rev. Immunol. 20:825 (2002); Coggeshall, Curr. Dir. Autoimm. 5:1 (2002); Mimura et al., Adv. Exp. Med. Biol. 495:49 (2001); Baumann et al., Adv. Exp. Med. Biol. 495:219 (2001); Santoso et al., Ital. Heart J. 2:811 (2001); Novak et al., Curr. Opin. Immunol. 13:721 (2001); Fossati et al., Eur. J. Clin. Invest. 31:821 (2001)), each of which is incorporated by reference herein in its entirety.

Cells that are capable of mediating ADCC are examples of immune effector cells. Other immune effector cells include Natural Killer cells, tumor-infiltrating T lymphocytes (TILs), cytotoxic T lymphocytes, and granulocytic cells such as cells that comprise allergic response mechanisms. Immune effector cells thus include, but are not limited to, cells of hematopoietic origin including cells at various stages of differentiation within myeloid and lymphoid lineages and which may (but need not) express one or more types of functional cell surface FcR, such as T lymphocytes, B lymphocytes, NK cells, monocytes, macrophages, dendritic cells, neutrophils, basophils, eosinophils, mast cells, platelets, erythrocytes, and precursors, progenitors (e.g., hematopoietic stem cells), as well as quiescent, activated, and mature forms of such cells. Other immune effector cells may include cells of non-hematopoietic origin that are capable of mediating immune functions, for example, endothelial cells, keratinocytes, fibroblasts, osteoclasts, epithelial cells, and other cells. Immune effector cells can also include cells that mediate cytotoxic or cytostatic events, or endocytic, phagocytic, or pinocytotic events, or that effect induction of apoptosis, or that effect microbial immunity or neutralization of microbial infection, or cells that mediate allergic, inflammatory, hypersensitivity and/or autoimmune reactions.

DBDpp as Albumin Fusions

Nucleic acid molecules encoding the DBDpp-albumin fusion proteins are also encompassed herein, as are vectors containing these nucleic acids, host cells containing these nucleic acids vectors, and methods of making the DBDpp-albumin fusion proteins and using these nucleic acids, vectors, and/or host cells. The invention also encompasses pharmaceutical formulations comprising a DBDpp-albumin fusion protein and a pharmaceutically acceptable diluent or carrier. Such formulations can be used in methods of treating, preventing, ameliorating or diagnosing a disease or disease symptom in a patient, preferably a mammal, most preferably a human, comprising the step of administering the pharmaceutical formulation to the patient.

DBDpp as Chimeric Receptors

In addition to the incorporation of DBD into soluble multi-domain proteins, the present invention provides a means by which to create cell-associated DBDpp, comprised of at least one DBDpp designed to impart binding specificity a membrane bound fusion protein. DBDpp-receptors may be expressed by any cell type.

Figure 5B:
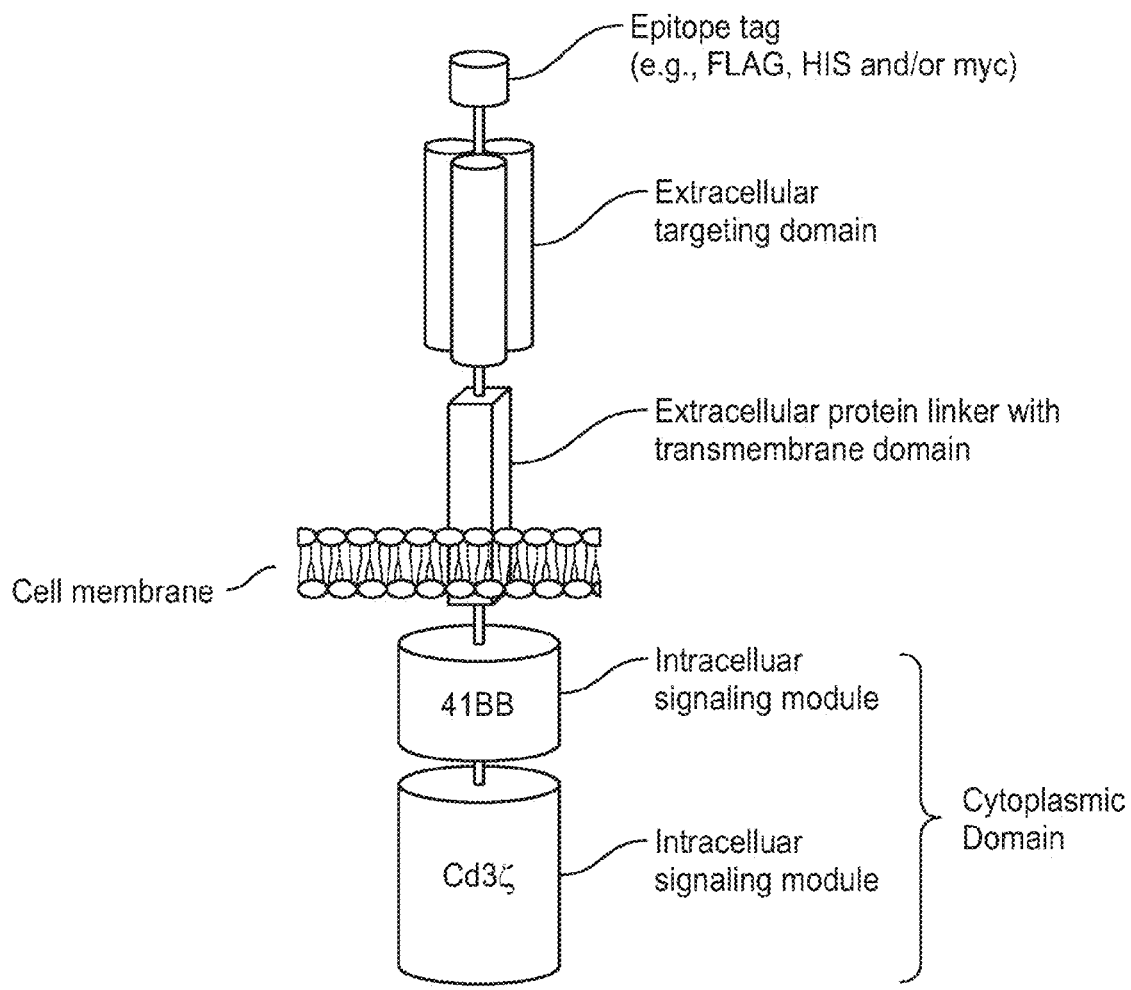

In one embodiment, the DBDpp-receptor fusion protein comprises a chimeric antigen receptor (CAR), or DBDpp-CAR, composed of the following elements: an extracellular targeting domain, a transmembrane domain and a cytoplasmic domain wherein the cytoplasmic domain comprises the signaling domain. In another embodiment the DBDpp-CAR is composed of an extracellular targeting domain and a transmembrane domain. In a further embodiment the DBDpp-CAR is comprised of an extracellular domain composed of one or more DBDpp, in which each DBDpp constitutes a target-specific binding domain with the same or different specificities. In several embodiments, the target-specific domain is directed to one (or more) of the cancer or tumor antigens disclosed herein, such as CD123, CD137, PD-L1, CD19, CD22, NY-ESO, or MAGE A3, as non-limiting examples. In one embodiment, the intracellular domain (e.g., the cytoplasmic domain) of the DBDpp-CAR comprises the intracellular domain of CD3 zeta chain. In another embodiment the intracellular signaling domain of the DBDpp is comprised of part of the intracellular domain of CD3 zeta chain. In a further embodiment, the intracellular domain of the DBDpp-CAR comprises the intracellular domain of CD3 zeta chain and a costimulatory signaling region. The costimulatory signaling region refers to a portion of the DBDpp-CAR comprising all or part of the intracellular domain of a costimulatory molecule. Costimulatory molecules are cell surface molecules other than antigens receptors or their ligands that are required for an efficient response of lymphocytes to antigen. Costimulatory molecules and portions of these molecules that are able to confer costimulatory properties to a CAR are known in the art and can routinely be incorporated into the DBDpp-CAR. In addition, truncations or mutation to these intracellular signaling and costimulatory domains may be incorporated to further enhance or reduce receptor signaling. In preferred embodiments, a T cell is genetically modified to stably express a DBDpp-CAR. In such embodiments the cytoplasmic domain of the DBDpp-CAR can be designed to comprise the CD28 and/or 4-1BB signaling domain by itself or be combined with any other desired cytoplasmic domain(s) useful in the context of the invention. In one embodiment, the cytoplasmic domain of the DBDpp-CAR can be designed to further comprise the signaling domain of CD3-zeta. For example, as depicted schematically in FIG. 5B, in one embodiment, the DBDpp-CAR comprises an extracellular targeting domain, an extracellular protein linker with a transmembrane domain that passes through the cellular membrane (such as found in T cells or NK cells), and a cytoplasmic domain, optionally comprising multiple signaling modules. In several embodiments, the DBDpp-CAR may also comprise an epitope tag. In several embodiments, the cytoplasmic domain of the DBDpp-CAR can include but is not limited to CD3-zeta, 4-1BB and CD28 signaling modules and combinations thereof.

Extracellular Domain

Depending on the desired antigen to be targeted, the DBDpp-CAR can be engineered to include the appropriate antigen binding DBDpp that is specific to the desired antigen target. For example, if CD19 is the desired antigen that is to be targeted, one or more CD19-binding DBDpp can be incorporated into the target specific binding domain of the DBDpp-CAR. Alternatively DBDpp-CAR may include more than one DBDpp, imparting multi-specificity or multi-valency to the DBDpp-CAR.

The choice of DBDpp incorporated into the extracellular domain of the DBDpp receptor (e.g., DBDpp-CAR) depends upon the identity of the cell or cells to be targeted. For example, a DBDpp-CAR may specifically bind to cell surface proteins such as a receptor on the same cell or another cell. In other embodiments, DBDpp-CAR specifically binds to a soluble molecule, such as an immunoglobulin. In other embodiments the targets of interest bound by the DBDpp-CAR include those associated with viral, bacterial and parasitic infections, diseases and disorders of the immune system (e.g., autoimmune disease).

In other embodiments a DBDpp-CAR may be chosen to recognize a ligand that acts as a cell surface marker on target cells associated with a cancer. A DBDpp-CAR can in some embodiments target and bind a tumor antigen (e.g., a TAA or other tumor antigen described herein or otherwise known in the art. Accordingly, provided herein are methods for creating DBDpp-CAR, their use in creating chimeric cells such as, human T cells and natural killer cells and the use of these chimeric T cells in adoptive immunotherapy.

In the context provided herein, "tumor antigen" refers to antigens that are common to specific hyperproliferative disorders such as cancer. Tumor antigens that can be specifically bound by a DBDpp in a DBDpp-CAR are disclosed herein. In one embodiment, a DBDpp in a DBDpp-CAR specifically binds a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells. Non-limiting examples of TSA or TAA antigens that can be specifically bound by a DBDpp in a DBDpp-CAR includes a member selected from: a differentiation antigen such as MART1/MelanA (MARTI), gp100 (Pmel 17), tyrosinase, TRP1, TRP2; a tumor-specific multi-lineage antigen such as MAGE1, MAGE5, BAGE, GAGE1, GAGE2, pi5; an overexpressed embryonic antigen such as CEA; and overexpressed oncogene or mutated tumor-suppressor gene such as p53, Ras, HER-2/neu; a unique tumor antigen resulting from chromosomal translocation such as BCR-ABL, E2A-PRL, H4-RET, 1GH-IGK, MYL-RAR; a viral antigen, such as the Epstein Barr virus antigens EBVA and the human papillomavirus (HPV) antigens E6 and E7; TSP-180, MAGE4, MAGE5, MAGE6, RAGE, NY-ESO, p185erbB2, p180erbB3, cmet, nm-23H1, PSA, TAG72, CA 19-9, CA72-4, CAM 17.1, NuMa, K-ras, beta-Catenin, CDK4, Mum-1, p15, p16, 43-9F, 5T4(791Tgp72) alpha-fetoprotem, beta-HCG, BCA225, BTAA, CA125, CA 15-3\CA 27.29\BCAA, CA195, CA242, CA50, CAM43, CD68\I, CO-029, FGF5, G250, Ga733VEpCAM, HTgp-175, M344, MA50, MG7-Ag, MOV 18, NB/70K, NY-CO-1, RCAS1, SDCCAG16, TA90\Mac-2, TAAL6, TAG72, TLP, and TPS; a glioma-associated antigen, carcinoembryonic antigen (CEA), β-human chorionic gonadotropin, alphafetoprotein (AFP), lectin-reactive AFP, thyroglobulm, RAGE-1, MN-CA IX, human telomerase reverse transcriptase, RU1, RU2 (AS), intestinal carboxylesterase, mut hsp70-2, MCSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA1), MAGE, ELF2M, neutrophil elastase, ephrinB2, TACI (CD267), BAFF-R (CD268), BCMA (CD269), TLR4, insulin growth factor (IGF)I, IGFII, IGFI receptor and mesothelin.

In a particular embodiment, a DBDpp in the antigen binding moiety portion of a DBDpp-CAR specifically binds a target selected from: CD123, HVEM, BTLA, DR3, CD19, CD20, CD22, ROR 1, Mesothelin, CD33/1L3Ra, cMet, PSMA, Glycolipid F77, EGFRvIII, GD2, MY-ESO-1TCR, CD133, CD47 and MAGE A3 TCR. In another preferred embodiment, the DBDpp in the antigen binding moiety portion of a DBDpp-CAR specifically bind all classes of immunoglobulin or specific isotypes, allotypes or idiotypes.

In one embodiment, a DBDpp in a DBDpp-CAR specifically binds a tumor antigen associated with a malignant tumor. Malignant tumors express a number of tumor antigens that a DBDpp-CAR can be engineered to bind. In one embodiment, a DBDpp of a DBDpp-CAR binds to an antigen selected from: a tissue-specific antigen such as MART-1, tyrosinase and GP 100 in melanoma and prostatic acid phosphatase (PAP) and prostate-specific antigen (PSA) in prostate cancer; a transformation-related molecule such as the oncogene HER2/Neu ErbB2; an onco-fetal antigen such as carcinoembryonic antigen (CEA); a B-cell lymphoma-specific idiotype immunoglobulin; a B-cell differentiation antigen such as CD19, CD20 and CD37; TSLPR and IL-7R on myeloid cells and cancer testis (CT) antigens (e.g. NY-ESO-1, LAGE-1a), CS-1, CD38, CD138, MUC1, HM1.24, CYP1B1, SP17, PRAME, Wilms' tumour 1 (WT1), and heat shock protein gp96 on multiple myeloma cells.

Transmembrane Domain

"Transmembrane domain" (TMD) as used herein refers to the region of a cell surface expressed DBDpp fusion protein such as a DBDpp-CAR, which crosses the plasma membrane. In some embodiments, the transmembrane domain of the DBDpp-CAR is the transmembrane region of a transmembrane protein (for example Type I transmembrane proteins), an artificial hydrophobic sequence or a combination thereof. Other transmembrane domains will be apparent to those of skill in the art and may be used in connection with alternate embodiments of the invention.

The DBDpp receptor (e.g., DBDpp-CAR) can be designed to contain a transmembrane domain that is fused to the extracellular domain of the DBDpp receptor. As described above, the fusion of the extracellular and transmembrane domains can be accomplished with or without a linker. In one embodiment, the transmembrane domain that is naturally associated with one of the domains in the DBDpp-CAR is used. In a specific embodiment, the transmembrane domain in the DBDpp-CAR is the CD8 transmembrane domain. In some instances, the transmembrane domain of the DBDpp-CAR comprises the CD8 hinge domain. In some embodiments, the transmembrane domain is be selected or modified by amino acid substitution to promote or inhibit association with other surface membrane proteins.

The transmembrane domain can be derived either from a natural or from a synthetic source. Where the source is natural, the domain can be derived from any membrane-bound or transmembrane protein. Transmembrane regions of particular use for the purposes herein may be derived from (i.e., comprise at least the transmembrane region(s) of) a member selected from the group: the alpha, beta or zeta chain of the T-cell receptor; CD28, CD3 epsilon, CD45, CD4, CD5, CD8, CD9, CD16, CD22, CD33, CD37, CD64, CD80, CD86, CD134, CD137, and CD154. Alternatively the transmembrane domain can be synthetic, in which case the DBDpp-CAR transmembrane domain will comprise predominantly hydrophobic residues such as leucine and valine. In further embodiments, the transmembrane domain comprises the triplet of phenylalanine, tryptophan and valine at each end of a synthetic transmembrane domain.

"Extracellular spacer domain" (ESD) as used herein refers to the hydrophilic region which is between the antigen-specific targeting region and the transmembrane domain. In some embodiments, the DBDpp-CAR comprise an extracellular spacer domain. In other embodiments, the DBDpp-CAR does not comprise an extracellular spacer domain. The extracellular spacer domains include but are not limited to Fc fragments of antibodies or fragments or derivatives thereof, hinge regions of antibodies or fragments or derivatives thereof, CH2 regions of antibodies, CH3 regions of antibodies, artificial spacer sequences or combinations thereof. Additional examples of extracellular spacer domains include but are not limited to CD8a hinge, and artificial spacers made of polypeptides which may be as small as, for example, Gly3 or CHI and CH3 domains of IgGs (such as human IgG4). In some embodiments, the extracellular spacer domain is any one or more of (i) a hinge, CH2 and CH3 regions of IgG4, (ii) a hinge region of IgG4, (iii) a hinge and CH2 of IgG4, (iv) a hinge region of CD8a, (v) a hinge, CH2 and CH3 regions of IgG1, (vi) a hinge region of IgG1 or (vi) a hinge and CH2 region of IgG1. Other extracellular spacer domains will be apparent to those of skill in the art and may be used in connection with alternate embodiments provided herein.

In some embodiments, a short oligo- or polypeptide linker, from about 1 to 100 amino acids in length, is used to link together any of the domains of a DBDpp-CAR. Linkers can be composed of flexible residues like glycine and serine (or any other amino acid) so that the adjacent protein domains are free to move relative to one another. The amino acids sequence composition of the linker may be selected to minimize potential immunogenicity of the DBDpp-CAR or DBDpp fusion protein. Longer linkers can be used when it is desirable to ensure that two adjacent domains do not sterically interfere with one another. In some embodiments, preferably between 2 and 10 amino acids in length forms the linkage between the transmembrane domain and the cytoplasmic signaling domain of the DBDpp-CAR. In further embodiments, the linker is between 10 and 15 amino acids in length, or between 15 and 20, or between 20 and 30, or between 30 and 60, or between 60 and 100 amino acids in length (or any range in between those listed). In further embodiments, the linker is a glycine-serine doublet sequence. Further embodiments employ a fragment of the hinge region derived from the human T-cell surface glycoprotein CD8 alpha-chain (for example ranging from amino acid positions 138 to 182 CD8 alpha chain; Swiss-Prot accession number P01732). Further embodiments employ a fragment of the CD8 hinge region that has been further modified, through amino acid substitution, to improve expression function or immunogenicity. Further embodiments employ a fragment of the extracellular region derived from the human CD28 Further embodiments employ a fragment of the CD28 extracellular region that has been further modified, through amino acid substitution, to improve expression function or immunogenicity.

Intracellular Domain

"Intracellular signaling domain" (ISD) or "cytoplasmic domain" as used herein refer to the portion of the DBDpp-CAR which transduces the effector function signal and directs the cell to perform its specialized function. The cytoplasmic domain (i.e., intracellular signaling domain) of a DBDpp-CAR is responsible for activation of at least one of the normal effector functions of an immune cell engineered to express a DBDpp-CAR. The term "effector function" refers to a specialized function of a cell. The effector function of a T cell, for example, includes cytolytic activity and helper activity including the secretion of cytokines. Thus the term "intracellular signaling domain" refers to the portion of a DBDpp-CAR protein which transduces the effector function signal and directs the cell to perform a specialized function. While typically the entire intracellular signaling domain corresponding to a naturally occurring receptor can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal. In one embodiment, an intracellular signaling domain in the DBDpp-CAR includes the cytoplasmic sequences of the T cell receptor (TCR) and also the sequence of co-receptors that act in concert to initiate signal transduction following antigen receptor engagement, or any derivative or variant of these sequences that has functional capability. Examples of domains that transduce an effector function signal include but are not limited to the ζ chain of the T-cell receptor complex or any of its homologs (e.g., η chain, FcsRly and β chains, MB 1 (Iga) chain, B29 (Ig) chain, etc.), human CD3 zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs (ITAMs).

Examples of ITAM containing primary cytoplasmic signaling sequences that are of particular use in the invention include those derived from TCR zeta, FcR gamma, FcR beta, CD3 gamma, CD3 delta, CD3 epsilon, CD22, CD79a, CD79b, and CD66d. It is particularly preferred that cytoplasmic signaling molecule in the CAR comprises a cytoplasmic signaling sequence derived from CD3 zeta.

"Co-stimulatory domain" (CSD) as used herein refers to the portion of a CAR or DBDpp-CAR which enhances the proliferation, survival and/or development of memory cells. The DBDpp-CAR may comprise one or more co-stimulatory domains. Each co-stimulatory domain comprises the costimulatory domain of any one or more of, for example, a member of the TNFR superfamily, selected from CD28, CD137 (4-1BB), CD134 (OX40), Dap10, CD27, CD2, CD5, ICAM-1, LFA-1(CD1 la/CD18), Lck, TNFR-I, TNFR-II, Fas, CD30, and CD40 or a combination thereof. Other co-stimulatory domains (e.g., from other proteins) will be apparent to those of skill in the art and may be used in connection with alternate embodiments of the invention.

In a preferred embodiment, the cytoplasmic domain of a DBDpp-CAR comprises the CD3-zeta signaling domain by itself or combined with any other desired cytoplasmic domain(s) useful in the context of the DBDpp-CAR. For example, the cytoplasmic domain of the DBDpp-CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD 137), OX40, CD30, CD40, PD1, ICOS, lymphocyte function-associated antigen-1 (LFA1), CD2, CD7, LIGHT, NKG2C, B7H3, TIM1, and LAG-3.

Polypeptide linkers may be positioned between adjacent elements of the DBDpp-CAR. For example linkers may be positioned between adjacent DBDpp or between DBDpp and the transmembrane domain or between the transmembrane domain and the cytoplasmic domain or between adjacent cytoplasmic domains. The cytoplasmic signaling sequences within the cytoplasmic signaling portion of the DBDpp-CAR may be linked to each other in a random or specified order. Optionally, a short linker, preferably between 2 and 10 amino acids in length may form the linkage. A glycine-serine doublet provides a particularly suitable linker.

Epitope Tag

In some embodiments, the DBDpp fusion protein comprises a peptide epitope tag. In some embodiments, the peptide tag is selected from the group consisting of a hexahistidyl (His6) tag, a myc tag and a FLAG tag. In additional embodiments, peptide tags include, but are not limited to, avitag (allows biotinylation of the tag and isolation with streptavidin), calmodulin, E-tag, hemagglutinin (HA), S-tag, SBP-tag, softag 1, streptavidin, tetra or polycysteine, V5, VSV, and Xpress tag. Additionally polyhistidyl tags (other than 6 residues) can be used. In additional embodiments, covalent peptide tags, protein tags, and the like can be used. Covalent peptide tags include, but are not limited to, isopeptag (covalently binds pilinC protein), Spy-tag (covalently binds to the SpyCatcher protein), and Snooptag (covalently binds to the SnoopCatcher protein). In still additional embodiments, protein tags, including but not limited to biotin carboxyl carrier protein (BCCP), glutathione-s-transferase, green fluorescent protein (or other fluorophore), Halo tag, Nus tag, thioredoxin, and Fc tags may optionally be used. In still additional embodiments, multiple types of tags may be used. In still additional embodiments, no tag is used. Any combination of extracellular, transmembrane and intracellular domains disclosed herein may be used, depending on the embodiment.

Linkers

The terms "linker" and spacer are used interchangeably herein to refer to a peptide or other chemical linkage that functions to link otherwise independent functional domains. In one embodiment, a linker in a DBDpp is located between a DBDpp and another polypeptide component containing an otherwise independent functional domain. Suitable linkers for coupling the two or more linked DBDpp will be clear to the persons skilled in the art and may generally be any linker used in the art to link peptides, proteins or other organic molecules. In particular embodiments, such a linker is suitable for constructing proteins or polypeptides that are intended for pharmaceutical use.

Suitable linkers for operably linking a DBDpp and an additional component of a DBDpp fusion protein in a single-chain amino acid sequence include but are not limited to, polypeptide linkers such as glycine linkers, serine linkers, mixed glycine/serine linkers, glycine- and serine-rich linkers or linkers composed of largely polar polypeptide fragments.

In one embodiment, the linker is made up of a majority of amino acids selected from glycine, alanine, proline, asparagine, glutamine, and lysine. In one embodiment, the linker is made up of a majority of amino acids selected from glycine, alanine, proline, asparagine, aspartic acid, threonine, glutamine, and lysine. In one embodiment, the DBDpp fusion protein linker is made up of one or more of the amino acids selected from glycine, alanine, proline, asparagine, glutamine, and lysine. In one embodiment, the DBDpp fusion protein linker is made up of one or more of the amino acids selected from glycine, alanine, proline, asparagine, aspartic acid, threonine, glutamine, and lysine. In another embodiment, the DBDpp fusion protein linker is made up of a majority of amino acids that are sterically unhindered. In another embodiment, a linker in which the majority of amino acids are glycine, serine, and/or alanine. In some embodiments, the peptide linker is selected from polyglycines (such as (Gly)5 (SEQ ID NO: 188), and (Gly)8 (SEQ ID NO: 189), poly(Gly-Ala), and polyalanines. In some embodiments, the peptide linker contains the sequence of Gly-Gly-Gly-Gly-Thr-Gly-Gly-Gly-Ser (SEQ ID NO: 190). In some embodiments, the peptide linker contains the sequence of Gly-Gly-Gly-Gly-Asp-Gly-Gly-Gly-Gly-Ser (SEQ ID NO: 191).

In one embodiment, a DBDpp fusion comprises a DBDpp directly attached (i.e., without a linker) to another component of the DBDpp fusion protein. In one embodiment, a DBDpp fusion comprises at least 2, at least 3, at least 4, DBDpp directly attached to another component of the DBDpp fusion.

In another embodiment, a DBDpp can be operably linked to another component of a DBDpp fusion protein through a linker. DBDpp fusion proteins can contain a single linker, multiple linkers, or no linkers. In one embodiment, a DBDpp fusion comprises a DBDpp operably linked to another component of the DBDpp fusion protein through a linker peptide. In one embodiment, a DBDpp fusion comprises at least 2, 3, 4, or 5 DBD operably linked to another component of the DBDpp fusion protein through a linker peptide.

Linkers can be of any size or composition so long as they are able to operably link a DBDpp in a manner that enables the DBDpp to bind a target of interest. In some embodiments, linkers are about 1 to about 100 amino acids, about 1 to 50 amino acids, about 1 to 20 amino acids, about 1 to 15 amino acids, about 1 to 10 amino acids, about 1 to 5 amino acids, about 2 to 20 amino acids, about 2 to 15 amino acids, about 2 to 10 amino acids, or about 2 to 5 amino acids. It should be clear that the length, the degree of flexibility and/or other properties of the linker(s) may have some influence on the properties of the final polypeptide of the invention, including but not limited to the affinity, specificity or avidity for a target of interest, or for one or more other target proteins of interest. When two or more linkers are used in the DBDpp fusion proteins, these linkers may be the same or different. In the context and disclosure provided herein, a person skilled in the art will be able to routinely determine the optimal linker composition and length for the purpose of operably linking a DBDpp and other components of a DBDpp fusion protein.

The linker can also be a non-peptide linker such as an alkyl linker, or a PEG linker. For example, alkyl linkers such as —NH—(CH2)s-C(0)-, wherein s=2-20 can be used. These alkyl linkers may further be substituted by any non-sterically hindering group such as lower alkyl e.g., C1 C6) lower acyl, halogen (e.g., CI, Br), CN, NH2, phenyl, etc. An exemplary non-peptide linker is a PEG linker. In certain embodiments, the PEG linker has a molecular weight of about 100 to 5000 kDa, or about 100 to 500 kDa.

Suitable linkers for coupling DBDpp and DBDpp fusion protein components by chemical cross-linking include, but are not limited to, homo-bifunctional chemical cross-linking compounds such as glutaraldehyde, imidoesters such as dimethyl adipimidate (DMA), dimethyl suberimidate (DMS) and dimethyl pimelimidate (DMP) or N-hydroxysuccinimide (NHS) esters such as dithiobis(succinimidyl-propionate) (DSP) and dithiobis (sulfosuccinimidylpropionate) (DTSSP). Examples of suitable linkers for coupling DBDpp and DBDpp fusion protein components of heterobifunctional reagents for cross-linking include, but are not limited to, cross-linkers with one amine-reactive end and a sulfhydryl-reactive moiety at the other end, or with a NHS ester at one end and an SH-reactive group (e.g., a maleimide or pyridyl).

In additional embodiments, one or more of the linkers in the DBDpp fusion protein is cleavable. Examples of cleavable linkers include, without limitation, a peptide sequence recognized by proteases (in vitro or in vivo) of varying type, such as Tev, thrombin, factor Xa, plasmin (blood proteases), metalloproteases, cathepsins (e.g., GFLG, etc.), and proteases found in other corporeal compartments.

In one embodiment, the linker is a "cleavable linker" that facilitates the release of a DBDpp or cytotoxic agent in a cell. For example, an acid-labile linker (e.g., hydrazone), protease-sensitive (e.g., peptidase-sensitive) linker, photolabile linker, dimethyl linker or disulfide-containing linker (Chari, Can. Res. 52:127-131 (1992); U.S. Pat. No. 5,208, 020; U.S. Appl. Pub. No. 20090110753; each incorporated by reference in their entireties) can be used wherein it is desirable that the covalent attachment between a DBDpp or a cytotoxic agent and the fusion partner is intracellularly cleaved when the composition is internalized into the cell. The terms "intracellularly cleaved" and "intracellular cleavage" refer to a metabolic process or reaction inside a cell on an DBDpp drug conjugate whereby the covalent attachment, i.e., linked via a linker between the DBDpp and cytotoxic agent, DBDpp and fusion partner, or between two DBDpp is broken, resulting in the free DBDpp and/or cytotoxic agent dissociated inside the cell.

Linker optimization can be evaluated using techniques described herein and/or otherwise known in the art. In some embodiments, linkers do not disrupt the ability of a DBDpp to bind a target molecule and/or another DBDpp fusion protein component such as an antibody domain or fragment to bind an antigen.

DBDpp as Chemical Conjugates

DBDpp that promote specific binding to targets of interest can be chemically conjugated with a variety of compound such as fluorescent dyes, radioisotopes, chromatography compositions (e.g., beads, resins, gels, etc.) and chemotherapeutic agents. DBDpp conjugates have uses that include but are not limited to purification, diagnostic, analytic, manufacturing and therapeutic applications.

The inherent lack of cysteines in the DBD sequence provides the opportunity for introduction of unique cysteines for purposes of site-specific conjugation.

In some embodiments, the DBDpp (e.g., a DBDpp fusion protein) contains at least one reactive residue. Reactive residues are useful, for example, as sites for the attachment of conjugates such as chemotherapeutic drugs. The reactive residue can be, for example, a cysteine, a lysine, or another reactive residue. Thus, a cysteine can be added to a DBDpp at either the N or C terminus, or within the DBDpp sequence. A cysteine can be substituted for another amino acid in the sequence of a DBDpp. In addition, a lysine can be added to a DBDpp at either end or within the DBDpp sequence and/or a lysine can be substituted for another amino acid in the sequence of a DBDpp. In one embodiment, a reactive residue (e.g., cysteine, lysine, etc.) is located in a loop sequence of a DBD (e.g., $Z_1$ and $Z_2$ of SEQ ID NOS:7-11). In one embodiment, a reactive residue is located between components of a DBDpp fusion, e.g., in a linker located between a DBDpp and other component of a DBDpp fusion protein. The reactive residue (e.g., cysteine, lysine, etc.) can also be located within the sequence of a DBDpp, or other component of the DBDpp fusion protein. In one embodiment, a DBDpp or a DBDpp fusion protein comprises at least one, at least two, at least three reactive residues. In one embodiment, a DBDpp such as a DBDpp fusion protein comprises at least one, at least two, or at least three, cysteine residues.

Production of DBDpp

The production of the DBDpp, useful in practicing the provided methods, may be carried out using a variety of standard techniques for chemical synthesis, semi-synthetic methods, and recombinant DNA methodologies known in the art. Also provided is a method for producing a DBDpp, individually or as part of multi-domain fusion protein, as soluble agents and cell associated proteins.

In several embodiments, the overall production scheme for DBDpp comprises obtaining a reference protein scaffold and identifying a plurality of residues within the scaffold for modification. Depending on the embodiment, the reference scaffold may comprise a protein structure with one or more alpha-helical regions, or other tertiary structure. Once identified, the plurality of residues can be modified, for example by substitution of an amino acid. In some embodiments substitution is conservative, while in other embodiments non-conservative substitutions are made. In some embodiments a natural amino acid (e.g., one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine) is substituted into the reference scaffold at the targeted position for modification. In certain embodiments, the modifications do not include substituting in either a cysteine or a proline. After modifications have been made at all the identified positions desired in a particular embodiment, the resulting modified polypeptides (e.g., candidate DBDpp) can be recombinantly expressed, for example in a plasmid, bacteria, phage, or other vector (e.g. to increase the number of each of the modified polypeptides). The modified polypeptides can then be purified and screened to identify those modified polypeptides that have specific binding to a particular target of interest. In several embodiments, certain modified polypeptides will show enhanced binding specificity for a target of interest vis-à-vis the reference scaffold, which in some embodiments may exhibit little or no binding to a given target of interest. In additional embodiments, depending on the target of interest the reference scaffold may show some interaction (e.g. nonspecific interaction) with a target of interest, while certain modified polypeptides will exhibit at least about two fold, at least about five fold, at least about 10 fold, at least about 20 fold, at least about 50 fold, or at least about 100 fold (or more) increased binding specificity for the target of interest. Optionally, the reference sequence and/or the modified polypeptides (e.g., DBDpp) can be de-immunized. For example, residues or motifs that are potentially immunogenic can be identified and modified in order to reduce or eliminate potential immune responses to the DBDpp. Additional details regarding various embodiments of the production, selection, and isolation of DBDpp are provided in more detail below.

Recombinant Expression of DBDpp

In some embodiments, a DBDpp such as a DBDpp fusion protein is "recombinantly produced," (i.e., produced using recombinant DNA technology). Exemplary recombinant methods available for synthesizing DBDpp fusion proteins, include, but are not limited to polymerase chain reaction (PCR) based synthesis, concatemerization, seamless cloning, and recursive directional ligation (RDL) (see, e.g., Meyer et al., Biomacromolecules 3:357-367 (2002), Kurihara et al., Biotechnol. Lett. 27:665-670 (2005), Haider et al., Mol. Pharm. 2:139-150 (2005); and McMillan et al., 32:3643-3646 (1999), the contents of each of which is herein incorporated by reference in its entirety).

Nucleic acids comprising a polynucleotide sequence encoding a DBDpp are also provided. Such polynucleotides optionally further comprise, one or more expression control elements. For example, the polynucleotide can comprise one or more promoters or transcriptional enhancers, ribosomal binding sites, transcription termination signals, and polyadenylation signals, as expression control elements. The polynucleotide can be inserted within any suitable vector, which can be contained within any suitable host cell for expression.

The expression of nucleic acids encoding DBDpp is typically achieved by operably linking a nucleic acid encoding the DBDpp to a promoter in an expression vector. Typical expression vectors contain transcription and translation terminators, initiation sequences, and promoters useful for regulation of the expression of the desired nucleic acid sequence. Methods known in the art can be used to routinely construct expression vectors containing the nucleic acid sequence encoding a DBDpp along with appropriate transcriptional/translational control signals. These methods include, but are not limited to in vitro recombinant DNA techniques, synthetic techniques and in vivo recombination/genetic recombination. The expression of the polynucleotide can be performed in any suitable expression host known in the art including, but not limited to bacterial cells, yeast cells, insect cells, plant cells or mammalian cells. In one embodiment, a nucleic acid sequence encoding a DBDpp is operably linked to a suitable promoter sequence such that the nucleic acid sequence is transcribed and/or translated into DBDpp in a host. Promoters useful for expression in *E. coli*, include but are not limited to, the T7 promoter.

In one embodiment, a vector comprising a DBDpp encoding nucleic acid is introduced into a host cell (e.g., phagemid) for expression of a DBDpp. The vector can remain episomal or become chromosomally integrated, as long as the insert encoding therapeutic agent can be transcribed. Vectors can be constructed by standard recombinant DNA technology. Vectors can be plasmids, phages, cosmids, phagemids, viruses, or any other types known in the art, which are used for replication and expression in prokaryotic or eukaryotic cells. It will be appreciated by one of skill in the art that a wide variety of components known in the art (such as expression control elements) can be included in such vectors, including a wide variety of transcription signals, such as promoters and other sequences that regulate the binding of RNA polymerase onto the promoter. Any promoter known or demonstrated to be effective in the cells in which the vector will be expressed can be used to initiate expression of DBDpp. Suitable promoters can be inducible (e.g., regulated) or constitutive. Non-limiting examples of suitable promoters include the SV40 early promoter region, the promoter contained in the 3' long terminal repeat of Rous sarcoma virus, the HSV-1 (herpes simplex virus-1) thymidine kinase promoter, the regulatory sequences of the metallothionein gene, etc., as well as the following animal transcriptional control regions, which exhibit tissue specificity and have been utilized in transgenic animals: elastase I gene control region which is active in pancreatic acinar cells; insulin gene control region which is active in pancreatic beta cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in erythroid cells, myelin basic protein gene control region which is active in oligodendrocyte cells in the brain, myosin light chain-2 gene control region which is active in skeletal muscle, and gonadotropin releasing hormone gene control region which is active in the hypothalamus. In a particular embodiment, the promoter is an immunoglobulin gene control region which is active in lymphoid cells.

In one embodiment, one or several nucleic acids encoding a DBDpp is expressed under the control of a constitutive promoter or, alternately, a regulated expression system. Suitable regulated expression systems include, but are not limited to, a tetracycline-regulated expression system, an ecdysone inducible expression system, a lac-switch expression system, a glucocorticoid-inducible expression system, a temperature-inducible promoter system, and a metallothionein metal-inducible expression system. If several different nucleic acids encoding a DBDpp are contained within the host cell system, some of the nucleic acids may be expressed under the control of a constitutive promoter, while others may be expressed under the control of a regulated promoter. Expression levels may be determined by methods known in the art, including Western blot analysis and Northern blot analysis.

A variety of host-expression vector systems can be utilized to express a nucleic acid encoding a DBDpp. Vectors containing the nucleic acids encoding the DBDpp (e.g., individual DBD subunits or DBDpp fusions) or portions or fragments thereof, include plasmid vectors, a single and double-stranded phage vectors, as well as single and double-stranded RNA or DNA viral vectors. Phage and viral vectors may also be introduced into host cells in the form of packaged or encapsulated virus using known techniques for infection and transduction. Moreover, viral vectors may be replication competent or alternatively, replication defective. Alternatively, cell-free translation systems may also be used to produce the protein using RNAs derived from the DNA expression constructs (see, e.g., WO86/05807 and WO89/01036; and U.S. Pat. No. 5,122,464, each incorporated in its entirety by reference herein).

Generally, any type of cells or cultured cell line can be used to express a DBDpp provided herein. In some embodiments the background cell line used to generate an engineered host cells is a phage, a bacterial cell, a yeast cell or a mammalian cell. A variety of host-expression vector systems may be used to express the coding sequence a DBDpp fusion protein. Mammalian cells can be used as host cell systems transfected with recombinant plasmid DNA or cosmid DNA expression vectors containing the coding sequence of the target of interest and the coding sequence of the fusion polypeptide.

The cells can be primary isolates from organisms (including human), cultures, or cell lines of transformed or transgenic nature. In some embodiments the host cell is a human cell. In some embodiments, the host cell is human T cell. In some embodiments, the host cell is derived from a human patient.

Useful host cells include but are not limited to microorganisms such as, bacteria (e.g., *E. coli, B. subtilis*) transformed with recombinant bacteriophage DNA, plasmid DNA or cosmid DNA expression vectors containing DBDpp coding sequences; yeast (e.g., *Saccharomyces, Pichia*) transformed with recombinant yeast expression vectors containing DBDpp coding sequences; insect cell systems infected with recombinant virus expression vectors (e.g., Baculovirus) containing DBDpp coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing DBDpp coding sequences. In particular embodiments, the mammalian cell systems are used to produce the DBDpp. Mammalian cell systems typically utilize recombinant expression constructs containing promoters derived from the genome of mammalian cells (e.g., metallothionein promoter) or from mammalian viruses (e.g., the adenovirus late promoter; the vaccinia virus 7.5K promoter).

Prokaryotes useful as host cells in producing a DBDpp such as DBDpp fusion protein, include gram negative or gram positive organisms such as, *E. coli* and *B. subtilis*. Expression vectors for use in prokaryotic host cells generally contain one or more phenotypic selectable marker genes (e.g., genes encoding proteins that confer antibiotic resistance or that supply an autotrophic requirement). Examples of useful prokaryotic host expression vectors include the pKK223-3 (Pharmacia, Uppsala, Sweden), pGEM1 (Promega, Wis., USA), pET (Novagen, Wis., USA) and pRSET (Invitrogen, Calif., USA) series of vectors (see, e.g., Studier, J. Mol. Biol. 219:37 (1991) and Schoepfer, Gene 124:83 (1993)). Exemplary promoter sequences frequently used in prokaryotic host cell expression vectors include T7, (Rosenberg et al., Gene 56:125-135 (1987)), beta-lactamase (penicillinase), lactose promoter system (Chang et al., Nature 275:615 (1978)); and Goeddel et al., Nature 281:544 (1979)), tryptophan (trp) promoter system (Goeddel et al., Nucl. Acids Res. 8:4057, (1980)), and tac promoter (Sambrook et al., 1990, Molecular Cloning, A Laboratory Manual, 2d Ed., Cold Spring Harbor Laboratory, Cold Spring Harbor, N.Y.).

In one embodiment, a eukaryotic host cell systems is be used, including yeast cells transformed with recombinant yeast expression vectors containing the coding sequence of a DBDpp, such as, the expression systems taught in U.S. Appl. No. 60/344,169 and WO03/056914 (methods for producing humanlike glycoprotein in a non-human eukaryotic host cell) (the contents of each of which are incorporated by reference in their entirety). Exemplary yeast that can be used to produce compositions of the invention, such as, DBD, include yeast from the genus *Saccharomyces, Pichia*, Actinomycetes and *Kluyveromyces*. Yeast vectors typically contain an origin of replication sequence from a 2mu yeast plasmid, an autonomously replicating sequence (ARS), a promoter region, sequences for polyadenylation, sequences for transcription termination, and a selectable marker gene. Examples of promoter sequences in yeast expression constructs include, promoters from metallothionein, 3-phosphoglycerate kinase (Hitzeman, J. Biol. Chem. 255:2073 (1980)) and other glycolytic enzymes, such as, enolase, glyceraldehyde-3-phosphate dehydrogenase, hexokinase, pyruvate decarboxylase, phosphofructokinase, glucose-6-phosphate isomerase, 3-phospho glycerate mutase, pyruvate kinase, triosephosphate isomerase, phosphoglucose isomerase, and glucokinase. Additional suitable vectors and promoters for use in yeast expression as well as yeast transformation protocols are known in the art. See, e.g., Fleer, Gene 107:285-195 (1991) and Hinnen, PNAS 75:1929 (1978).

Insect and plant host cell culture systems are also useful for producing the compositions of the invention. Such host cell systems include for example, insect cell systems infected with recombinant virus expression vectors (e.g., baculovirus) containing the coding sequence of a DBD; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of a DBD, including, but not limited to, the expression systems taught in U.S. Pat. No. 6,815,184; U.S. Publ. Nos. 60/365,769, and 60/368,047; and WO2004/057002, WO2004/024927, and WO2003/078614, the contents of each of which is herein incorporated by reference in its entirety.

In an additional embodiment the host cell systems may be used, including animal cell systems infected with recombinant virus expression vectors (e.g., adenoviruses, retroviruses, adeno-associated viruses, herpes viruses, lentiviruses) including cell lines engineered to contain multiple copies of the DNA encoding a DBDpp either stably amplified (CHO/dhfr) or unstably amplified in double-minute chromosomes (e.g., murine cell lines). In one embodiment, the vector comprising the polynucleotide(s) encoding the DBDpp is polycistronic. Exemplary mammalian cells useful for producing these compositions include 293 cells (e.g., 293T and 293F), CHO cells, BHK cells, NS0 cells, SP2/0 cells, YO myeloma cells, $P3X_{63}$ mouse myeloma cells, PER cells, PER.C6 (Crucell, Netherlands) cells VERY, Hela cells, COS cells, MDCK cells, 3T3 cells, W138 cells, BT483 cells, Hs578T cells, HTB2 cells, BT20 cells, T47D cells, CRL7O30 cells, HsS78Bst cells, hybridoma cells, and other mammalian cells. Additional exemplary mammalian host cells that are useful in practicing the invention include but are not limited, to T cells. Some examples of expression systems and selection methods are described in the following references and references cited therein: Borth et al., Biotechnol. Bioen. 71(4):266-73 (2000), in Werner et al., Arzneimittelforschung/Drug Res. 48(8):870-80 (1998), Andersen et al., Curr. Op. Biotechnol. 13:117-123 (2002), Chadd et al., Curr. Op, Biotechnol. 12:188-194 (2001), and Giddings, Curr. Op. Biotechnol. 12:450-454 (2001). Additional examples of expression systems and selection methods are described in Logan et al., PNAS 81:355-359 (1984), Birtner et al. Methods Enzymol. 153:51-544 (1987)). Transcriptional and translational control sequences for mammalian host cell expression vectors are frequently derived from viral genomes. Commonly used promoter sequences and enhancer sequences in mammalian expression vectors include, sequences derived from Polyoma virus, Adenovirus 2, Simian Virus 40 (SV40), and human cytomegalovirus (CMV). Exemplary commercially available expression vectors for use in mammalian host cells include pCEP4 (Invitrogen) and pcDNA3 (Invitrogen).

Physical methods for introducing a nucleic acid into a host cell (e.g., a mammalian host cell) include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian (e.g., human) cells. Other viral vectors can be derived from lentivirus, poxviruses, herpes simplex virus I, adenoviruses and adeno-associated viruses, and the like. See, for example, U.S. Pat. Nos. 5,350,674 and 5,585,362, the contents of each of which is herein incorporated by reference in its entirety.

Methods for introducing a DNA and RNA polynucleotides of interest into a host cell include electroporation of cells, in which an electrical field is applied to cells in order to increase the permeability of the cell membrane, allowing chemicals, drugs, or polynucleotides to be introduced into the cell. DBDpp containing DNA or RNA constructs may be introduced into mammalian or prokaryotic cells using electroporation.

In a preferred embodiment, electroporation of cells results in the expression of a DBDpp-CAR on the surface of T cells, NK cells, NKT cells. Such expression may be transient or stable over the life of the cell. Electroporation may be accomplished with methods known in the art including MaxCyte GT® and STX® Transfection Systems (MaxCyte, Gaithersburg, Md., USA).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristoyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristoyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5:505-510 (1991)). However, compositions that have different structures in solution than the normal vesicular structure are also encompassed. For example, the lipids can assume a micellar structure or merely exist as non-uniform aggregates of lipid molecules. Also contemplated are lipofectamine-nucleic acid complexes.

Regardless of the method used to introduce exogenous nucleic acids into a host cell, or the presence of the recombinant nucleic acid sequence in the host cell can routinely be confirmed through a variety of assays known in the art. Such assays include, for example, "molecular biological" assays known in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Reporter genes are used for identifying potentially transfected cells and for evaluating the functionality of regulatory sequences. In general, a reporter gene is a gene that is not present in or expressed by the recipient organism, tissue, or cell and that encodes a polypeptide whose expression is manifested by some easily detectable property, e.g., enzymatic activity. Expression of the reporter gene is assayed at a suitable time after the DNA has been introduced into the recipient cells. A non-limiting list of suitable reporter genes can include genes encoding luciferase, beta-galactosidase, chloramphenicol acetyl transferase, secreted alkaline phosphatase, or the green fluorescent protein gene (e.g., Ui-Tei et al., FEBS Lett. 479:79-82 (2000)). Suitable expression systems are known in the art and can be prepared using known techniques or obtained commercially. In general, the construct with the minimal 5' flanking region showing the highest level of expression of reporter gene is identified as the promoter. Such promoter regions can routinely be linked to a reporter gene and used to evaluate agents for the ability to modulate promoter-driven transcription.

A number of selection systems can be used in mammalian host-vector expression systems, including, but not limited to, the herpes simplex virus thymidine kinase, hypoxanthine-guanine phosphoribosyltransferase and adenine phosphoribosyltransferase (Lowy et al., Cell 22:817 (1980)) genes, which can be employed in tk$^-$, hgprt$^-$ or aprt$^-$ cells, respectively. Additionally, antimetabolite resistance can be used as the basis of selection for e.g., dhfr, gpt, neo, hygro, trpB, hisD, ODC (ornithine decarboxylase), and the glutamine synthase system.

DBDpp Purification

Once a DBDpp such as a DBDpp fusion protein has been produced by recombinant expression, it can be purified by any method known in the art for purification of a recombinant protein, for example, by chromatography (e.g., ion exchange, affinity, and sizing column chromatography), centrifugation, differential solubility, or by any other standard technique for the purification of proteins. In additional embodiments, the DBDpp are optionally fused to heterologous polypeptide sequences described herein or otherwise known in the art to facilitate purification. More particularly, it is envisioned that ligands (e.g., antibodies and other affinity matrices) for DBDpp affinity columns for affinity purification and that optionally, the DBDpp or other components of the DBDpp fusion composition that are bound by these ligands are removed from the composition prior to final preparation of the DBDpp using techniques known in the art.

Expression of Cell Associated DBDpp

In another embodiment of the invention, production of DBDpp result in cell associated DBDpp compositions. For example, the expression of recombinant vectors that encode DBDpp operably linked to a cell membrane anchor or transmembrane domain have the potential to remain cell associated. DBDpp comprising chimeric antigen receptors are intentionally cell associated and used in the context of the cell in which they are expressed. One particular embodiment relates to a strategy of adoptive cell transfer of T cells which have been transduced to express a DBDpp chimeric antigen receptor (CAR). Preferably, the cell can be genetically modified to stably express a DBDpp on its surface, conferring novel target specificity that is MHC independent.

A variety of viral-derived vectors can be used in applications in which viruses are used for transfection and integration into a mammalian cell genome. Viruses, which are useful as vectors include, but are not limited to, retroviruses, adenoviruses, adeno-associated viruses, herpes viruses, and lentiviruses. Lentiviral vectors are particularly suitable to achieving long-term gene transfer (e.g., adoptive T cell immune therapy) since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In general, a suitable vector contains an origin of replication functional in at least one organism, a promoter sequence, convenient restriction endonuclease sites, and one or more selectable markers, (e.g., WO 01/96584 and WO 01/29058; and U.S. Pat. No. 6,326,193). Several vector promoter sequences are available for expression of the transgenes. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is EF-1a. However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters include, but are not limited to a metallothionein promoter, a glucocorticoid promoter, a progesterone promoter, and a tetracycline promoter.

In order to assess the expression of a DBDpp-CAR polypeptide or portions thereof, the expression vector to be introduced into a cell can also contain either a selectable marker gene or a reporter gene or both to facilitate identification and selection of expressing cells from the population of cells sought to be transfected or infected through viral vectors, in other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments provided herein, any number of T cell lines available in the art, may be used.

A full discussion of T cell isolation, culturing, activation and expansion methods may be found in WO 2012079000, the contents of which is herein incorporated by reference in its entirety.

Additionally provided is a host cell comprising nucleic acids encoding a DBDpp described herein. Further provided is a composition comprising a nucleic acid sequence encoding the DBDpp.

"Co-express" as used herein refers to simultaneous expression of two or more protein coding sequences. The coding sequences may be nucleic acids encoding, for example, a single protein or a chimeric protein as a single polypeptide chain.

Chemical Synthesis of DBDpp

In addition to recombinant methods, DBDpp production may also be carried out using organic chemical synthesis of the desired polypeptide using a variety of liquid and solid phase chemical processes known in the art. Various automatic synthesizers are commercially available and can be used in accordance with known protocols. See, for example, Tam et al., J. Am. Chem. Soc, 105:6442 (1983); Merrifield, Science 232:341-347 (1986); Barany and Merrifield, The Peptides, Gross and Meienhofer, eds, Academic Press, New York, 1-284; Barany et al., Int. J. Pep. Protein Res., 30:705 739 (1987); Kelley et al. in Genetic Engineering Principles and Methods, Setlow, J. K., ed. Plenum Press, N Y. 1990, vol. 12, pp. 1-19; Stewart et al., Solid-Phase Peptide Synthesis, W.H. Freeman Co., San Francisco, 1989. One advantage of these methodologies is that they allow for the incorporation of non-natural amino acid residues into the sequence of the DBDpp.

The DBDpp that are used in the methods of the present invention may be modified during or after synthesis or translation, e.g., by glycosylation, acetylation, benzylation, phosphorylation, amidation, pegylation, formylation, derivatization by known protecting/blocking groups, proteolytic cleavage, linkage to an antibody molecule, hydroxylation, iodination, methylation, myristoylation, oxidation, pegylation, proteolytic processing, phosphorylation, prenylation, racemization, selenoylation, sulfation, ubiquitination, etc. (See, e.g., Creighton, Proteins: Structures and Molecular Properties, 2d Ed. (W.H. Freeman and Co., N.Y., 1992); Postranslational Covalent Modification of Proteins, Johnson, ed. (Academic Press, New York, 1983), pp. 1-12; Seifter, Meth. Enzymol., 182:626-646 (1990); Rattan, Ann. NY Acad. Sci., 663:48-62 (1992).) In specific embodiments, the peptides are acetylated at the N-terminus and/or amidated at the C-terminus.

Any of numerous chemical modifications may be carried out by known techniques, including, but not limited to acetylation, formylation, etc. Additionally, the derivative may contain one or more non-classical amino acids.

Populations of DBDpp can be Represented by Libraries of Polypeptides

A "library" of DBDpp refers to a plurality of unique DBDpp. A "vector library" of DBDpp refers to a plurality of unique nucleic acids encoding DBDpp. These libraries of DBDpp can be used to select for and identify sequences that promote binding to specific predetermined targets.

In one embodiment, DBDpp are represented by a mixed population, or library, of different DBDpp molecules. A library of DBDpp does not imply any particular size limitation to the number unique polypeptide molecules. A library can contain as few as 3, 5, 6, 6, 7, 8, 9, 10, 15, 20, 25, 30, 35, 40, 45, 50, 75, or 100 unique DBDpp, and can range to greater than 1020 different DBDpp. In some embodiments the library has up to about $10^4$, $10^5$, $10^6$, $10^7$, or $10^8$ unique DBDpp. In further embodiments the library has up to about $10^{12}$ different DBDpp.

In one embodiment, a population of polypeptide variants is based on a sequence of core residues and variant residues. For example, SEQ ID NO:3 variant residues are denoted by an X, where X can be any amino acid residue independent of the identity of any other residue denoted X in the sequence. In certain embodiments, X can comprise a null position (e.g., no amino acid at that site). In the scaffold amino acid sequence the different varied amino acids X may be chosen from all 20 naturally occurring amino acid residues in such a way that any of these 20 naturally occurring amino acid residues may be present at the corresponding X position in any given variant. The selection of amino acid residue in each position is more or less randomized, depending on the embodiment. It is also possible to limit the group from which the different varied amino acid residues are selected to 19, 18, 17, 16 or less of the 20 naturally occurring amino acid residues. For example, in some embodiments, the variant residues are not replaced by cysteine and/or proline. The variability in different positions can be adjusted individually, between one, meaning no randomization, up to all 20 amino acids. Random introduction of a smaller subset of amino acids may be obtained by careful selection of the deoxyribonucleotide bases introduced, for example the codons T(A/C)C may be introduced to obtain a random introduction of either serine or tyrosine at a given position in the polypeptide chain. Likewise, the codons (T/C/A/G)CC can be introduced to obtain a random introduction of phenylalanine, leucine, alanine and valine at a given position in the polypeptide chain. As would be understood by a person of ordinary skill in the art many alternatives of deoxyribonucleotide base combinations can be used to obtain different combinations of amino acids at a given position in the polypeptide chain. The set of amino acids that can appear at a given position in the polypeptide chain can also be determined by the introduction of trinucleotides during the oligonucleotide synthesis, instead of one deoxyribonucleotide base at a time.

Also provided is a library containing a plurality of DBDpp. In some embodiments, the DBDpp library comprises a plurality of different DBDpp that comprise the amino acid sequence of SEQ ID NO:1 wherein 5 to 25, 5 to 30, 5 to 35, 5 to 40, 5 to 45, 5 to 50, 5 to 55, or 5 to 60 amino acid residues have been modified; and wherein the DBDpp specifically binds a target of interest. In some embodiments, 5 to 25, 5 to 30, 5 to 35, 5 to 40, 5 to 45, 5 to 50, 5 to 55, or 5 to 60 of the modified amino acid residues are substitutions. In some embodiments, 5 to 25, 5 to 30, 5 to 35, 5 to 40, 5 to 45, or 5 to 50 of the modified amino acid residues are conservative substitutions. In some embodiments, 5 to 25, 5 to 30, 5 to 35, 5 to 40, 5 to 45, or 5 to 50 of the modified amino acid residues are non-conservative substitutions. In a further embodiment, 5 to 15, 5 to 20, 5 to 25, 5 to 30, 5 to 35, 5 to 40, or 5 to 45 of the amino acid residue modifications are conservative substitutions and 5 to 15, 5 to 20, 5 to 25, 5 to 30, 5 to 35, 5 to 40, or 5 to 45 of the amino acid residue modifications are non-conservative substitutions. In additional embodiments, 5 to 25, 5 to 30, 5 to 35, 5 to 40, 5 to 45, 5 to 50, 5 to 55, or 5 to 60 of the substitutions are at amino acid residues of SEQ ID NO:1 selected from the group consisting of: M1, G2, S3, W4, A5, E6, K8, Q9, R10, A12, A13, K15, T16, R17, E19, A20, L21, G22, G23, S24, E25, A26, E27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 of the substitutions are at amino acid residues of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In another embodiment, the library comprises at least 2, 3, 4, 5, 10, 25, 50, 75, 100, 250, 500, or 1000 different DBDpp that specifically binding different targets. In a further embodiment, the different targets bound by DBDpp in the library are selected from the group consisting of: a nucleic acid, an oligosaccharide, a peptide, a protein, a cell surface antigen, and a small organic molecule. In a further embodiment, the library comprises at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a sequence tag. In a further embodiment, the library comprises at least 2, 3, 4, 5, 10, 25, 50, 75, 100, 250, 500, or 1000 different DBDpp that specifically bind a target disclosed herein. In an additional embodiment, the library is a vector library or a host cell library. In an additional embodiment, the vector library is a library of host cells. In another embodiment, the host cell library comprises a plurality of host cells that display the DBDpp on their surface. In a further embodiment, the host cells are phage that display the DBDpp on their surface.

In some embodiments, the DBDpp library comprises: (a) 3 DBDpp that specifically bind to different targets; (b) 3, 4, 5, 6, 7, 8, 9, 10, or more than 10 DBDpp having different sequences that specifically bind to the same target; (c) 3, 4, 5, 6, 7, 8, 9, 10, or more than 10 DBDpp having different sequences that specifically bind to the same epitope of a target of interest; (d) 3, 4, 5, 6, 7, 8, 9, 10, or more than 10 DBDpp having different sequences that specifically bind to different epitopes of a target; or (e) 3, 4, 5, 6, 7, 8, 9, 10, or more than 10 DBDpp having different sequences that compete for binding to the same target.

Also provided is a library containing a plurality of DBDpp. In some embodiments, the DBDpp library comprises a plurality of different DBDpp that comprise the amino acid sequence of SEQ ID NO:1 wherein 5 to 25, 5 to 30, 5 to 35, 5 to 40, 5 to 45, 5 to 50, 5 to 55, or 5 to 60 amino acid residues have been modified; and wherein the DBDpp specifically binds a target of interest. In some embodiments, 5 to 25, 5 to 30, 5 to 35, 5 to 40, 5 to 45, 5 to 50, 5 to 55, or 5 to 60 of the modified amino acid residues are substitutions. In some embodiments, 5 to 25, 5 to 30, 5 to 35, 5 to 40, 5 to 45, or 5 to 50 of the modified amino acid residues are conservative substitutions. In some embodiments, 5 to 25, 5 to 30, 5 to 35, 5 to 40, 5 to 45, or 5 to 50 of the modified amino acid residues are non-conservative substitutions. In a further embodiment, 5 to 15, 5 to 20, 5 to 25, 5 to 30, 5 to 35, 5 to 40, or 5 to 45 of the amino acid residue modifications are conservative substitutions and 5 to 15, 5 to 20, 5 to 25, 5 to 30, 5 to 35, 5 to 40, or 5 to 45 of the amino acid residue modifications are non-conservative substitutions. In additional embodiments, 5 to 25, 5 to 30, 5 to 35, 5 to 40, 5 to 45, 5 to 50, 5 to 55, or 5 to 60 of the substitutions are at amino acid residues of SEQ ID NO:1 selected from the group consisting of: M1, G2, S3, W4, A5, E6, K8, Q9, R10, A12, A13, K15, T16, R17, E19, A20, L21, G22, G23, S24, E25, A26, E27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 of the substitutions are at amino acid residues of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In another embodiment, the library comprises at least 2, 3, 4, 5, 10, 25, 50, 75, 100, 250, 500, or 1000 different DBDpp that specifically binding different targets. In a further embodiment, the different targets bound by DBDpp in the library are selected from the group consisting of: a nucleic acid, an oligosaccharide, a peptide, a protein, a cell surface antigen, and a small organic molecule. In a further embodiment, the library comprises at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises at least 2, 3, 4, 5, 10, 25, 50, 75, 100, 250, 500, or 1000 different DBDpp that specifically bind a target disclosed herein. In an additional embodiment, the library is a vector library or a host cell [including viral particles] library. In an additional embodiment, the vector library is a library of host cells. In another embodiment, the host cell library comprises a plurality of host cells that display the DBDpp on their surface. In a further embodiment, the host cells are phage that display the DBDpp on their surface.

In some embodiments, the DBDpp library comprises: (a) 3, 4, 5, 6, 7, 8, 9, 10, or more than 10 DBDpp that specifically bind to different targets; (b) 3, 4, 5, 6, 7, 8, 9, 10, or more than 10 DBDpp having different sequences that specifically bind to the same target; (c) 3, 4, 5, 6, 7, 8, 9, 10, or more than 10 DBDpp having different sequences that specifically bind to the same epitope of a target of interest; (d) 3, 4, 5, 6, 7, 8, 9, 10, or more than 10 DBDpp having different sequences that specifically bind to different epitopes of a target; or (e) 3, 4, 5, 6, 7, 8, 9, 10, or more than 10 DBDpp having different sequences that compete for binding to the same target.

In an additional embodiment, the DBDpp library contains a plurality of different nucleic acid sequences encoding DBDpp, that comprise the amino acid sequence of SEQ ID NO:1 wherein a total of 5 to 25, 5 to 30, 5 to 35, 5 to 40, 5 to 45, 5 to 50, 5 to 55, or 5 to 60 amino acid residues have been modified; and wherein the DBDpp specifically binds a target of interest. In another embodiment, 5 to 25, 5 to 30, 5 to 35, 5 to 40, 5 to 45, 5 to 50, 5 to 55, or 5 to 60 of the modified amino acid residues encoded by the nucleic acids sequences are substitutions. In another embodiment, 5 to 25, 5 to 30, 5 to 35, 5 to 40, 5 to 45, or 5 to 50 of the modified amino acid residues are conservative substitutions. In another embodiment, 5 to 25, 5 to 30, 5 to 35, 5 to 40, 5 to 45, or 5 to 50 of the encoded modified amino acid residues are non-conservative substitutions. In a further embodiment, 5 to 15, 5 to 20, 5 to 25, 5 to 30, 5 to 35, 5 to 40, or 5 to 45 of the encoded amino acid residue modifications are conservative substitutions and 5 to 15, 5 to 20, 5 to 25, 5 to 30, 5 to 35, 5 to 40, or 5 to 45 of the encoded amino acid residue modifications are non-conservative substitutions. In additional embodiments, 5 to 25, 5 to 30, 5 to 35, 5 to 40, 5 to 45, 5 to 50, 5 to 55, or 5 to 60 of the encoded substitutions are at amino acid residues of SEQ ID NO:1 selected from the group consisting of: Ml, G2, S3, W4, A5, E6, K8, Q9, R10, A12, A13, K15, T16, R17, E19, A20, L21, G22, G23, S24, E25, A26, E27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 of the encoded substitutions are at amino acid residues of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In a further embodiment, the nucleic acids optionally encode a DBDpp that further comprises an amino acid sequence wherein 1 to 5, 5 to 15, 5 to 20, 5 to 25, 5 to 30, 5 to 35, 5 to 40, or 5 to 45 of the residues corresponding to the solvent inaccessible residues of the amino acid sequence of SEQ ID NO:1 are substituted and wherein the DBDpp specifically binds a target of interest. In another embodiment, the library comprises nucleic acids encoding at least 2, 3, 4, 5, 10, 25, 50, 75, 100, 250, 500, or 1000 different DBDpp that specifically bind different targets. In a further embodiment, the different targets bound by DBDpp in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, the vector library is contained in host cells (e.g., viral particles). In another embodiment, the library comprises a plurality of host cells that display the DBDpp on their surface. In a further embodiment, the host cells are phage that display the DBDpp on their surface. In some embodiments, the DBDpp library comprises: (a) 3, 4, 5, 6, 7, 8, 9, 10, or more than 10 DBDpp that specifically bind to different targets; (b) 3, 4, 5, 6, 7, 8, 9, 10, or more than 10 DBDpp having different sequences that specifically bind to the same target; (c) 3, 4, 5, 6, 7, 8, 9, 10, or more than 10 DBDpp having different sequences that specifically bind to the same epitope of a target; (d) 3, 4, 5, 6, 7, 8, 9, 10, or more than 10 DBDpp having different sequences that specifically bind to different epitopes of a target; or (e) 3, 4, 5, 6, 7, 8, 9, 10, or more than 10 DBDpp having different sequences that compete for binding to the same target.

Nucleic acids encoding DBDpp such as DBDpp fusion proteins are also provided. In some embodiments the host cell containing the nucleic acids is a bacteria, yeast, fungal or mammalian cell. In a further embodiment, the host cell is an immune cell. In a further embodiment, the host cell is a human immune cell. In a further embodiment, the human immune cell expresses the DBDpp on its cell surface. In particular embodiments, the nucleic acid encode a DBDpp fusion protein. In a further embodiment, the host cell expresses the DBDpp as a fusion protein on the cell surface. Additionally provided herein are vector libraries comprising a plurality of nucleic acids encoding the DBDpp.

In one embodiment, a vector library comprises a plurality of different nucleic acids encoding DBDpp, wherein the encoded DBDpp comprises an amino acid sequence selected from the group consisting of: (a) MGSWX$_5$EFX$_8$X$_9$RLX$_{12}$AIX$_{15}$X$_{16}$RL X$_{19}$ALGGSEAELAAFEKEIAAFESELQAYKGKGNPE VEX$_{55}$LRX$_{58}$X$_{59}$AAX$_{62}$IRX$_{65}$X$_{66}$L QAYRHN (SEQ ID NO:4), wherein X$_5$, X$_8$, X$_9$, X$_{12}$, X$_{15}$, X$_{16}$, X$_{19}$, X$_{55}$, X$_{58}$, X$_{59}$, X$_{62}$, X$_{65}$, and X$_{66}$, is a natural and/or non-natural amino acid residue; (b) MGSWX$_5$X$_6$FKX$_9$X$_{10}$LA X$_{13}$IKX$_{16}$X$_{17}$LEALGGSEAELAX$_{30}$FEX$_{33}$X$_{34}$IAX$_{37}$ FEX$_{40}$X$_{41}$LQX$_{44}$YKGKGNPEVEALRK EAAAIRD-ELQAYRHN (SEQ ID NO:2), wherein X$_5$, X$_6$, X$_9$, X$_{10}$, X$_{13}$, X$_{16}$, X$_{17}$, X$_{30}$, X$_{33}$, X$_{34}$, X$_{37}$, X$_{40}$, X$_{41}$, and X$_{44}$, is a natural and/or non-natural amino acid residue; (c) MGSWAEFKQRLAAIKTRLEALGGSEAELAAFX$_{32}$X$_{33}$ EIX$_{36}$AFX$_{39}$X$_{40}$ELX$_{43}$AYKGKG NPEVEALX$_{57}$X$_{58}$EAX$_{61}$AIX$_{64}$X$_{65}$ELX$_{68}$AYRHN (SEQ ID NO:3), wherein X$_{32}$, X$_{33}$, X$_{36}$, X$_{39}$, X$_{40}$, X$_{43}$, X$_{57}$, X$_{58}$, X$_{61}$, X$_{64}$, X$_{65}$, and X$_{68}$, is a natural and/or non-natural amino acid residue, and; (d) MGSWX$_5$X$_6$FKX$_9$X$_{10}$LAX$_{13}$IKX$_{16}$X$_{17}$LEALGGSEAEL AAFX$_{32}$X$_{33}$EIX$_{36}$A FX$_{39}$X$_{40}$ELX$_{43}$AYKGKGNPEVEX$_{55}$LRX$_{58}$X$_{59}$AAX$_{62}$ IRX$_{65}$X$_{66}$LQAYRHN (SEQ ID NO:5), wherein X$_5$, X$_6$, X$_9$, X$_{10}$, X$_{13}$, X$_{16}$, X$_{17}$, X$_{32}$, X$_{33}$, X$_{36}$, X$_{39}$, X$_{40}$, X$_{43}$, X$_{55}$, X$_{58}$, X$_{59}$, X$_{62}$, X$_{65}$, and X$_{66}$, is a natural and/or non-natural amino acid residue; and (e) MGSWX$_5$EFX$_8$X$_9$RLX$_{12}$AI X$_{15}$X$_{16}$RLX$_{19}$ALGGSEAELAX$_{30}$FEX$_{33}$X$_{34}$IAX$_{37}$FEX$_{40}$ X$_{41}$LQX$_{44}$YKGKGNPEVEALX$_{57}$X$_{58}$EAX$_{61}$AIX$_{64}$X$_{65}$ ELX$_{68}$AYRHN (SEQ ID NO:6), wherein X$_5$, X$_8$, X$_9$, X$_{12}$, X$_{15}$, X$_{16}$, X$_{19}$, X$_{30}$, X$_{33}$, X$_{34}$, X$_{37}$, X$_{40}$, X$_{41}$, X$_{44}$, X$_{57}$, X$_{58}$, X$_{61}$, X$_{64}$, X$_{65}$, and X$_{68}$, is a natural and/or non-natural amino acid residue; and wherein the DBDpp specifically binds a target of interest. In an additional embodiment, X$_n$ is a natural amino acid residue. In a further embodiment, X$_n$ is a natural amino acid residue other than cysteine or proline. In an additional embodiment, a plurality of the vectors in the library encode a DBDpp fusion protein. In another embodiment, the library comprises nucleic acids encoding at least 2, 3, 4, 5, 10, 25, 50, 75, 100, 250, 500, or 1000 different DBDpp that specifically bind different targets. In a further embodiment, the different targets bound by DBDpp encoded by the nucleic acids in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, a plurality of the vectors of the vector library are contained in host cells (e.g., viral particles such as phage), E. coli, yeast, and mammalian cells. In another embodiment, the host cells display DBDpp on their surface. In a further embodiment, the host cells are phage that display DBDpp on their surface. In some embodiments, the vector library comprises: (a) nucleic acids encoding 3, 4, 5, 6, 7, 8, 9, 10, or more than 10 DBDpp that specifically bind to different targets; (b) nucleic acids encoding 3, 4, 5, 6, 7, 8, 9, 10, or more than 10 DBDpp 3, 4, 5, 6, 7, 8, 9, 10, or more than 10 DBDpp having different sequences that specifically bind to the same target; (c) nucleic acids encoding 3, 4, 5, 6, 7, 8, 9, 10, or more than 10 DBDpp having different sequences that specifically bind to the same epitope of a target; (d) nucleic acids encoding 3, 4, 5, 6, 7, 8, 9, 10, or more than 10 DBDpp having different sequences that specifically bind to different epitopes of a target; (e) nucleic acids encoding 3, 4, 5, 6, 7, 8, 9, 10, or more than 10 DBDpp having different sequences that compete for binding to the same target; or (f) 3, 4, 5, 6, 7, 8, 9, 10, or more than 10 different nucleic acids encoding the same DBDpp. Host cells containing the vectors are also provided.

In one embodiment, a vector library comprises a plurality of nucleic acids encoding DBDpp comprising an amino acid sequence selected from the group consisting of: (a) MGSWX$_5$EFX$_8$X$_9$RLX$_{12}$AIX$_{15}$X$_{16}$RLX$_{19}$ALZ$_1$EAELAA FEKEIAAFESELQAYZ$_2$NPEVEX$_{50}$LR X$_{53}$X$_{54}$AAX$_{57}$IRX$_{60}$X$_{61}$LQAYRHN (SEQ ID NO:9), wherein X$_5$, X$_8$, X$_9$, X$_{12}$, X$_{15}$, X$_{16}$, X$_{19}$, X$_{50}$, X$_{53}$, X$_{54}$, X$_{57}$, X$_{60}$, and X$_{61}$, is a natural and/or non-natural amino acid residue, and Z$_1$ and Z$_2$ is 2 to natural and/or non-natural amino acid residues; (b) MGSWX$_5$X$_6$FKX$_9$X$_{10}$LAX$_{13}$IKX$_{16}$X$_{17}$LEALZ$_1$EAELAX$_{28}$FEX$_{31}$X$_{32}$IAX$_{35}$FEX$_{38}$X$_{39}$LQX$_{42}$YZ$_2$NPEVEALRKEAAA IRDELQAYRHN (SEQ ID NO:7), wherein X$_5$, X$_6$, X$_9$, X$_{10}$, X$_{13}$, X$_{16}$, X$_{17}$, X$_{28}$, X$_{31}$, X$_{32}$, X$_{35}$, X$_{38}$, X$_{39}$, and X$_{42}$, is a natural and/or non-natural amino acid residue, and Z$_1$ and Z$_2$ is 2 to 30 natural and/or non-natural amino acid residues; (c) MGSWAEFKQRLAAIKTRLEALZ$_1$EAEL AAFX$_{30}$X$_{31}$EIX$_{34}$AFX$_{37}$X$_{38}$ELX$_{41}$AYZ$_2$NPEVEALX$_{52}$ X$_{53}$EAX$_{56}$AIX$_{59}$X$_{60}$ELX$_{63}$AYRHN (SEQ ID NO:8), wherein X$_{30}$, X$_{31}$, X$_{34}$, X$_{37}$, X$_{38}$, X$_{41}$, X$_{52}$, X$_{53}$, X$_{56}$, X$_{59}$, X$_{60}$, and X$_{63}$, is a natural and/or non-natural amino acid residue, and Z$_1$ and Z$_2$ is 2 to 30 natural and/or non-natural amino acid residues; (d) MGSWX$_5$X$_6$FKX$_9$X$_{10}$LAX$_{13}$IKX$_{16}$X$_{17}$LEALZ$_1$EAELA AFX$_{30}$X$_{31}$EIX$_{34}$AFX$_{37}$X$_{38}$ELX$_{41}$AYZ$_2$NPEVEX$_{50}$LRX$_{53}$ X$_{54}$AAX$_{571}$RX$_{60}$X$_{61}$LQAYRHN (SEQ ID NO:10), wherein X$_5$, X$_6$, X$_9$, X$_{10}$, X$_{13}$, X$_{16}$, X$_{17}$, X$_{30}$, X$_{31}$, X$_{34}$, X$_{37}$, X$_{38}$, X$_{41}$, X$_{50}$, X$_{53}$, X$_{54}$, X$_{57}$, X$_{60}$, and X$_{61}$, is a natural and/or non-natural amino acid residue, and Z$_1$ and Z$_2$ is 2 to 30 natural and/or non-natural amino acid residues; and (e) MGSWX$_5$EFX$_8$X$_9$RLX$_{12}$AIX$_{15}$X$_{16}$RL X$_{19}$ALZ$_1$EAELAX$_{28}$FEX$_{31}$X$_{32}$IAX$_{35}$FEX$_{38}$X$_{39}$LQX$_{42}$ YZ$_2$NPEVEALX$_{52}$X$_{53}$EAX$_{56}$AIX$_{59}$X$_{60}$ELX$_{63}$AYRHN (SEQ ID NO:11), wherein X$_5$, X$_8$, X$_9$, X$_{12}$, X$_{15}$, X$_{16}$, X$_{19}$, X$_{28}$, X$_{31}$, X$_{32}$, X$_{35}$, X$_{38}$, X$_{39}$, X$_{42}$, X$_{52}$, X$_{53}$, X$_{56}$, X$_{59}$, X$_{60}$, and X$_{63}$, is a natural and/or non-natural amino acid residue, and Z$_1$ and Z$_2$ is 2 to 30 natural and/or non-natural amino acid residues; and wherein the DBDpp specifically binds a target of interest. In an additional embodiment, X$_n$ is a natural amino acid residue. In a further embodiment, X$_n$ is a natural amino acid residue other than cysteine or proline. In an additional embodiment, a plurality of the vectors in the library encode a DBDpp fusion protein. In another embodiment, the library comprises nucleic acids encoding at least 2, 3, 4, 5, 10, 25, 50, 75, 100, 250, 500, or 1000 different DBDpp that specifically bind different targets. In a further embodiment, the different targets bound by DBDpp encoded by the nucleic acids in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, a plurality of the vectors of the vector library are contained in host cells. In another embodiment, the host cells (e.g., viral particles) display DBDpp on their surface. In a further embodiment, the host cells are phage that display DBDpp on their surface. In some embodiments, the vector library comprises: (a) nucleic acids encoding 3, 4, 5, 6, 7, 8, 9, 10, or more than 10 DBDpp that specifically bind to different targets; (b) nucleic acids encoding 3, 4, 5, 6, 7, 8, 9, 10, or more than 10 DBDpp having different sequences that specifically bind to the same target; (c) nucleic acids encoding 3, 4, 5, 6, 7, 8, 9, 10, or more than 10 DBDpp having different sequences that specifically bind to the same epitope of a target; (d) nucleic acids encoding 3, 4, 5, 6, 7, 8, 9, 10, or more than 10 DBDpp having different sequences that specifically bind to different epitopes of a target; (e) nucleic acids encoding 3, 4, 5, 6, 7, 8, 9, 10, or more than 10 DBDpp having different sequences that compete for binding to the same target; or (f) 3, 4, 5, 6, 7, 8, 9, 10, or more than 10 different nucleic acid sequences encoding the same DBDpp sequence. Host cells containing the vectors are also provided.

In some embodiments, 4, 5, 10 or more DBDpp encoded by the nucleic acids in the library specifically bind different targets.

In one embodiment, a vector library comprises comprising a plurality of different nucleic acid sequences encoding DBDpp, that comprise the amino acid sequence of SEQ ID NO:1 wherein a total of 5 to 25, 5 to 30, 5 to 35, 5 to 40, 5 to 45, 5 to 50, 5 to 55, or 5 to 60 amino acid residues have been modified; and wherein the DBDpp specifically binds a target of interest. In another embodiment, 5 to 25, 5 to 30, 5 to 35, 5 to 40, 5 to 45, 5 to 50, 5 to 55, or 5 to 60 of the modified amino acid residues encoded by the nucleic acids sequences are substitutions. In another embodiment, 5 to 25, 5 to 30, 5 to 35, 5 to 40, 5 to 45, or 5 to 50 of the modified amino acid residues are conservative substitutions. In another embodiment, 5 to 25, 5 to 30, 5 to 35, 5 to 40, 5 to 45, or 5 to 50 of the encoded modified amino acid residues are non-conservative substitutions. In a further embodiment, 5 to 15, 5 to 20, 5 to 25, 5 to 30, 5 to 35, 5 to 40, or 5 to 45 of the encoded amino acid residue modifications are conservative substitutions and 5 to 15, 5 to 20, 5 to 25, 5 to 30, 5 to 35, 5 to 40, or 5 to 45 of the encoded amino acid residue modifications are non-conservative substitutions. In additional embodiments, 5 to 25, 5 to 30, 5 to 35, 5 to 40, 5 to 45, 5 to 50, 5 to 55, or 5 to 60 of the encoded substitutions are at amino acid residues of SEQ ID NO:1 selected from the group consisting of: M1, G2, S3, W4, A5, E6, K8, Q9, R10, A12, A13, K15, T16, R17, E19, A20, L21, G22, G23, S24, E25, A26, E27, A29, A30, E32, K33, E34, A36, A37, E39, S40, E41, Q43, A44, Y45, K46, G47, K48, G49, N50, P51, E52, E54, A55, R57, K58, E59, A61, A62, R64, D65, E66, Q68, A69, Y70, R71, H72, and N73. In a further embodiment, 1 to 20, 1 to 30, or 1 to 40 of the encoded substitutions are at amino acid residues of SEQ ID NO:1 selected from the group consisting of: G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70. In a further embodiment, the nucleic acids optionally encode a DBDpp that further comprises an amino acid sequence wherein 1 to 5, 5 to 15, 5 to 20, 5 to 25, 5 to 30, 5 to 35, 5 to 40, or 5 to 45 of the residues corresponding to the solvent inaccessible residues of the amino acid sequence of SEQ ID NO:1 are substituted and wherein the DBDpp specifically binds a target of interest. In another embodiment, the library comprises nucleic acids encoding at least 2, 3, 4, 5, 10, 25, 50, 75, 100, 250, 500, or 1000 different DBDpp that specifically bind different targets. In a further embodiment, the different targets bound by DBDpp in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, the vector library is contained in host cells (e.g., viral particles). In another embodiment, the library comprises a plurality of host cells that display the DBDpp on their surface. In a further embodiment, the host cells are phage that display the DBDpp on their surface. In some embodiments, the vector library comprises: (a) nucleic acids encoding 3, 4, 5, 6, 7, 8, 9, 10, or more than 10 DBDpp that specifically bind to different targets; (b) nucleic acids encoding 3, 4, 5, 6, 7, 8, 9, 10, or more than 10 DBDpp having different sequences that specifically bind to the same target; (c) nucleic acids encoding 3, 4, 5, 6, 7, 8, 9, 10, or more than 10 DBDpp having different sequences that specifically bind to the same epitope of a target; (d) nucleic acids encoding 3, 4, 5, 6, 7, 8, 9, 10, or more than 10 DBDpp having different sequences that specifically bind to different epitopes of a target; or (e) nucleic acids encoding 3, 4, 5, 6, 7, 8, 9, 10, or more than 10 DBDpp having different sequences that compete for binding to the same target; or (f) 3, 4, 5, 6, 7, 8, 9, 10, or more than 10 different nucleic acids encoding the same DBDpp. Host cells containing the vectors are also provided.

In some embodiments, the vector library comprises: (a) nucleic acids encoding 3 DBDpp that specifically bind to different targets of interest; (b) nucleic acids encoding 3, 4, 5, 6, 7, 8, 9, 10, or more than 10 DBDpp having different sequences that specifically bind to the same target of interest; (c) nucleic acids encoding 3, 4, 5, 6, 7, 8, 9, 10, or more than 10 DBDpp having different sequences that specifically bind to the same epitope of a target of interest; (d) nucleic acids encoding 3, 4, 5, 6, 7, 8, 9, 10, or more than 10 DBDpp having different sequences that specifically bind to different epitopes of a target of interest; (e) nucleic acids encoding 3, 4, 5, 6, 7, 8, 9, 10, or more than 10 DBDpp having different sequences that compete for binding to the same target of interest; or (f) 3 different nucleic acid sequences encoding the same DBDpp sequence.

In one embodiment, the vector library comprises a plurality of nucleic acids encoding DBDpp comprising an amino acid selected from the group consisting of: (a) MGSWX$_5$EFX$_8$X$_9$RLX$_{12}$AIX$_{15}$X$_{16}$RLX$_{19}$ALZ$_1$EAELAA FEKEIAAFESELQAYZ$_2$NPEVEX$_{50}$LRX$_{53}$X$_{54}$AA X$_{57}$IRX$_{60}$X$_{61}$LQAYRHN (SEQ ID NO:9), wherein X$_5$, X$_8$, X$_9$, X$_{12}$, X$_{15}$, X$_{16}$, X$_{19}$, X$_{50}$, X$_{53}$, X$_{54}$, X$_{57}$, X$_{60}$, and X$_{61}$, is a natural and/or non-natural amino acid residue, and Z$_1$ and Z$_2$ is 2 to 30 natural and/or non-natural amino acid residues; (b) MGSWX$_5$X$_6$FKX$_9$X$_{10}$LAX$_{13}$IK X$_{16}$X$_{17}$LEALZ$_1$EAELAX$_{28}$FEX$_{31}$X$_{32}$IAX$_{35}$FEX$_{38}$X$_{39}$ LQX$_{42}$YZ$_2$NPEVEALRKEAAAIRDE LQAYRHN (SEQ ID NO:7), wherein X$_5$, X$_6$, X$_9$, X$_{10}$, X$_{13}$, X$_{16}$, X$_{17}$, X$_{28}$, X$_{31}$, X$_{32}$, X$_{35}$, X$_{38}$, X$_{39}$, and X$_{42}$, is a natural and/or non-natural amino acid residue, and Z$_1$ and Z$_2$ is 2 to 30 natural and/or non-natural amino acid residues; (c) MGSWAEFKQRLAAIKTRLEALZ$_1$E AELAAFX$_{30}$X$_{31}$EIX$_{34}$AFX$_{37}$X$_{38}$ELX41AYZ$_2$NPEVEA LX$_{52}$X$_{53}$EAX$_{56}$AIX$_{59}$X$_{60}$ELX$_{63}$AYRHN (SEQ ID NO:8), wherein X$_{30}$, X$_{31}$, X$_{34}$, X$_{37}$, X$_{38}$, X$_{41}$, X$_{52}$, X$_{53}$, X$_{56}$, X$_{59}$, X$_{60}$, and X$_{63}$ is a natural and/or non-natural amino acid residue, and Z$_1$ and Z$_2$ is 2 to 30 natural and/or non-natural amino acid residues; (d) MGSWX$_5$X$_6$FKX$_9$X$_{10}$LAX$_{13}$IKX$_{16}$X$_{17}$LEALZ$_1$EAELAAF X$_{30}$X$_{31}$EIX$_{34}$AFX$_{37}$X$_{38}$ELX$_{41}$AYZ$_2$NPEVEX$_{50}$LRX$_{53}$ X$_{54}$AAX$_{57}$IRX$_{60}$X$_{61}$LQAYRHN (SEQ ID NO:10), wherein X$_5$, X$_6$, X$_9$, X$_{10}$, X$_{13}$, X$_{16}$, X$_{17}$, X$_{30}$, X$_{31}$, X$_{34}$, X$_{37}$, X$_{38}$, X$_{41}$, X$_{50}$, X$_{53}$, X$_{54}$, X$_{57}$, X$_{60}$, and X$_{61}$, is a natural and/or non-natural amino acid residue, and Z$_1$ and Z$_2$ is 2 to 30 natural and/or non-natural amino acid residues; and (e) MGSWX$_5$EFX$_8$X$_9$RLX$_{12}$AIX$_{15}$X$_{16}$RL X$_{19}$ALZ$_1$EAELAX$_{28}$FEX$_{31}$X$_{32}$IAX$_{35}$FEX$_{38}$X$_{39}$LQX$_{42}$ YZ$_2$NPEVEALX$_{52}$X$_{53}$EAX$_{56}$AIX$_{59}$X$_{60}$ELX$_{63}$A YRHN (SEQ ID NO:11), wherein X$_5$, X$_8$, X$_9$, X$_{12}$, X$_{15}$, X$_{16}$, X$_{19}$, X$_{28}$, X$_{31}$, X$_{32}$, X$_{35}$, X$_{38}$, X$_{39}$, X$_{42}$, X$_{52}$, X$_{53}$, X$_{56}$, X$_{59}$, X$_{60}$, and X$_{63}$, is a natural and/or non-natural amino acid residue, and Z$_1$ and Z$_2$ is 2 to 30 natural and/or non-natural amino acid residues; and wherein the DBDpp specifically binds a target of interest. In an additional embodiment, X$_n$ is a natural amino acid residue. In a further embodiment, X$_n$ is a natural amino acid residue other than cysteine or proline. In an additional embodiment, a plurality of the vectors in the library encode a DBDpp fusion protein. In another embodiment, the library comprises nucleic acids encoding at least 2, 3, 4, 5, 10, 25, 50, 75, 100, 250, 500, or 1000 different DBDpp that specifically bind different targets. In a further embodiment, the different targets bound by DBDpp encoded by the nucleic acids in the library are selected from the group consisting of: a nucleic acid, an oligosaccharide, a peptide, a protein, a cell surface antigen, and a small organic molecule. In a further embodiment, the library comprises nucleic acids encoding at least 2, 3, 4, 5, 10, 25, 50, 75, 100, 250, 500, or 1000 different DBDpp that specifically bind a protein target selected from the group consisting of: an immunoglobulin, an enzyme, a hormone, a serum protein, a cell surface protein, a therapeutic protein, a TSA, a CSA, and a protein containing a peptide tag. In a further embodiment, the library comprises nucleic acids encoding at least 2, 3, 4, 5, 10, 25, 50, 75, 100, 250, 500, or 1000 different DBDpp that specifically bind a target disclosed herein. In an additional embodiment, a plurality of the vectors of the vector library is contained in host cells (including viral particles). In another embodiment, the host cells (e.g., viral particles) display DBDpp on their surface. In a further embodiment, the host cells are phage that display DBDpp on their surface. In some embodiments, at least two, three, four, five, or ten of the DBDpp encoded in the vector library specifically bind different targets. In some embodiments, the DBDpp binds a target of interest selected from the group consisting of: a nucleic acid, an oligosaccharide, a peptide, a protein, a cell surface antigen, and a small organic molecule. In a further embodiment, the DBDpp target of interest is a protein selected from the group consisting of: an immunoglobulin, an enzyme, a hormone, a serum protein, a cell surface protein, a therapeutic protein, a TSA, a CSA, and a protein containing a peptide tag. In a further embodiment, the DBDpp specifically binds a target disclosed herein. Also provided is a library of host cells (e.g., viral particles) containing the vector library. In some embodiments, the library contains a plurality of host cells (e.g., viral particles) that display the DBDpp on their surface. In particular embodiments, the host cells are phage that display the DBDpp on their surface. In some embodiments, the vector library comprises: (a) nucleic acids encoding 3, 4, 5, 6, 7, 8, 9, 10, or more than 10 DBDpp that specifically bind to different targets of interest; (b) nucleic acids encoding 3, 4, 5, 6, 7, 8, 9, 10, or more than 10 DBDpp having different sequences that specifically bind to the same target of interest; (c) nucleic acids encoding 3, 4, 5, 6, 7, 8, 9, 10, or more than 10 DBDpp having different sequences that specifically bind to the same epitope of a target of interest; (d) nucleic acids encoding 3, 4, 5, 6, 7, 8, 9, 10, or more than 10 DBDpp having different sequences that specifically bind to different epitopes of a target of interest; (e) nucleic acids encoding 3, 4, 5, 6, 7, 8, 9, 10, or more than 10 DBDpp having different sequences that compete for binding to the same target of interest; or (f) 3, 4, 5, 6, 7, 8, 9, 10, or more than 10 different nucleic acid sequences encoding the same DBDpp sequence.

It is envisioned that the DBDpp can be modified to tailor the polypeptides to the specific use intended, without departing from the scope provided herein. Such modifications may comprise additional amino acids at the N- or C-terminus of the DBDpp and/or labels or therapeutic agents that are chemically conjugated or otherwise bound to the DBDpp. The additional amino acid residues discussed above may also constitute one or more polypeptide domain(s) with any desired function, such as another binding function, or an enzymatic function, or a metal ion chelating function, or a fluorescent function, or mixtures thereof.

Selecting, Isolating and Identifying DBDpp

Methods for selecting, isolating and identifying DBDpp that specifically bind a target of interest from a plurality of DBDpp, such as those in a library, are also provided. In one embodiment, a method of screening a library of DBDpp for binding with a binding partner, comprises: (a) obtaining a population displaying a library of DBDpp; (b) contacting the population with the target of interest under conditions suitable for binding; and (c) identifying those DBDpp that bind to the target. Two exemplary DBDpp display selection processes include panning and cell-based screening selection.

In illustrative examples provided herein, DBDpp phage display libraries are prepared and screened for DBDpp having desired properties, including the ability to specifically bind numerous validated therapeutic and diagnostic targets. Representative DBDpp identified in these screens are further characterized and demonstrated to display desirable properties useful in for example, purification, diagnostic, and therapeutic applications.

Display Library

As described herein, substitutions in the reference scaffold of SEQ ID NO:1 provide a versatile molecular recognition platform. Such DBDpp can be used in methods for preparing libraries of DBDpp which can be screened against targets of interest. Such screening methods can be used to identify DBDpp with desired properties such as the ability to bind a target of interest. The population of DBDpp used in the selection of target-specific DBDpp can be in different forms, and can be but are not limited to protein libraries, nucleic acid libraries, vector libraries and host cell libraries.

Various methods known in the art for preparing modifications of nucleic acid can be used to prepare (encode) DBDpp having modification in one or more amino acid residues compared to another DBDpp and/or the reference scaffold of SEQ ID NO:1. Nucleic acids encoding DBDpp may be obtained using standard methods in the art, such as chemical synthesis, recombinant methods and/or obtained from biological sources. Nucleic acid of interest may be placed under the control of one or more elements necessary for their expression in any particular host cell. A variety of host cells are available to propagate nucleic acids encoding DBDpp, and display methods are known in the art and described herein that may be used in display DBDpp on their surface. Display methods include without limitation phage display, bacterial display, yeast display, ribosome display, and mRNA display.

In some embodiments, the generation of a (partially) randomized DBDpp library requires the (partial) randomization of specific positions within the reference scaffold sequence of SEQ ID NO:1. In additional embodiments, other reference sequences may be used and modified according to the methods disclosed herein. In one embodiment, a DBDpp library for use in the methods provided herein are generated by recombinant DNA techniques. In particular, libraries of nucleic acid sequences encoding DBDpp each differing in sequence at particular amino acid positions can be obtained by site-directed or random mutagenesis of a template sequence. Random amino acid residues can be introduced at specific positions in an amino acid sequence using techniques known in the art such as selecting (introducing) 'NNK' or 'NNS' codons at corresponding positions in the nucleotide sequence encoding said amino acid sequence. Methods for producing such libraries are known in the art and commercial services are available for generating such libraries. The nucleotide(s) determining the relevant amino acid residues in the positions of interest are mutated in different ways such as to obtain a library of sequences encoding different DBDpp.

Libraries are optionally created through the selective or random mutation of specific solvent exposed amino acid sequence positions of the DBD.

In some embodiments, the number of substituted amino acid residue positions in DBDpp libraries provided herein range from 5 to 20 amino acid residue positions. Thus, a defined set of substituted amino acid residue positions in a DBDpp library provided herein comprise 5 to 20 defined substituted amino acid residue positions, such as 5, 6, 7, 8, 9, 10, 11, 12, 13, 14, 15, 16, 17, 18, 19, or 20, defined substituted amino acid residue positions. In several embodiments, the substituted amino acid residues are natural or non-natural amino acids. In several embodiments, any of the 20 natural amino acids can be used. However, in some embodiments, the substitutions do not result in the replacement of any amino acids with a cysteine and/or a proline.

A library of DBDpp can contain any suitable number of different DBDpp sequences. In some embodiments, the library of DBDpp contain least 2, at least 5, at least 10, at least 50, at least 100, at least 1000, at least 10,000, at least 105, at least 106, at least 107, at least 108, at least 109 or more different DBDpp sequences (e.g., DBDpp fusion proteins).

The notion "substituted amino acid residue position", when referring to a library of different-DBDpp sequences, refers to an amino acid residue position at which at least two different amino acid residue types are located when at least two of the amino acid sequences of the different DBDpp from a library of DBDpp are compared to each other.

In one embodiment, the disclosure encompasses methods of producing a library (i.e., a collection or plurality) of DBDpp which differ from each other in at least one of a defined set of 5 to 20 substituted amino acid residue positions. Therefore, the sequences within a library of DBDpp differ from each other at any one or more particular amino acid positions that are comprised in a selected, defined, or random set. Accordingly, the term "different sequences" or "different DBDpp sequences" refers to the occurrence of sequence variation or sequence differences in a defined set of amino acid residue positions between two or more DBDpp in a library.

Display Vehicle

The population or library of molecules is displayed on a typical display vehicle (e.g., bacteriophage, E. coli, ribosome) that affords the coupling of phenotype to genotype.

In some embodiments, the DBDpp of the library are displayed on the surface of a phage particle, a ribosome, a bacterium, a yeast cell, a mammalian cell or any other suitable (micro)organism, so as to facilitate screening or selection to isolate the desired DBDpp sequences having detectable binding affinity for, or detectable in vitro activity on the target of interest. A major advantage of this technology is the coupling of genotype (i.e., the encapsulated DNA encoding the displayed protein) and phenotype (i.e., the displayed protein such as a DBDpp provided herein) which allows affinity-based selection from libraries with millions to trillions of polypeptide variants in a relatively simple in vitro assay.

Suitable methods, techniques and host organisms for displaying and selecting or screening a library of substituted DBDpp sequences or nucleotide sequences encoding such substituted DBDpp sequences, and which are applicable to DBDpp having desired features, are known to the person skilled in the art. Such methods are described, for example, in Georgiou, Nat. Biotechnol. 15:29-34 (1997); Wittrup, Curr. Opin. Biotechnol. 12:395-399 (2001); Lipovsek and Pluckthun, J Immunol Methods 290:51-67 (2004); Reiersen, Nucl Acids Res, 33:e10, 2005; Levin, Mol BioSyst, 2:49-57 (2006); Bratkovic, Cell. Mol. Life. Sci. 67:749-767 (2010). For example, the technology of phage library display, and the selection by means of a phage display technique may be chosen as a method for high-throughput identification of protein-specific binders, because it is one of the most robust and versatile selection techniques available (Scott, Science 249:386-390 (1990); Bratkovic, Cell. Mol. Life Sci. 67:749-767 (2010)).

Additionally, display technology can be used to alter, e.g., improve the binding properties of DBDpp. See, for example, Scott, Science 249: 386 (1990); Devlin, Science 249: 404 (1990); U.S. Pat. Nos. 5,223,409, 5,733,731, 5,498,530, 5,432,018, 5,338,665, and 5,922,545; WO 96/40987 and WO 98/15833, the contents of each of which is herein incorporated by reference in its entirety. In peptide phage display libraries, natural and/or non-naturally occurring peptide sequences can be displayed by fusion with coat proteins of filamentous phage. The displayed peptides can be affinity-eluted against a target of interest if desired. The retained phage can be enriched by successive rounds of affinity purification and repropagation. The best binding DBDpp can be sequenced to identify key residues and mutagenesis libraries may be created and screened to further optimize the sequence of the best binders. Lowman, Ann. Rev. Biophys. Biomol. Struct. 26: 401-24 (1997).

Phage Display

A typical phage display protocol involves the use of a filamentous phage (phagemid) surface expression system, production of phage particles in a bacterial host with each particle displaying the gene product of one member of the gene library as a fusion with one type of its coat proteins (gIII or gVIII proteins). A library of phage particles is taken through a selection process for binding to an immobilized target molecule ('biopanning') involving binding of the phage library to the target, washing steps to remove non-bound phage DBDpp, and elution of bound particles. Usually several rounds of panning are necessary to select molecules with the desired characteristics involving reamplification of eluted phage in the bacterial host and selection on the immobilized target.

For example, using a phagemid display (Kay et al., Phage Display of Peptides and Proteins. A Laboratory Manual, B. K. Kay et al. 1996) a given DBDpp library may be represented by a collection of phagemids each of which encodes for a fusion protein comprising a member of the DBDpp library fused to the minor coat protein pIII. These phagemids can be introduced into suitable E. coli cells (e.g. TG1) by electroporation or other means. Using infection with helper phage, phage are produced (packaging also the phagemid genome) that display the DBDpp-fusion protein. These phage can be used to select binders against a given target and the selected phage can be propagated by infecting E. coli TG1 (Stratagene).

Thus, in particular embodiments, the DBDpp libraries are provided as a phage library and binding DBDpp are identified by contacting the phage with the labeled target of interest, after which binding phages are retrieved by detection or selective collection of the labeled, bound target. In one embodiment, a biotinylated target is used, whereby phage which generate a DBDpp that specifically binds to the target are captured with a streptavidin-coated support (e.g., magnetic beads). In some embodiments, the selection steps of the methods for producing one or more DBDpp having detectable binding affinity for a target of interest, may comprise the (further) enrichment of the DBDpp library or the mixture of DBDpp libraries for DBDpp having detectable binding affinity for the target of interest by iterative execution of the steps of contacting a target of interest with a DBDpp library or with a mixture of DBDpp libraries (including a plurality of DBDpp) of the invention and subsequently identifying from the DBDpp library or mixture of DBDpp libraries being contacted with the protein, one or more DBDpp having detectable binding affinity for the target of interest. The step of selecting a DBDpp that has detectable in vitro activity by interacting with a target of interest may comprises: (a) contacting a DBDpp library or a mixture of DBDpp libraries of the invention with the cytokine or growth factor or cytokine or growth factor receptor of interest, and (b) identifying from the DBDpp library or mixture of DBDpp libraries, the one or more DBDpp having detectable in vitro activity on the target of interest.

In illustrative embodiments disclosed herein in the Examples, phage display methods are used to display and screen DBDpp for the ability to specifically bind a target of interest It is demonstrated herein that the DBD domain can be displayed and selected on the surface of phage. Different libraries of DBDpp, based on the scaffold of SEQ ID NO:1, and described herein in the examples, were prepared and subjected to phage display methods to demonstrate that DBDpp can be produced that specifically bind to different targets of interest including CD137, CD47, CTLA4, DR5, KIR, PD-L1, PD1 and TIM3.

Cell Display

In some embodiments, the library screening techniques include a cell surface display system. The cell surface display system may comprise prokaryotic cells, such as Gram+ cells, or eukaryotic cells, such as yeast cells. Numerous cell surface display systems are known in the art and can routinely be adapted for screening DBDpp libraries. Prokaryotic systems are, for example, described in Francisco et al., PNAS 90:10444-10448 (1993) and Lee et al., Trends Biotechnol 21:45-52 (2003). Eukaryotic systems are described for example in Boder et al., Nat. Biotechnol. 15:553-557 (1997) and Gal et al., Curr. Opin. Struct. Biol. 17:467-473 (2007). "*E. coli* display" methods such as peptidoglycan-associated lipoprotein (PAL) fusion are also encompassed herein. For example, a DBDpp peptide can be fused to the carboxyl terminus of the lac repressor and expressed in *E. coli*.

The bacterial display and yeast display technologies known in the art allow expression of recombinant proteins on the surface of yeast cells *S. cerevisiae* (Boder, Nat. Biotechnol. 15:553-557 (1997) or bacteria (*E. coli, Staphylococcus carnosus*) (Daugherty., 1998, Wernerus, Appl. Environ. Microbiol. 69(9):5328-5335 (2003)) as a fusion with the a-agglutinin yeast adhesion receptor or a bacterial outer membrane protein (OMP) respectively.

In some embodiments, the expressed fusion proteins also contain a peptide tag allowing quantification of the library surface expression by flow cytometry. Combined with indirect fluorescent labeling of the ligand, anti-tag labeling allows cell sorting by FACS (fluorescence activated cell sorting) and the determination of the binding affinities of the interactions (Feldhaus et al., Nat. Biotechnol. 21:163-70 (2003); Wernerus et al. Appl. Environ. Microbiol. 69(9): 5328-35 (2003)).

In Vitro Display

In vitro (also known as cell-free or acellular) display methods may also be employed to select for, isolate and identify DBDpp that bind a target of interest. In one example, translation of random RNA is halted prior to ribosome release, resulting in a library of polypeptides with their associated RNA still attached. This and related methods are collectively referred to as "ribosome display." Other known methods employ chemical linkage of peptides to RNA. See, for example, Roberts et al., PNAS 94:12297-303 (1997). This and related methods are collectively referred to as "RNA-peptide screening, RNA display and mRNA display." Alternatively, in vitro display methods may employ DNA as the genetic component to which the expressed polypeptide is coupled. A method known as cis-display affords the in vitro selection of peptides from libraries of protein—DNA complexes and is described in U.S. Pat. No. 7,842,476 B2, the contents of which are herein incorporated by reference in its entirety. Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. These and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells, Curr. Opin. Biotechnol. 3:355-362 (1992).

Selection of DBDpp

Biopanning is a known iterative selection and screening method to enrich an initial population of different molecules (such as a DBDpp library) for molecules having an affinity for a target of choice. Library members that have affinity for the target are allowed to bind. Non-specifically or weakly bound members are washed from the support. Then the bound library members are recovered (e.g., by elution) from the support. Recovered library members are collected for further analysis (e.g., screening) or pooled for an additional round of selection.

In one embodiment, the target is captured on the solid support after incubation with the phage library. The immobilization of the target can be performed by many different methods known in the art. Examples of solid support are microtiter plates or tubes (e.g. Maxisorp plates, Maxisorp tubes, Nunc) or magnetic beads (Dynabead®, Invitrogen). The target can either be directly coated on the plastic or the beads (surface activated Dynabeads, e.g. Dynabeads M270 Epoxy, Invitrogen) or via streptavidin when the target is biotinylated (e.g. Dynabeads MyOne Streptavidin T1, Invitrogen).

In addition the target may be bound non-covalently to the bead via an intermediate affinity molecule such as an antibody or protein A directed against the target or a target-associated peptide tag. Peptide tags such as His-tags or alternatively, an antibody directed against the target can also be used to capture the target on the support. These alternative peptide tags are also compatible with the Dynabeads (Dynabeads His-tag isolation and pull down, Invitrogen) and Protein A or Protein G coupled Dynabeads (Dynabeads-Protein A/G, Invitrogen). To immobilize the target on magnetic beads, the recommendations of the manufacturer are followed for each specific bead type.

The capturing step may then consist of trapping the target to coated magnetic beads, thereby capturing indirectly phage bound to the target. The target-phage interaction is performed in solution. To be able to wash away the non-binding phage, the target needs to be immobilized on a solid support. The immobilization of the target in the soluble biopanning method is identical to the immobilization possibilities in the direct biopanning protocols.

A classical biopanning protocol consists of 2, 3 to 5 or more selection rounds, depending on the type of target and library. Each selection round consists of typically different steps: (1) immobilization of the target of choice to a support. This step is optional, as biopanning can also be performed in a format wherein the target is not-immobilized but kept in solution (in case of soluble target) or remains anchored on a cell (in case of e.g. a membrane anchored target such as a receptor), (2) incubation of the library with the target, (3) washing steps to eliminate non-specific binders, (4) optionally elution of the binders and (5) amplification of the eluted binders from step (4) or from step (3) (in case step (4)) was omitted in consecutive screening rounds). The steps 1 to 5 will be repeated two, three, four or more times to isolate from the initial library target-specific binders. After the biopanning, the target—specificity of the binders isolated from the different selection rounds is typically analyzed in ELISA assays or similar assays.

In one embodiment, a method of screening for DBDpp that specifically bind a target of interest comprises the steps of: (a) contacting a target of interest with a plurality of DBDpp; and (b) identifying a DBDpp that specifically binds the target of interest. The step of contacting the target of interest with the plurality of DBDpp may be affected in any way known in the art. For example, in one embodiment, the target of interest is immobilized on a solid support and contacting a solution containing the plurality of DBDpp molecules with the immobilized target of interest. Such a procedure is akin to an affinity chromatographic process, with the affinity matrix being comprised of the immobilized target of interest. The DBDpp having a selective affinity for the target of interest can then be purified using techniques known in the art, such as affinity selection. The composition of the solid support, process for attaching the target of interest to the solid support, and the reagents, conditions and methods of screening for and isolating DBDpp having a selective affinity for a target of interest are largely conventional and known to those of ordinary skill in the art. In certain situations, it may be desirable to wash away any unbound DBDpp from a mixture of the target of interest and/or one or more DBDpp bound to the target of interest prior to attempting to determine or to detect the presence of a selective affinity interaction. Such a wash step may be particularly desirable when the target of interest is bound to a solid support.

It will be understood that the selection step of the methods described herein can be performed by way of a method commonly known as a selection method or a by way of a method commonly known as a screening method. Both methods envisage the identification and subsequent isolation (e.g., the selection step) of desirable components (e.g., DBDpp library members) from an original ensemble comprising both desirable and non-desirable components (e.g., a DBDpp library). In the case of a selection method, library members will typically be isolated by a step wherein the desired property is applied to obtain the desired goal; in such case, the desired property is usually restricted to the property of a high affinity for a given target interest. Such method is generally known as an affinity selection method and, such affinity selection method will be applied to a DBDpp library for the purpose of selecting DBDpp having a high affinity for a target of interest. In additional embodiments, the library is screened DBDpp having desired kinetic properties such as high on-rate for binding to a given target of interest, or low off-rate for library members bound to said target by adjusting the appropriate selection conditions (e.g. short incubation times or long wash cycles, or other conditions as is known by someone skilled in the art of library selection techniques). Alternatively, in the case of a screening method, library members will typically be isolated by a step wherein all library members, or at least a substantial collection of library members, are individually examined with respect to a given desired property, and wherein members having such desired property are retained whereas members not having such desired property are discarded; in such case, and in the context provided herein, desired properties may relate to either a high affinity for a target of interest, or a functional activity such as, the inhibition, reduction and/or prevention of the activity of a target of interest. Accordingly, it is submitted that the selection step of the methods may be accomplished by either an (affinity) selection technique or by an affinity-based or activity-based functional screening technique, both techniques resulting in the selection of one or more DBDpp having beneficial (favorable, desirable, superior) affinity or activity properties compared to the non-selected DBDpp of the DBDpp.

Screening of DBDpp

After selection, the identified members of the library can be individually isolated and screened.

A screening differs from a selection in that a screen is characterized by the analysis of library members individually (or in pools) whereas a selection is characterized by analysis of library members that are separated from other members during the process (e.g., retained, eluted, or washed off). In one embodiment, a collection of library members is directly screened, without being subjected to a selection step. This approach, for example, can be used during affinity maturation protocols that are known and can be routinely applied.

The ability of a DBDpp to specifically bind a target of interest can be determined using or routinely modifying assays and other methodologies described herein or otherwise known in the art. For example, DBDpp-target interaction can be assayed as described in the Examples below or alternatively, using in vitro or in vivo binding assays such as western blots, radioimmunoassays, ELISA (enzyme linked immunosorbent assay), "sandwich" immunoassays, immunoprecipitation assays, fluorescent immunoassays, protein A immunoassays, immunohistochemistry (IHC) and BIAcore analysis. Similarly, the ability of a DBDpp to specifically bind a target of interest and to alter the biological activity of the target can be determined using or routinely modifying assays and other methodologies described herein or otherwise known in the art. Assays evaluating the ability of a DBDpp to functionally affect its target (e.g., assays to measure signaling, proliferation, migration etc.) can also be used to indirectly assess DBDpp-target interaction. Additionally, DBDpp can be identified based on their effects in assays that measure particular pathways or activities. For example, assays that measure signaling pathways (e.g., phosphorylation studies or multimerization), ion channel fluxes, intracellular cAMP levels, cellular activities such as migration, adherence, proliferation, or apoptosis, and viral entry, replication, budding, or integration can be used to identify, characterize, and improve the desired properties of the DBDpp. The ability of a DBDpp to competitively inhibit another DBDpp-containing sequence can be determined using techniques known in the art, including ELISA and BIAcore analysis.

Identification of DBDpp

Where a DBDpp candidate contained in a library of DBDpp, is displayed on a suitable cell or phage or particle, the nucleic acid coding sequence can be isolated and routinely determined. It is possible to isolate from said cell or phage or particle, the nucleotide sequence that encodes that DBDpp sequence. In this way, the nucleotide sequence of the selected DBDpp library member(s) can be determined by routine sequencing methods.

DBDpp library members that are specific for the target can be characterized by nucleic acid sequencing. Sequence information is used to classify the members and to remove redundant members (i.e., members that encode that same DBDpp). DBDpp libraries and library members (including some members in which epitope tags have been added) according to several embodiments include, but are not limited to those identified in below in Table 1. Additionally included are those DBDpp that correspond to any of SEQ ID NOS: 2, 3, 4, 5, 6, 7, 8, 9, 10, or 11, wherein one or more of the $X_n$ positions are substituted with a natural or non-natural amino acid. In some embodiments, the DBDpp that correspond to any of SEQ ID NOS: 2, 3, 4, 5, 6, 7, 8, 9, 10, or 11 do not include cysteine and/or proline residues that are substituted into an $X_n$ position.

TABLE 1

Non-limiting Examples of DBDpp Libraries and Library Members

| SEQ ID NO | Sequence | Target | Library |
|---|---|---|---|
| 2 | MGSWX$_5$X$_6$FKX$_9$X$_{10}$LAX$_{13}$IKX$_{16}$X$_{17}$LEALGGSEAELAX$_{30}$FEX$_{33}$X$_{34}$IAX$_{37}$FEX$_{40}$X$_{41}$LQX$_{44}$YKGKGNPEVEALRKEAAAIRDELQAYRHN | | F1 |
| 3 | MGSWAEFKQRLAAIKTRLEALGGSEAELAAFX$_{32}$X$_{33}$EIX$_{36}$AFX$_{39}$X$_{40}$ELX$_{43}$AYKGKGNPEVEALX$_{57}$X$_{58}$EAX$_{61}$AIX$_{64}$X$_{65}$ELX$_{68}$AYRHN | | F2 |
| 4 | MGSWX$_5$EFX$_8$X$_9$RLX$_{12}$AIX$_{15}$X$_{16}$RLX$_{19}$ALGGSEAELAAFEKEIAAFESELQAYKGKGNPEVEX$_{55}$LRX$_{58}$X$_{59}$AAX$_{62}$IRX$_{65}$X$_{66}$LQAYRHN | | F3 |
| 5 | MGSWX$_5$X$_6$FKX$_9$X$_{10}$LAX$_{13}$IKX$_{16}$X$_{17}$LEALGGSEAELAAFX$_{32}$X$_{33}$EIX$_{36}$AFX$_{39}$X$_{40}$ELX$_{43}$AYKGKGNPEVEX$_{55}$LRX$_{58}$X$_{59}$AAX$_{62}$IRX$_{65}$X$_{66}$LQAYRHN | | C1 |
| 6 | MGSWX$_5$EFX$_8$X$_9$RLX$_{12}$AIX$_{15}$X$_{16}$RLX$_{19}$ALGGSEAELAX$_{30}$FEX$_{33}$X$_{34}$IAN$_{37}$FEX$_{40}$X$_{41}$LQX$_{44}$YKGKGNPEVEALX$_{57}$X$_{58}$EAX$_{61}$AIX$_{64}$X$_{65}$ELX$_{68}$AYRHN | | C2 |
| 7 | MGSWX$_5$X$_6$FKX$_9$X$_{10}$LAX$_{13}$IKX$_{16}$X$_{17}$LEALZ$_1$EAELAX$_{28}$FEX$_{31}$X$_{32}$IAX$_{35}$FEX$_{38}$X$_{39}$LQX$_{42}$YZ$_2$NPEVEALRKEAAAIRDELQAYRHN | | |
| 8 | MGSWAEFKQRLAAIKTRLEALZ$_1$EAELAAFX$_{30}$X$_{31}$EIX$_{34}$AFX$_{37}$X$_{38}$ELX$_{41}$AYZ$_2$NPEVEALX$_{52}$X$_{53}$EAX$_{56}$AIX$_{59}$X$_{60}$ELX$_{63}$AYRHN | | |
| 9 | MGSWX$_5$EFX$_8$X$_9$RLX$_{12}$AIX$_{15}$X$_{16}$RLX$_{19}$ALZ$_1$EAELAAFEKEIAAFESELQAYZ$_2$NPEVEX$_{50}$LRX$_{53}$X$_{54}$AAX$_{57}$IRX$_{60}$X$_{61}$LQAYRHN | | |
| 10 | MGSWX$_5$X$_6$FKX$_9$X$_{10}$LAX$_{13}$IKX$_{16}$X$_{17}$LEALZ$_1$EAELAAFX$_{30}$X$_{31}$EIX$_{34}$AFX$_{37}$X$_{38}$ELX$_{41}$AYZ$_2$NPEVEX$_{50}$LRX$_{53}$X$_{54}$AAX$_{57}$IRX$_{60}$X$_{61}$LQAYRHN | | |
| 11 | MGSWX$_5$EFX$_8$X$_9$RLX$_{12}$AIX$_{15}$X$_{16}$RLX$_{19}$ALZ$_1$EAELAX$_{28}$FEX$_{31}$X$_{32}$IAX$_{35}$FEX$_{38}$X$_{39}$LQX$_{42}$YZ$_2$NPEVEALX$_{52}$X$_{53}$EAX$_{56}$AIX$_{59}$X$_{60}$ELX$_{63}$AYRHN | | |
| 12 | MGSWVEFGHRLWAIDQRLYALGGSEAELAAFEKEIAAFESELQAYKGKGNPEVEKLRQRAAFIRFRLQAYRHN | CD137 | F3 |
| 13 | MGSWVEFANRLWAIDQRLFALGGSEAELAAFEKEIAAFESELQAYKGKGNPEVEHLRDQAAFIRHKLQAYRHN | CD137 | F3 |
| 14 | MGSWYEFRHRLWAIDQRLYALGGSEAELAAFEKEIAAFESELQAYKGKGNPEVEGLREAAAFIRAKLQAYRHN | CD137 | F3 |
| 15 | MGSWYEFSMRLWAIDQRLYALGGSEAELAAFEKEIAAFESELQAYKGKGNPEVEALRAKAAYIRWKLQAYRHN | CD137 | F3 |
| 16 | MGSWFEFNHRLWAINERLYALGGSEAELAAFEKEIAAFESELQAYKGKGNPEVERLRSMAAFIRYKLQAYRHN | CD137 | F3 |
| 17 | MGSWYEFGHRLWAIDQRLYALGGSEAELAAFEKEIAAFESELQAYKGKGNPEVEYLRETAAHIRTRLQAYRHN | CD137 | F3 |
| 18 | MGSWYEFHYRLHAIDQRLYALGGSEAELAAFEKEIAAFESELQAYKGKGNPEVEELRIKAAFIRDRLQAYRHN | CD137 | F3 |
| 19 | MGSWAEFKQRLAAIKTRLEALGGSEAELAAFLGEIWAFEMELAAYKGKGNPEVALGREAAAIRMELQAYRHN | CD137 | F2 |
| 20 | MGSWYEFDLRLHAIYDRLVALGGSEAELAAFEKEIAAFESELQAYKGKGNPEVEILRDNAAYIRQMLQAYRHN | CD47 | F3 |
| 21 | MGSWTEFTYRLSAIEWRLWALGGSEAELAWFEQKIAFFEDFLQYYKGKGNPEVEALKHEAGAILNELMAYRHN | CD47 | C2 |
| 22 | MGSWAEFDHRLHAIRERLHALGGSEAELAAFEKEIAAFESELQAYKGKGNPEVEILRGNAAYIRALLQAYRHN | CD47 | F3 |
| 23 | MGSWTEFVGRLAAIEFRLWALGGSEAELAWFEAHIAFFEDYLQWYKGKGNPEVEALREEAGAIMEELKAYRHN | CD47 | C2 |
| 24 | MGSWTEFYSRLEAIWVRLQALGGSEAELAMFEDRIAHFEWFLQQYKGKGNPEVEALHEEAIAIRKELAAYRHN | CD47 | C2 |
| 25 | MGSWHEFHDRLQAIHERLYALGGSEAELAAFEKEIAAFESELQAYKGKGNPEVESLRIAAAHIRQVLQAYRHN | CTLA4 | F3 |
| 26 | MGSWNYFKDHLAWIKNSLEALGGSEAELAHFETAIASFERQLQEYKGKGNPEVEALRKEAAAIRDELQAYRHN | DR5 | F1 |

TABLE 1-continued

Non-limiting Examples of DBDpp Libraries and Library Members

| SEQ ID NO | Sequence | Target | Library |
|---|---|---|---|
| 27 | MGSWLYFKEHLAHIKAWLEALGGSEAELAHFELAIADFEYHLQEYK GKGNPEVEALRKEAAAIRDELQAYRHN | DR5 | F1 |
| 28 | MGSWVYFKEHLAWIKTELEALGGSEAELAHFEHSIADFEMSLQFYKG KGNPEVEALRKEAAAIRDELQAYRHN | DR5 | F1 |
| 29 | MGSWFYFKQHLAWIKSYLEALGGSEAELAHFERAIAAFEQHLQMYK GKGNPEVEALRKEAAAIRDELQAYRHN | DR5 | F1 |
| 30 | MGSWHYFKDHLAEIKGLLEALGGSEAELAHFEMAIADFEHNLQYYK GKGNPEVEALRKEAAAIRDELQAYRHN | DR5 | F1 |
| 31 | MGSWHYFKGHLAEIKNHLEALGGSEAELAHFERAIAAFERSLQWYK GKGNPEVEALRKEAAAIRDELQAYRHN | DR5 | F1 |
| 32 | MGSWIYFKEHLAYIKKELEALGGSEAELAHFESAIAVFESTLQYYKGK GNPEVEALRKEAAAIRDELQAYRHN | DR5 | F1 |
| 33 | MGSWTYFKEHLAEIKYMLEALGGSEAELAHFEVAIADFEKMLQYYK GKGNPEVEALRKEAAAIRDELQAYRHN | DR5 | F1 |
| 34 | MGSWWLFKDHLAEIKTALEALGGSEAELAHFEMAIAAFEKQLQYYK GKGNPEVEALRKEAAAIRDELQAYRHN | DR5 | F1 |
| 35 | MGSWSEFYNRLDAIESRLLALGGSEAELALFEIQIARFEKVLQAYKGK GNPEVEALRGEARAIFAELYAYRHN | KIR | C2 |
| 36 | MGSWYEFYNRLYAIEIRLYALGGSEAELAAFEKEIAAFESELQAYKG KGNPEVERLRVRAAKIRVILQAYRHN | KIR | F3 |
| 37 | MGSWLWFKIFLAEIKYFLEALGGSEAELAAFDFEIHAFHVELFAYKG KGNPEVEVLREVAAEIRWDLQAYRHN | KIR | C1 |
| 38 | MGSWTEFQSRLDAIHSRLRALGGSEAELAAFEKEIAAFESELQAYKG KGNPEVELLRDDAAFIRHFLQAYRHN | PD-L1 | F3 |
| 39 | MGSWQEFDDRLNAIKARLQALGGSEAELAAFEKEIAAFESELQAYKG KGNPEVEDLRDDAAFIRRFLQAYRHN | PD-L1 | F3 |
| 40 | MGSWYEFQNRLHAIHERLNALGGSEAELAAFEKEIAAFESELQAYKG KGNPEVELLRDDAAFIRHFLQAYRHN | PD-L1 | F3 |
| 41 | MGSWFEFQDRLTAINERLSALGGSEAELAAFEKEIAAFESELQAYKGK GNPEVETLRSDAAFIRRFLQAYRHN | PD-L1 | F3 |
| 42 | MGSWYEFESRLDAIHERLHALGGSEAELAAFEKEIAAFESELQAYKG KGNPEVENLRGDAAFIRHFLQAYRHN | PD-L1 | F3 |
| 43 | MGSWYEFNHRLDAISKRLNALGGSEAELAAFEKEIAAFESELQAYKG KGNPEVEELRGDAAFIRHFLQAYRHN | PD-L1 | F3 |
| 44 | MGSWFEFENRLHAIVHRLGALGGSEAELAAFEKEIAAFESELQAYKG KGNPEVETLRADAAFIRHYLQAYRHN | PD-L1 | F3 |
| 45 | MGSWVVFKVDLATIKYILEALGGSEAELAEFEGEIAGFEYSLQFYKGK GNPEVEALRKEAAAIRDELQAYRHN | TIM3 | F1 |
| 46 | MGSWTIFKEWLAFIKTDLEALGGSEAELAFFEGWIASFEMELQKYKG KGNPEVEALRKEAAAIRDELQAYRHN | PD1 | F1 |
| 47 | MGSWVMFKWLLADIKSHLEALGGSEAELAFFEGFIAAFETHLQVYKG KGNPEVEALRKEAAAIRDELQAYRHN | PD1 | F1 |
| 48 | MGSWYAFKDYLADIKGWLEALGGSEAELAFFEIFIARFELELQAYKG KGNPEVEALRKEAAAIRDELQAYRHN | PD1 | F1 |
| 49 | MGSWAEFKQRLAAIKTRLQALGGSEAELAAFEKEIAAFESELQAYKG KGNPEVEALRKEAAAIRDELQAYRHN | None | |
| 51 | MGSWVEFGHRLWAIDQRLYALGGSEAELAAFEKEIAAFESELQAYK GKGNPEVEKLRQRAAFIRFRLQAYRHNGGGGSHHHHHH | CD137 | F3 |

TABLE 1-continued

Non-limiting Examples of DBDpp Libraries and Library Members

| SEQ ID NO | Sequence | Target | Library |
|---|---|---|---|
| 52 | MGSWVEFANRLWAIDQRLFALGGSEAELAAFEKEIAAFESELQAYKG KGNPEVEHLRDQAAFIRHKLQAYRHNGGGGSHHHHHH | CD137 | F3 |
| 53 | MGSWYEFRHRLWAIDQRLYALGGSEAELAAFEKEIAAFESELQAYKG KGNPEVEGLREAAAFIRAKLQAYRHNGGGGSHHHHHH | CD137 | F3 |
| 54 | MGSWYEFSMRLWAIDQRLYALGGSEAELAAFEKEIAAFESELQAYK GKGNPEVEALRAKAAYIRWKLQAYRHNGGGGSHHHHHH | CD137 | F3 |
| 55 | MGSWFEFNHRLWAINERLYALGGSEAELAAFEKEIAAFESELQAYKG KGNPEVERLRSMAAFIRYKLQAYRHNGGGGSHHHHHH | CD137 | F3 |
| 56 | MGSWYEFGHRLWAIDQRLYALGGSEAELAAFEKEIAAFESELQAYK GKGNPEVEYLRETAAHIRTRLQAYRHNGGGGSHHHHHH | CD137 | F3 |
| 57 | MGSWYEFHYRLHAIDQRLYALGGSEAELAAFEKEIAAFESELQAYKG KGNPEVEELRIKAAFIRDRLQAYRHNGGGGSHHHHHH | CD137 | F3 |
| 58 | MGSWAEFKQRLAAIKTRLEALGGSEAELAAFLGEIWAFEMELAAYK GKGNPEVEALGREAAAIRMELQAYRHNGGGGSHHHHHH | CD137 | F2 |
| 60 | MGSWIEFEDRLDAITDRLWALGGSEAELAEFEHQIAFFEEDLQWYKG KGNPEVEALHMEAEAIMEELGAYRHN | CD123 | C2 |
| 61 | MGSWVEFEYRLDAISDRLWALGGSEAELAFFENEIASFESDLQFYKG KGNPEVEALMFEAEAIDDELHAYRHN | CD123 | C2 |
| 62 | MGSWYEFEDRLAAIEARLWALGGSEAELADFEEEIAYFEHGLQWYK GKGNPEVEALESEAMAIIDELHAYRHN | CD123 | C2 |
| 63 | MGSWYEFEERLDAIEDRLIALGGSEAELAIFEDIIAFFEQDLQYYKGKG NPEVEALEMEAEAISIELDAYRHN | CD123 | C2 |
| 64 | MGSWWEFEDRLWAIDRRLMALGGSEAELAVFEQMIAHFEQILQVYK GKGNPEVEALHFEAHAIGMELAAYRHN | CD123 | C2 |
| 65 | MGSWEEFHERLDAIDERLEALGGSEAELAFFEDDIASFEDWLQWYKG KGNPEVEALSREADAINFELEAYRHN | CD123 | C2 |
| 66 | MGSWEEFDKRLDAITRRLMALGGSEAELAEFESTIAWFEWDLQEYK GKGNPEVEALDWEAYAIDYELGAYRHN | CD123 | C2 |
| 67 | MGSWSEFVDRLDAIFDRLWALGGSEAELAWFEDTIAHFEWNLQEYK GKGNPEVEALNGEADAITDELHAYRHN | CD123 | C2 |
| 68 | MGSWWEFTDRLDAIFDRLWALGGSEAELAAFEESIAIFEQDLQYYKG KGNPEVEALEYEANAIQYELEAYRHN | CD123 | C2 |
| 69 | MGSWWEFTDRLEAIEDRLWALGGSEAELAHFEDSIAQFEQELQWYK GKGNPEVEALADEADAIESELHAYRHN | CD123 | C2 |
| 70 | MGSWEWFKSDLASIKWELEALGGSEAELAWFEHDIAEFEEDLQWYK GKGNPEVEALRKEAAAIRDELQAYRHN | CD123 | F1 |
| 71 | MGSWDHFKNDLAWIKKHLEALGGSEAELAEFEAVIAYFELYLQGYK GKGNPEVEALRKEAAAIRDELQAYRHN | CD123 | F1 |
| 72 | MGSWEFFKEVLAEIKYDLEALGGSEAELAWFETDIAGFEIDLQVYKG KGNPEVEALRKEAAAIRDELQAYRHN | CD123 | F1 |
| 73 | MGSWYDFKEDLADIKWMLEALGGSEAELAEFENVIAYFENDLQEYK GKGNPEVEALRKEAAAIRDELQAYRHN | CD123 | F1 |
| 74 | MGSWSFFKDDLAEIKYFLEALGGSEAELAMFEQTIAEFEYDLQDYKG KGNPEVEALRKEAAAIRDELQAYRHN | CD123 | F1 |
| 75 | MGSWVTFKDELADIKDFLEALGGSEAELAFFEVDIAEFEALQFYKG KGNPEVEALRKEAAAIRDELQAYRHN | CD123 | F1 |
| 76 | MGSWSWFKEDLADIKFELEALGGSEAELAWFELDIADFEQALQQYK GKGNPEVEALRKEAAAIRDELQAYRHN | CD123 | F1 |

TABLE 1-continued

Non-limiting Examples of DBDpp Libraries and Library Members

| SEQ ID NO | Sequence | Target | Library |
|---|---|---|---|
| 77 | MGSWWEFKEDLAEIKWFLEALGGSEAELAWFEHDIAKFEFELQYYKGKGNPEVEALRKEAAAIRDELQAYRHN | CD123 | F1 |
| 78 | MGSWDEFKEDLAHIKTDLEALGGSEAELALFEDEIADFEMYLQHYKGKGNPEVEALRKEAAAIRDELQAYRHN | CD123 | F1 |
| 79 | MGSWFMFKEELADIKDWLEALGGSEAELASFESYIAWFEQDLQWYKGKGNPEVEALRKEAAAIRDELQAYRHN | CD123 | F1 |
| 80 | MGSWQIFKGELAYIKQYLEALGGSEAELAFFEFDIAEFEEDLQYYKGKGNPEVEALRKEAAAIRDELQAYRHN | CD123 | F1 |
| 81 | MGSWYIFKEDLAEIKEELEALGGSEAELAYFEEEIALFEMELQWYKGKGNPEVEALRKEAAAIRDELQAYRHN | CD123 | F1 |
| 82 | MGSWYYFKDELADIKWDLEALGGSEAELAWFEMLIAQFELDLQWYKGKGNPEVEALRKEAAAIRDELQAYRHN | CD123 | F1 |
| 83 | MGSWFNFKEELAVIKFQLEALGGSEAELAFFEWVIADFEDDLQEYKGKGNPEVEALRKEAAAIRDELQAYRHN | CD123 | F1 |
| 84 | MGSWYMFKEELADIKWYLEALGGSEAELAWFEDDIAGFEWDLQAYKGKGNPEVEALRKEAAAIRDELQAYRHN | CD123 | F1 |
| 85 | MGSWHVFKTELADIKFYLEALGGSEAELAMFELWIAEFEHELQDYKGKGNPEVEALRKEAAAIRDELQAYRHN | CD123 | F1 |
| 86 | MGSWYVFKDELAEIKQFLEALGGSEAELAWFEDDIAEFETQLQHYKGKGNPEVEALRKEAAAIRDELQAYRHN | CD123 | F1 |
| 87 | MGSWTEFKGELAEIKWILEALGGSEAELAFFEDEIAAFEWDLQKYKGKGNPEVEALRKEAAAIRDELQAYRHN | CD123 | F1 |
| 88 | MGSWFWFKEDLAFIKEDLEALGGSEAELAWFEDGIAFFEWDLQDYKGKGNPEVEALRKEAAAIRDELQAYRHN | CD123 | F1 |
| 89 | MGSWSWFKEDLASIKAVLEALGGSEAELAFFESDIAEFEQELQYYKGKGNPEVEALRKEAAAIRDELQAYRHN | CD123 | F1 |
| 90 | MGSWILFKDDLAWIKETLEALGGSEAELAFFEDNIADFEEQLQGYKGKGNPEVEALRKEAAAIRDELQAYRHN | CD123 | F1 |
| 91 | MGSWQWFKDDLAYIKETLEALGGSEAELALFEDMIADFEFELQWYKGKGNPEVEALRKEAAAIRDELQAYRHN | CD123 | F1 |
| 92 | MGSWEEFHSRLDAIDDRLWALGGSEAELAAFEKEIAAFESELQAYKGKGNPEVEWLRWEAATIRETLQAYRHN | CD123 | F3 |
| 93 | MGSWSEFWQRLEAIEDRLWALGGSEAELAAFEKEIAAFESELQAYKGKGNPEVEWLRENAAMIRDELQAYRHN | CD123 | F3 |
| 94 | MGSWTEFAWRLDAIYDRLLALGGSEAELAAFEKEIAAFESELQAYKGKGNPEVEWLRHVAANIRRELQAYRHN | CD123 | F3 |
| 95 | MGSWDEFYYRLEAIEMRLGALGGSEAELAAFEKEIAAFESELQAYKGKGNPEVEELRHYAAQIRHMLQAYRHN | CD123 | F3 |
| 96 | MGSWIEFNMRLDAIYERLVALGGSEAELAAFEKEIAAFESELQAYKGKGNPEVEWLRKVAANIRLELQAYRHN | CD123 | F3 |
| 97 | MGSWSEFNMRLDAIYERLTALGGSEAELAAFEKEIAAFESELQAYKGKGNPEVEWLRHSAARIRLELQAYRHN | CD123 | F3 |
| 98 | MGSWVEFNIRLDAIYERLYALGGSEAELAAFEKEIAAFESELQAYKGKGNPEVEKLRHWAASIRRELQAYRHN | CD123 | F3 |
| 99 | MGSWDEFGRRLYAIEWRLYALGGSEAELAAFEKEIAAFESELQAYKGKGNPEVEKLREIAAVIRSNLQAYRHN | CD123 | F3 |
| 100 | MGSWIEFYDRLEAIYDRLDALGGSEAELAAFEKEIAAFESELQAYKGKGNPEVEWLREDAAFIRSWLQAYRHN | CD123 | F3 |

TABLE 1-continued

Non-limiting Examples of DBDpp Libraries and Library Members

| SEQ ID NO | Sequence | Target | Library |
|---|---|---|---|
| 101 | MGSWTEFDRRLDAIWDRLFALGGSEAELAAFEKEIAAFESELQAYKGKGNPEVEWLREEAADIRDYLQAYRHN | CD123 | F3 |
| 102 | MGSWTEFDRRLDAIWDRLFALGGSEAELAAFEKEIAAFESELQAYKGKGNPEVEWLREEAADIRDYLQAYRHN | CD123 | F3 |
| 103 | MGSWIEFEVRLDAIYNRLAALGGSEAELAAFEKEIAAFESELQAYKGKGNPEVERLRRYAANIRHELQAYRHN | CD123 | F3 |
| 104 | MGSWTEFHDRLEAIDDRLWALGGSEAELAAFEKEIAAFESELQAYKGKGNPEVEYLREEAAQIRWELQAYRHN | CD123 | F3 |
| 105 | MGSWYEFHHRLDAIYERLLALGGSEAELAAFEKEIAAFESELQAYKGKGNPEVEWLRSSAANIRKELQAYRHN | CD123 | F3 |
| 106 | MGSWHEFDQRLWAIEERLWALGGSEAELAAFEKEIAAFESELQAYKGKGNPEVETLRLYAALIRHDLQAYRHN | CD123 | F3 |
| 107 | MGSWIEFESRLWAIEDRLLALGGSEAELAAFEKEIAAFESELQAYKGKGNPEVEFLRLEAADIREDLQAYRHN | CD123 | F3 |
| 108 | MGSWYEFENREGAIGDRLWALGGSEAELAAFEKEIAAFESELQAYKGKGNPEVEWLRDEAAYIRAVLQAYRHN | CD123 | F3 |
| 109 | MGSWNEFYDRLSAIYFRLQALGGSEAELAAFEKEIAAFESELQAYKGKGNPEVEHLRWYAADIRMILQAYRHN | CD123 | F3 |
| 110 | MGSWYEFEYRLEAIEDRLWALGGSEAELAAFEKEIAAFESELQAYKGKGNPEVEYLREEAAWIRVWLQAYRHN | CD123 | F3 |
| 111 | MGSWVEFENRLEAIENRLWALGGSEAELAAFEKEIAAFESELQAYKGKGNPEVEWLREDAAQIRMMLQAYRHN | CD123 | F3 |
| 112 | MGSWYEFWDRLEAIDDRLWALGGSEAELAAFEKEIAAFESELQAYKGKGNPEVEALRQEAAWIREELQAYRHN | CD123 | F3 |
| 113 | MGSWFEFWDRLDAIEDRLYALGGSEAELAAFEKEIAAFESELQAYKGKGNPEVEELRDEAAWIRGTLQAYRHN | CD123 | F3 |
| 114 | MGSWTEFDRRLDAIWDRLFALGGSEAELAAFEKEIAAFESELQAYKGKGNPEVEWLREEAADIRDYLQAYRHN | CD123 | F3 |
| 115 | MGSWWEFEMRLEAIEDRLFALGGSEAELAAFEKEIAAFESELQAYKGKGNPEVESLRWEAAFIRDILQAYRHN | CD123 | F3 |
| 116 | MGSWVEFYDRLHAIYFRLLALGGSEAELAAFEKEIAAFESELQAYKGKGNPEVEDERWYAADIRLVLQAYRHN | CD123 | F3 |
| 117 | MGSWYEFYNRLSAIYARLQALGGSEAELAAFEKEIAAFESELQAYKGKGNPEVEDLRWYAADIRYMLQAYRHN | CD123 | F3 |
| 118 | MGSWFEFWGRLEAIESRLKALGGSEAELAAFEKEIAAFESELQAYKGKGNPEVEELREHAAWIRAYLQAYRHN | CD123 | F3 |
| 119 | MGSWTEFSIRLEAIYDREVALGGSEAELAAFEKEIAAFESELQAYKGKGNPEVEVLRTYAANIRHELQAYRHN | CD123 | F3 |
| 120 | MGSWYEFENRLEAIEERLWALGGSEAELAAFEKEIAAFESELQAYKGKGNPEVEMLREEAAFIRDWLQAYRHN | CD123 | F3 |
| 121 | MGSWYEFVIRLEAIEDRLWALGGSEAELAAFEKEIAAFESELQAYKGKGNPEVEVLRWYAADIRHELQAYRHN | CD123 | F3 |
| 122 | MGSWIEFEDRLEAIEDRLFALGGSEAELAAFEKEIAAFESELQAYKGKGNPEVEWLRQEAAEIRLMLQAYRHN | CD123 | F3 |
| 123 | MGSWTEFNERLDAIYDREMALGGSEAELAAFEKEIAAFESELQAYKGKGNPEVEWLRASAAAIRVELQAYRHN | CD123 | F3 |
| 124 | MGSWSEFYLRLDAIYDRLDALGGSEAELAAFEKEIAAFESELQAYKGKGNPEVEWLRKTAANIREELQAYRHN | CD123 | F3 |

TABLE 1-continued

Non-limiting Examples of DBDpp Libraries and Library Members

| SEQ ID NO | Sequence | Target | Library |
|---|---|---|---|
| 125 | MGSWSEFHVRLDAIYARLDALGGSEAELAAFEKEIAAFESELQAYKGKGNPEVERLREWAANIRRELQAYRHN | CD123 | F3 |
| 126 | MGSWHEFGVRLDAIYDRLMALGGSEAELAAFEKEIAAFESELQAYKGKGNPEVEFLRQAAANIRSELQAYRHN | CD123 | F3 |
| 127 | MGSWYEFSMRLDAIYDRLMALGGSEAELAAFEKEIAAFESELQAYKGKGNPEVEQLRGYAANIRNELQAYRHN | CD123 | F3 |
| 128 | MGSWDEFGRRLYAIEWQLYALGGSEAELAAFEKEIAAFESELQAYKGKGNPEVEKLREIAAVIRSNLQAYRHN | CD123 | F3 |
| 129 | MGSWDEFGRRLYAIEWRLYALGGEEAELAAFEKEIAAFESELQAYKGKGNPEVEKLREIAAVIRSNLQAYRHN | CD123 | F3 |
| 130 | MGSWDEFGRRLYAIEWRLYALGGSEAELAAFEKEIAAFESELQAYKGKGNPEVEKLREIAAVIRENLQAYRHN | CD123 | F3 |
| 131 | MGSWDEFGRRLYAIEWQLYALGGEEAELAAFEKEIAAFESELQAYKGKGNPEVEKLREIAAVIRSNLQAYRHN | CD123 | F3 |
| 132 | MGSWDEFGRRLYAIEWQLYALGGTEAELAAFEKEIAAFESELQAYKGKGNPEVEKLREIAAVIRSNLQAYRHN | CD123 | F3 |
| 133 | MGSWDEFGRRLYAIEWQLYALGGGEAELAAFEKEIAAFESELQAYKGKGNPEVEKLREIAAVIRSNLQAYRHN | CD123 | F3 |
| 134 | MGSWDEFGRRLYAIEWQLYALGGEEAELAAFEKEIAAFESELQAYKGKGNPEVEKLREIAAVIRENLQAYRHN | CD123 | F3 |
| 135 | MGSWDEFGRRLYAIEWQLYALGGTEAELAAFEKEIAAFESELQAYKGKGNPEVEKLREIAAVIRENLQAYRHN | CD123 | F3 |
| 136 | MGSWDEFGRRLYAIEWQLYALGGGEAELAAFEKEIAAFESELQAYKGKGNPEVEKLREIAAVIRENLQAYRHN | CD123 | F3 |
| 137 | MGSWEEFELRLNAIEERLYALGGSEAELAYFEYVIADFEGNLQRYKGKGNPEVEALYFEADAIFEELVAYRHN | CD19 | C2 |
| 138 | MGSWFEFNHRLWAIFERLMALGGSEAELAAFEKEIAAFESELQAYKGKGNPEVEYLRAMAAVIRYHLQAYRHN | CD19 | F3 |
| 139 | MGSWEEFDGRLFAIEQRLQALGGSEAELAAFEKEIAAFESELQAYKGKGNPEVEVLRWFAAGIRDFLQAYRHN | CD19 | F3 |
| 140 | MGSWAEFYHRLYAIETRLSALGGSEAELAAFEKEIAAFESELQAYKGKGNPEVEYLRHWAAWIRTYLQAYRHN | CD19 | F3 |
| 141 | MGSWVEFSDRLYAIEERLWALGGSEAELAAFEKEIAAFESELQAYKGKGNPEVEELRELAAIIRHSLQAYRHN | CD19 | F3 |
| 142 | MGSWWEFEGRLYAIEERLTALGGSEAELAAFEKEIAAFESELQAYKGKGNPEVEYLREWAAWIRQMLQAYRHN | CD19 | F3 |
| 143 | MGSWWEFEHRLYAIEERLVALGGSEAELAAFEKEIAAFESELQAYKGKGNPEVEYLRNWAAYIRMALQAYRHN | CD19 | F3 |
| 144 | MGSWWEFEARLYAIEFRLSALGGSEAELAAFEKEIAAFESELQAYKGKGNPEVEYLRSWAAYIRTSLQAYRHN | CD19 | F3 |
| 145 | MGSWWEFEARLWAIESRLKALGGSEAELAAFEKEIAAFESELQAYKGKGNPEVEYLRHWAAYIRVILQAYRHN | CD19 | F3 |
| 146 | MGSWWEFEARLYAIEFRLSALGGSEAELAAFEKEIAAFESELQAYKGKGNPEVEYLRSWAAYIRTSLQAYRHN | CD19 | F3 |
| 147 | MGSWEEFYHRLDAIELRLYALGGSEAELAAFEKEIAAFESELQAYKGKGNPEVEYLRWYAAEIREILQAYRHN | CD19 | F3 |
| 148 | MGSWYEFYERLDAIDTRLWALGGSEAELAAFEKEIAAFESELQAYKGKGNPEVEFLREYAAEIRHFLQAYRHN | CD19 | F3 |

TABLE 1-continued

Non-limiting Examples of DBDpp Libraries and Library Members

| SEQ ID NO | Sequence | Target | Library |
|---|---|---|---|
| 149 | MGSWNEFFDRLDAILYRLDALGGSEAELAAFEKEIAAFESELQAYKGKGNPEVEYLRFVAADIRSWLQAYRHN | CD19 | F3 |
| 150 | MGSWIEFDDRLLAIMDRLWALGGSEAELAAFEKEIAAFESELQAYKGKGNPEVEDLRDVAADIRHYLQAYRHN | CD19 | F3 |
| 151 | MGSWYEFWERLDAITFRLYALGGSEAELAAFEKEIAAFESELQAYKGKGNPEVEDLRTWAADIRAILQAYRHN | CD19 | F3 |
| 152 | MGSWEEFYIRLDAIMERLWALGGSEAELAAFEKEIAAFESELQAYKGKGNPEVEDLRYAAADIRHFLQAYRHN | CD19 | F3 |
| 153 | MGSWIEFEERLYAIETRELALGGSEAELAAFEKEIAAFESELQAYKGKGNPEVEFLRVVAADIREWLQAYRHN | CD19 | F3 |
| 154 | MGSWIEFEHRLSAINDRLYALGGSEAELAAFEKEIAAFESELQAYKGKGNPEVEDLREWAADIRSLLQAYRHN | CD19 | F3 |
| 155 | MGSWFEFEMRLDAIMARLWALGGSEAELAAFEKEIAAFESELQAYKGKGNPEVEDLRYAAADIRDYLQAYRHN | CD19 | F3 |
| 156 | MGSWYEFVYRLDAIYDRLWALGGSEAELAAFEKEIAAFESELQAYKGKGNPEVEDLRYAAADIRDFLQAYRHN | CD19 | F3 |
| 157 | MGSWVEFEDRLDAILERLWALGGSEAELAAFEKEIAAFESELQAYKGKGNPEVEDLRELAADIRDFLQAYRHN | CD19 | F3 |
| 158 | MGSWFEFEERLIAIEERLFALGGSEAELAAFEKEIAAFESELQAYKGKGNPEVEYLRWIAADIRDVLQAYRHN | CD19 | F3 |
| 159 | MGSWIEFADRLDAILDRLDALGGSEAELAAFEKEIAAFESELQAYKGKGNPEVEWLREIAADIRAYLQAYRHN | CD19 | F3 |
| 160 | MGSWLEFEYRLDAILDRLFALGGSEAELAAFEKEIAAFESELQAYKGKGNPEVEDLREVAADIRMLLQAYRHN | CD19 | F3 |
| 161 | MGSWYEFHDRLDAITNRLYALGGSEAELAAFEKEIAAFESELQAYKGKGNPEVEDLRDWAADIRVWLQAYRHN | CD19 | F3 |
| 162 | MGSWQEFEQRLDAINWRLWALGGSEAELAAFEKEIAAFESELQAYKGKGNPEVEELREWAADIRIFLQAYRHN | CD19 | F3 |
| 163 | MGSWYEFYSRLDAIDSRLYALGGSEAELAAFEKEIAAFESELQAYKGKGNPEVEFLRDYAAEIRRYLQAYRHN | CD19 | F3 |
| 164 | MGSWEEFHDRLEAISDRLWALGGSEAELAAFEKEIAAFESELQAYKGKGNPEVEDLRDWAADIRFYLQAYRHN | CD19 | F3 |
| 165 | MGSWWEFDERLYAIEDRLFALGGSEAELAAFEKEIAAFESELQAYKGKGNPEVEWLRIVAADIREILQAYRHN | CD19 | F3 |
| 166 | MGSWEEFEYRLMAIEVRLWALGGSEAELAAFEKEIAAFESELQAYKGKGNPEVEVLREIAADIRQILQAYRHN | CD19 | F3 |
| 167 | MGSWVVFKQRLAYIKDLLEALGGSEAELAYFEMSIAFFEEDLQVYKGKGNPEVEALRKEAAAIRDELQAYRHN | CD22 | F1 |
| 168 | MGSWYEFKNDLAWIKVHLEALGGSEAELAYFEFRIAHFENALQYYKGKGNPEVEALRKEAAAIRDELQAYRHN | CD22 | F1 |
| 169 | MGSWVEFYNRLWAIDHRLHALGGSEAELAAFEKEIAAFESELQAYKGKGNPEVEVLRYHAASIRVTLQAYRHN | CD22 | F3 |
| 170 | MGSWSEFYDRLHAIHHRLYALGGSEAELAAFEKEIAAFESELQAYKGKGNPEVEALRDTAAFIRTRLQAYRHN | CD22 | F3 |
| 171 | MGSWKEFHFRLHAIEHRLIALGGSEAELAAFEKEIAAFESELQAYKGKGNPEVEFLRAKAANIRTHLQAYRHN | CD22 | F3 |
| 172 | MGSWFEFHGRLHAIYGRLSALGGSEAELAAFEKEIAAFESELQAYKGKGNPEVEHLRAHAAHIRDHLQAYRHN | CD22 | F3 |
| 173 | MGSWYEFADRLHAIHQRLYALGGSEAELAAFEKEIAAFESELQAYKGKGNPEVEALRMTAAFIRSRLQAYRHN | CD22 | F3 |

TABLE 1-continued

Non-limiting Examples of DBDpp Libraries and Library Members

| SEQ ID NO | Sequence | Target | Library |
|---|---|---|---|
| 174 | MGSWNEFYNRLHAIHQRLYALGGSEAELAAFEKEIAAFESELQAYKG KGNPEVESLRQTAAYIRDRLQAYRHN | CD22 | F3 |
| 175 | MGSWNEFADRLHAIHQRLYALGGSEAELAAFEKEIAAFESELQAYKG KGNPEVESLRMTAAFIRSRLQAYRHN | CD22 | F3 |
| 176 | MGSWTEFSYRLGAIQSRLHALGGSEAELAAFEKEIAAFESELQAYKG KGNPEVEHLRYNAAKIRHFLQAYRHN | CD22 | F3 |
| 177 | MGSWQEFTTRLEAIYHRLRALGGSEAELANFEGFIAEFEGNLQMYKG KGNPEVEALVHEAYAIMEELHAYRHN | DR5 | C2 |
| 178 | MGSWVEFFDRLKAIHDRLEALGGSEAELAHFEKLIAHFEHRLQNYKG KGNPEVEALEKEADAILYELAAYRHN | DR5 | C2 |
| 179 | MGSWYYFKHHLAWIKMELEALGGSEAELAHFESSIASFERDLQQYK GKGNPEVEALRKEAAAIRDELQAYRHN | DR5 | F1 |
| 180 | MGSWVEFHIRLHAIQYRLYALGGSEAELAAFEKEIAAFESELQAYKG KGNPEVEELRHWAAFIRLQLQAYRHN | DR5 | F3 |
| 181 | MGSWNEFHDRLNAIHARLHALGGSEAELAAFEKEIAAFESELQAYKG KGNPEVENLRDDAAFIRRFLQAYRHN | PD-L1 | F3 |
| 182 | MGSWYEFTVRLEAIHERLKALGGSEAELAAFEKEIAAFESELQAYKG KGNPEVEILRDDAAFIRRFLQAYRHN | PD-L1 | F3 |
| 183 | MGSWKEFDDRLNAIKARLQALGGSEAELAAFEKEIAAFESELQAYKG KGNPEVEDLRDDAAFIRRFLQAYRHN | PD-L1 | F3 |
| 184 | MGSWYEFDDRENAIHDRLQALGGSEAELAAFEKEIAAFESELQAYKG KGNPEVEDLRDDAAFIRRFLQAYRHN | PD-L1 | F3 |
| 185 | MGSWNEFKNRLDAIHKRLNALGGSEAELAAFEKEIAAFESELQAYKG KGNPEVENLRDDAAFIRHFLQAYRHN | PD-L1 | F3 |
| 186 | MGSWTEFEQRLEAIHNRLQALGGSEAELAAFEKEIAAFESELQAYKG KGNPEVEELRNDAAFIRHFLQAYRHN | PD-L1 | F3 |

In some embodiments, the invention comprises one or more the sequences identified on Table 1. In other embodiments, the invention comprises one or more the sequences with 60-70%, 70-75%, 75-80%, 80-85%, 85-90%, 95-99% homology (and overlapping ranges therein) with those sequences identified on Table 1. In several embodiments, the sequences having such homology are functionally similar or identical as compared to the respective sequence identified on Table 1. In several embodiments, the invention comprises one or more polypeptides that compete with (wholly or partially) one or more of the sequences in Table 1 for its respective target. In several embodiments, the competition can be assessed by a standard competition assay. In some embodiments, competition does not require that the competing polypeptide compete for the same specific target as those polypeptides of Table 1, rather they can compete by binding a sterically inhibiting epitope, an overlapping epitope, etc.

Affinity Maturation of DBDpp

Affinity maturation strategies can be used to generate high affinity DBDpp that can be used in the DBDpp fusion proteins described herein.

Mutagenesis libraries may be created and screened to further optimize the sequence of the best binders. Lowman, Ann. Rev. Biophys. Biomol. Struct. 26: 401-24 (1997).

An improved DBDpp that specifically binds a desired target can also be prepared based on a known DBDpp sequence. For example, at least one, two, three, four, five, or more amino acid mutations (e.g., conservative or non-conservative substitutions), deletions or insertions can be introduced into a known DBDpp sequence and the resulting DBDpp can be screened for binding to the desired target and biological activity, such as the ability to antagonize target biological activity or agonize target biological activity.

Articles of Manufacture

Articles of manufacture, including, kits, are provided herein. The article of manufacture may comprise a container and a label or package insert on or associated with the container. Suitable containers include, for example, bottles, vials or syringes. The containers may be formed from a variety of materials such as glass or plastic. The container holds one or more DBDpp, nucleic acids encoding DBDpp and/or vectors or host cells of the present disclosure. The label or package insert may include directions for performing affinity based screening, detection, and/or purification.

Also provided are kits containing a DBDpp. Such kits have uses including, but not limited to detecting or isolating the target of interest to which the DBDpp specifically binds. Such assay kit may be useful in screening for the presence of a target of interest and/or quantitating the concentrations of a target of interest in a fluid, such as, a biological fluid (e.g., blood, serum, or synovial fluid).

In one embodiment a DBDpp assay kit is contemplated which comprises one or more containers of a DBDpp that specifically binds a target of interest and, optionally, a detection means for determining the presence or absence of a target/DBDpp interaction or the absence thereof. The kit further optionally contains target of interest protein that may be used, for example as a control or standard. The DBDpp may be free or expressed on the surface of a host cell or on the surface of a bacteriophage. In a specific embodiment, the DBDpp or target of interest provided in the kit is labeled. Any label known in the art can be used. In some embodiments, the label is selected from the group consisting of biotin, a fluorogen, an enzyme, an epitope, a chromogen, or a radionuclide. In some embodiments, the DBDpp is immobilized on a solid support. The detection means employed to detect the label will depend on the nature of the label and can be any known in the art, e.g., film to detect a radionuclide; an enzyme substrate that gives rise to or amplifies a detectable signal to detect the presence of a target of interest.

Preferably, the kit further comprises a solid support for the DBDpp, which may be provided as a separate element or on which a DBDpp that specifically binds a target of interest is immobilized. Hence, the DBDpp that specifically binds the target of interest in the kit may be immobilized on a solid support, or they may be immobilized on such support that is included with the kit or provided separately from the kit. Preferably, DBDpp is coated on a microtiter plate. In some embodiments, the detection involves a signal amplifying molecule. Where the signal amplifying molecule is an enzyme, the kit optionally further includes substrates and cofactors required by the enzyme, and where the amplifying molecule is a fluorophore. The kit optionally further includes a dye precursor that provides the detectable chromophore.

The kit may also contain instructions for carrying out the assay as well as other additives such as stabilizers, washing and incubation buffers, and the like. The components of the kit will be provided in predetermined ratios, with the relative amounts of the various reagents suitably varied to provide for concentrations in solution of the reagents that substantially maximize the sensitivity of the assay and/or the ability to purify the target of interest. Particularly, the reagents can be provided as dry powders, usually lyophilized, including excipients, which on dissolution will provide for a reagent solution having the appropriate concentration for combining with the sample to be tested.

Various formats and techniques for binding assays that can be used are known in the art and include but are not limited to, immobilization to filters such as nylon or nitrocellulose; two-dimensional arrays, enzyme linked immunosorbent assay (ELISA), radioimmuno-assay (RIA), competitive binding assays, direct and indirect sandwich assays, immunoprecipitation assays, fluorimetric microvolume assay technology (FMAT™), Luminex™ system assays, fluorescent resonance energy transfer (FRET), bioluminescence resonance energy transfer (BRET), electroimmunoassays, AlphaScreen™, nanoparticle-derived techniques, and surface plasmon resonance (SPR).

Binding assays can be homogeneous or semi-homogeneous. A homogeneous assay is an assay where all the components are mixed together, incubated, and then analyzed. A semi-homogeneous assay is one where the majority of the reaction takes place as a complex mixture, but a washing step is required prior to the addition of a final reagent and analysis, in contrast to a typical stepwise assembly sandwich assay where each component is added then washed off before the next component is added. In some embodiments the assay is an immunoassay. In certain embodiments the assay is a semi-homogeneous Enzyme Immuno-Assay (EIA), Applications DBDpp, whether alone, as fusion proteins, as chemical conjugates or as other embodiments described herein, have a variety of applications. In some embodiments, DBDpp are used as detection reagents, capture reagents, separation reagents, diagnostic reagents or analytical reagents. Some embodiments have in vivo, in vitro and/or ex vivo applications. Methods that employ the DBDpp in vitro can be performed in different formats, such as in microtiter plates, in protein arrays, on biosensor surfaces, on tissue sections, and in additional formats that would be apparent to a person skilled in the art. Likewise, methods that employ the DBDpp in vivo can be used in different formats that include but are not limited to DBDpp-Fc fusion proteins, CAR cells, and DBDpp multi-specific antibodies. In particular embodiments DBDpp such as DBDpp fusion proteins are used as a therapeutic agent.

Analytical and Diagnostic Applications

Whether alone, as fusion proteins, as chemical conjugates or as other embodiments described herein, DBDpp have a variety of applications. In some embodiments, DBDpp are used as detection reagents of targets of interest in a variety of different sample types.

In one embodiment a DBDpp are used to detect targets of interest in solutions involved in manufacturing processes, such as protein expression and purification. Samples may include, but are not limited to, water, buffers, in-process purification samples, bulk drug substance and final drug product. In still additional embodiments, the DBDpp can be used to detect and/or remove impurities or contaminants from a sample, such as a water supply source or water (or other fluid) used in manufacturing.

In another embodiment, DBDpp are used to detect targets of interest in diagnostic samples. Samples may include, but are not limited to tissue homogenates, cell extracts, biopsy samples, sera, plasma, lymph, blood, blood fractions, urine, synovial fluid, spinal fluid, saliva, mucous, sputum, pleural fluid, nipple aspirates, fluid of the respiratory, intestinal, and genitourinary tracts, tear fluid, breast milk, fluid from the lymphatic system, semen, cerebrospinal fluid, intra-organ system fluid, ascitic fluid, tumor cyst fluid, amniotic fluid, and media or lysate from cultured cells.

In one embodiment, the DBDpp are useful for detecting the presence of a factor or multiple factors (e.g., antigens or organisms) in a biological sample. The term "detecting" as used herein encompasses quantitative or qualitative detection. In certain embodiments, a biological sample comprises a cell, tissue or fluid. In certain embodiments, such tissues include normal and/or cancerous tissues.

Various formats and techniques for detection are known in the art and include but are not limited to Western Blot analysis, Immunohistochemistry, ELISA, FACS analysis, enzymatic assays, autoradiography and any of the binding assays mentioned herein.

In one embodiment, a method is provided for detecting a target of interest in a solution containing the target comprising: (a) contacting the solution with a DBDpp that specifically binds the target of interest under conditions suitable for specific binding of the DBDpp to the target and (b) detecting binding of the DBDpp and target. The DBDpp may be either free or immobilized. Sufficient time is allowed to permit binding between the target of interest and the DBDpp, and non-binding components in the solution or mixture are removed or washed away. The formation of a binding complex between the DBDpp and the target of interest can then be detected, for example, by detecting the signal from a label on the DBDpp, which is one component of the binding complex. A label may be any label that generates a signal that can be detected by standard methods, such as a fluorescent label, a radioactive compound, or an enzyme that reacts with a substrate to generate a detectable signal. Examples of suitable labels for such purposes are described herein and/or otherwise known in the art.

DBDpp that bind to a of interest can be detectably labeled through the use of radioisotopes, affinity labels (such as biotin, avidin, etc.), enzymatic labels (such as horseradish peroxidase, alkaline phosphatase, etc.) using methods known in the art, such as described in WO 00/70023 and (Harlow and Lane (1989) Antibodies, Cold Spring Harbor Laboratory, pp. 1-726).

The detectable marker or label can be any which is capable of producing, either directly or indirectly, a measurable signal, such as a radioactive, chromogenic, luminescence, or fluorescent signal, which can be used to quantitate the amount of bound detectable moiety or label in a sample. Detectable labels known in the art include radioisotopes, such as 3H, 14C, 32P, 35S, or 125I, electrochemiluminescent labels (such as Ruthenium (Ru)-based catalyst in conjunction with substrates, etc.), luminescent or bioluminescent labels (e.g., Europium, Vanadium), fluorescent or chemiluminescent compounds, such as fluorescein isothiocyanate, rhodamine, or luciferin, enzymes (e.g., enzyme, such as alkaline phosphatase, beta-galactosidase, or horseradish peroxidase), colorimetric labels such as colloidal gold, colored glass or plastic beads (e.g., polystyrene, polypropylene, latex, etc.), paramagnetic atoms or magnetic agents, electron-dense reagents, a nano- or micro-bead containing a fluorescent dye, nanocrystals, a quantum dot, a quantum bead, a nanotag, dendrimers with a fluorescent label, a micro-transponder, an electron donor molecule or molecular structure, or a light reflecting particle, the microparticles may be nanocrystals or quantum dots. Nanocrystals are substances that absorb photons of light, then re-emit photons at a different wavelength (fluorophores). In addition, additional fluorescent labels, or secondary antibodies may be conjugated to the nanocrystals. Nanocrystals are commercially available from sources such as Invitrogen and Evident Technologies (Troy, N.Y.). Other labels include E)-5-[2-(methoxycarbonyl) ethenyl]cytidine, which is a nonfluorescent molecule that when subjected to ultraviolet (UV) irradiation yields a product, 3 beta-D-ribofuranosyl-2,7-dioxopyrido[2,3-d]pyrimidine, which displays a strong fluorescence signal.

Competitive inhibition can be determined by any method known in the art, for example, competition ELISA assays. A DBDpp, such as a DBDpp fusion protein (e.g., a DBDpp-Fc, DBDpp-CAR, a DBDpp-scFv), or other molecule is said to "competitively inhibit" binding of a reference molecule to a given epitope if it binds to that epitope to the extent that it blocks, to some degree, binding of the reference molecule to the epitope. As used herein, a DBDpp (e.g., a DBDpp fusion protein), or other molecule can be said to competitively inhibit binding of the reference molecule to a given epitope, for example, by at least 90%, at least 80%, at least 70%, at least 60%, at least 50%, by at least 40%, at least 30%, or at least 20%. The terms "compete," "ability to compete" and "competes with" are relative terms used to describe a DBDpp, such as a DBDpp fusion protein, that produce at least 20%, at least 30%, at least 40%, or at least 50% inhibition of binding of a reference molecule to a target by a DBDpp such as DBDpp fusion protein (e.g., a DBDpp-Fc, DBDpp CAR, a DBDpp-scFv, and an antibody-comprising a DBDpp) as determined in a standard competition assay as described herein or otherwise known in the art, including, but not limited to, competitive assay systems using techniques such as radioimmunoassays (RIA), enzyme immunoassays (EIA), preferably the enzyme linked immunosorbent assay (ELISA), "sandwich" immunoassays, immunoradiometric assays, fluorescent immunoassays, luminescent, electrochemical luminescent, and immunoelectrophoresis assays. Methods for determining binding and affinity of candidate binding molecules are known in the art and include, but are not limited to, affinity chromatography, size exclusion chromatography, equilibrium dialysis, fluorescent probe displacement, and plasma resonance.

Affinity Purification

In purification based on affinity chromatography, target proteins are selectively isolated according to their ability to specifically and reversibly bind to a ligand that has typically been covalently coupled to a chromatographic matrix. In one embodiment, DBDpp can be used as reagents for affinity purification of targets of interest from either recombinant sources or natural sources such as biological samples (e.g., serum).

In another embodiment, a method for isolating a target of interest from a solution that contains the target of interest is provided. Such method comprises: (a) contacting the solution with a DBDpp under conditions that permit binding of the DBDpp to the target of interest; and (b) recovering the target of interest. In another embodiment, a method is provided for isolating a target of interest from a solution that contains the target of interest, comprising: (a) contacting the solution with a DBDpp under conditions suitable for specific binding of the DBDpp to the target; and (b) separating the complex(es) formed by the target of interest and/or DBDpp from other components of the solution. In a further embodiment, the method further comprises the steps of: (c) dissociating the DBDpp from the target of interest, and (d) recovering the dissociated target of interest.

In some embodiments, the DBDpp that specifically binds a target of interest is immobilized on beads and then used to affinity purify the target protein.

Methods of covalently coupling proteins to a surface are known by those of skill in the art, and peptide tags that can be used to attach DBDpp to a solid surface are known to those of skill in the art. Further, DBDpp can be attached (i.e., coupled, linked, or adhered) to a solid surface using any reagents or techniques known in the art. In some embodiments, the solid support is selected from: beads, glass, slides, chips and gelatin. Thus, a series of DBDpp can be used to make an array on a solid surface using techniques known in the art. For example, U.S. Publ. No. 2004/0009530 discloses methods for preparing arrays. The contents of U.S. Publ. No. 2004/0009530 are herein incorporated by reference in its entirety.

In another embodiment, a DBDpp is used to isolate a target of interest by affinity chromatography. Any conventional method of chromatography may be employed. In some embodiments, a DBDpp is immobilized on a solid support. The DBDpp can be immobilized on the solid support using techniques and reagents described herein or otherwise known in the art. Suitable solid supports are described herein or otherwise known in the art and in specific embodiments are suitable for packing a chromatography column. The immobilized DBDpp can then be loaded or contacted with a solution under conditions favorable to form a complex between the DBDpp and the target of interest. Non-binding materials can be washed away. Suitable wash conditions can readily be determined by one of skill in the art. Examples of suitable wash conditions include but are not limited to PBS/0.01% Tween 20, pH7.2 and 1M NaCl/10 mM Tris, pH7.5. Tris wash buffers may be preferable since phosphates can precipitate in 50% ethylene glycol. In general, non-limiting terms, wash buffers are pH7.0, optionally containing 0.0 to 1.5 M NaCl, more preferably 1M NaCl. Additionally, wash buffers may optionally contain a mild detergent, such as, Tween 20, Tween 80, or NP-80. The target of interest can be eluted from the DBDpp binding complex by introducing solution conditions that favor dissociation of the binding complex. Suitable elution solutions can readily be determined by one of skill in the art and include but are not limited to 50% ethylene glycol/10 mM NaOAc. By way of non-limiting example, useful elution buffers, contain 40-60% ethylene glycol, preferably 50% ethylene glycol; and 50-100 mM NaOAc with a pH in the range of pH 4-7, more preferably, pH 4-6 and most preferably pH 4.5-5.5. Preferably, a fast flow affinity chromatographic technique is used to bind the DBDpp to the target of interest and from which the purified target of interest is eluted.

Alternatively, chromatography can be carried out by mixing a solution containing the target of interest and the DBDpp, then isolating complexes of the target of interest and DBDpp. For this type of separation, many methods are known and can routinely be applied. For example, the DBDpp may be immobilized on a solid support such as beads, then separated from a solution along with the target of interest by filtration. In another example, the DBDpp may be a fusion protein that contains a peptide tag, such as a poly-HIS tail or streptavidin binding region, which can be used to isolate the DBDpp after complexes have formed using an immobilized metal affinity chromatographic resin or steptavidin-coated substrate. Once separated, the target of interest can be released from the DBDpp under elution conditions and recovered in a purified form.

Therapeutics

The DBD described herein are useful in a variety of applications including, but not limited to, therapeutic treatment methods, which may be in vitro, ex vivo, or in vivo methods.

The application as a therapeutic entity is an attribute of the target binding specificity of the DBDpp. The incorporation of DBDpp within various molecular compositions, (e.g., a DBD-antibody fusions, DBD-drug conjugates and DBD-chimeric receptors) affords application in a variety of therapeutic indications and modalities, which include, but not limited to soluble and cell-associated compositions.

Figure 5C:
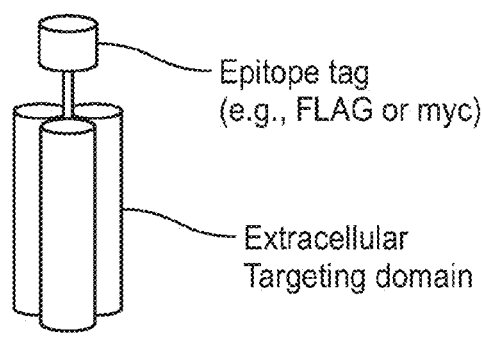

In one embodiment, the DBDpp is a soluble fusion protein (schematically shown in FIG. 5C and made up of an optional epitope tag 10 and a targeting domain 20) that binds to a target that is associated with a disease or disorder of the metabolic, cardiovascular, musculoskeletal, neurological, or skeletal system. In other embodiments, the DBDpp is a soluble fusion protein that binds to a target that is associated with yeast, fungal, viral or bacterial infection or disease. In some embodiments, the DBDpp is a soluble fusion protein that binds to a target that is associated with a disease or disorder of the immune system.

Also provided are therapeutic compositions useful for practicing therapeutic methods described herein. In one embodiment, therapeutic compositions provided herein contain a physiologically tolerable carrier together with at least one species of DBDpp fusion as described herein, dissolved or dispersed therein as an active ingredient. In another embodiment, therapeutic compositions provided herein contain a physiologically tolerable carrier together with at least one species of a DBDpp as described herein, dissolved or dispersed therein as an active ingredient. In a preferred embodiment, therapeutic composition is not immunogenic when administered to a human patient for therapeutic purposes.

The preparation of a pharmacological composition that contains active ingredients dissolved or dispersed therein is well understood in the art. Typically such compositions are prepared as sterile injectables either as liquid solutions or suspensions, aqueous or non-aqueous. However, solid forms suitable for solution, or suspensions, in liquid prior to use can also be prepared. The preparation can also be emulsified. Thus, a DBDpp-containing composition can take the form of solutions, suspensions, tablets, capsules, sustained release formulations or powders, or other compositional forms. In some embodiments, the DBDpp compositions (e.g., a DBDpp fusion proteins) are formulated to ensure or optimize distribution in vivo, For example, the blood-brain barrier (BBB) excludes many highly hydrophilic compounds and if so desired, the compositions are prepared so as to increase transfer across the BBB, by for example, formulation in liposomes. For methods of manufacturing liposomes, see, e.g., U.S. Pat. Nos. 4,522,811, 5,374,548, and 5,399,331. The liposomes can comprise one or more moieties that are selectively transported into specific cells or organs, thus enhance targeted drug delivery (see, e.g., Ranade, Clin. Pharmacol. 29:685 (1989)).

The DBDpp (e.g. DBDpp fusion protein) can be mixed other active ingredients and/or excipients that are pharmaceutically acceptable and compatible with the active ingredient and in amounts suitable for use in therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

Therapeutic DBDpp can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylarnine, 2-ethylamino ethanol, histidine, procaine and the like.

Physiologically tolerable carriers are known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to, and to the exclusion of water. Exemplary of such additional liquid phases are glycerin, vegetable oils such as cottonseed oil, organic esters such as ethyl oleate, and water-oil emulsions.

In one embodiment, a therapeutic composition contains a DBDpp fusion protein, typically in an amount of at least 0.1 weight percent of DBDpp fusion protein per weight of total therapeutic composition. A weight percent is a ratio by weight of DBDpp fusion per total composition. Thus, for example, 0.1 weight percent is 0.1 grams of DBDpp per 100 grams of total composition.

A DBDpp fusion protein-containing therapeutic composition typically contains about 10 micrograms (μg) per milliliter (ml) to about 100 milligrams (mg) per ml of DBDpp fusion protein as active ingredient per volume of composition, and more preferably contains about 1 mg/ml to about 10 mg/ml (i.e., about 0.1 to 1 weight percent).

The dosage ranges for the administration of the DBDpp (e.g., a DBDpp fusion protein) are those large enough to produce the desired effect in which the disease symptoms mediated by the target molecule are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

The DBDpp (e.g., a DBDpp fusion protein) can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, DBDpp can be administered intravenously, intraperitoneally, intramuscularly, subcutaneously, intracavity, transdermally, and can be delivered by peristaltic means. DBDpp fusion proteins can also be delivered by aerosol to airways and lungs.

Therapeutic compositions containing a DBDpp can be conventionally administered intravenously, as by injection of a unit dose, for example. The term "unit dose" when used in reference to a therapeutic composition provided herein refers to physically discrete units suitable as unitary dosage for the subject, each unit containing a predetermined quantity of active material calculated to produce the desired therapeutic effect in association with the required diluent; e.g., carrier, or vehicle. In a specific embodiment, therapeutic compositions containing a DBDpp are administered subcutaneously.

In some embodiments, the DBDpp (e.g., a DBDpp fusion protein) is administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The DBDpp compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The dosage ranges for the administration of the DBDpp are those large enough to produce the desired effect in which the disease symptoms mediated by the target molecule are ameliorated. The dosage should not be so large as to cause adverse side effects, such as, hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

The dosage schedule and amounts effective for therapeutic and prophylactic uses, i.e., the "dosing regimen," will depend upon a variety of factors, including the cause, stage and severity of the disease or disorder, the health, physical status, age of the mammal being treated, and the site and mode of the delivery of the DBD. Therapeutic efficacy and toxicity of the complex and formation can be determined by standard pharmaceutical, pharmacological, and toxicological procedures in cell cultures or experimental animals. Data obtained from these procedures can likewise be used in formulating a range of dosages for human use. Moreover, therapeutic index (i.e., the dose therapeutically effective in 50 percent of the population divided by the dose lethal to 50 percent of the population (ED50/LD50)) can readily be determined using known procedures. The dosage is preferably within a range of concentrations that includes the ED50 with little or no toxicity, and may vary within this range depending on the dosage form employed, sensitivity of the patient, and the route of administration.

The dosage regimen also takes into consideration pharmacokinetics parameters known in the art, such as, drug absorption rate, bioavailability, metabolism and clearance (see, e.g., Hidalgo-Aragones, J. Steroid Biochem. Mol. Biol. 58:611-617 (1996); Groning et al., Pharmazie 51:337-341 (1996); Fotherby, Contraception 54:59-69 (1996); and Johnson et al., J. Pharm. Sci. 84:1144-1146 (1995)). It is well within the state of the art for the clinician to determine the dosage regimen for each subject being treated. Moreover, single or multiple administrations of DBDpp compositions can be administered depending on the dosage and frequency as required and tolerated by the subject. The duration of prophylactic and therapeutic treatment will vary depending on the particular disease or condition being treated. Some diseases are amenable to acute treatment whereas others require long-term, chronic therapy. DBDpp can be administered serially, or simultaneously with the additional therapeutic agent.

In some embodiments, the DBDpp is administered at about 1 mg/kg to about 50 mg/kg, about 1 mg/kg to about 25 mg/kg, about 1 mg/kg to about 20 mg/kg, about 1 mg/kg to about 15 mg/kg, about 1 mg/kg to about 10 mg/kg, or about 1 mg/kg to about 5 mg/kg.

In another embodiment, a DBDpp is administered in combination with more one or more additional therapeutics.

A therapeutically effective amount of a DBDpp, such as a DBDpp fusion protein, can be an amount such that when administered in a physiologically tolerable composition is sufficient to achieve a plasma concentration of from about 0.1 microgram (μg) per milliliter (ml) to about 100 μg/ml, preferably from about 1 μg/ml to about 5 μg/ml, and usually about 5 μg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

In one embodiment the disease or disorder is a disease or disorder of the immune system, such as inflammation or an autoimmune disease.

In some embodiments, the DBDpp is a soluble protein that specifically binds to a target that is associated with a disease or disorder of the metabolic, cardiovascular, musculoskeletal, neurological, or skeletal system.

In other embodiments, the DBDpp is a soluble protein that specifically binds to a target that is associated with yeast, fungal, viral or bacterial infection or disease. In some embodiments, the DBDpp is a soluble protein that specifically binds to a target that is associated with a disease or disorder of the immune system.

In one embodiments, the DBDpp fusion proteins are useful for inhibiting tumor growth, reducing neovascularization, reducing angiogenesis, inducing differentiation, reducing tumor volume, and/or reducing the tumorigenicity of a tumor.

In some embodiments, the DBDpp described herein are useful for treating cancer. Thus, in some embodiments, the invention provides methods of treating cancer comprise administering a therapeutically effective amount of a DBDpp (e.g. a DBDpp fusion) to a patient.

Cancers that can be treated include tumors that are not vascularized, or not yet substantially vascularized, as well as vascularized tumors. The cancers can comprise non-solid tumors (such as hematological tumors, for example, leukemias and lymphomas) or can comprise solid tumors. Types of cancers to be treated with the DBDpp include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases).

In another embodiment, the DBDpp described herein are useful for treating a patient having hematological cancers. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In additional embodiments, the DBDpp fusion protein binds (1) a target on a cell or tissue of interest (e.g., a tumor antigen on a tumor cell) and (2) a target on an effector cell, such as, a T-cell receptor molecule. According to one embodiment, the binding of one or more targets by the DBDpp fusion protein is used to direct an immune response to an infectious agent, cell, tissue, or other location of interest in a patient. For example, in some embodiments a DBDpp specifically binds a target on the surface of an effector cell. Thus, in some embodiments, a DBDpp specifically binds a target on the surface of a T cell. In specific embodiments a DBDpp specifically binds CD3. In other embodiments, a DBDpp specifically binds CD2. In a further embodiment, a DBDpp specifically binds the T-cell receptor (TCR). According to additional embodiments, a DBDpp specifically binds a target on the surface of a Natural Killer Cell. Thus, in some embodiments, a DBDpp specifically binds a NKG2D (Natural Killer Group 2D) receptor. In additional embodiments a DBDpp specifically binds CD16 (i.e., Fc gamma RIII) CD64 (i.e., Fc gamma RI), or CD32 (i.e., Fc gamma RII).

In one embodiment, a DBDpp fusion protein binds a target on a leukocyte and a tumor antigen on a tumor cell. In some embodiments, the DBDpp fusion protein binds NKG2D. In a further embodiment, a DBDpp fusion protein binds NKG2D and a target selected from ErbB2, EGFR, IGF1R, CD19, CD20, CD80 and EPCAM. In one embodiment, a DBDpp fusion protein binds CD3. In particular embodiments, the DBDpp specifically binds CD3 epsilon. In one embodiment, a DBDpp fusion protein binds CD4.

In one embodiment, the DBDpp fusion is bispecific and specifically binds to two different targets expressed on the surface of two different cell types. In one embodiment the bispecific DBDpp fusion protein specifically binds to a cancer cell target and an immune effector cell target. In one embodiment the bispecific DBDpp fusion protein specifically binds a target expressed on a cancer cell (e.g. CD19) and a target expressed on the surface of a T lymphocyte (e.g., CD3).

In some embodiments, DBDpp can mimic ligand binding. In certain embodiments, a DBDpp can mimic the biological activity of a ligand (an agonist DBDpp) or inhibit the bioactivity of the ligand (an antagonist DBDpp), e.g., through competitive binding. DBDpp in DBDpp fusion proteins can also affect targets in other ways, e.g., by neutralizing, blocking, stabilizing, aggregating, or crosslinking a DBDpp target.

DBDpp Drug Conjugates

In a further embodiment a DBDpp fusion protein may be linked to other organic or inorganic molecules or substrates through the use of chemically conjugation. In one embodiment, DBDpp-drug conjugates are intended to facilitate the local delivery of cytotoxic agents through the targeting specificity of the DBDpp. This combination of targeting specificity and cytotoxic agent, allows targeted delivery of the drug to tumors, and intracellular accumulation therein, where systemic administration of these unconjugated drug agents may result in unacceptable levels of toxicity to normal cells as well as the tumor cells sought to be eliminated (Baldwin et al., Lancet pages 603-05 (1986); Thorpe, "Antibody Carriers Of Cytotoxic agents In Cancer Therapy: A Review," in Monoclonal Antibodies '84: Biological And Clinical Applications, A. Pinchera et al., (ed.s), pp. 475-506) (1985)).

Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Chemotherapeutic agents useful in the generation of such immunoconjugates also include antitubulin drugs, such as auristatins, including monomethyl auristatin E (MMAE) and monomethyl auristatin F (MMAF). Enzymatically active toxins and fragments thereof that can be used according to the invention include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In one embodiment, a DBDpp (e.g., a DBDpp fusion protein) is conjugated to a radioisotope. In a further embodiment, a DBDpp is conjugated to an isotope selected from 90Y, 125I, 131I, 123I, 111In, 105Rh, 153Sm, 67Cu, 67Ga, 166Ho, 177Lu, 186Re and 188Re using anyone of a number of known chelators or direct labeling. In other embodiments, the DBDpp is coupled to drugs, prodrugs or lymphokines such as interferon. Conjugates of the DBDpp and cytotoxin can routinely be made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). In a specific embodiment, the toxin is conjugated to a DBDpp fusion protein through an enzyme-cleavable linker system (e.g., such as that present in SGN-35). Conjugates of a DBDpp and one or more small molecule toxins, such as a calicheamicin, maytansinoids, a trichothene, and CC1065, and the derivatives of these toxins that have toxin activity, can also be used.

In some embodiments, the cytotoxic agent is covalently attached to a DBDpp by a linker. In some embodiments, the linker attaching the DBDpp and the cytotoxic agent is cleavable by a protease.

Therapeutic Use as Cell Associated Receptor

In one embodiment of the invention, DBDpp-CAR are used for purposes of redirecting transduced T cells to a tumor target defined by the binding specificity of the DBDpp-CAR. In one example primary T cells are transduced with a lentiviral vector encoding a CAR that combines a DBD target binding domain with a transmembrane domain and an intracellular domain of CD3-zeta, CD28, 4-1BB. The resultant population of transduced T cells may therefore elicit a DBDpp-CAR-mediated T-cell response. In one embodiment T cells are genetically modified to express DBDpp-CAR and the DBDpp-CAR T cell is infused to a recipient in need thereof. The infused cell is able to kill tumor cells in the recipient. Several embodiments of the invention are particularly advantageous because they include one, several or all of the following benefits: (i) target-binding specificity, (ii) enhanced therapeutic efficacy, (iii) reduced off-target side effects, (iv) customizability for markers of a particular patient or patient population, (v) enhanced stability during production and processing, and (vi) ability to target one, two, or more specific targets to enhance target-directed therapy.

"Genetically modified cells", "redirected cells", "genetically engineered cells" or "modified cells" as used herein refer to cells that express a DBDpp provided herein. In a particular embodiment, the genetically modified cells express a DBDpp fusion protein such as a DBDpp-CAR. In a further embodiment, the genetically modified cells express and display a DBDpp-CAR on the cell surface.

"Disease targeted by genetically modified cells" as used herein encompasses the targeting of any cell involved in any manner in any disease by the genetically modified cells, irrespective of whether the genetically modified cells target diseased cells or healthy cells to effectuate a therapeutically beneficial result. The genetically modified cells include but are not limited to genetically modified T-cells, NK cells, hematopoietic stem cells, pluripotent embryonic stem cells or embryonic stem cells. The genetically modified cells express the DBDpp-CAR, which can target any of the antigens expressed on the surface of target cells.

In one embodiment, the DBDpp portion of the DBDpp-CAR is designed to treat a particular cancer. Cancers that can be treated include tumors that are not vascularized, or not yet substantially vascularized, as well as vascularized tumors. The cancers can comprise non-solid tumors (such as hematological tumors, for example, leukemias and lymphomas) or can comprise solid tumors. Types of cancers to be treated with the DBDpp-CARs include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Examples of hematological (or hematogenous) cancers include leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases).

In one embodiment, cancers and disorders can be treated using cell expressing DBDpp-CAR that target CD19, CD20, CD22, and ROR1. In one specific embodiment, the DBD-CAR can be designed to target CD22 to treat B-cell lymphoma. In another embodiment the cell expressing DBDpp-CAR contain a DBDpp designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

"B-cell associated diseases" as used herein include B-cell immunodeficiencies, autoimmune diseases and/or excessive/uncontrolled cell proliferation associated with B-cells (including lymphomas and/or leukemias). Examples of such diseases, wherein DBDpp-CAR may be used for therapeutic approaches include but are not limited to systemic lupus erythematosus (SLE), diabetes, rheumatoid arthritis (RA), reactive arthritis, multiple sclerosis (MS), pemphigus vulgaris, celiac disease, Crohn's disease, inflammatory bowel disease, ulcerative colitis, autoimmune thyroid disease, X-linked agammaglobulinaemis, pre-B acute lymphoblastic leukemia, systemic lupus erythematosus, common variable immunodeficiency, chronic lymphocytic leukemia, diseases associated with selective IgA deficiency and/or IgG subclass deficiency, B lineage lymphomas (Hodgkin's lymphoma and/or non-Hodgkin's lymphoma), immunodeficiency with thymoma, transient hypogammaglobulinemia and/or hyper IgM syndrome, as well as virally-mediated B-cell diseases such as EBV mediated lymphoproliferative disease, and chronic infections in which B-cells participate in the pathophysiology.

In one embodiment, the DBDpp-CAR can be designed to target mesothelin to treat mesothelioma, pancreatic cancer, ovarian cancer, and the like. In one embodiment, the DBDpp-CAR can be designed to target CD33/IL3Ra to treat acute myelogenous leukemia and the like. In one embodiment, the DBDpp-CAR can be designed to target c-Met to treat triple negative breast cancer, non-small cell lung cancer, and the like. In one embodiment, the DBDpp-CAR can be designed to target PSMA to treat prostate cancer and the like. In one embodiment, the DBDpp-CAR can be designed to target Glycolipid F77 to treat prostate cancer and the like. In one embodiment, the DBDpp-CAR can be designed to target EGFRvIII to treat gliobastoma and the like. In one embodiment, the DBDpp-CAR can be designed to target GD-2 to treat neuroblastoma, melanoma, and the like. In one embodiment, the DBDpp-CAR can be designed to target NY-ESO-1 to treat myeloma, sarcoma, melanoma, and the like. In one embodiment, the DBDpp-CAR can be designed to target MAGE A3 to treat myeloma, sarcoma, melanoma, and the like. However, the invention should not be construed to be limited to solely to the antigen targets and diseases disclosed herein. Rather, the invention should be construed to include any antigenic target that is associated with a disease where a DBDpp-CAR can be used to treat the disease.

In a preferred embodiment, the DBDpp-CAR is expressed in a T cell and provides a method for treating or preventing cancer, comprising the administration of host cells expressing DBDpp-CAR to a cancer patient in which the cancer cell expresses a tumor antigen on its surface, and wherein the DBDpp specifically binds the target antigen. Exemplary target antigens that the DBDpp and DBDpp-CAR bind include, but are not limited to, CD19, CD123, TSLPR, and CD267.

The DBDpp-CAR-modified T cells can also serve as a type of vaccine for ex vivo immunization and/or in vivo therapy in a mammal. Preferably, the mammal is a human.

The DBDpp-CAR-modified T cells provided herein can be administered either alone, or as a pharmaceutical composition in combination with diluents and/or with other components such as chemotherapeutics, antibodies, cytokines or cell populations. Compositions provided herein are preferably formulated for intravenous administration that can be administered one or more times.

"Antigen loss escape variants" as used herein refer to cells which exhibit reduced or loss of expression of the target antigen, which antigens are targeted by a CAR provided herein.

Various embodiments of the invention will now be illustrated through the description of experiments conducted in accordance therewith. The examples that follow are provided to facilitate the practice of the disclosed embodiments, and are not to be construed as limiting in any way the remainder of the disclosure. In the examples, reference is made to the appended figures.

EXAMPLES

Example 1. Immunogenicity Assessment of DBDpp

The sequences of DBDpp, particularly those administered to a subject and/or used in purifying a composition administered to a subject, are preferably not antigenic with respect to the subject (e.g., human). In some embodiments, the sequence of the DBDpp does not contain a human HLA-DR binding motif or cleavage sites for proteasomes and immune-proteasomes. In particular embodiments, the DBDpp sequence does not contain an antigenic sequence as determined by a computer prediction model version existent on the filing date of this specification. In particular embodiments, the DBDpp sequence does not contain an MHC (class I or class II) binding site sequence as predicted by an algorithm selected from ProPred (see, e.g., Singh, Bioinformatics 17(12):1236-1237 (2001)), ProPred1 (Singh, Bioinformatics 19(8):1009-14 (2003)), SYFPEITHI (see, e.g., Schuler, Immunoinf. Meth. in Mol. Biol. 409(1):75-93 (2007)), SMM-align (see, e.g., Nielsen, BMC Bioinformatics 8:238 (2007)), RANKPEP (see, e.g., Reche, Hum Immunol 63: 701-709. (2004)), or TEPITOPE (see, Sturniolo, Nat Biotechnol 17:555-561 (1999)), wherein the version of the algorithm and the applied database are in existence on the filing date of this application.

In silico analysis of the amino acid sequence of alpha3D (MGSWAEFKQRLAAIKT RLQALGGSEAELAAFEKE-IAAFESELQAYKGKGNPEVEALRKEAAAIRD-ELQAYRH N (SEQ ID NO:49) revealed a 9 amino acid sequence (i.e., LAAIKTRLQ (SEQ ID NO:50)), that shares characteristics with that of high affinity (binding threshold less than 6%) and promiscuous (present in greater than 50% of relevant alleles) T cell epitopes (Singh, Bioinformatics 17:1236-1237, 2001). This epitope resides within an invariant region of some of the DBDpp libraries. Therefore, with the aim of reducing the potential for immunogenicity, a Q19E substitution was introduced into SEQ ID NO:49. This conserved and surface exposed substitution appeared unlikely to significantly disrupt the hydrophobic core (see, e.g., FIG. 1B). In silico analysis of the resultant sequence (SEQ ID NO:1) yielded lower immunogenicity scores.

Example 2. DBDpp Library Design, Construction and Screening

Unlike natural ligands and binding proteins, the synthetic scaffold sequence of DBD (i.e., SEQ ID NO:1) has no known binding partner. In the construction of DBDpp that bind to targets, residues were considered for mutation (i.e., randomization within the library) if they were considered to be surface exposed—exhibiting significant solvent accessibility. A variety of methods are available to assess solvent accessibility of defined molecular structures. For example, PyMOL is an open source software package developed for molecular visualization and analysis and may be used to calculate solvent accessible surface area using the method of Lee and Richards (Lee et al., J. Mol. Biol. 55:379-400 (1971)). More specifically, using PyMOL (version 1.4.1) with the "'dot solvent" set to 1, "solvent radius" to 1.4 Å, and "dot density" set to 4, the solvent accessible surface area can be calculated for each amino acid of a homology model of the SEQ ID NO:1 based on the template, PDB 2A3D. Table 2 lists the calculated area (in square angstroms) for each residue, as measured in the context of the domain (area D) and as an isolated amino acid, independent of steric hindrances imposed by neighboring residues (area I). The relative accessibility of a residue within the domain (area D) as compared to the isolated state (area I) is represented as a percent value (% A).

TABLE 2

Solvent Accessibility of the Reference Scaffold Sequence (SEQ ID NO:1)

| position | aa | Area I | Area D | % A | position | aa | Area I | Area D | % A |
|---|---|---|---|---|---|---|---|---|---|
| 1 | M | 295.0 | 156.9 | 53.2 | 38 | F | 316.3 | 12.6 | 4.0 |
| 2 | G | 187.1 | 56.6 | 30.2 | 39 | E | 289.6 | 112.0 | 38.7 |
| 3 | S | 227.0 | 23.6 | 10.4 | 40 | S | 227.0 | 93.7 | 41.3 |
| 4 | W | 345.8 | 107.4 | 31.1 | 41 | E | 285.0 | 57.9 | 20.3 |
| 5 | A | 211.9 | 53.7 | 25.4 | 42 | L | 281.8 | 21.5 | 7.6 |
| 6 | E | 286.8 | 104.7 | 36.5 | 43 | Q | 294.3 | 120.5 | 41.0 |
| 7 | F | 318.1 | 7.8 | 2.5 | 44 | A | 209.6 | 79.0 | 37.7 |
| 8 | K | 303.7 | 142.0 | 46.8 | 45 | Y | 323.7 | 33.1 | 10.2 |
| 9 | Q | 293.7 | 123.0 | 41.9 | 46 | K | 303.8 | 70.1 | 23.1 |
| 10 | R | 341.2 | 102.9 | 30.2 | 47 | G | 187.2 | 64.4 | 34.4 |
| 11 | L | 274.1 | 19.0 | 6.9 | 48 | K | 298.8 | 149.1 | 49.9 |
| 12 | A | 211.5 | 54.8 | 25.9 | 49 | G | 185.6 | 6.9 | 3.7 |
| 13 | A | 211.3 | 43.4 | 20.6 | 50 | N | 267.4 | 80.5 | 30.1 |
| 14 | I | 279.0 | 18.0 | 6.5 | 51 | P | 238.9 | 92.8 | 38.8 |
| 15 | K | 300.5 | 134.3 | 44.7 | 52 | E | 293.1 | 110.3 | 37.6 |
| 16 | T | 246.5 | 89.7 | 36.4 | 53 | V | 249.2 | 5.7 | 2.3 |
| 17 | R | 339.6 | 131.8 | 38.8 | 54 | E | 290.7 | 91.0 | 31.3 |
| 18 | L | 279.6 | 27.8 | 9.9 | 55 | A | 211.2 | 67.2 | 31.8 |
| 19 | E | 269.3 | 135.1 | 50.2 | 56 | L | 274.5 | 10.5 | 3.8 |
| 20 | A | 211.6 | 61.6 | 29.1 | 57 | R | 336.4 | 146.8 | 43.6 |
| 21 | L | 278.0 | 8.9 | 3.2 | 58 | K | 306.7 | 165.1 | 53.8 |
| 22 | G | 186.9 | 67.8 | 36.3 | 59 | E | 290.1 | 114.0 | 39.3 |
| 23 | G | 186.6 | 47.9 | 25.7 | 60 | A | 211.1 | 13.2 | 6.3 |
| 24 | S | 225.9 | 12.2 | 5.4 | 61 | A | 211.7 | 47.6 | 22.5 |
| 25 | E | 286.9 | 130.2 | 45.4 | 62 | A | 211.0 | 56.7 | 26.9 |
| 26 | A | 210.5 | 92.4 | 43.9 | 63 | I | 275.2 | 26.3 | 9.5 |
| 27 | E | 281.6 | 57.7 | 20.5 | 64 | R | 337.5 | 119.5 | 35.4 |
| 28 | L | 269.8 | 4.4 | 1.6 | 65 | D | 261.1 | 106.5 | 40.8 |
| 29 | A | 211.4 | 53.0 | 25.1 | 66 | E | 284.7 | 102.5 | 36.0 |
| 30 | A | 210.7 | 54.2 | 25.7 | 67 | L | 272.8 | 7.3 | 2.7 |
| 31 | F | 317.0 | 14.8 | 4.7 | 68 | Q | 277.9 | 131.3 | 47.2 |
| 32 | E | 284.7 | 96.0 | 33.7 | 69 | A | 211.4 | 40.4 | 19.1 |
| 33 | K | 306.8 | 158.8 | 51.8 | 70 | Y | 329.3 | 50.8 | 15.4 |
| 34 | E | 281.1 | 83.1 | 29.5 | 71 | R | 341.0 | 149.1 | 43.7 |
| 35 | I | 276.3 | 22.9 | 8.3 | 72 | H | 279.1 | 135.5 | 48.5 |
| 36 | A | 211.4 | 58.5 | 27.7 | 73 | N | 275.1 | 130.5 | 47.4 |
| 37 | A | 209.8 | 51.4 | 24.5 | | | | | |

Domain residues with % A values that are less than 10% to 11% (e.g., F7, L11, I14, L18, L21, S24, L28, F31, I35, F38, L42, Y45, G49, V53, L56, A60, I63, and L67 of SEQ ID NO:1; Table 2A), were considered to be relatively inaccessible to the exterior solvent and were therefore considered interior core residues of the DBD. Conversely, residues with % A values that were greater than 10% to 11% (e.g., G2, S3, W4, A5, E6, K8, Q9, R10, A12, A13, K15, T16, R17, E19, A20, A29, A30, E32, K33, E34, A36, A37, E39, S40, E41, Q43, A44, E52, E54, A55, R57, K58, E59, A61, A62, R64, D65, E66, Q68, A69, and Y70 of SEQ ID NO:1) are predicted to be located within regions of the polypeptide associated with alpha-helical secondary structure and to occupy positions that have greater potential for interaction with macromolecular targets of interest. These solvent accessible, alpha helical residues were considered to be candidates for the greatest degree of substitutional diversity (including conserved and non-conserved substitutions) in the library.

The non-alpha helical residues of the reference scaffold sequence correspond to, in several embodiments, positions Ml, L21, G22, G23, S24, E25, A26, E27, Y45, K46, G47, K48, G49, N50, P51, R71, H72, and N73 of SEQ ID NO:1. In additional embodiments, non-alpha helical residues of the reference scaffold sequence correspond to positions Ml, G22, G23, S24, E25, A26, E27, K46, G47, K48, G49, N50, P51, R71, H72, and N73 of SEQ ID NO:1. These residues were likewise considered to be candidates for conserved and non-conserved substitutions in the library.

Figure 1B:
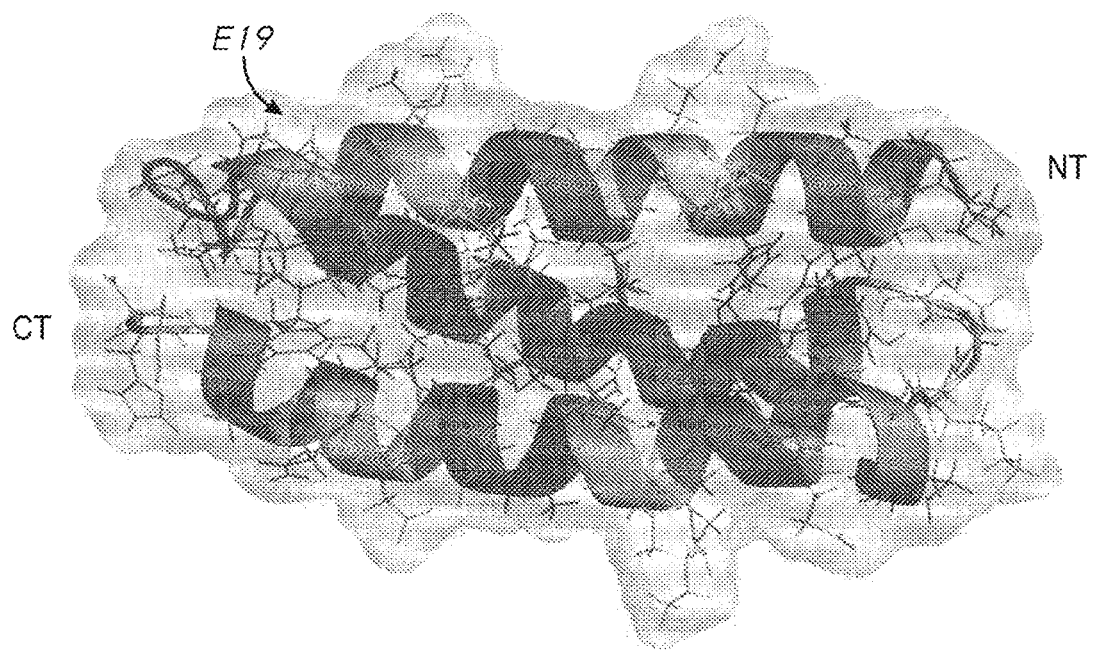

Some DBDpp libraries were created through the selective or random mutation of specific solvent exposed amino acid sequence positions of the DBDpp. In one series of experiments, libraries, referred to herein as "face" libraries or "F libraries", were designed such that the substituted residues of the reference scaffold structure of the polypeptide of SEQ ID NO:1 were clustered on a single face of the domain and to create a single, contiguous binding surface. Face libraries were constructed for all three faces (F1, F2 & F3) of the structure of the polypeptide of SEQ ID NO:1. Due to the asymmetry of the domain structure, each pair of alpha helices—and therefore each face—forms a unique geometric topology (FIGS. 1 and 2). As modeled in the reference scaffold, the large number targeted residues correspond to contiguous surface area greater than 1400 square angstroms—significantly greater than the binding surfaces measured for a survey of non-antibody binding scaffolds. (Gilbreth et al., Curr. Opin. Struct. Biol. 22:413-420 (2012)).

In another of set of experiments, libraries referred to herein as "combined" libraries or "C libraries" were constructed to identify DBDpp that potentially exhibit multifaceted binding to a target of interest (Table 3 and FIGS. 1 and 2). The combined libraries (C1 and C2) were constructed by combining residues from each of the three helices used in the F series libraries.

In these experiments, a total of 32 residue positions were subjected to mutagenesis. Each mutagenized position is present in at least 2 libraries. Furthermore, each mutagenized position is represented in each of the two library "architectures"; F and C.

TABLE 3

DBDpp Library Sequence Profiles

| Library | Sequence Profile |
| --- | --- |
| F1 | MGSW$X_5X_6$FK$X_9X_{10}$LA$X_{13}$IK$X_{16}X_{17}$LEALGGSEAELA$X_{30}$FE$X_{33}X_{34}$IA$X_{37}$FE$X_{40}X_{41}$LQ$X_{44}$YKGKGNPEVEALRKEAAAIRDELQAYRHN (SEQ ID NO: 2) |
| F2 | MGSWAEFKQRLAAIKTRLEALGGSEAELAAF$X_{32}X_{33}$EI$X_{36}$AF$X_{39}X_{40}$EL$X_{43}$AYKGKGNPEVEAL$X_{57}X_{58}$EA$X_{61}$AI$X_{64}X_{65}$EL$X_{68}$AYRHN (SEQ ID NO: 3) |
| F3 | MGSW$X_5$EF$X_8X_9$RL$X_{12}$AI$X_{15}X_{16}$RL$X_{19}$ALGGSEAELAAFEKEIAAFESELQAYKGKGNPEVE$X_{55}$LR$X_{58}X_{59}$AA$X_{62}$IR$X_{65}X_{66}$LQAYRHN (SEQ ID NO: 4) |
| C1 | MGSW$X_5X_6$FK$X_9X_{10}$LA$X_{13}$IK$X_{16}X_{17}$LEALGGSEAELAAF$X_{32}X_{33}$EI$X_{36}$AF$X_{39}X_{40}$EL$X_{43}$AYKGKGNPEVE$X_{55}$LR$X_{58}X_{59}$AA$X_{62}$IR$X_{65}X_{66}$LQAYRHN (SEQ ID NO: 5) |
| C2 | MGSW$X_5$EF$X_8X_9$RL$X_{12}$AI$X_{15}X_{16}$RL$X_{19}$ALGGSEAELA$X_{30}$FE$X_{33}X_{34}$IA$X_{37}$FE$X_{40}X_{41}$LQ$X_{44}$YKGKGNPEVEAL$X_{57}X_{58}$EA$X_{61}$AI$X_{64}X_{65}$EL$X_{68}$AYRHN (SEQ ID NO: 6) |
| F1Lp$_X$ | MGSW$X_5X_6$FK$X_9X_{10}$LA$X_{13}$IK$X_{16}X_{17}$LEAL$Z_1$EAELA$X_{28}$FE$X_{31}X_{32}$IA$X_{35}$FE$X_{38}X_{39}$LQ$X_{42}$Y$Z_2$NPEVEALRKEAAAIRDELQAYRHN (SEQ ID NO: 7) |
| F2Lp$_X$ | MGSWAEFKQRLAAIKTRLEAL$Z_1$EAELAAF$X_{30}X_{31}$EI$X_{34}$AF$X_{37}X_{38}$EL$X_{41}$AY$Z_2$NPEVEAL$X_{52}X_{53}$EA$X_{56}$AI$X_{59}X_{60}$EL$X_{63}$AYRHN (SEQ ID NO: 8) |
| F3Lp$_X$ | MGSW$X_5$EF$X_8X_9$RL$X_{12}$AI$X_{15}X_{16}$RL$X_{19}$AL$Z_1$EAELAAFEKEIAAFESELQAY$Z_2$NPEVE$X_{50}$LR$X_{53}X_{54}$AA$X_{57}$IR$X_{60}X_{61}$LQAYRHN (SEQ ID NO: 9) |
| C1Lp$_X$ | MGSW$X_5X_6$FK$X_9X_{10}$LA$X_{13}$IK$X_{16}X_{17}$LEAL$Z_1$EAELAAF$X_{30}X_{31}$EI$X_{34}$AF$X_{37}X_{38}$EL$X_{41}$AY$Z_2$NPEVE$X_{50}$LFI$X_{53}X_{54}$AA$X_{57}$IR$X_{60}X_{61}$LQAYRHN (SEQ ID NO: 10) |

TABLE 3-continued

DBDpp Library Sequence Profiles

| Library | Sequence Profile |
| --- | --- |
| C2Lp$_X$ | MGSW$X_5$EF$X_8X_9$RL$X_{12}$AI$X_{15}X_{16}$RL$X_{19}$AL$Z_1$EAELA$X_{28}$FE$X_{31}X_{32}$IA$X_{35}$FE$X_{38}X_{39}$LQ$X_{42}$Y$Z_2X_{52}X_{53}$EA$X_{56}$AI$X_{59}X_{60}$EL$X_{63}$AYRHN (SEQ ID NO: 11) |

X = all amino acid residues

Z = amino acid sequence corresponding to loop1 ($Z_1$) or loop2 ($Z_2$) as described herein DBDpp F2NNK Library Construction An F2 library was constructed that targeted 12 surface-exposed residues on face 2 (helixes 2 and 3) (Table 3 and FIGS. 2C and 2D). This library, designated F2NNK, was created through Kunkel mutagenesis, utilizing oligos containing NNK codons. Libraries were constructed using a modified pComb phagmid vector in which DBDpp are fused at the C-terminus to the N-terminus of M13 pIII. These DBDpp are also fused at their N-terminus to the C-terminus of the FLAG epitope tag. The entire DBDpp fusion protein is under the secretory control of a DsbA signal peptide (FIG. 3B).

DBDpp Trinucleotide Phosphoramidite Library Construction

Subsequent libraries were constructed through Kunkel mutagenesis in the same modified pComb phagemid vector as the F2NNK library. In several embodiments, the FLAG tag is optional (see e.g., FIG. 3C), or can be replaced with another tag. These libraries were constructed using trinucleotide phosphoramidite (codon) mixtures. These mixtures were designed to exclude termination, cysteine and proline codons and provided an equal representation of the remaining amino acids. Libraries were built using all five sequence profiles (F1, F2, F3, C1 & C2) as shown in Table 3.

Selection Using F2$_{NNK}$ Library

The F2NNK DBD library was used in five rounds of selection against recombinant, biotinylated, Human 4-1BB/TNFRSF9/CD137-Fc. ELISA screening of rescued phage revealed that 89 of 95 clones bound 4-1BB/CD137 with an average OD 5.3-fold greater than control (IgG Fc). The distribution of binding (ELISA absorbance values) for the 89 clones: CD137 0.353 (0.134-0.617), control 0.067 (0.056-0.125). Sequencing of individual phage indicated that all 89 clones were identical at the nucleotide level. Notably, this clone, named bb10, contained substitutions in only 8 (in bold in the sequence below) of the 12 randomized positions of sequence of SEQ ID NO:1 that are underlined in sequence:

(bb10: SEQ ID NO: 19)

MGSWAEFKQRLAAIKTRLEALGGSEAELAAFLGEIWAFEMELAAYKGKGN

PEVEALGREAAAIRMELQAYRHN.

Selection Using F1, F2, F3, C1 & C2 Trinucleotide Phosphoramidite Libraries

Selections were also performed using F1, F2, F3, C1 & C2 trinucleotide phosphoramidite libraries. In most cases, libraries were pooled prior to use in selection. By combining equal volumes of the individual libraries, Pool F (libraries F1, F2 and F3) and Pool C (libraries C1 and C2) were generated. These libraries were used in selections for DBDpp binders to 4-1BB/CD137 as well as a larger panel of purified recombinant "target"-Fc proteins, including CD47, CTLA4, DR5, KIR, LAG3, OX40, PD1, PD-L1 and TIM3. (Many of these targets are considered immuno-regulatory factors (Pardoll et al., Nat. Rev. Cancer 12:252-264 (2012)).

After incubation of the target with the pools of DBDpp phage libraries, bound phage-target complexes were captured and separated from unbound phage with protein A beads (target proteins were Fc fusions). After three rounds of selection, rescued phage clones were screened by ELISA for binding to the selected target.

For each target, approximately 90 DBDpp phage clones were screened by ELISA for binding to the target protein and as well as a non-specific control (e.g., IgG1-Fc). Sequencing was performed on individual DBDpp clones that exhibited a target-specific binding signal that was 3 fold higher than the non-specific control. In some instances, for the ELISA screening plate in which the majority of DBDpp clones were positive, the entire plate was sequenced. Sequence results indicated that, in total, approximately 70% of DBDpp clones were in the correct reading frame and conformed to one of the five anticipated library sequence profiles (Table 3). Sequences that did not conform to an expected profile were typically composed of either failed sequencing reads, frameshift mutations, truncations, concatemerizations or other cloning artifacts.

DBDpp Bind to a Variety of Targets

Table 4 shows the distribution of clones for each of the libraries as a function of target and binding data. The three sub-tables tally the distribution for all sequences (top) and those with target-specific binding ratios equal to or greater than 2 (middle) or 3 (bottom). (Where sequences are represented by more than one clone, the average binding value is used.) Of the 794 total sequences, 330 are unique clones, of which 278 yielded an ELISA signal 3 fold above background.

TABLE 4

Distribution of DBDpp clones and unique sequences (T-Total; U-Unique)

| Library | CD137 T | CD137 U | CD47 T | CD47 U | CTLA T | CTLA U | DR5 T | DR5 U | KIR T | KIR U | LAG3 T | LAG3 U | OX40 T | OX40 U | PD1 T | PD1 U | PDL1 T | PDL1 U | TIM3 T | TIM3 U |
|---|---|---|---|---|---|---|---|---|---|---|---|---|---|---|---|---|---|---|---|---|
| ALL Sequences ||||||||||||||||||||| 
| F1 | 182 | 78 | 1 | 1 | 1 | 1 | | | 74 | 26 | 5 | 3 | 3 | 3 | | | 51 | 30 | | | 47 | 14 |
| F2 | 7 | 7 | | | | | | | | | | | 5 | 5 | 2 | 2 | | | | | | |
| F3 | 416 | 223 | 114 | 49 | 55 | 34 | 74 | 2 | 2 | 1 | 17 | 16 | 3 | 3 | | | 53 | 41 | 76 | 63 | 22 | 14 |
| C1 | 4 | 4 | | | 1 | 1 | | | | | 1 | 1 | | | | | 2 | 2 | | | | |
| C2 | 95 | 17 | 3 | 2 | 73 | 12 | | | 14 | 2 | 5 | 1 | | | | | | | | | | |
| F2$^{NNK}$ | 90 | 1 | 90 | 1 | | | | | | | | | | | | | | | | | | |
| Total | 794 | 330 | 208 | 53 | 130 | 48 | 74 | 2 | 90 | 29 | 28 | 21 | 11 | 11 | 4 | 4 | 104 | 71 | 76 | 63 | 69 | 28 |
| Sequences with ELISA ratios greater or equal to 2 |||||||||||||||||||||
| F1 | 162 | 64 | 1 | 1 | 1 | 1 | | | 74 | 26 | 5 | 3 | 2 | 2 | | | 43 | 24 | | | 36 | 7 |
| F2 | 7 | 7 | | | | | | | | | | | 5 | 5 | 2 | 2 | | | | | | |
| F3 | 402 | 409 | 114 | 49 | 52 | 31 | 74 | 2 | 2 | 1 | 15 | 14 | 3 | 3 | | | 52 | 40 | 75 | 62 | 15 | 7 |
| C1 | 3 | 3 | | | | | | | | | 1 | 1 | | | | | 2 | 2 | | | | |
| C2 | 92 | 14 | 3 | 2 | 70 | 9 | | | 14 | 2 | 5 | 1 | | | | | | | | | | |
| F2$^{NNK}$ | 90 | 1 | 90 | 1 | | | | | | | | | | | | | | | | | | |
| Total | 756 | 298 | 208 | 53 | 123 | 41 | 74 | 2 | 90 | 29 | 26 | 19 | 10 | 10 | 4 | 4 | 95 | 64 | 75 | 62 | 51 | 14 |
| Sequences with ELISA ratios greater or equal to 3 |||||||||||||||||||||
| F1 | 159 | 61 | | | 1 | 1 | | | 74 | 26 | 5 | 3 | 2 | 2 | | | 42 | 23 | | | 35 | 6 |
| F2 | 5 | 5 | | | | | | | | | | | 4 | 4 | 1 | 1 | | | | | | |
| F3 | 310 | 195 | 114 | 49 | 51 | 30 | | | 2 | 1 | 14 | 13 | 3 | 3 | | | 49 | 38 | 66 | 55 | 11 | 6 |
| C1 | 2 | 2 | | | | | | | | | 1 | 1 | | | | | 1 | 1 | | | | |
| C2 | 92 | 14 | 3 | 2 | 70 | 9 | | | 14 | 2 | 5 | 1 | | | | | | | | | | |
| F2$^{NNK}$ | 90 | 1 | 90 | 1 | | | | | | | | | | | | | | | | | | |
| Total | 658 | 278 | 207 | 52 | 122 | 40 | | | 90 | 29 | 25 | 18 | 9 | 9 | 2 | 2 | 91 | 61 | 66 | 55 | 46 | 12 |

Table 5 lists exemplary sequences derived from the experiments described above. For each sequence, the Target, library of origin (Lib.), number of screening occurrences (Count) and target to background ratio (ELISA ratio) are indicated. In several embodiments, DBDpp with at least 80%, at least 85%, at least 90%, at least 92%, at least 95% or at least 98% homology to those described above (and elsewhere herein) retain significant functional equivalence. In several embodiments, this is advantageous as the divergence in homology may present certain advantages, such as reduced immunogenicity, increased cross-reactivity, increased specificity, etc.

TABLE 5

Sequences of DBDpp Library Clones Isolated from the Screened Libraries

| SEQ ID NO: | Sequence | Target | Lib. | Count | ELISA ratio |
|---|---|---|---|---|---|
| 12 | MGSWVEFGHRLWAIDQRLYALGGSEAELAAFEKEIAAFES ELQAYKGKGNPEVEKLRQRAAFIRFRLQAYRHN | CD137 | F3 | 3 | 20.606 |
| 13 | MGSWVEFANRLWAIDQRLFALGGSEAELAAFEKEIAAFESE LQAYKGKGNPEVEHLRDQAAFIRHKLQAYRHN | CD137 | F3 | 7 | 16.055 |
| 14 | MGSWYEFRHRLWAIDQRLYALGGSEAELAAFEKEIAAFES ELQAYKGKGNPEVEGLREAAAFIRAKLQAYRHN | CD137 | F3 | 4 | 12.974 |
| 15 | MGSWYEFSMRLWAIDQRLYALGGSEAELAAFEKEIAAFES ELQAYKGKGNPEVEALRAKAAYIRWKLQAYRHN | CD137 | F3 | 2 | 12.040 |
| 16 | MGSWFEFNHRLWAINERLYALGGSEAELAAFEKEIAAFESE LQAYKGKGNPEVERLRSMAAFIRYKLQAYRHN | CD137 | F3 | 4 | 11.925 |
| 17 | MGSWYEFGHRLWAIDQRLYALGGSEAELAAFEKEIAAFES ELQAYKGKGNPEVEYLRETAAHIRTRLQAYRHN | CD137 | F3 | 3 | 7.707 |
| 18 | MGSWYEFHYRLHAIDQRLYALGGSEAELAAFEKEIAAFESE LQAYKGKGNPEVEELRIKAAFIRDRLQAYRHN | CD137 | F3 | 3 | 7.262 |
| 19 | MGSWAEFKQRLAAIKTRLEALGGSEAELAAFLGEIWAFEME LAAYKGKGNPEVEALGREAAAIRMELQAYRHN | CD137 | F2 | 90 | 5.269 |
| 20 | MGSWYEFDLRLHAIYDRLVALGGSEAELAAFEKEIAAFESE LQAYKGKGNPEVEILRDNAAYIRQMLQAYRHN | CD47 | F3 | 2 | 14.087 |
| 21 | MGSWTEFTYRLSAIEWRLWALGGSEAELAWFEQKIAFFED FLQYYKGKGNPEVEALKHEAGAILNELMAYRHN | CD47 | C2 | 24 | 12.517 |
| 22 | MGSWAEFDHRLHAIRERLHALGGSEAELAAFEKEIAAFESE LQAYKGKGNPEVEILRGNAAYIRALLQAYRHN | CD47 | F3 | 3 | 11.651 |
| 23 | MGSWTEFVGRLAAIEFRLWALGGSEAELAWFEAHIAFFED YLQWYKGKGNPEVEALREEAGAIMEELKAYRHN | CD47 | C2 | 3 | 8.230 |
| 24 | MGSWTEFYSRLEAIWVRLQALGGSEAELAMFEDRIAHFEW FLQQYKGKGNPEVEALHEEAIAIRKELAAYRHN | CD47 | C2 | 37 | 4.578 |
| 25 | MGSWHEFHDRLQAIHERLYALGGSEAELAAFEKEIAAFESE LQAYKGKGNPEVESLRIAAAHIRQVLQAYRHN | CTLA4 | F3 | 73 | 2.950 |
| 26 | MGSWNYFKDHLAWIKNSLEALGGSEAELAHFETAIASFER QLQEYKGKGNPEVEALRKEAAAIRDELQAYRHN | DR5 | F1 | 12 | 12.993 |
| 27 | MGSWLYFKEHLAHIKAWLEALGGSEAELAHFELAIADFEYH LQEYKGKGNPEVEALRKEAAAIRDELQAYRHN | DR5 | F1 | 5 | 12.309 |
| 28 | MGSWVYFKEHLAWIKTELEALGGSEAELAHFEHSIADFEMS LQFYKGKGNPEVEALRKEAAAIRDELQAYRHN | DR5 | F1 | 4 | 12.117 |
| 29 | MGSWFYFKQHLAWIKSYLEALGGSEAELAHFERAIAAFEQ HLQMYKGKGNPEVEALRKEAAAIRDELQAYRHN | DR5 | F1 | 5 | 11.836 |
| 30 | MGSWHYFKDHLAEIKGLLEALGGSEAELAHFEMAIADFEHN LQYYKGKGNPEVEALRKEAAAIRDELQAYRHN | DR5 | F1 | 5 | 11.436 |
| 31 | MGSWHYFKGHLAEIKNHLEALGGSEAELAHFERAIAAFERS LQWYKGKGNPEVEALRKEAAAIRDELQAYRHN | DR5 | F1 | 7 | 10.822 |
| 32 | MGSWIYFKEHLAYIKKELEALGGSEAELAHFESAIAVFESTL QYYKGKGNPEVEALRKEAAAIRDELQAYRHN | DR5 | F1 | 4 | 10.677 |
| 33 | MGSWTYFKEHLAEIKYMLEALGGSEAELAHFEVAIADFEKM LQYYKGKGNPEVEALRKEAAAIRDELQAYRHN | DR5 | F1 | 8 | 10.256 |
| 34 | MGSWWLFKDHLAEIKTALEALGGSEAELAHFEMAIAAFEKQ LQYYKGKGNPEVEALRKEAAAIRDELQAYRHN | DR5 | F1 | 3 | 9.748 |
| 35 | MGSWSEFYNRLDAIESRLLALGGSEAELALFEIQIARFEKVL QAYKGKGNPEVEALRGEARAIFAELYAYRHN | KIR | C2 | 5 | 8.399 |
| 36 | MGSWYEFYNRLYAIEIRLYALGGSEAELAAFEKEIAAFESEL QAYKGKGNPEVERLRVRAAKIRVILQAYRHN | KIR | F3 | 2 | 4.244 |

TABLE 5-continued

Sequences of DBDpp Library Clones Isolated from the Screened Libraries

| SEQ ID NO: | Sequence | Target | Lib. | Count | ELISA ratio |
|---|---|---|---|---|---|
| 37 | MGSWLWFKIFLAEIKYFLEALGGSEAELAAFDFEIHAFHVEL FAYKGKGNPEVEVLREVAAEIRWDLQAYRHN | KIR | C1 | 1 | 4.170 |
| 38 | MGSWTEFQSRLDAIHSRLRALGGSEAELAAFEKEIAAFESE LQAYKGKGNPEVELLRDDAAFIRHFLQAYRHN | PD-L1 | F3 | 2 | 8.682 |
| 39 | MGSWQEFDDRLNAIKARLQALGGSEAELAAFEKEIAAFESE LQAYKGKGNPEVEDLRDDAAFIRRFLQAYRHN | PD-L1 | F3 | 2 | 7.413 |
| 40 | MGSWYEFQNRLHAIHERLNALGGSEAELAAFEKEIAAFESE LQAYKGKGNPEVELLRDDAAFIRHFLQAYRHN | PD-L1 | F3 | 2 | 6.345 |
| 41 | MGSWFEFQDRLTAINERLSALGGSEAELAAFEKEIAAFESE LQAYKGKGNPEVETLRSDAAFIRRFLQAYRHN | PD-L1 | F3 | 2 | 6.015 |
| 42 | MGSWYEFESRLDAIHERLHALGGSEAELAAFEKEIAAFESE LQAYKGKGNPEVENLRGDAAFIRHFLQAYRHN | PD-L1 | F3 | 6 | 4.882 |
| 43 | MGSWYEFNHRLDAISKRLNALGGSEAELAAFEKEIAAFESE LQAYKGKGNPEVEELRGDAAFIRHFLQAYRHN | PD-L1 | F3 | 2 | 2.982 |
| 44 | MGSWFEFENRLHAIVHRLGALGGSEAELAAFEKEIAAFESE LQAYKGKGNPEVETLRADAAFIRHYLQAYRHN | PD-L1 | F3 | 2 | 2.764 |
| 45 | MGSWVVFKVDLATIKYILEALGGSEAELAEFEGEIAGFEYSL QFYKGKGNPEVEALRKEAAAIRDELQAYRHN | TIM3 | F1 | 2 | 5.788 |
| 46 | MGSWTIFKEWLAFIKTDLEALGGSEAELAFFEGWIASFEME LQKYKGKGNPEVEALRKEAAAIRDELQAYRHN | PD1 | F1 | 14 | 17.145 |
| 47 | MGSWVMFKVVLLADIKSHLEALGGSEAELAFFEGFIAAFETH LQVYKGKGNPEVEALRKEAAAIRDELQAYRHN | PD1 | F1 | 4 | 8.132 |
| 48 | MGSWYAFKDYLADIKGWLEALGGSEAELAFFEIFIARFELEL QAYKGKGNPEVEALRKEAAAIRDELQAYRHN | PD1 | F1 | 2 | 3.295 |

N-terminal FLAG tag fusions of pb04 (SEQ ID NO: 182) and a3D (SEQ ID NO: 49) were expressed and purified from E. coli cultures. Through assessment by ELISA, purified FLAG-pb04 binds in a dose dependent manner to PD-L1-Fc coated microtiter wells. In contrast, FLAG-a3D exhibits no detectable binding to the PD-L1-Fc target protein (FIG. 3D). The results demonstrate that modification of reference scaffold sequence (SEQ ID NO:1) is effective in providing a robust source of DBDpp that are able to bind, with novel specificity, a diverse set of targets of interest.

Example 3. DBDpp Fusion Proteins

Figure 4B:
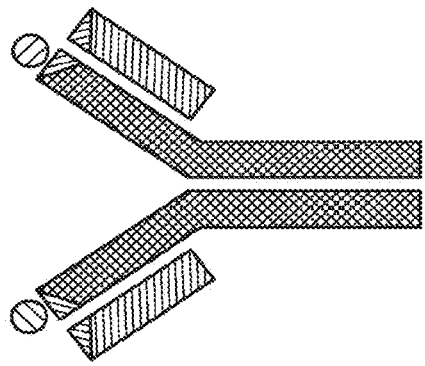
FIGS. 4A-D. DBDpp have novel binding specificities and impart these novel binding specificities to another molecule (e.g., an antibody) as part of a fusion protein (e.g., an antibody-DBDpp fusion protein). Schematic depicting the recombinant fusion of DBDpp (shown as circle) to the C-terminus (FIG. 4A) and N-terminus (FIG. 4B) of an antibody heavy chain. DBDpp—antibody fusions were created using an RSV-specific antibody (SYN) and either the targetless peptide of SEQ ID NO:1 (DBD) or the CD137-specific DBDpp (bb10). The DBDpp are fused to the N-terminus (bb10-SYN and DBD-SYN) or the C-terminus (SYN-bb10 and SYN-DBD). All four antibody fusions bind to RSV (FIG. 4C). However, the fusion of bb10 to either the N-terminus (bb10-SYN) or C-terminus (SYN-bb10) of the antibody heavy chain imparts a novel CD137 binding specificity to an otherwise mono-specific antibody (FIG. 4D).
Figure 4D:
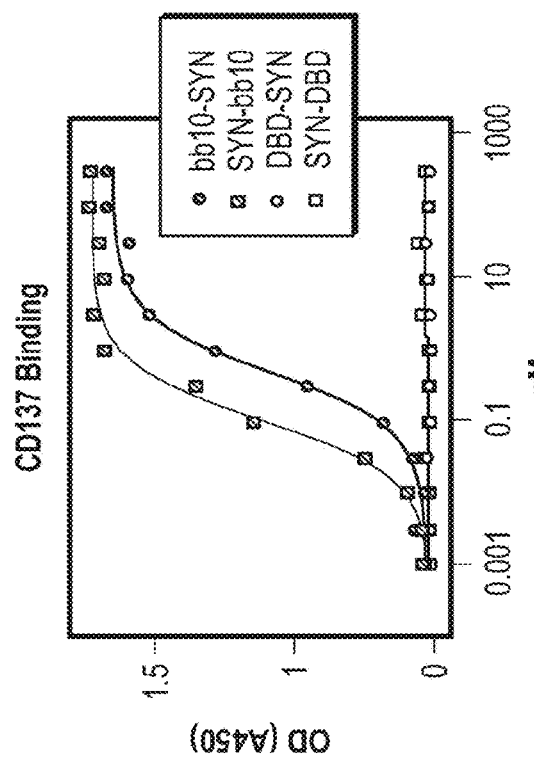
Figure 4A:
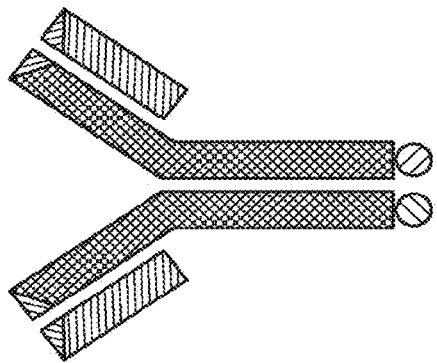

To assess the modular nature of DBDpp as a binding element, the DBDpp CD137-binder, bb10 (SEQ ID NO:19), was reformatted as a fusion to either the N or C terminus of the heavy chain of an antibody derived from the sequence of the RSV-specific monoclonal antibody palivizumab (SYNAGIS®) (shown schematically in FIGS. 4A and 4B, respectively). As a comparator analogous fusions were generated using the DBDpp parental sequence (SEQ ID NO:1), which is not known to exhibit any binding specificity. Proteins were produced in HEK293F suspension cells that were transiently transfected with equimolar ratios of independent heavy chain-bb10 fusion and light chain cDNA expression constructs, and purified through conventional protein A affinity methods. Separation by SDS-PAGE of purified samples indicated that the migration of heavy chain-bb10 (DBDpp) fusion proteins were commensurate with predictions based on molecular weight (data not shown).

Analysis by SEC indicated that the bb10 DBDpp antibody fusions were not aggregated and migrated as predicted relative to the size standards (data not shown). SYN-bb10 and bb10-SYN fusions demonstrate similar migration to each other, both ran faster than the parental SYNAGIS® antibody.

Figure 4C:
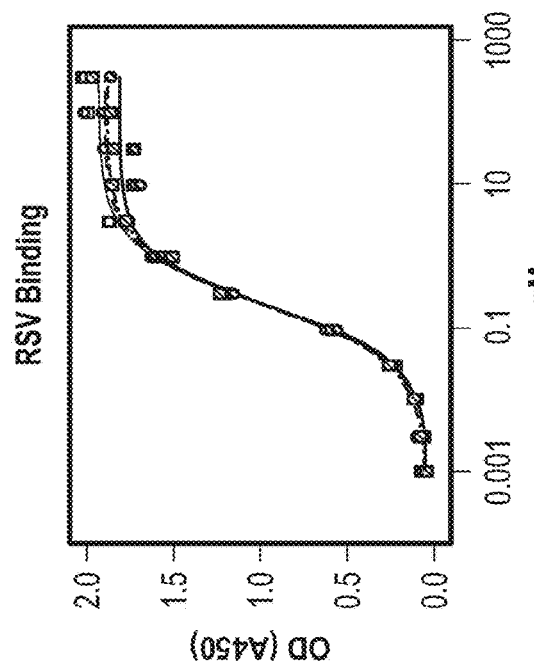

Bi-specific antibodies, SYN-bb10 and bb10-SYN exhibit binding to both CD137 and RSV (FIG. 4C-D; closed squares are bb10-SYN, closed circles are SYN-bb10)), demonstrating that a novel binding activity was imparted to the parental DBD sequence and the functionality of DBDpp is retained as both N and C-terminal fusion. In contrast, fusions between a targetless alpha-helical protein scaffold and SYN (DBD-SYN for N-terminal fusion, open circles; SYN-DBD for C-terminal fusion, open squares) showed binding only to RSV, but no binding to CD137 was imparted.

Figure 6A:
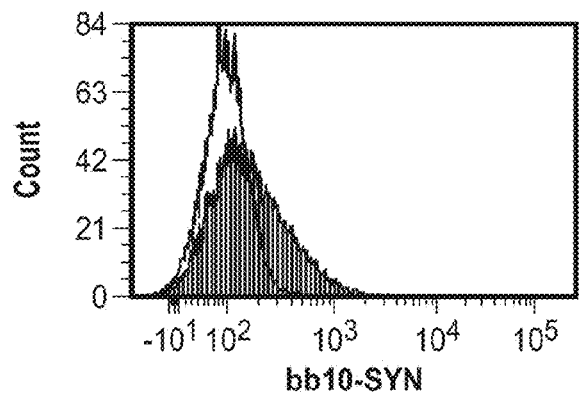
FIGS. 6A-C. Multi-specific DBDpp fusions recognize cell surface targets. FACS analysis indicates that bb10-SYN and SYNbb10 bispecific antibodies bind (shaded histogram) to activated CEM cell at levels greater than SYN alone (black outline). The weaker binding observed with the bb10 N-terminal fusion (FIG. 6A) as compared to the C-terminal fusion (FIG. 6B) is consistent with the above ELISA data. URE1 is a recombinant antibody constructed formed from variable domains of the CD137-targeting, urelumab fused to IgG scaffold. Binding of CEM cells was performed after activated with PMA (50 ng/ml) and ionomycin (500 ng/ml) for 48 hr. Detection of bound antibody was performed with anti-IgG1 Fc (FITC-A).
Figure 6B:
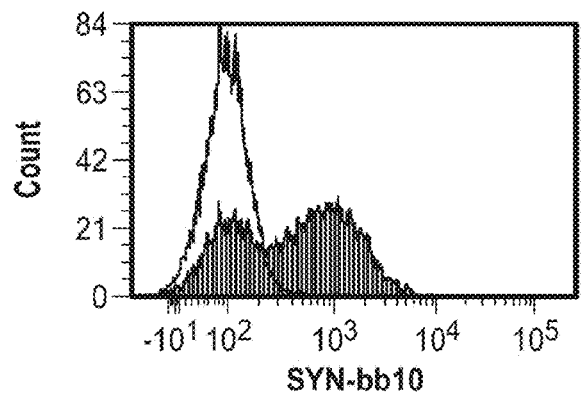
Figure 6C:
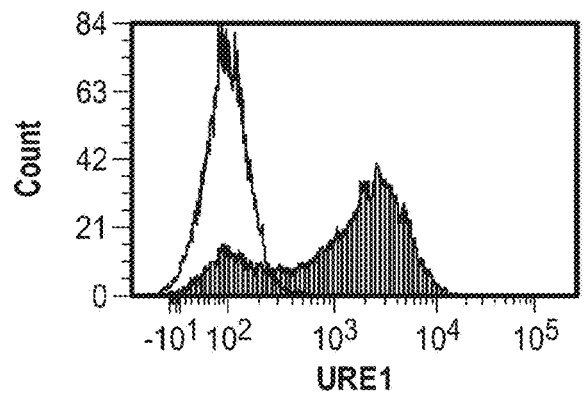
Figure 7A:
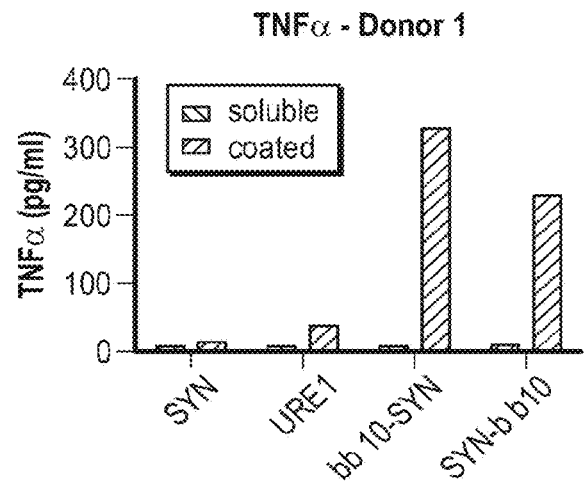
FIGS. 7A-D. DBDpp impart novel biological activity to an antibody-DBDpp fusion protein. Activation of CD137 by ligand or agonistic antibodies, such as urelumab, induces a signaling cascade that results in cytokine production, expression of anti-apoptotic molecules, and enhanced immune responses. The agonistic potential of the CD137-targeting DBDpp, bb10 was assessed by measuring the ability of bb10-SYN and SYN-bb10 to induce cytokine release from PBMC. bb10 fusions were tested in both soluble and plastic well-coated formats. PBMCs in complete RPMI medium were added to plates and incubated overnight. The cell culture supernatants were then measured for TNFa and IL8 using ELISA. For two donor PBMC populations, bb10 fusions induce secretion of IL8 and TNF alpha at levels equal to or greater than that of an agonistic anti-CD137 monoclonal antibody, URE1.
Figure 7B:
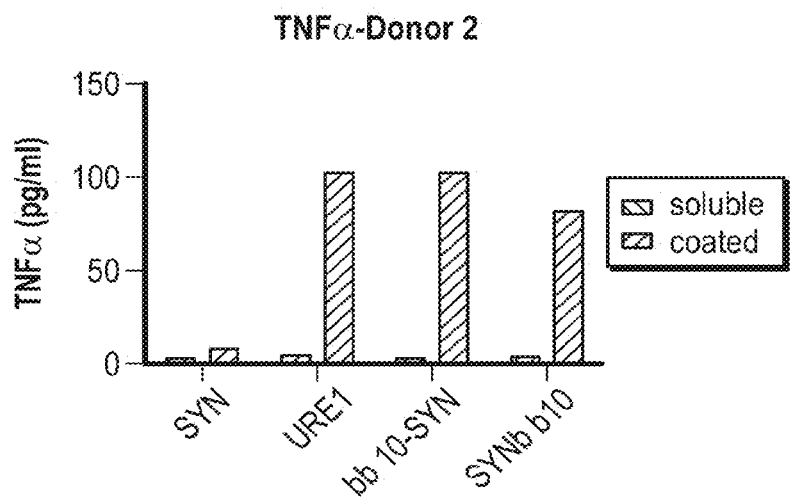
Figure 7C:
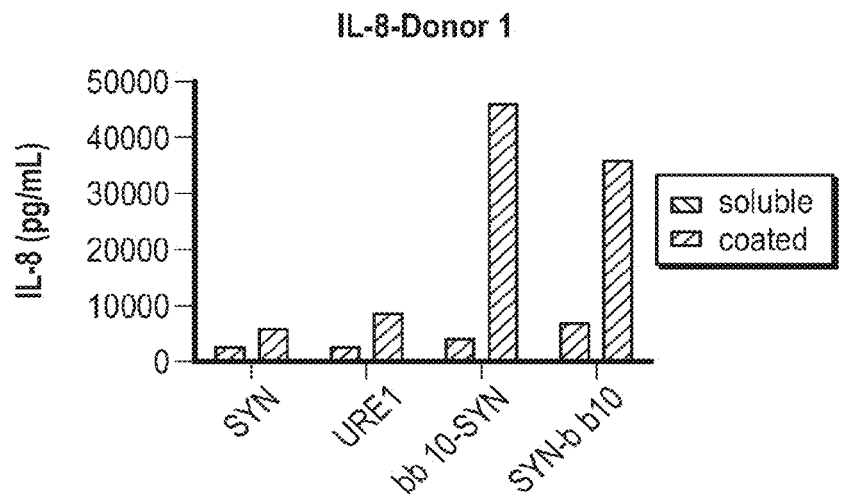
Figure 7D:
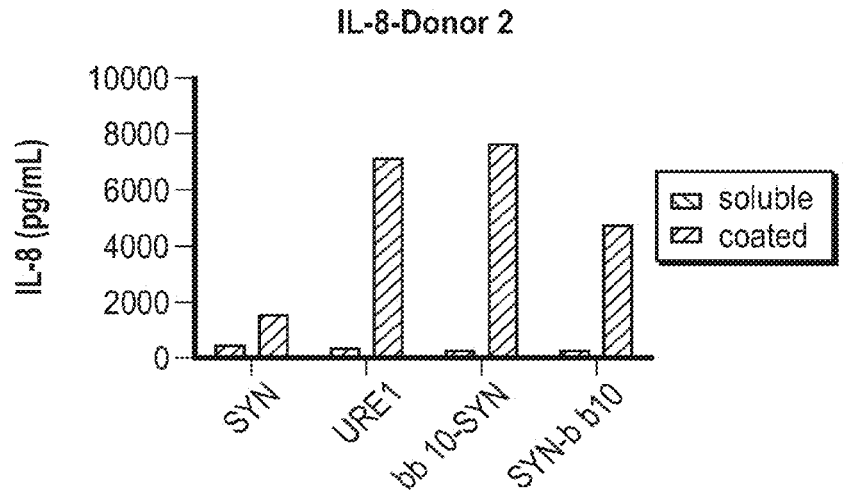

Binding of DBDpp, bb10 to CD137 is demonstrated using two different experimental methods: ELISA (FIG. 4C-D) and FACS (FIG. 6A-C). In these assays the target antigen is presented and ultimately recognized in three different formats: either directly bound to plastic (FIG. 4C-D) or in situ, as part of a cell membrane (FIG. 6A-C).

Treatment of PBMCs with SYN-bb10 and bb10-SYN demonstrates that in addition to binding, both fusion proteins are capable of inducing a downstream biological response in target cells (FIG. 7A-D).

Figure 8:
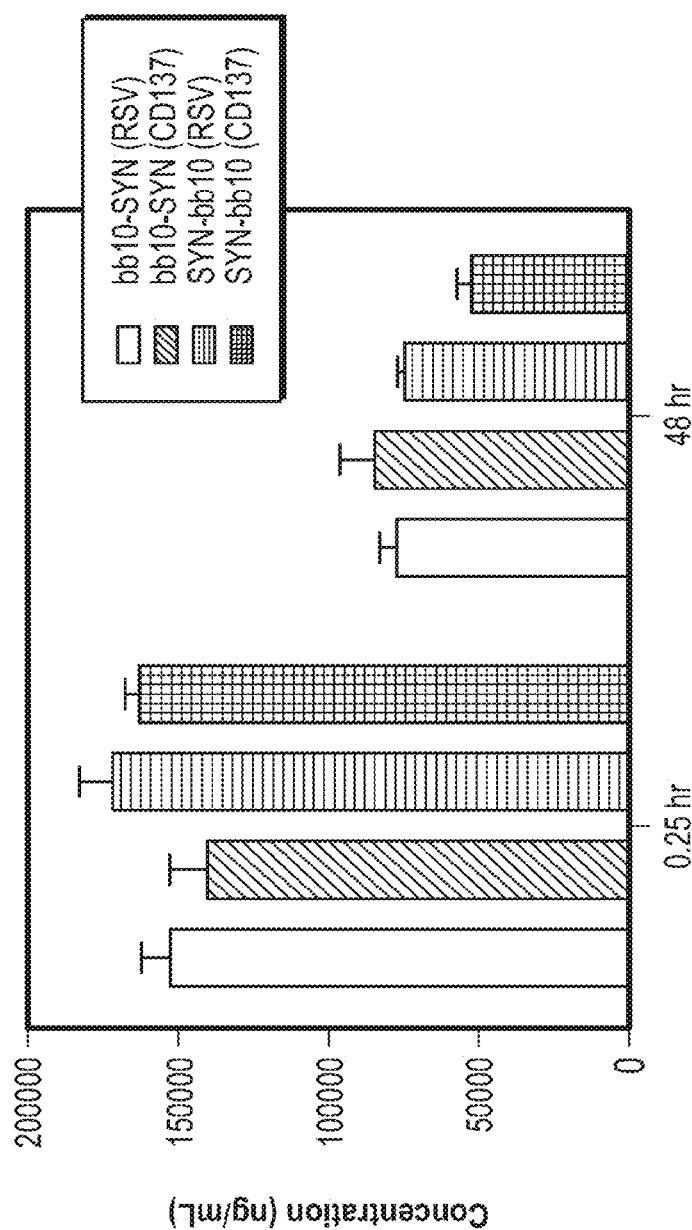
FIG. 8. In vivo stability is critical to the clinical efficacy of most biotherapeutics. Pharmacokinetic measurements of bb10 fusions were performed to assess the relative stability of DBDpp as compared to the antibody fusion partner. The in vivo stability was determined by analysis of both the RSV and CD137 binding of the bi-specific antibody present in serum from CD1 mice that received a single intravenous injection (1 mg/kg) of the fusion. Serum samples were collected at 15 minutes and 48 hours, and were assayed by ELISA. Both N-terminal and C-terminal DBDpp fusion proteins demonstrate sustained stability in vivo. As discussed in greater detail below, several embodiments involve DBDpp fusions with extended stability (e.g., on the order of 24 hours, 48 hours, 72 hours, 96 hours, 6 days, 8 days, 10 days, or greater, including times between those listed).

In vivo stability is critical to the clinical efficacy of most biotherapeutics. Pharmacokinetic measurements of bb10 fusions (SYN-bb10 and bb10-SYN) were performed to assess the relative stability of DBDpp as compared to the mAb fusion partner (FIG. 8). The in vivo stability was determined by analysis of both the RSV and CD137 binding of the bi-specific antibodies present in serum from CD1 mice that received a single intravenous injection (1 mg/kg) of the fusion proteins. Serum samples were collected at 15 minutes and 48 hours, and were assayed by ELISA. Both N-terminal and C-terminal DBDpp fusion proteins demonstrate sustained stability in vivo.

Example 4. Use of DBDpp in Affinity Purification

Eight CD137 binding DBDpp ligands (SEQ ID NO:12-19) were reformatted as N-terminal hexahistidine fusion proteins. Their tagged sequences and corresponding parent sequences are shown in Table 5.

TABLE 5

N-terminal hexahistidine fusion proteins prepared from SEQ ID NO: 12-19.

| Parent SEQ ID NO: | New Seq ID | His-Fusion Protein Sequence |
|---|---|---|
| 12 | 51 | MGSWVEFGHRLWAIDQRLYALGGSEAELAAFE KEIAAFESELQAYKGKGNPEVEKLRQRAAFIR FRLQAYRHNGGGGSHHHHHH |
| 13 | 52 | MGSWVEFANRLWAIDQRLFALGGSEAELAAFE KEIAAFESELQAYKGKGNPEVEHLRDQAAFIR HKLQAYRHNGGGGSHHHHHH |
| 14 | 53 | MGSWYEFRHRLWAIDQRLYALGGSEAELAAFE KEIAAFESELQAYKGKGNPEVEGLREAAAFIR AKLQAYRHNGGGGSHHHHHH |
| 15 | 54 | MGSWYEFSMRLWAIDQRLYALGGSEAELAAFE KEIAAFESELQAYKGKGNPEVEALRAKAAYIR WKLQAYRHNGGGGSHHHHHH |
| 16 | 55 | MGSWFEFNHRLWAINERLYALGGSEAELAAFE KEIAAFESELQAYKGKGNPEVERLRSMAAFIR YKLQAYRHNGGGGSHHHHHH |
| 17 | 56 | MGSWYEFGHRLWAIDQRLYALGGSEAELAAFE KEIAAFESELQAYKGKGNPEVEYLRETAAHIR TRLQAYRHNGGGGSHHHHHH |
| 18 | 57 | MGSWYEFHYRLHAIDQRLYALGGSEAELAAFE KEIAAFESELQAYKGKGNPEVEELRIKAAFIR DRLQAYRHNGGGGSHHHHHH |
| 19 | 58 | MGSWAEFKQRLAAIKTRLEALGGSEAELAAFL GEIWAFEMELAAYKGKGNPEVEALGREAAAIR MELQAYRHNGGGGSHHHHHH |

Figure 9:
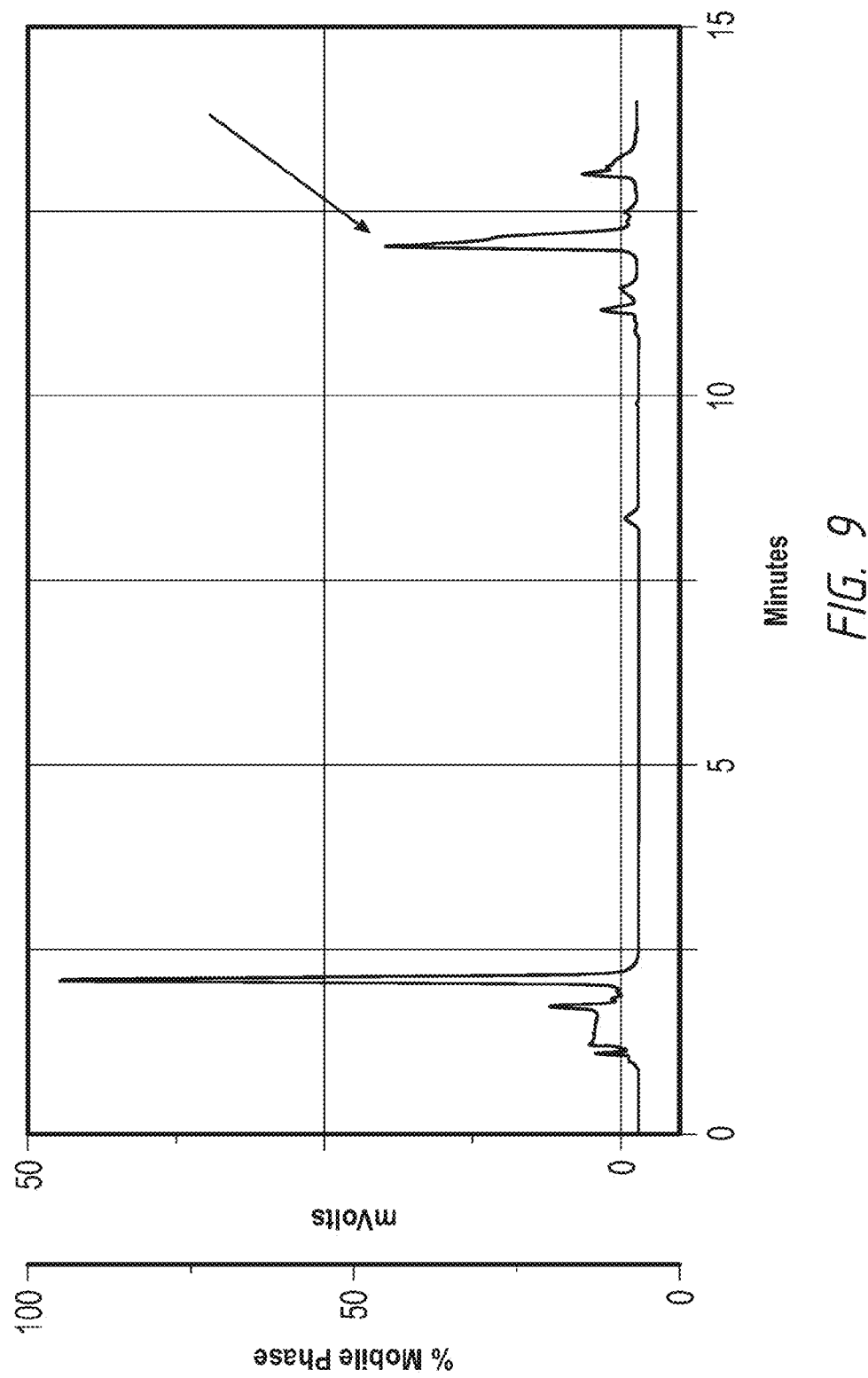
FIG. 9.

Each fusion was expressed separately in *E.Coli* BL21 (DE3) cells. After cell lysis and purification using immobilized metal ion chromatography each of the CD137 binding DBDpp ligands were re-purified using reverse-phase HPLC. The HPLC columns (20×100 mm C-4, Western Analytical) were each eluted with 0.1% TFA:Acetonitrile (88:12 for 2 minutes followed by a linear gradient to 58:42 at 15 minutes). The major peak at approximately 12 minutes corresponded to the target ligand (see arrow in FIG. 9). The purified ligands were lyophilized prior to further use.

Figure 10:
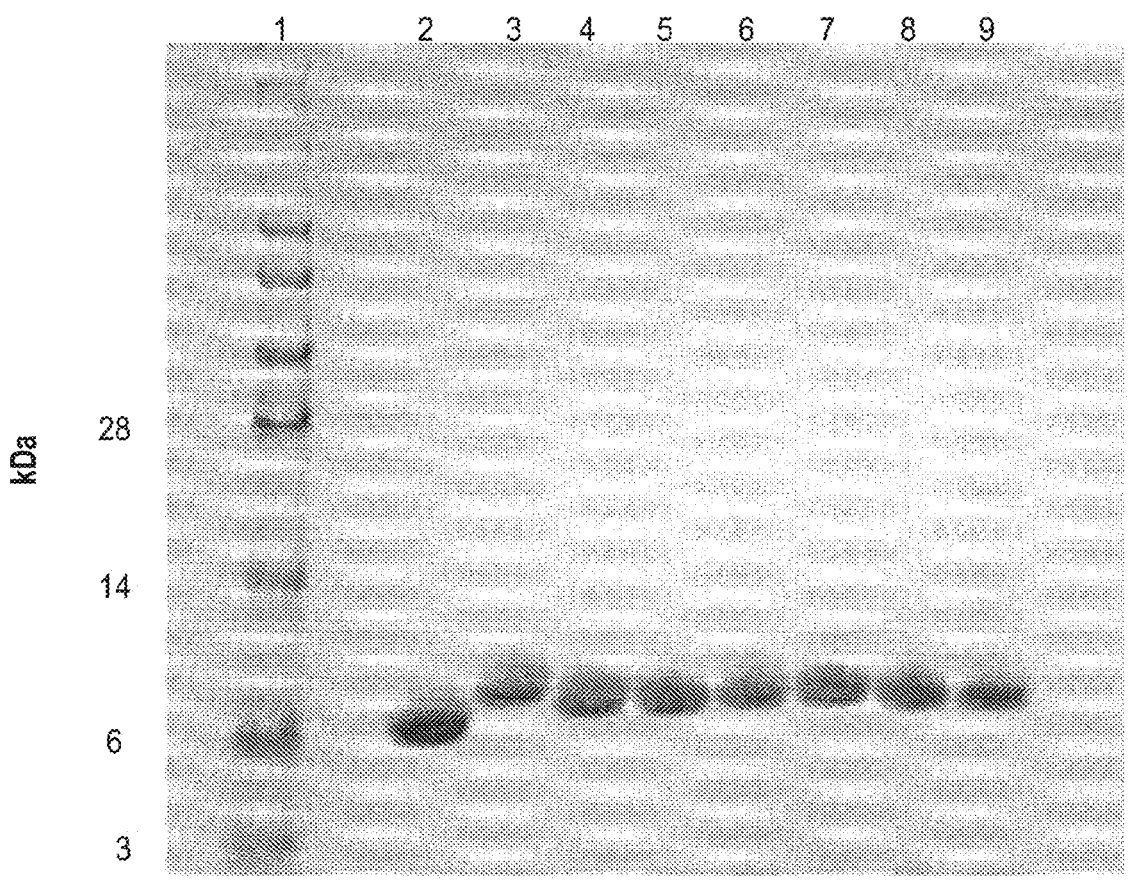
FIG. 10.

The identity and purity of each of the ligands was confirmed by electrospray mass spectrometry (Table 6) and SDS-PAGE (FIG. 10). Table 6 shows the calculated molecular weight for each of the CD137 targeting DBDpp, based on their sequence. Table 6 also shows the expected molecular weight for each of the DBDpp after replacement of the N-terminal methionine with a hexahistidine tag. Table 6 also shows the observed molecular weights. For each of the CD137 targeting DBDpps, with the exception of SEQ ID NO. 54, the observed molecular weight correlated well with the expected molecular weight, indicating that the dominant species in the purified sample included the hexahistidine tag. For SEQ ID NO: 54 the species containing the methionine was the major species.

TABLE 6

Comparison of expected molecular weight and observed molecular weight for the 8 proteins SEQ ID 51-58.

| Seq ID | Calc. MWt | Expected MWt (without Met) | Observed MWt |
|---|---|---|---|
| 51 | 9596 | 9465 | 9464 |
| 52 | 9501 | 9370 | 9369 |
| 53 | 9500 | 9369 | 9368 |
| 54 | 9569 | 9438 | 9568 |
| 55 | 9651 | 9520 | 9518 |
| 56 | 9585 | 9454 | 9453 |
| 57 | 9643 | 9512 | 9511 |
| 58 | 9207 | 9076 | 9075 |

FIG. 10 shows a Coomassie blue stained SDS-PAGE analysis of each of the CD137 targeting DBDpps with a hexahistidine tag. Lane 1 is a molecular weight ladder (kilodaltons), lane 2 is SEQ ID NO: 58, and lanes 3-9 correspond to SEQ ID NOS: 51-57, respectively. Each of the lanes shows a clean and precise band without smearing or evidence of smaller bands that would suggest breakdown of the DBDpp.

Figure 11:
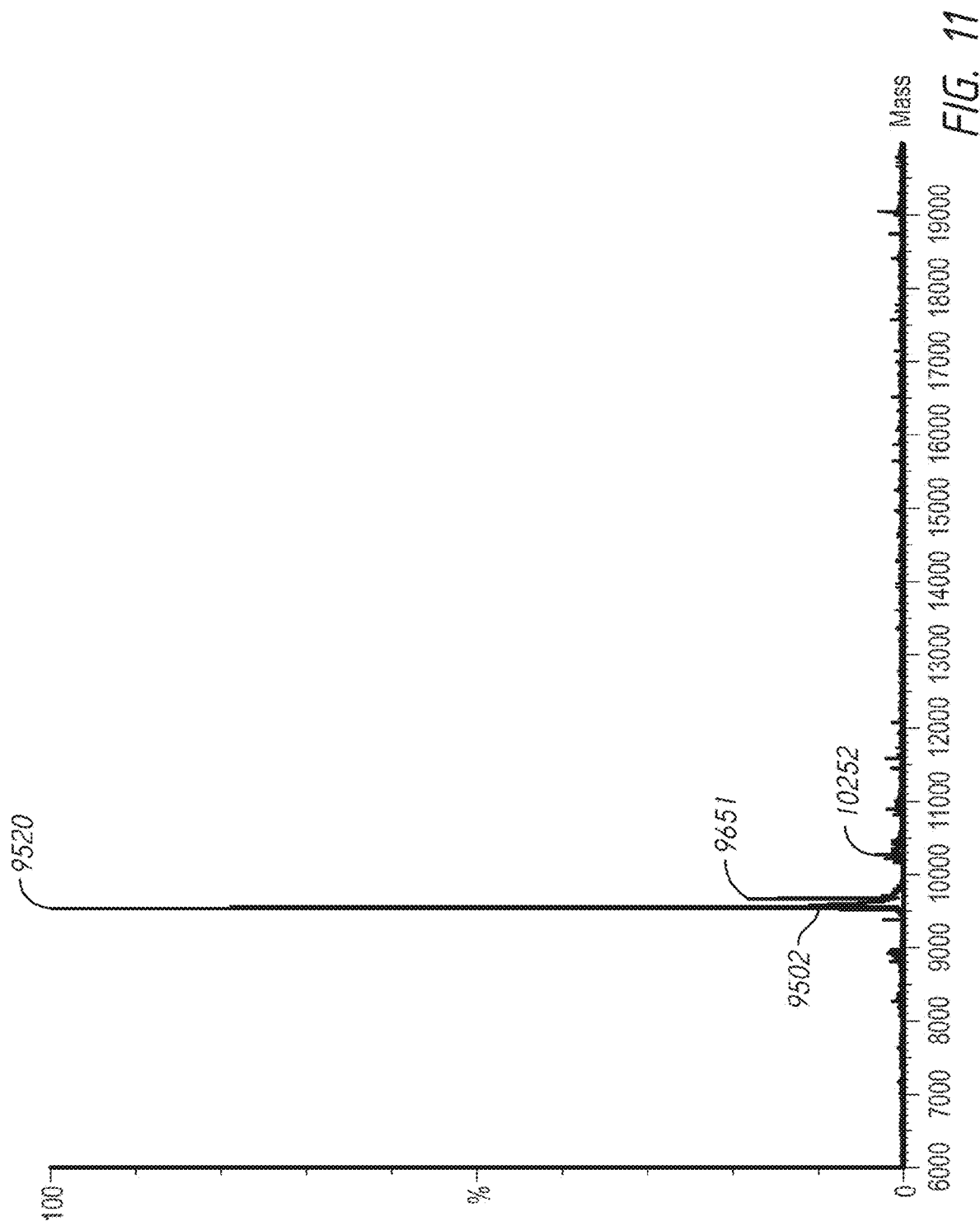
FIG. 11.
Figure 12A:
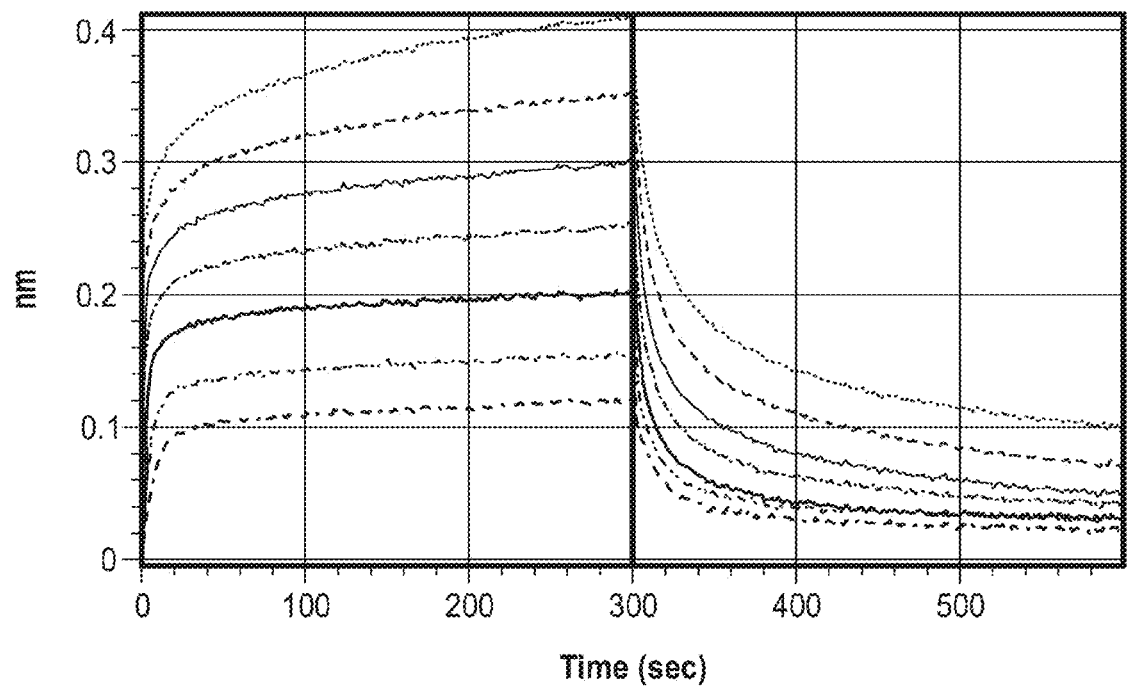
FIGS. 12A-12P.
Figure 12B:
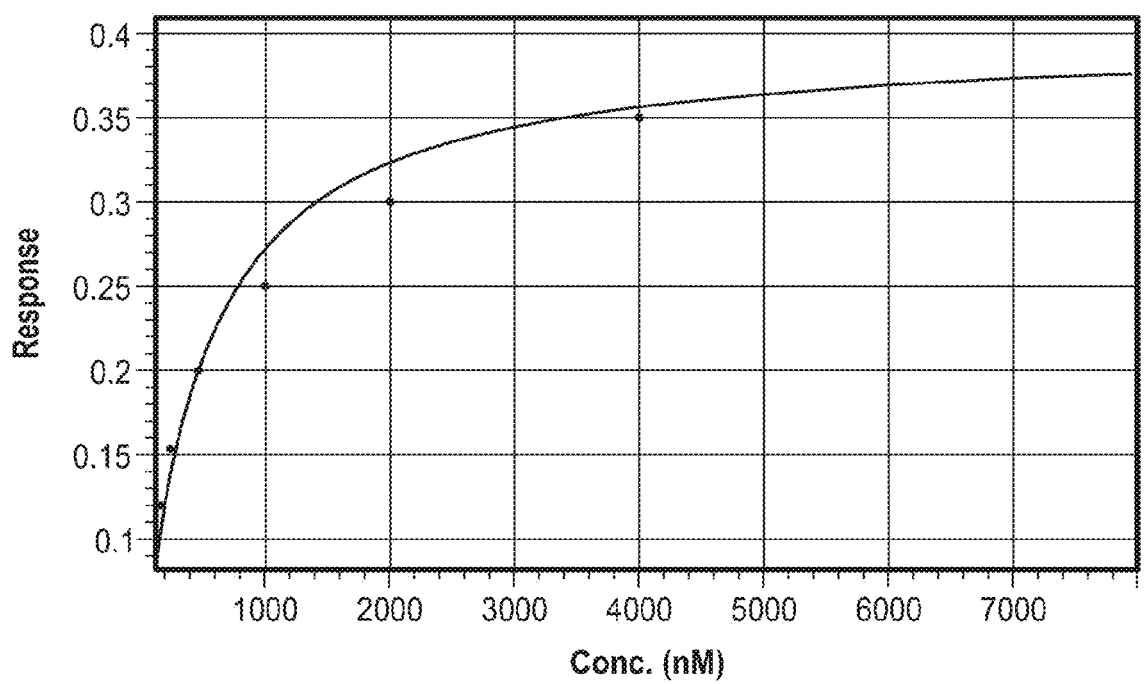
Figure 12C:
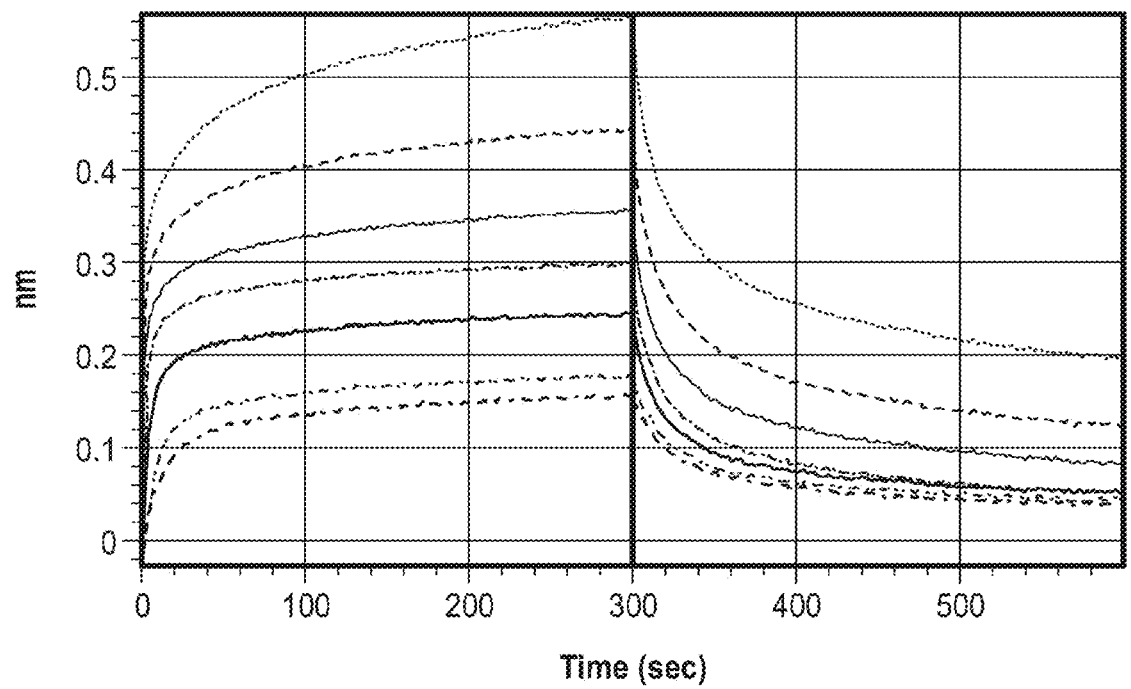
Figure 12D:
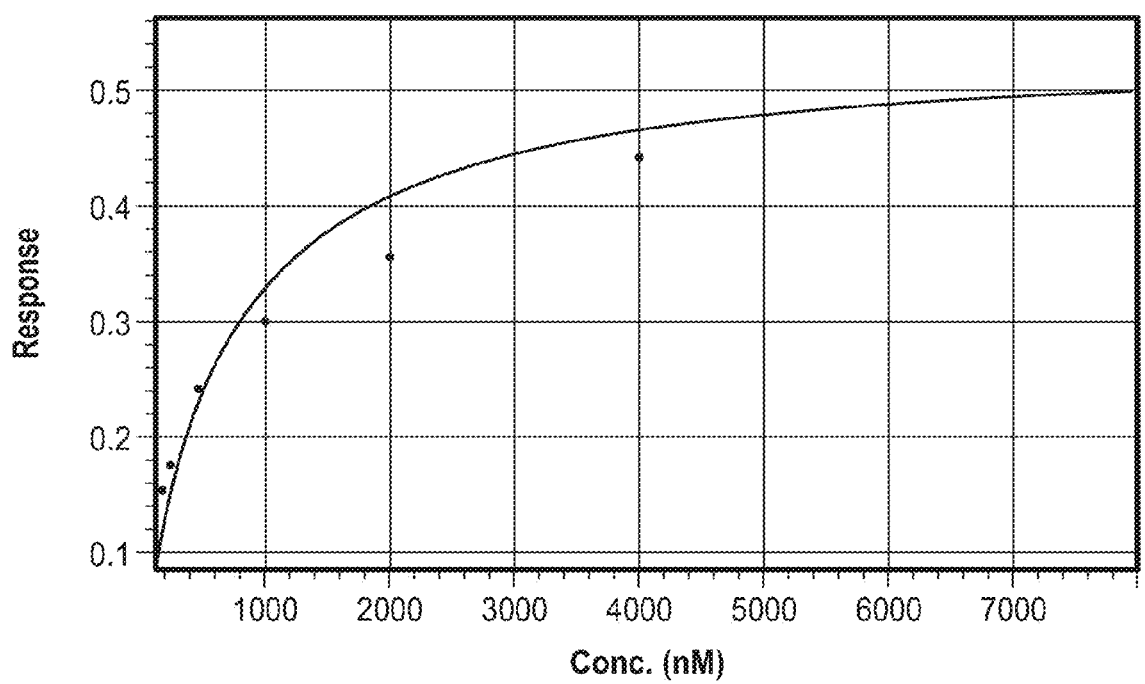
Figure 12E:
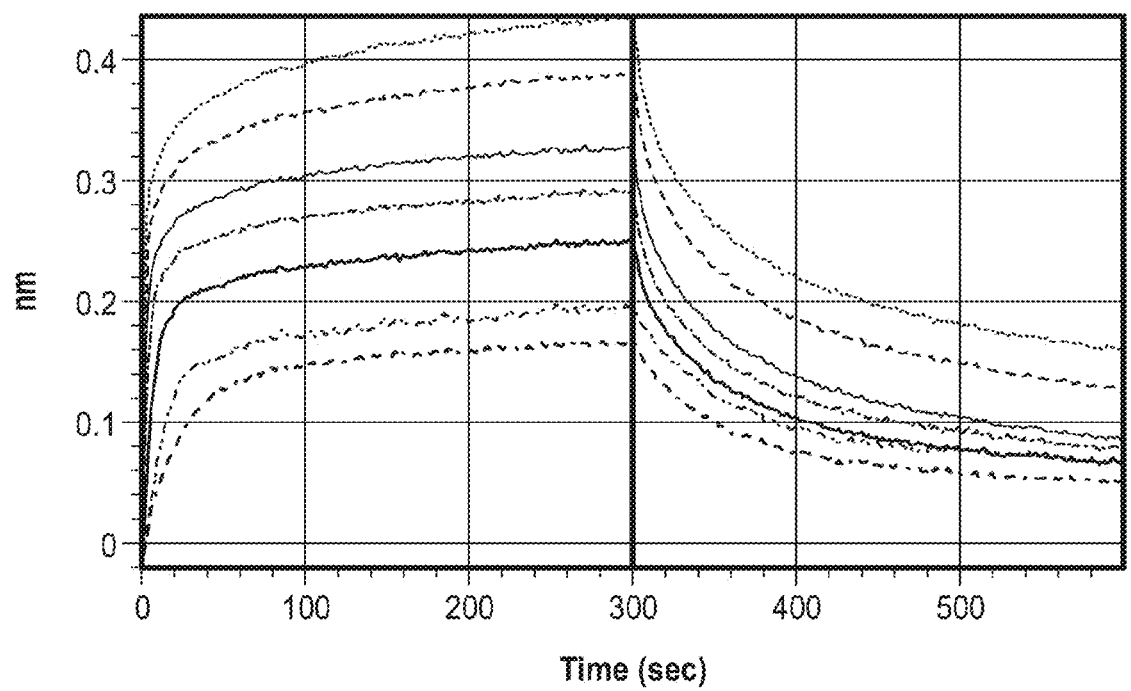
Figure 12F:
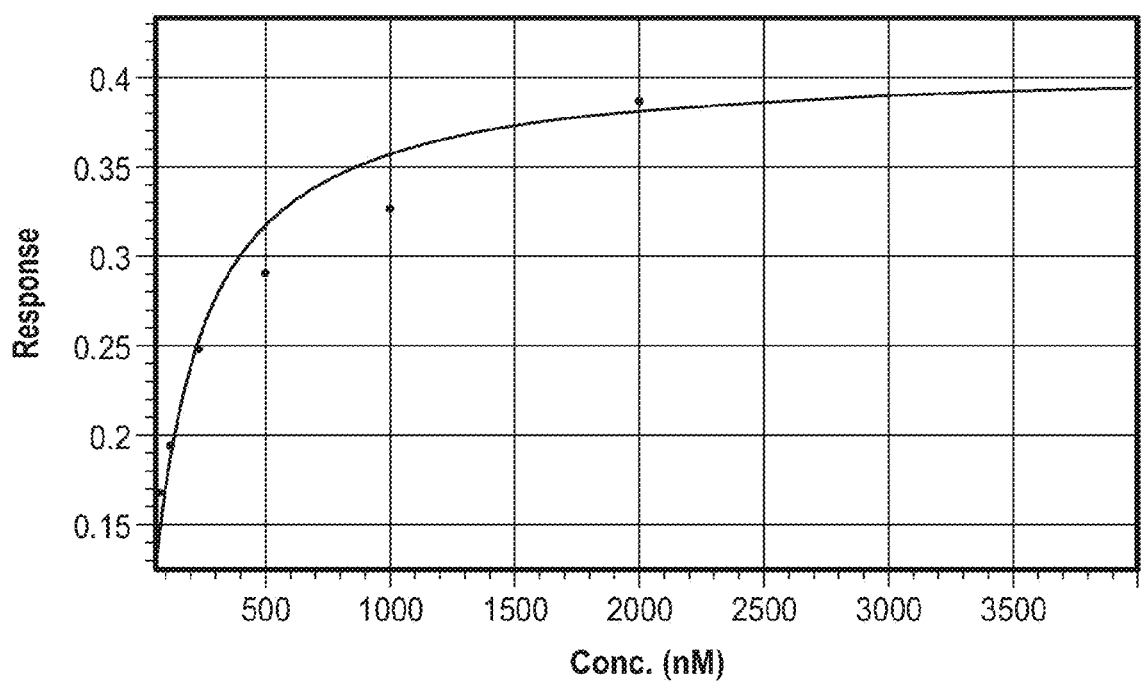
Figure 12G:
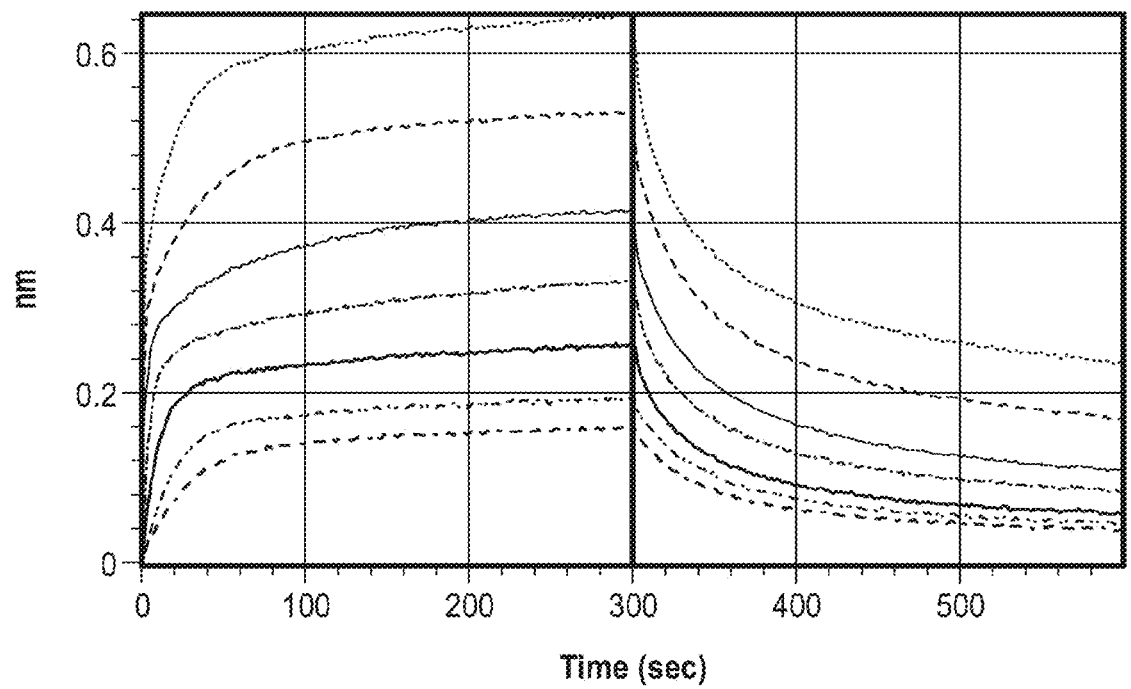
Figure 12H:
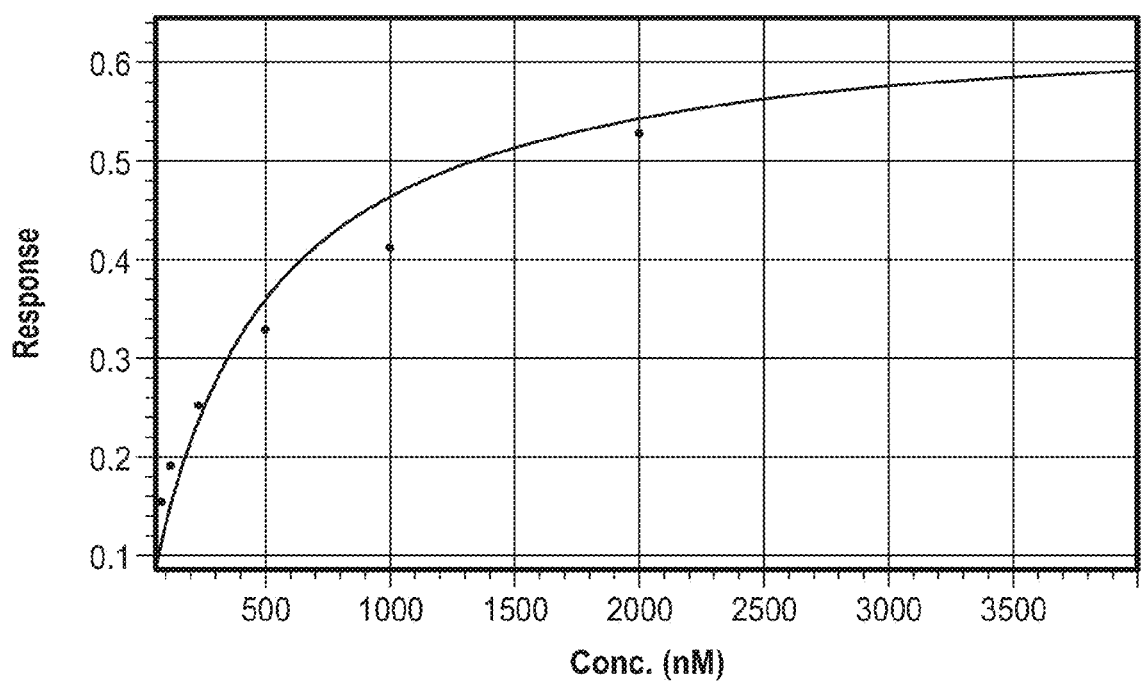
Figure 12I:
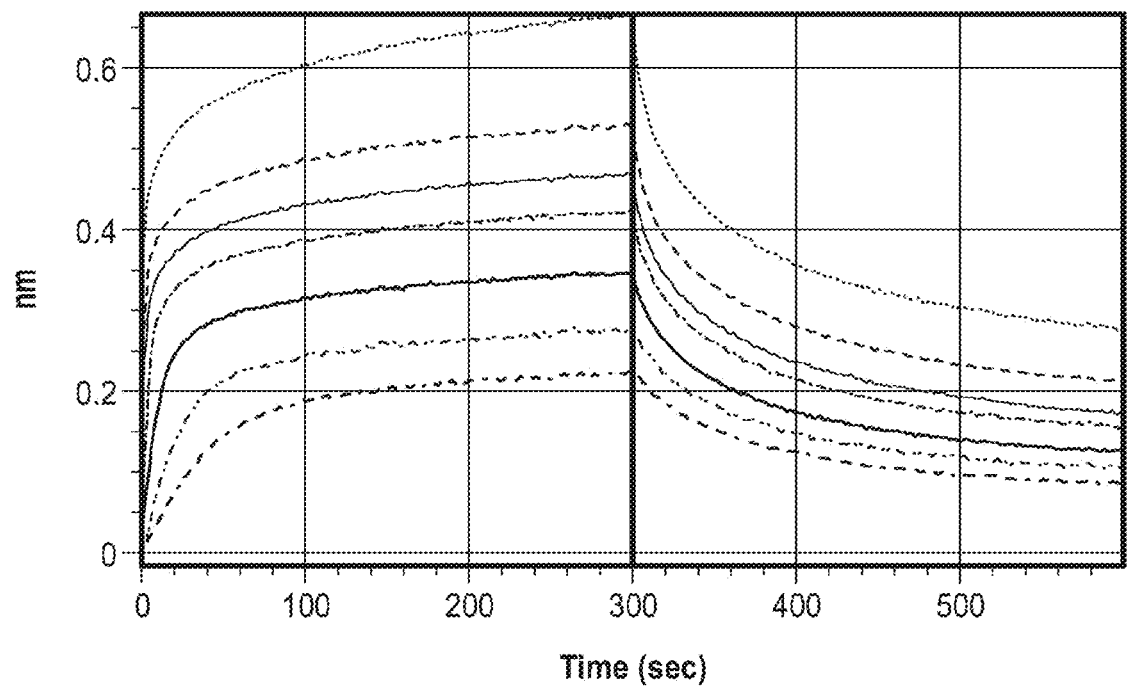
Figure 12J:
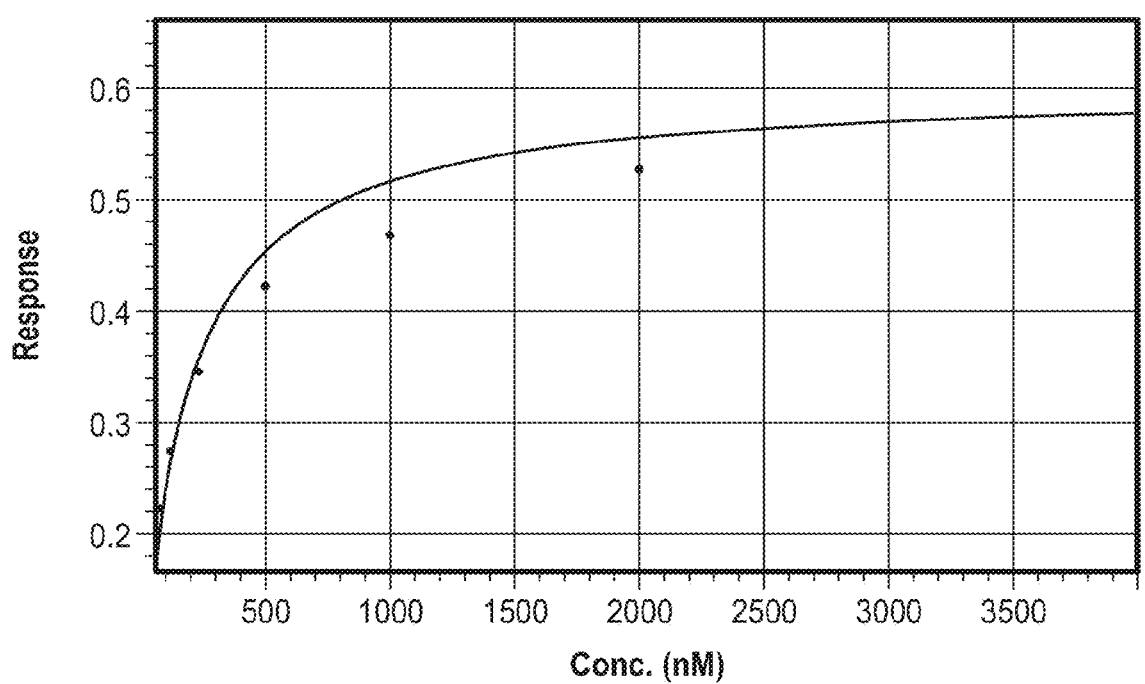
Figure 12K:
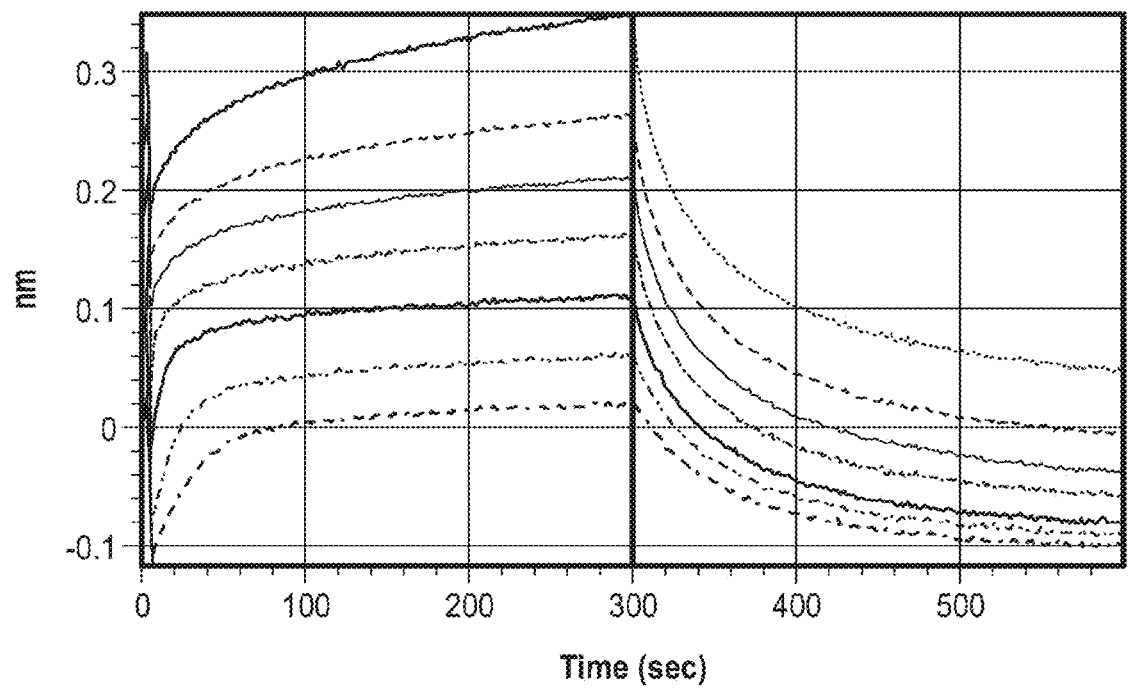
Figure 12L:
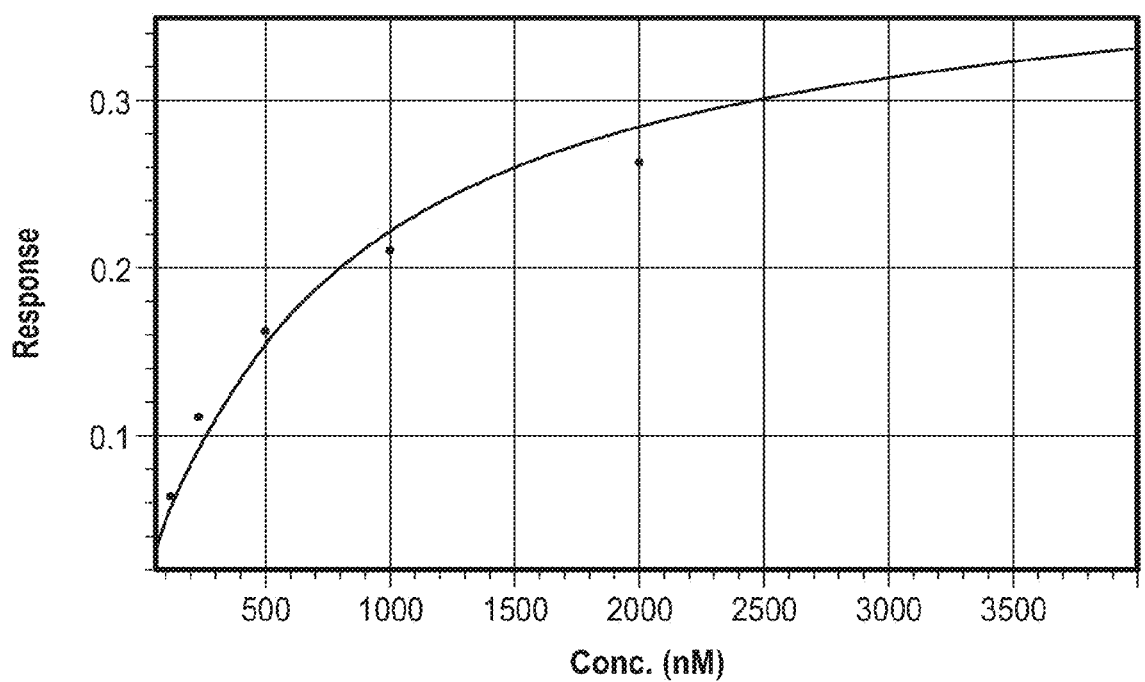
Figure 12M:
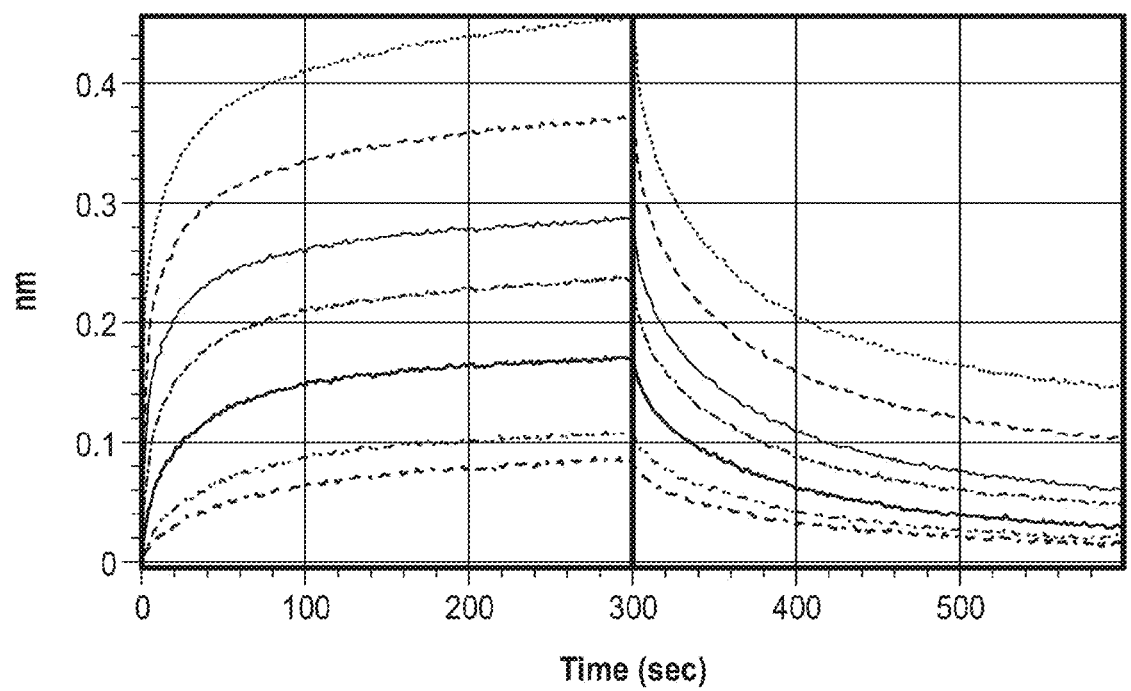
Figure 12N:
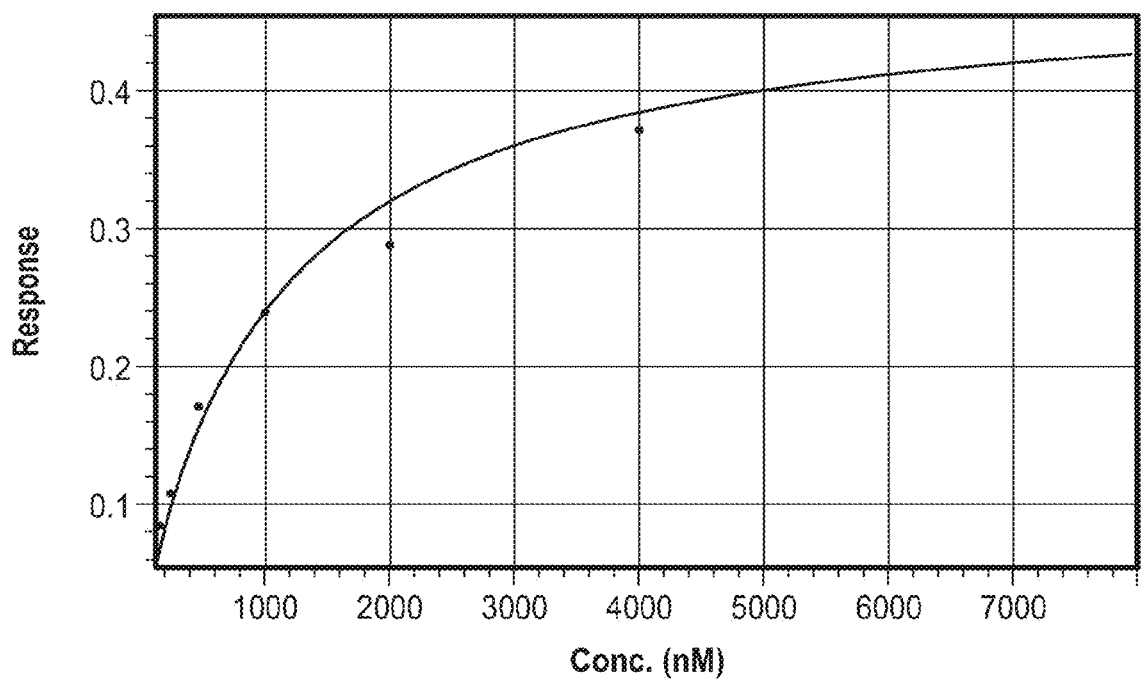
Figure 12O:
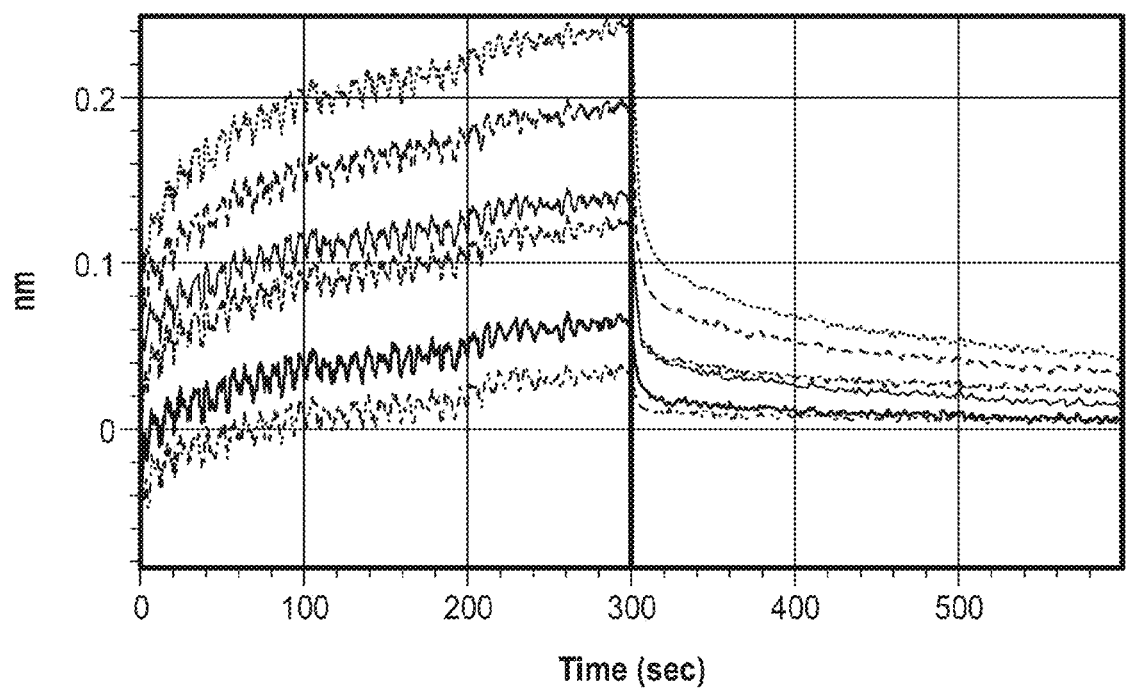
Figure 12P:
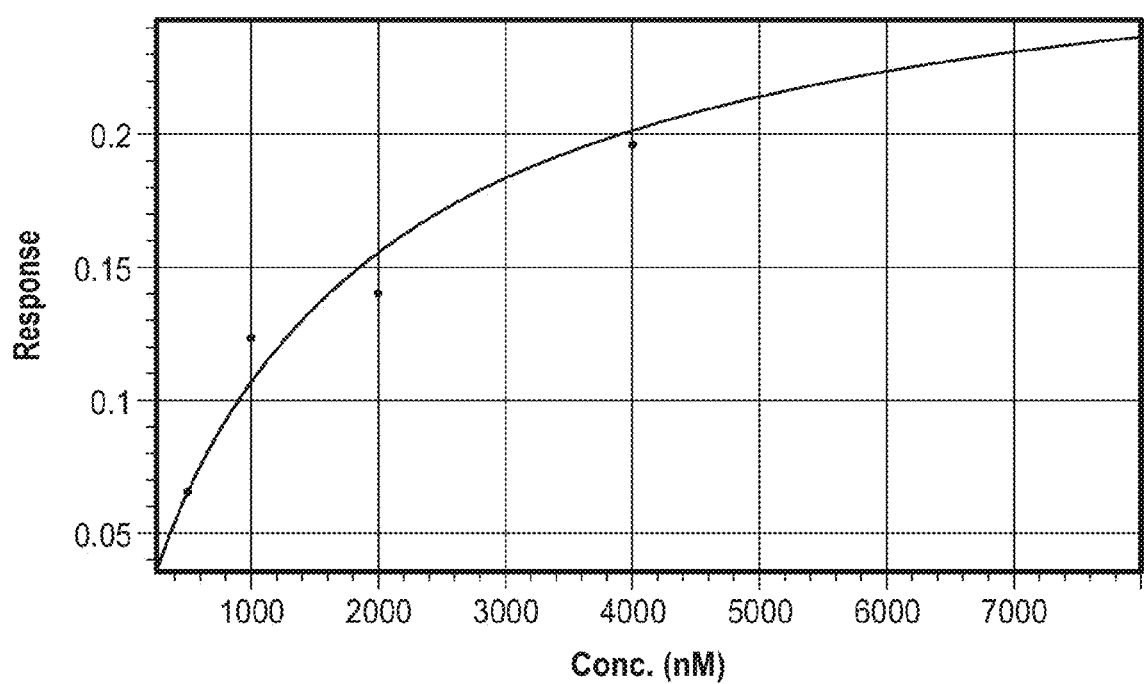

FIG. 11 shows the deconvoluted electrospray mass spectrum of the DBDpp according to SEQ ID NO: 54, in which it was clarified that the dominant species in the sample remained protein with the N-terminal methionine, as opposed to the His6 tag.

In accordance with several embodiments disclosed herein, the production methods disclosed herein for production of tagged DBDpp result in the dominant species (e.g., greater than 50%, greater than 60%, greater than 70%, greater than 80%, etc.) of a given production run being the tagged species. As discussed above, tags other than His6 may be used, depending on the embodiment.

The target protein, CD137, was constructed as a CD137-Fc-His6 fusion protein. A (Leu24-Gln186)/rHuman Fc (Lys100-Lys329) chimera (SEQ ID: 59) with hexahistidine tag was prepared by transient transfection of HEK293 cells and purified from the clarified cell supernatant using immobilized metal ion chromatography (IMAC) and then buffer exchanged into PBS. This material behaved identically to authentic protein purchased from commercial sources (RnD systems) and was used as a positive control for CD137.

SEQ ID: 59 is shown below:

LQDPCSNCPAGTFCDNNRNQICSPCPPNSFSSAGGQRTCDICRQCKGVFR

TRKECSSTSNAECDCTPGFHCLGAGCSMCEQDCKQGQELTKKGCKDCCFG

TFNDQKRGICRPWTNCSLDGKSVLVNGTKERDVVCGPSPADLSPGASSVT

PPAPAREPGHSPQDIEGRMDKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

-continued

LDSDGSFFLYSKLTVDKSRWQQGNVFSCSVMHEALHNHYTQKSLSLSPGK

HHHHHH

The binding of the eight his-tagged DBDpp ligands (SEQ ID NO:51-58) to the CD137 target protein was assessed using biolayer interferometry (ForteBio, Menlo Park, Calif.) according to established methods. The binding assay was constructed by immobilizing the CD137-Fc-His6 via protein A and then incubating in solutions of each of the DBDpp ligands for 5 minutes to measure the association (binding) phase. The sensors were then placed in buffer to monitor the dissociation phase and the complete sensorgrams (time in seconds on the X-axis and nm on the Y-axis) are shown in FIGS. 12A, 12C, 12E, 12G, 12I, 12K, 12M, and 12O for DBDpps of SEQ ID Nos: 51-58, respectively. The data was fitted by steady state analysis, which is depicted in each of FIGS. 12D, 12D, 12F, 12H, 12J, 12L, 12N, and 12P for the corresponding DBDpp. The data revealed yield affinity constants for CD137 in the range 140 nM-1.7 µM (Table 7).

TABLE 7

Calculated affinity constants for the 8 ligands SEQ ID 51-59.

| SEQ ID | $K_D$ (M) |
|---|---|
| 51 | $6.4 \times 10^{-7} \pm 1.8 \times 10^{-7}$ |
| 52 | $4.6 \times 10^{-7} \pm 8.5 \times 10^{-8}$ |
| 53 | $1.4 \times 10^{-7} \pm 3.0 \times 10^{-8}$ |
| 54 | $4.0 \times 10^{-7} \pm 9.4 \times 10^{-8}$ |
| 55 | $1.7 \times 10^{-7} \pm 4.0 \times 10^{-8}$ |
| 56 | $7.7 \times 10^{-7} \pm 1.2 \times 10^{-7}$ |
| 57 | $1.0 \times 10^{-6} \pm 1.7 \times 10^{-7}$ |
| 58 | $1.7 \times 10^{-6} \pm 2.6 \times 10^{-7}$ |

Four of the eight his-fusion proteins were coupled to NHS-activated Sepharose 4 Fast Flow (GE Healthcare Life Sciences) using the manufacturer's guidelines for 4 hours at room temperature and then washed before assaying the ligand density (Table 8).

TABLE 8

Measured ligand density of affinity resins

| Seq ID | Ligand coupling concentration mg/ml | Resin Ligand Density mg/ml |
|---|---|---|
| 51 | 4.9 | 10 |
| 52 | 1.7 | 3.3 |
| 53 | 3.9 | 7 |
| 56 | 3.3 | 6.5 |
| 58 | 3.9 | 5.4 |

For each of the resins a portion of the washed resin was packed into a 3×25 mm glass column (Omnifit) and fitted to a BioLogic chromatograph (Bio-Rad). The resins were equilibrated with 1 ml of phosphate buffered saline (PBS) at a flow rate of 0.5 mL/min. A sample of Chinese hamster ovary (CHO) cell supernatant containing CD137 (which had been added to a concentration of 0.25 mg/ml) was applied to the column (550 ug of CD137-Fc-His at 0.2 mL/min) and followed by washing (7.5 ml with PBS at 0.5 ml/min) and elution (2 ml with 50 mM Na Acetate pH 3 at 0.2 ml/min). Prior to evaluating binding of another sample, resins were regenerated with 1 ml with 6M Guanidine-HCl at 0.5 ml/min and re-equilibrated with 25 column volumes with PBS at 0.5 ml/min.

Figure 13:
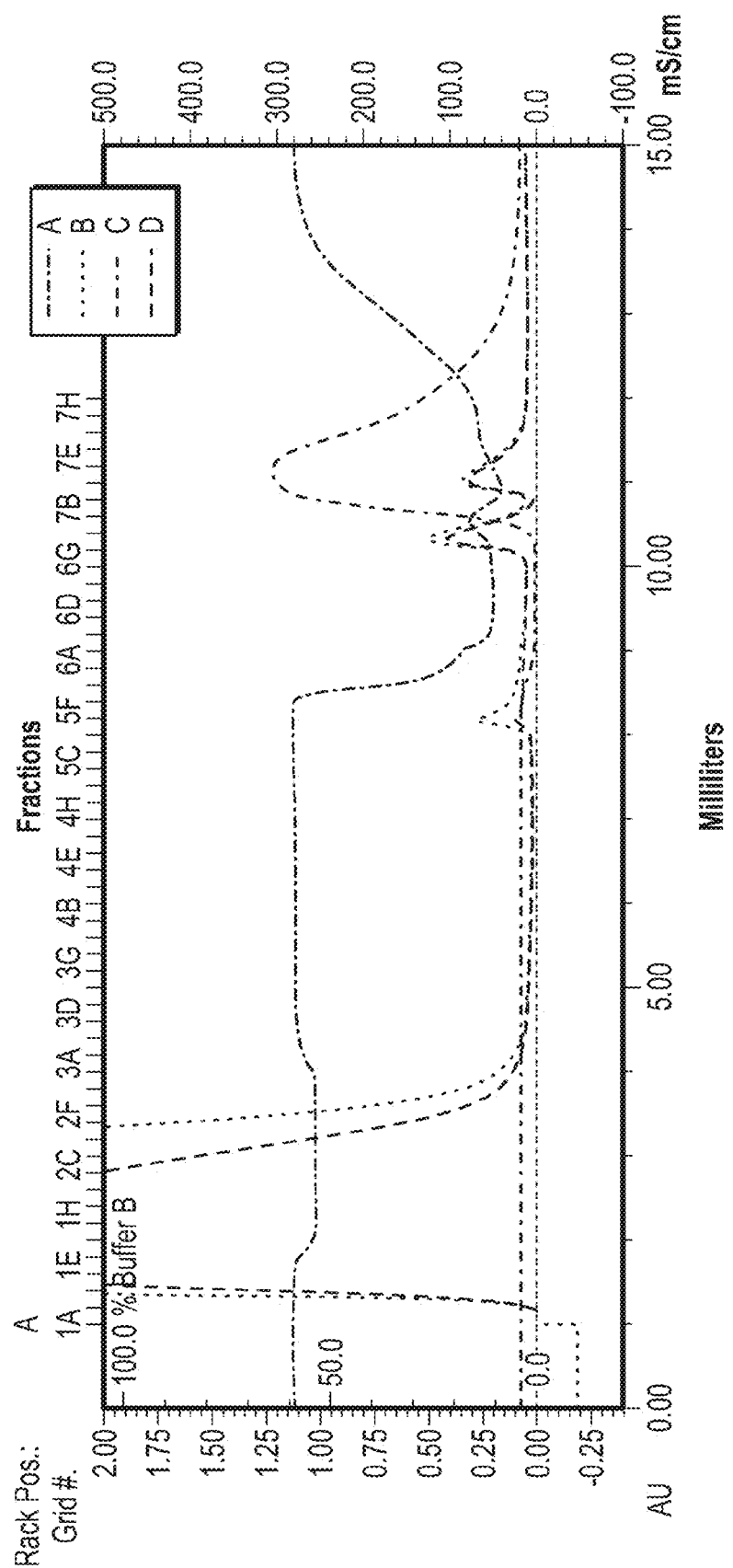
FIG. 13.

FIG. 13 depicts the chromatogram form the purification of CD137-Fc-His6 protein from the CHO supernatant. The peak eluting at 8-9 mL corresponds to the eluted CD137-Fc-His6 protein. This data demonstrates that the DBDpp disclosed herein can successfully be used to capture a target protein from a sample with a high degree of specificity, even when the input sample comprises a complex mixture of biological proteins that have the potential to interfere with target-binder interactions.

Figure 14A:
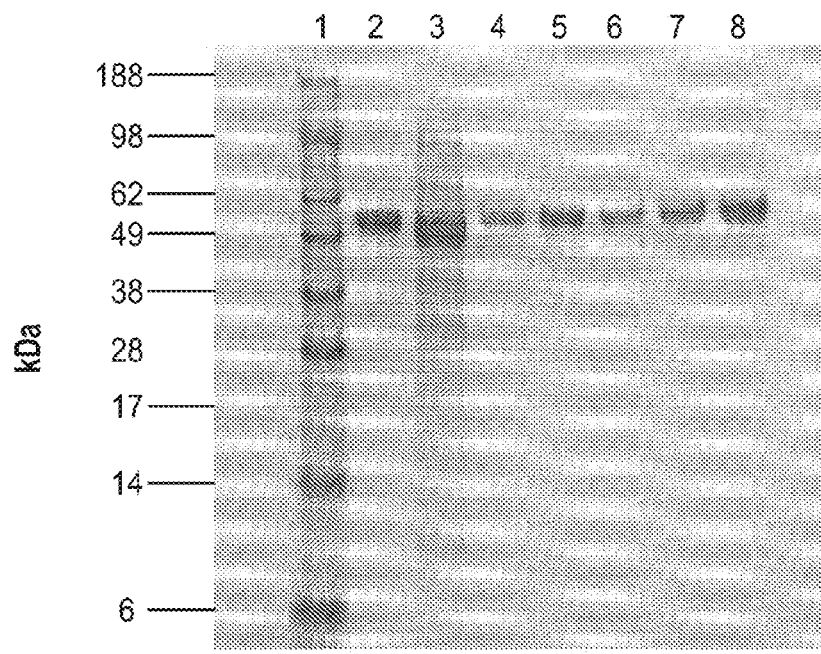
FIGS. 14A-14B. Analysis of proteins purified using DBDpp.

To further assess the specificity of binding, the fractions from the elution phase were assessed by SDS-PAGE to confirm that the affinity resin was able to purify CD137 while allowing removal of a considerable proportion of the host cell protein. FIG. 14A shows a Coomassie blue stained gel with a molecular weight ladder in Lane 1 (kilodaltons). Lane 2 shows a positive control IMAC-purified CD137 protein. Lane 3 depicts a negative control which is CD137-Fc-His6 spiked into CHO supernatant at a 0.25 mg/mL concentration, which represents lack of purification of the CD137 from the supernatant. Lane 4 is eluate after purification with the DBDpp of SEQ ID NO. 58, lane 5 is eluate after purification with the DBDpp of SEQ ID NO. 51, lane 6 is eluate after purification with the DBDpp of SEQ ID NO. 52, lane 7 is eluate after purification with the DBDpp of SEQ ID NO. 57, and lane 8 is eluate after purification with the DBDpp of SEQ ID NO. 57. These data show that the DBDpp specifically purify target proteins, of which CD137 is a non-limiting example. Lane 3 clearly shows additional protein matter in the lane, which is a result of the protein components of the CHO cell supernatant. In contrast lanes 4-8 show clean bands, with little or no other protein species, which is similar to the positive control IMAC purified CD137.

Figure 14B:
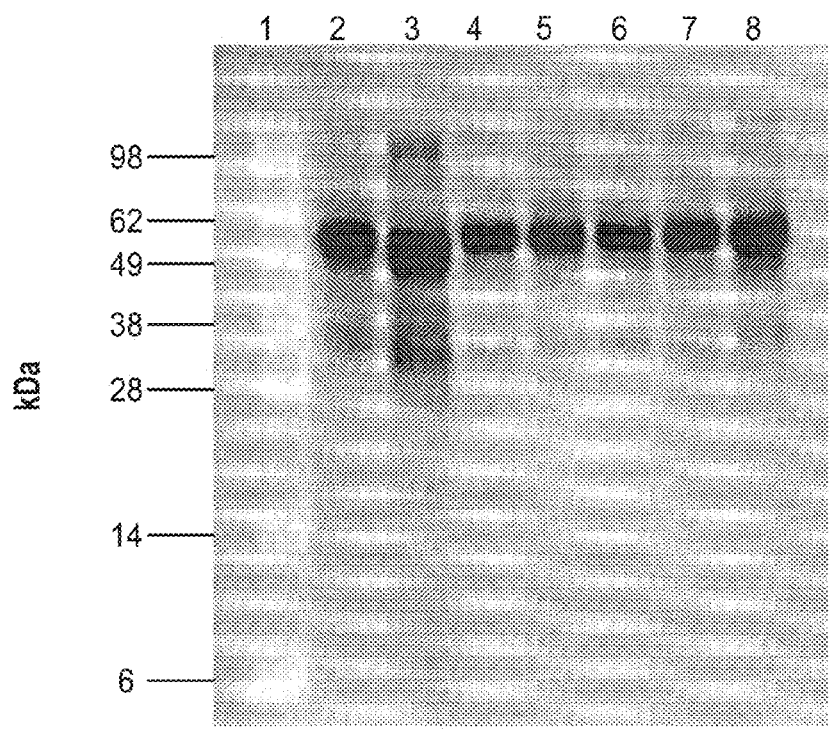

Additionally, the Western blot analysis shown in FIG. 14B further reinforce the ability of the DBDpp described herein to isolate a specific target protein from a complex protein-containing sample. The layout of the lanes is the same as that as described above for FIG. 14A. An anti-penta-His-HRP conjugate antibody (Qiagen) was used for detection. As initially suggested by the Coomassie stain, the Western blot analysis confirms that the DBDpp described herein can successfully bind a target protein with specificity, and then be used for specific isolation of that protein from a complex starting sample. Each of the CD137 targeting DBDpp in Lanes 4-8 show the ability to purify CD137 as well, if not better, as purification with immobilized metal ion chromatography (compare lanes 4-8 with lane 2). As CD137 is just one, nonlimiting embodiment, the DBDpp disclosed herein, according to additional embodiments can be used to purify a wide variety of target proteins from various starting samples. In some embodiments, the starting sample is a biological fluid while in other embodiments, other types of liquid or gaseous samples make up the starting material from which a target protein is to be captured and purified.

Example 5. Characterization of DBDpp Stability

The present example was performed to evaluate the stability of DBDpp according to embodiments disclosed herein.

DBDpp-6xHIS fusions (pb04 and pb06) and scFv-6xHIS fusions were expressed through in vitro transcription and translation reactions (NEB, PureExpress). Samples were diluted in ELISA blocking buffer (Thermo Fisher) 30 fold. Individual samples were subsequently incubated at either 25° C., 40° C., 55° C., 70° C. or 100° C. for 2 minutes and then rapidly returned to room temperature. The temperature increase, followed by rapid cooling can cause denaturation of the protein or other breakdown of the three-dimensional structure of proteins that reduce target interaction and/or binding. The ability of proteins to bind with a ligand, such as a target tumor antigen, after being exposed to denaturing conditions indicates either enhanced stability during exposure to elevated temperature or an ability to re-fold and maintain function after exposure. Regardless, the elevated thermal stability makes such proteins attractive candidates for maintaining function during and after the rigors of production, storage, thawing and clinical use.

Figure 15A:
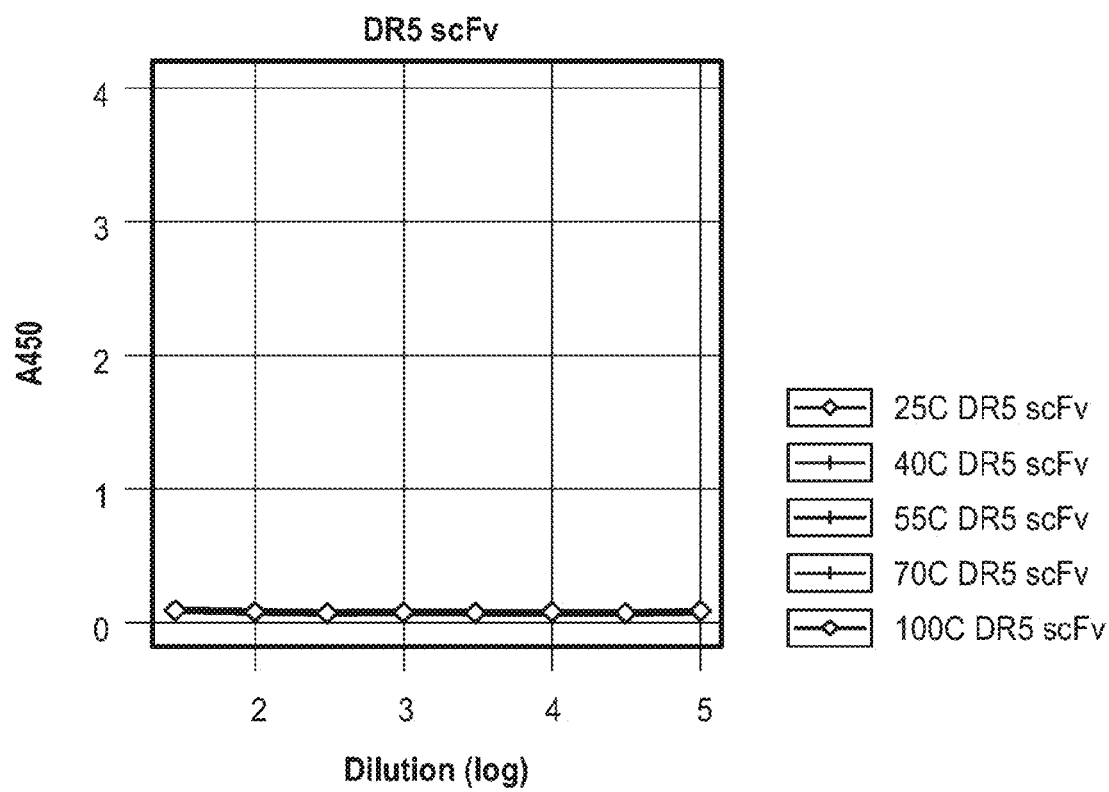
FIGS. 15A-15D. Thermal stability of DBDpp.
Figure 15B:
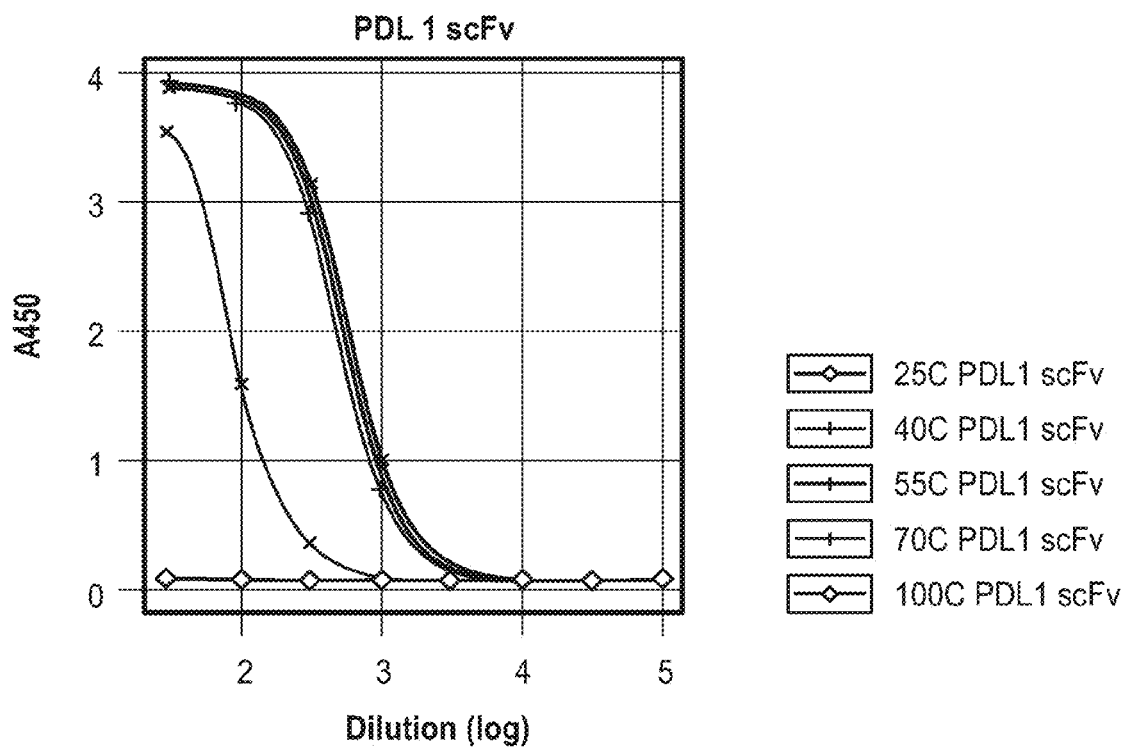

The heat-exposed samples were serially diluted in ELISA buffer and measured for binding to PD-L1-Fc in ELISA. Bound proteins were detected with HRP-conjugated rabbit anti-6xHIS polyclonal antibody (Abcam). FIG. 15A depicts the binding of DR5 scFv to cells expressing PD-L1. Since this particular scFv is not configured to bind PD-L1, this function as a negative control, and as expected, no binding is detected for any of the DR5 scFv, regardless of the temperatures they were exposed to. FIG. 15B shows that a scFv directed against PD-L1 will successfully bind to its target after exposure to elevated temperatures, up to about 55° C. However, exposure to temperatures of 70° C. show a decrease in the ability of the scFv to successfully bind to PD-L1, indicative of the heat labile nature of scFv. After heating the scFv to 100° C., binding of target PD-L1 is completely eliminated.

Figure 15C:
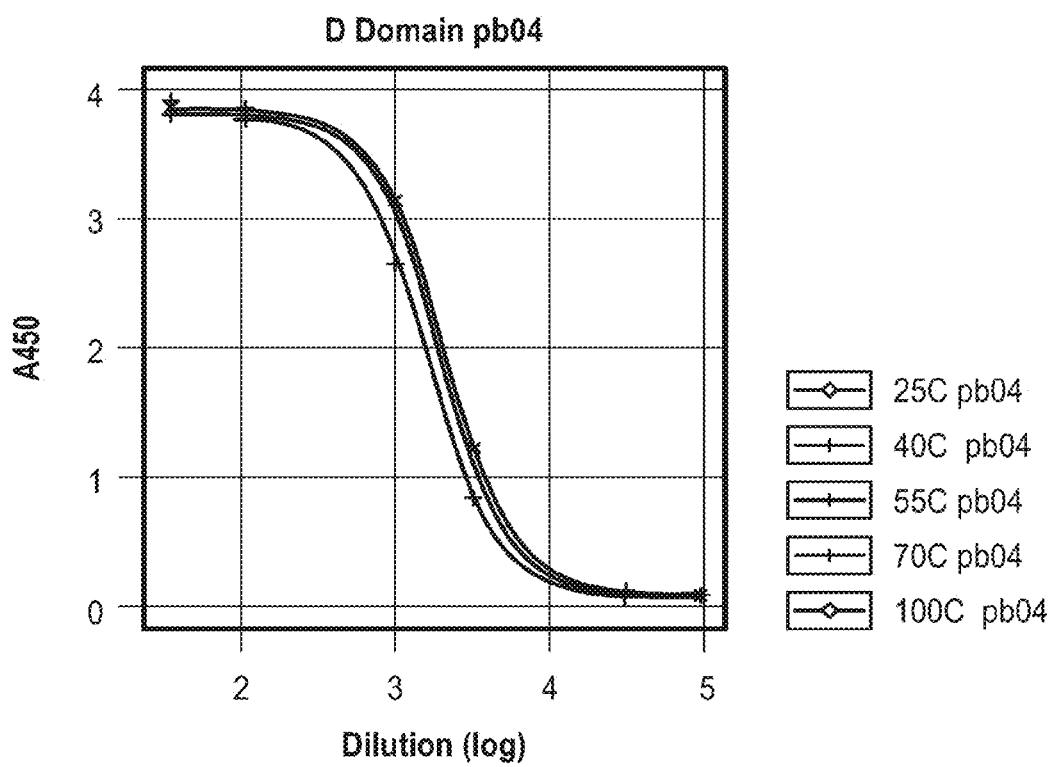
Figure 15D:
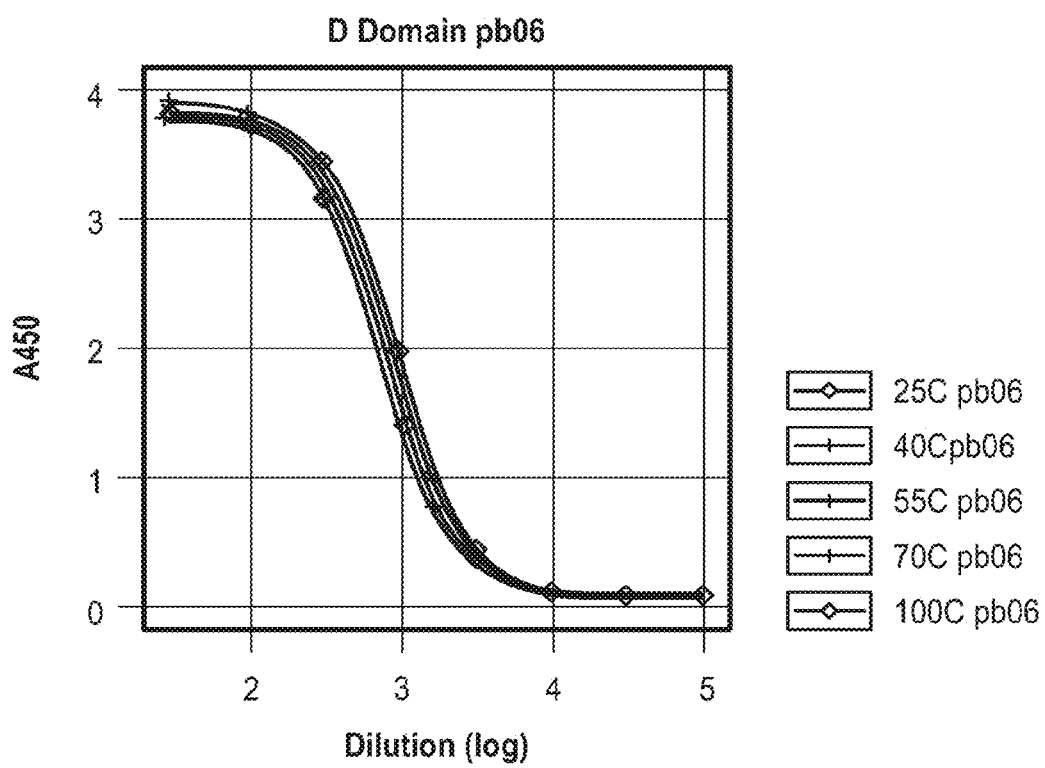

In contrast, DBDpp exhibit improved thermal stability. FIG. 15C depicts data exhibiting the ability of a DBDpp (pb04 in this nonlimiting embodiment) to bind to target PD-L1, even after being exposed to elevated temperatures of 100° C. FIG. 15D shows similar data for a different, non-limiting embodiment of a DBDpp (pb06). Again, the DBDpp retain the ability to bind its target after exposure of temperatures up to 100° C.

These data suggest that DBDpp, according to several embodiments disclosed herein, have the ability to resist denaturation and/or refold after exposure to elevated temperatures, and still retain the ability to bind a desired target. As discussed above, this makes DBDpp attractive targeting moiety is as their increased thermal stability suggests they are robust enough to handle manufacturing processes (or other production/handling protocols) which may involve elevated temperatures better than other types of targeting moieties, such as scFv.

Example 6. DBDpp Species Cross Reactivity

The present example was performed to establish the species specificity of DBDpp as disclosed herein.

Figure 16A:
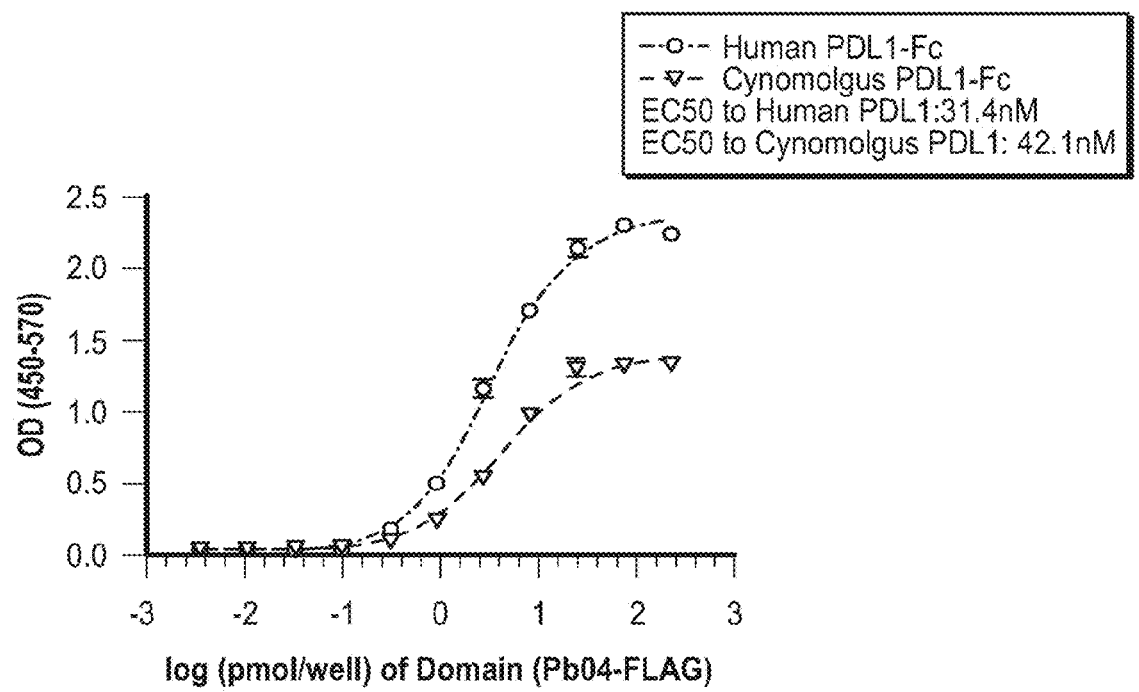
FIGS. 16A-16B. Cross-reactivity of DBDpp.
Figure 16B:
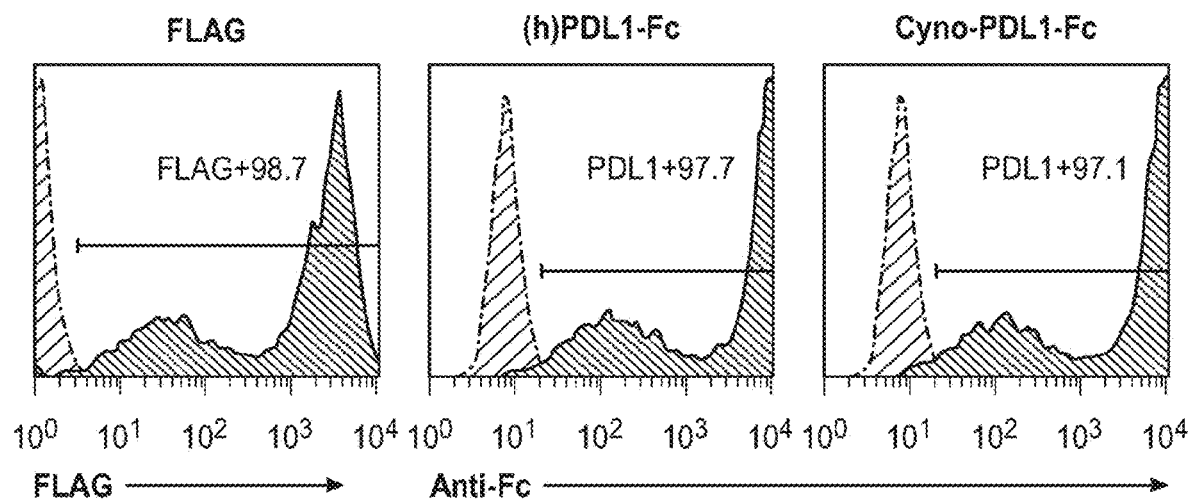

FIG. 16A establishes that a soluble DBDpp selected for binding to human PD-L1 (pb04 in this nonlimiting embodiment), can also bind PD-L1 of cynomolgus (*Macaca fascicularis*), as assessed by ELISA. Human PD-L1 or cynomolgus PD-L1 was immobilized in separate wells of an ELISA plate. Soluble DBDpp (FLAG tagged) directed against PD-L1 was incubated in the respective plates to assess the degree of binding with PD-L1 from each species. As shown, pb04 DBDpp binds to both human and cynomolgus PD-L1. FIG. 16B further demonstrates that PD-L1 of human and cynomolgus origin is bound by a CAR comprising a DBDpp (pb04 in this nonlimiting embodiment) expressed on the surface of human T cells. As exhibited by the flow cytometry data PD-L1-directed DBDpp CAR T cells can bind soluble human PD-L1 and cynomolgus PD-L1 (97.7% for human, and 97.1% for cynomolgus).

Example 7. CAR T Cells Expressing DBDpps Bind Target Molecules

The present example was performed to establish the ability of transiently expressed CARs comprising DBDpp in this nonlimiting embodiment, to bind a tumor target comprising an amino acid sequence that is at least 95% identical to residues 19-305 of SEQ ID NO: 187 (CD123).

293T cells were transiently transfected with pcDNA3 expression vectors encoding DBDpp containing CARs using (see, e.g., FIG. 5B) Lipofectamine 3000 (Life Technologies). After 24 hours, cells were collected using CellStripper™. Cells were assessed for CAR expression using a fluorescent-labeled anti-FLAG antibody. DBDpp containing CARs binding to CD123 was measured by incubating cells with a Fc-fusion protein comprising the extracellular domain of CD123 fused to human IgG1 Fc in cell culture media at 37° for 30 minutes, washing, and then detection with a PE anti-human IgG antibody. Both CD123 binding and CAR expression (FLAG Tag) were assayed by flow cytometry. Data are shown in FIG. 17, and each data point indicates the average FLAG expression and CD123-binding for each of the DBDpp-CARs from multiple experiments.

Figure 17:
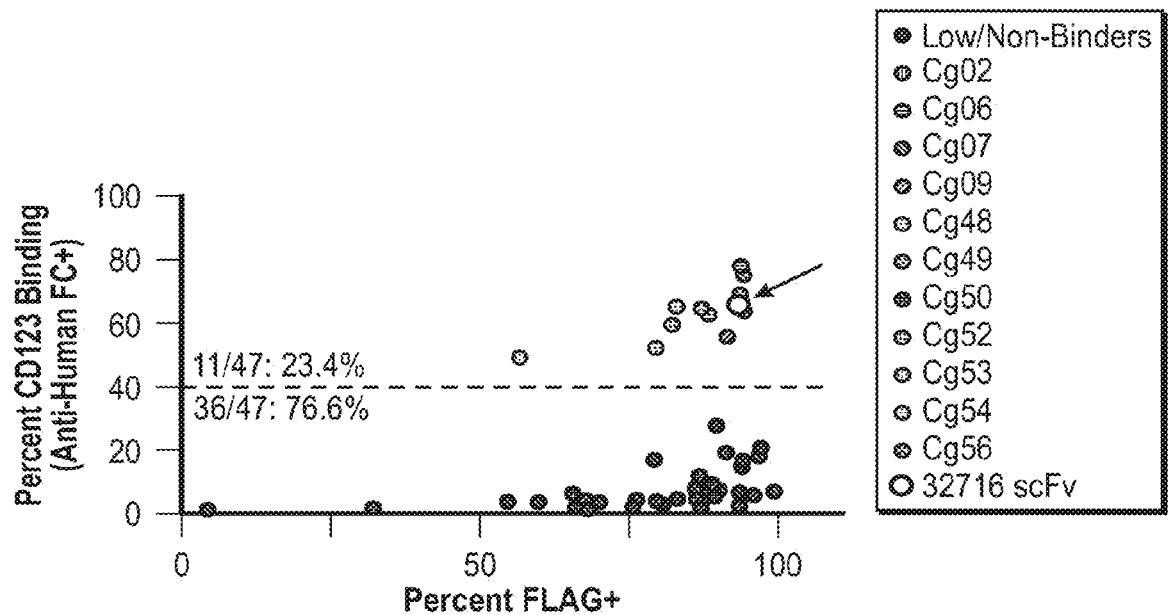
FIG. 17. Assessment of DBDpp-CAR expression and target binding.

FIG. 17 summarizes flow cytometry data demonstrating that CARs comprising a CD123 binding scFv (32716) or a DBDpp expressed in human T cells bind soluble CD123, as a non-limiting embodiment of a target of interest. The X-axis is a measure of CAR expression on human T cells. The Y-axis represents CAR binding of the Fc-CD123.

Figure 18:
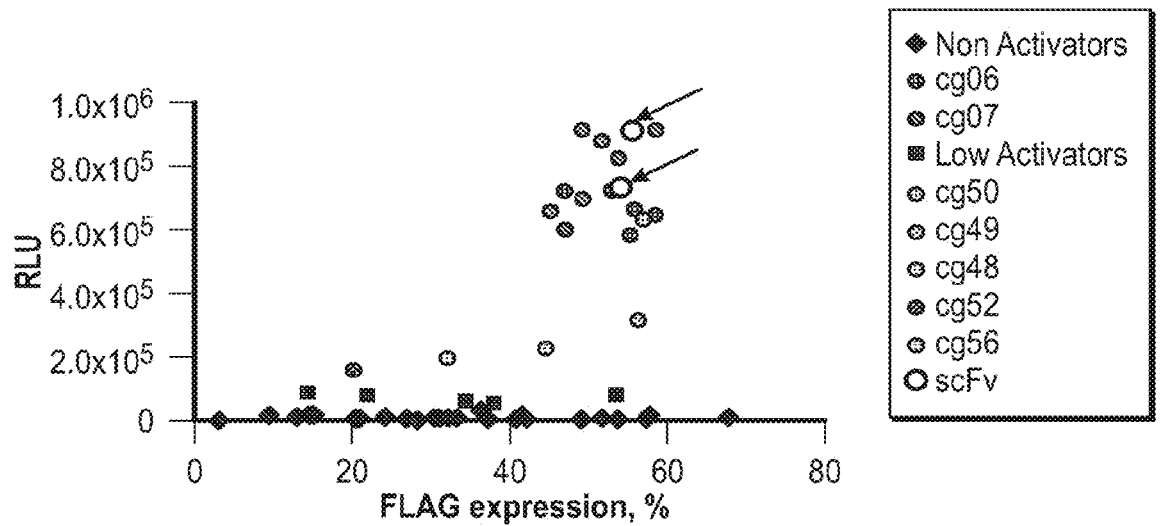
FIG. 18. DBDpp mediate signal transduction.

Example 8. T Cells Expressing CARs Comprising DBDpp (DBDpp-CAR) Induce Intracellular Signaling To assess the ability of CARs comprising a DBDpp (DBDpp-CAR) to initiate signal transduction, a Jurkat reporter cell line, containing Nuclear Factor of Activated T-cells (NFAT) enhancer coupled to luciferase reporter gene, was stably expressed in Jurkat cells. Various CAR constructs were electroporated into the Jurkat reporter cell line. After 24 hours post-electroporation, CAR expression was assessed by detection with a fluorescent labeled anti-FLAG monoclonal antibody. The DBDpp-CAR-expressing Jurkat cells were then co-cultured with CD123+ (BDCM, acute myelogenous leukemia, as a non-limiting embodiment) tumor cells for 6 hours after which NFAT mediated signaling was measured through the addition to the cells of luciferase assay reagent (Promega) and quantitation of relative luminescence units (RLU), as shown in FIG. 18.

These data demonstrate that, in this non-limiting embodiment, DBDpp-CARs are expressed on cells (e.g., human T cells), and when so expressed, can initiate an intracellular signaling cascade following exposure to a target (Fc-CD123 in this non-limiting embodiment) bound by the DBDpp.

Example 9. DBDpp-CARs Expressed in Human T Cells Produce Cytokines on Target Binding Engagement of a target by a CAR-expressing T cell can result in cytokine secretion.

Accordingly, 293T cells were transiently transfected with 3rd generation lentiviral packaging vectors (pRSV-REV, pMDLg/pRRE, and pMD2.G) with pELNS vectors encoding DBDpp-CARs using Lipofectamine 3000. Six hours post-transfection the media was changed, then lentivirus containing media was collected at 30 and 54 hours post-transfection, pooled, then centrifuged to remove cell debris.

Lentivirus was then aliquoted and stored at −80° C. until used for viral transduction. Transduction of human T-cells with CAR lentivirus was performed using total human PBMCs, activated with αCD3/CD28 T-cell activation beads in culture media supplemented with 40 U/ml of IL-2. After 24 hours, 2×10$^6$ PBMCs were plated per well in a 6-well tissue culture plate with 1 ml of culture media and 3 ml of lentivirus containing media supplemented with 40 U/ml of IL-2 and protamine sulfate. Plates were then centrifuged for 2 hours at 1000×g at 32° C. and then incubated overnight 37° C. The following day the lentivirus transduction procedure was repeated with fresh culture media and lentivirus-containing media. 72 hours after the initial cell activation, T-cell activation beads were removed, then T-cells were cultured for expansion at ~0.25-0.5×10$^6$ T-cells/ml in fresh media supplemented with 100 U/ml of IL-2. Every 2-3 days T-cells were supplemented with additional T-cell media and IL-2, until they were used for the cytokine assays (described below) 7-10 days after the initial activation.

Cytokine production in response to target antigen expression (CD123 in this non-limiting embodiment) was assessed by culturing 25,000 transduced T-cells (7 days post-activation) with 25,000 non-target (K562, CD123−) or target (BDCM, CD123+) tumor cells per well in 96-well plates. After 24 hours culture supernatants were collected and cytokine production was assessed by ELISA. Culture supernatants were diluted 1:5 prior to ELISA. Similarly, cytokine production in response to PD-L1 target antigen expression was assessed by culturing 25,000 transduced T-cells (7-days post activation) with 25,000 non-target (K562, PD-L1−) or target (SUDHL-1, PD-L1+) tumor cells per well in 96-well plates. After 24 hours culture supernatants were collected and cytokine production was assessed by ELISA. Culture supernatants were diluted 1:5 prior to ELISA.

Figure 19A:
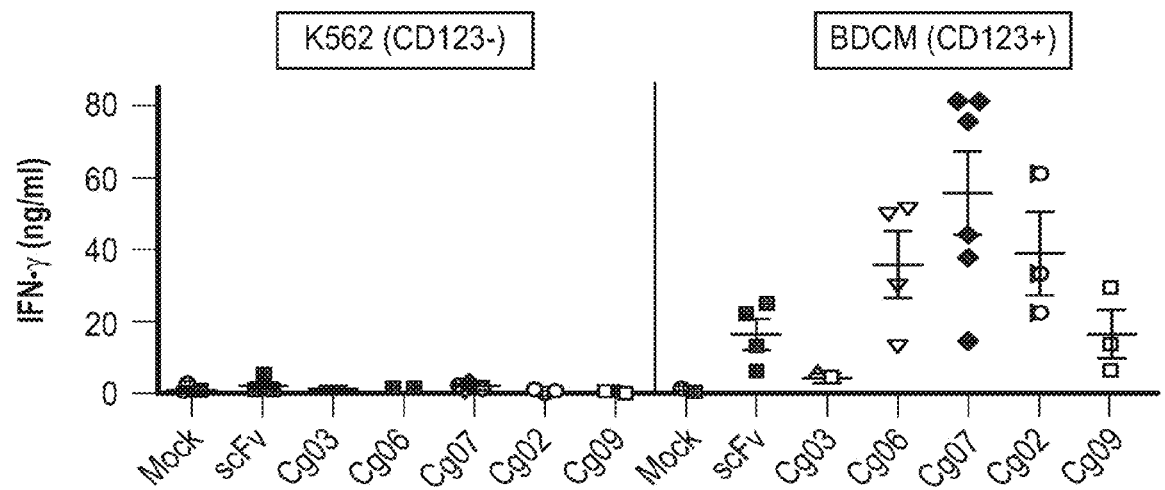
FIGS. 19A-19B. CD123-DBDpp-CAR T cells produce cytokines in response to target binding.
Figure 19B:
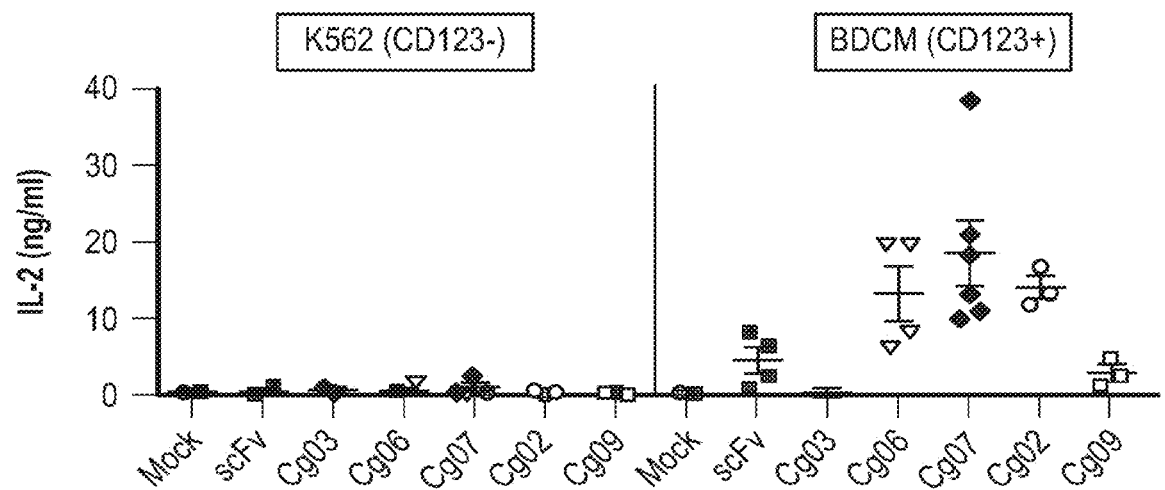
Figure 20A:
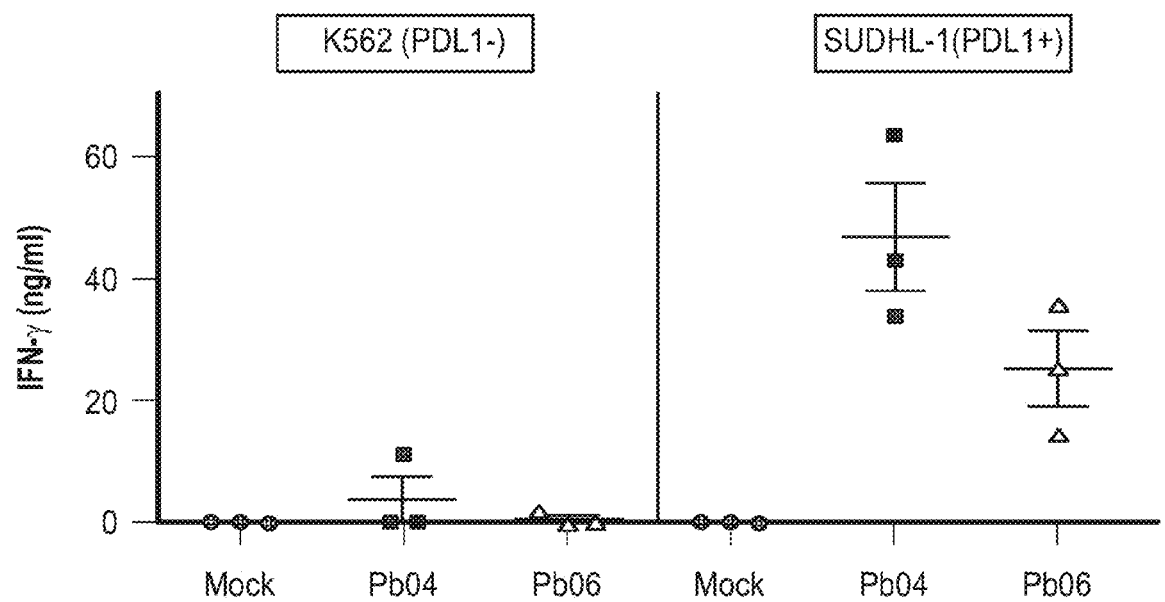
FIGS. 20A-20B. PD-L1-DBDpp-CAR T cells produce cytokines in response to target binding.
Figure 20B:
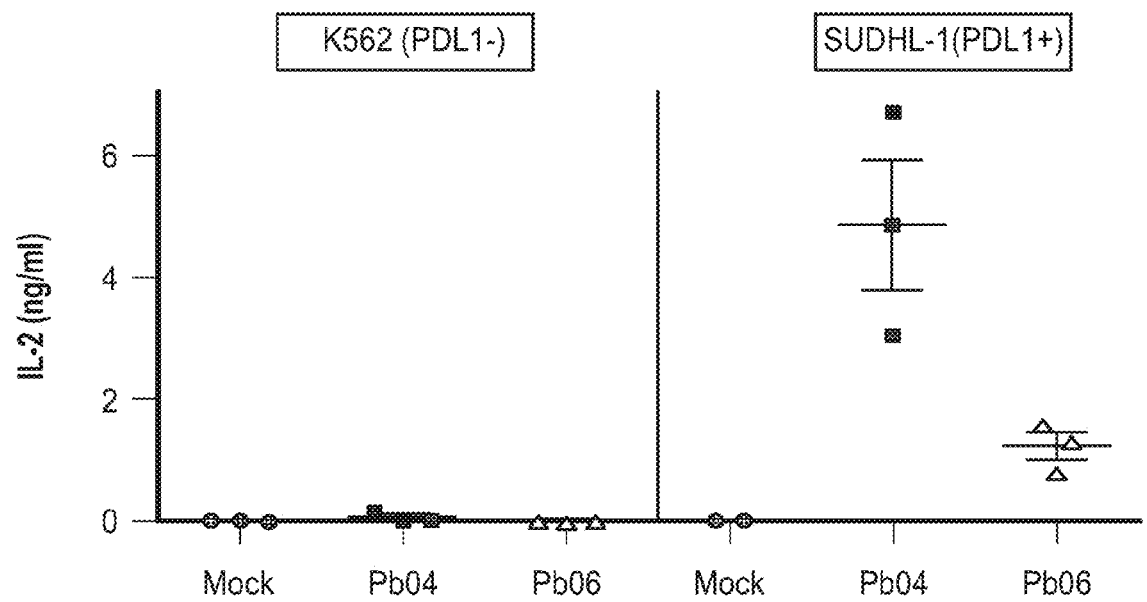

FIG. 19A demonstrates that T cells expressing CD123 binding DBDpp-CARs produce interferon gamma (IFNγ) following stimulation with CD123+ BDCM cells, but not the CD123-cell line K562. FIG. 19B demonstrates that T cells expressing CD123 binding DBDpp-CARs produce interleukin 2 (IL2) following stimulation with CD123+ BDCM cells, but not the CD123-cell line K562. FIG. 20A demonstrates that T cells expressing PD-L1 binding DBDpp-CARs produce interferon gamma (IFNγ) following stimulation with PD-L1+ SUDHL-1 cells but not the PD-L1− cell line K562. FIG. 20B demonstrates that T cells expressing PD-L1 binding DBDpp-CARs produce interleukin 2 (IL2) following stimulation with PD-L1+ SUDHL-1 cells but not the PD-L1− cell line K562.

Example 10. T Cells Expressing DBDpp-CARs Proliferate when Co-Cultured with Target-Expressing Tumor Cells T cells expressing target-binding CARs can proliferate following engagement of soluble target or target expressing tumor cells.

Proliferation of DBDpp-CAR transduced human T cells in response to tumor cells expressing target antigen (of which CD123 is a non-limiting example) was assessed by culturing transduced T-cells (1×10$^5$, day 10 post-activation) with 1×105 mitomycin-C pre-treated tumor cells in 24-well plates. Tumor cells included non-target expressing K562 (CD123−), intermediate target-expressing lines KG1a and MOLM-13 (CD123-intermediate), and BDCM (CD123-high). Transduced T cells were collected and counted after 96 hours of co-culturing with tumor cells. This approach was also used in assessing T-cell proliferation in response to tumor cells expressing PD-L1 target antigen. Tumor cells included non-target expressing K562 (PD-L1−), intermediate target-expressing lines BDCM and H460 (PD-L1-intermediate), and SUDHL-1 (PD-L1-high). Cells were collected and counted after culturing for 96-hours. Data from these proliferation experiments is shown in FIG. 21 and FIG. 22 respectively.

Figure 21:
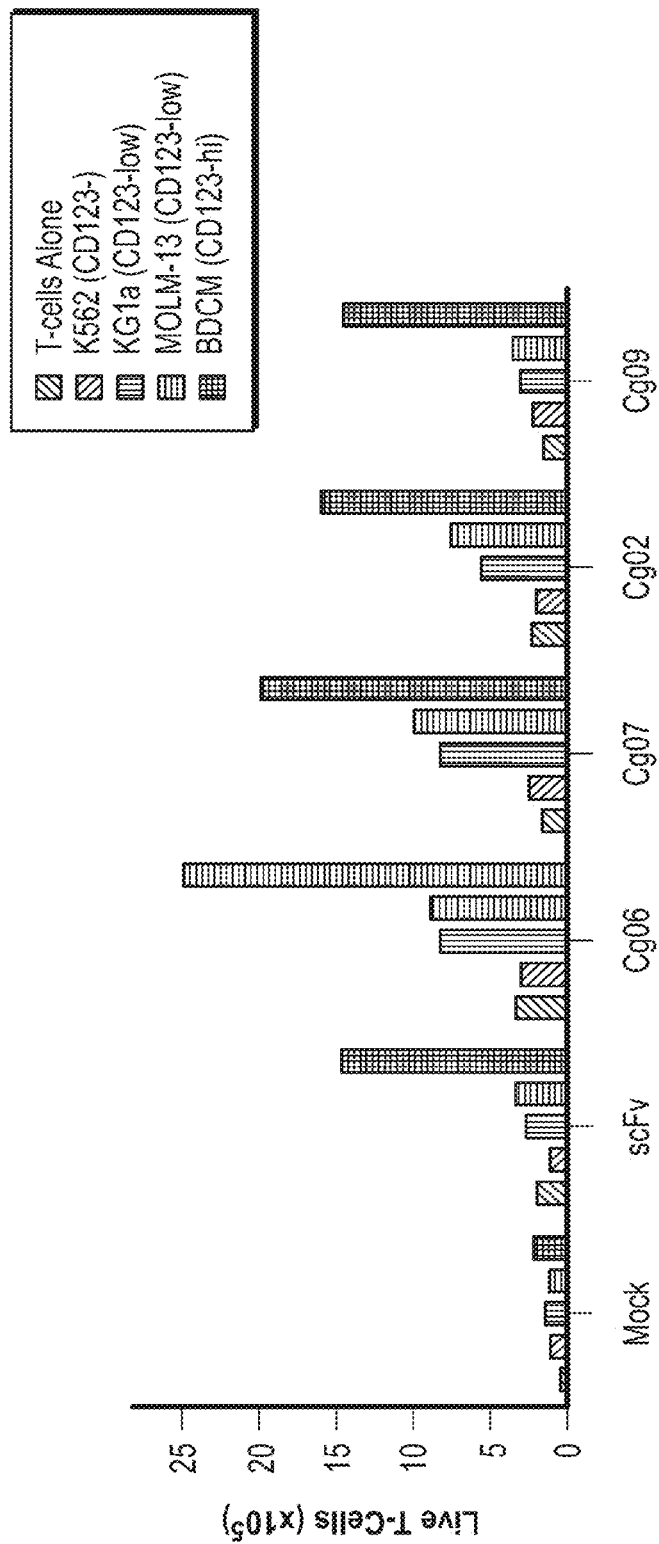
FIG. 21. CD123-DBDpp-CAR T cells proliferate in response to target binding.
Figure 22:
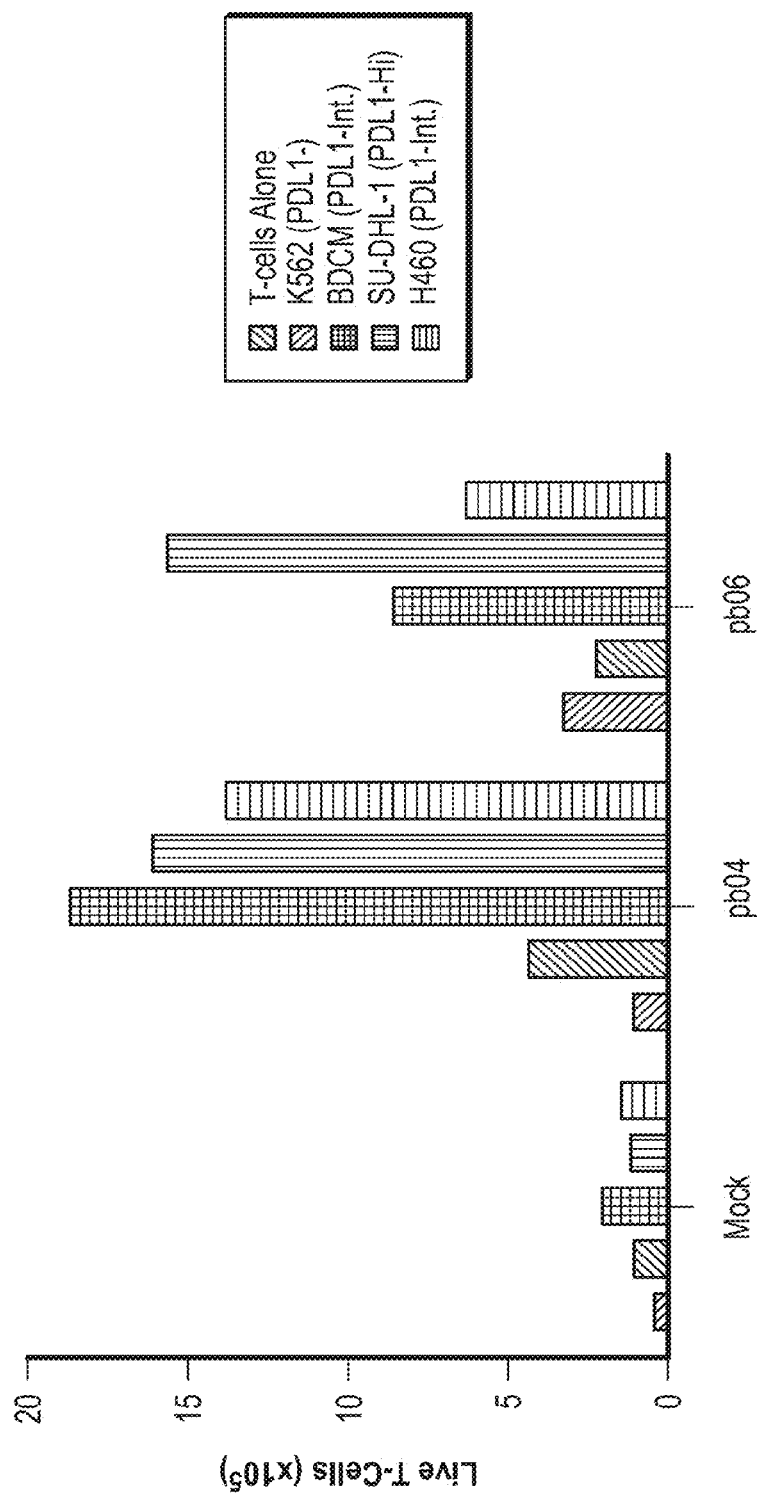
FIG. 22. PD-L1-DBDpp-CAR T cells proliferate in response to target binding.

The bars of the histogram in FIG. 21 represent (moving from left to right): culture of DBDpp-CAR T cells alone, co-culture with CD123 negative K562 cells, co-culture with low level CD123 expressing KG1a cells, co-culture with low level CD123 expressing MOLM-13 cells, and co-culture with high-level CD123 expressing BDCM cells. As indicated by the height of the histogram bars, when incubated with cells that express CD123 (in intermediate or high levels), there is a corresponding increase in T cell proliferation. These data indicate DBDpp-CAR T cells targeting CD123, proliferate in response to binding CD123 comparable to, or in some embodiments to a greater degree than, CD123 targeting scFv. Similarly, in FIG. 22, the bars of the histogram represent (moving from left to right): culture of PD-L1-DBDpp-CAR T cells alone, co-culture with PD-L1 negative K562 cells, co-culture with intermediate level PD-L1 expressing BDCM cells, co-culture with high level PDL2 expressing SUDHL-1 cells, and co-culture with intermediate level PD-L1 expressing H460 cells. These data show a specificity of the response of the T cells to the target of the DBDpp (e.g., there is limited to no response when the target is not present). Thus, as above, these data indicate DBDpp-CAR T cells targeting PD-L1, proliferate specifically in response to binding PD-L1. As discussed above, CD137, CD123, and PD-L1 are merely non-limiting examples of the targets that DBDpp can specifically bind and thus, can (in conjunction with a CAR in a T cell, NK cell, etc.) induce target-specific immune cell function.

Example 11. DBDpp-CAR Transduced T Cells Do Not Display Phenotypes Associated with T Cell Exhaustion Persistent exposure of T cells to antigen and/or inflammatory signals can result in T cell "exhaustion", characterized by the loss of effector function and expression of multiple inhibitory receptors, such as LAG-3, PD-1 and TIM-3. Such exhaustion can also result from spontaneous T cell stimulation through antigen-independent mechanisms that aggregate T cell receptors. A consequence of T cell exhaustion can be reduced tumor control, and thus avoidance of excessive exhaustion is a desirable attribute in cancer immunotherapy using T cells.

Figure 23A:
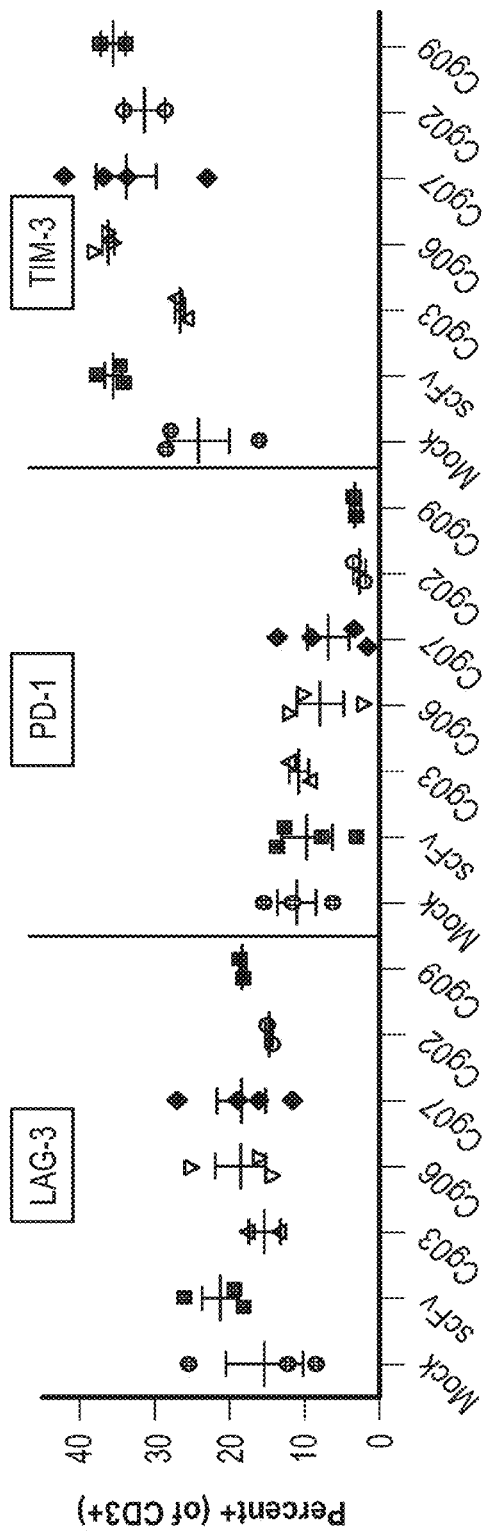
FIGS. 23A-23B. T cells expressing DBDpp-CARs do not undergo excessive exhaustion to a greater degree than scFv.
Figure 23B:
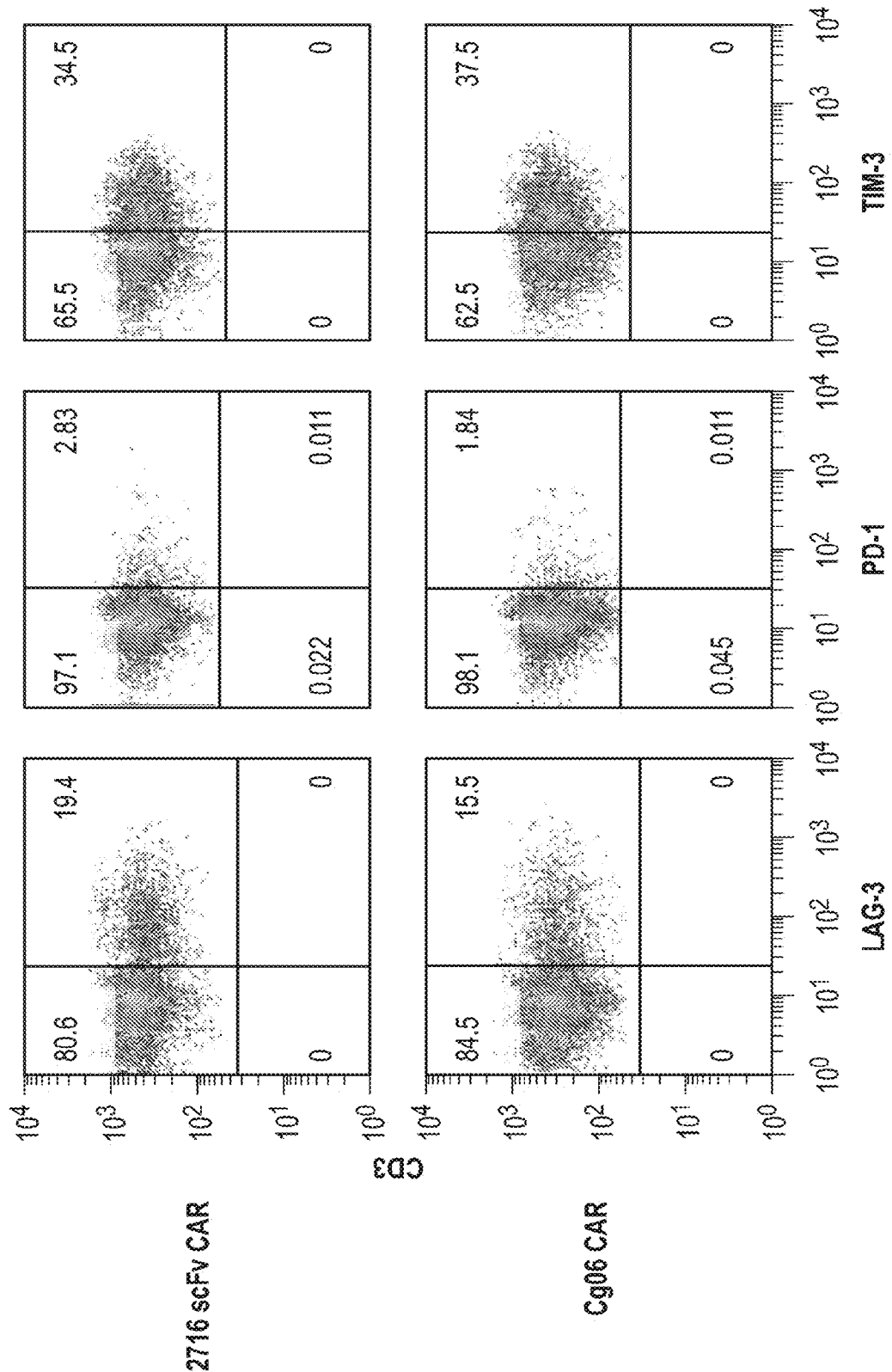

To assess potential antigen-independent exhaustion in T cells expressing DBDpp-CARs, transduced T-cells (day 10 post-activation) were stained with antibodies against CD3 and markers of T-cell exhaustion (LAG3, PD1, and TIM3). FIG. 23A summarizes data from individual experiments across several T cell donors. The data demonstrate that expression of the exhaustion markers was not enhanced in various CD123-binding DBDpp-CAR T cells. FIG. 23B shows representative flow cytometry data of LAG-3, PD1, and TIM-3 expression in T-cells transduced with either a scFv-containing CAR (top row) or a DBDpp-CAR (in this particular experiment CD123 targeting cg06) 10 days after the initial activation of the T cells. The similarity of these data again demonstrate that DBDpp-CAR T cells do not upregulate expression of exhaustion markers, which lends further support to their efficacy in cancer immunotherapy.

Example 12. DBDpp-CAR Expressing T Cells Exhibit Target-specific Degranulation and Tumor Cytotoxicity Degranulation of T cells, NK cells, and many monocytic lineage cells (all of which can be used depending on the embodiment). Degranulation can result in the release of, depending on the cell type, antimicrobial, cytotoxic or other molecules from secretory granules in the immune cell. Molecules like perforin (a pore forming cytotoxin) or granzymes (serine proteases that induce apoptosis in the target cell) aid T cells and NK cells in killing tumor cells (or other cell types).

To assess degranulation of T cells expressing DBDpp-CARs, $1 \times 10^5$ transduced T cells (day 9 post-activation) were cultured in T cell media for 4 hours in the presence of monensin and PE-conjugated CD107a/LAMP1. T-cells were cultured alone or in the presence of $2 \times 10^5$ non-target tumor cells (K562, which are CD123-) or target-expressing tumor cells (BDCM, CD123+), then washed and stained for CD3 expression. T-cell degranulation was then assessed by flow cytometry, first gating on the CD3+SSC-low cells (non-tumor), then the CD3+CD107a+ cells. Symbols represent samples from individual experiments using multiple donors.

Figure 24A:
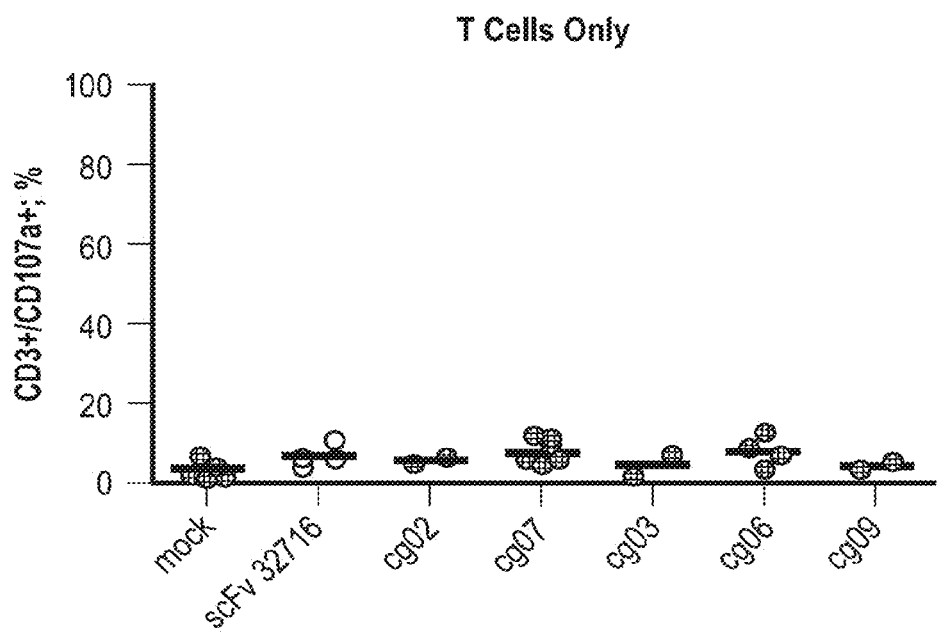
FIGS. 24A-24D. T cells expressing DBDpp-CARs degranulate in response to target binding.
Figure 24B:
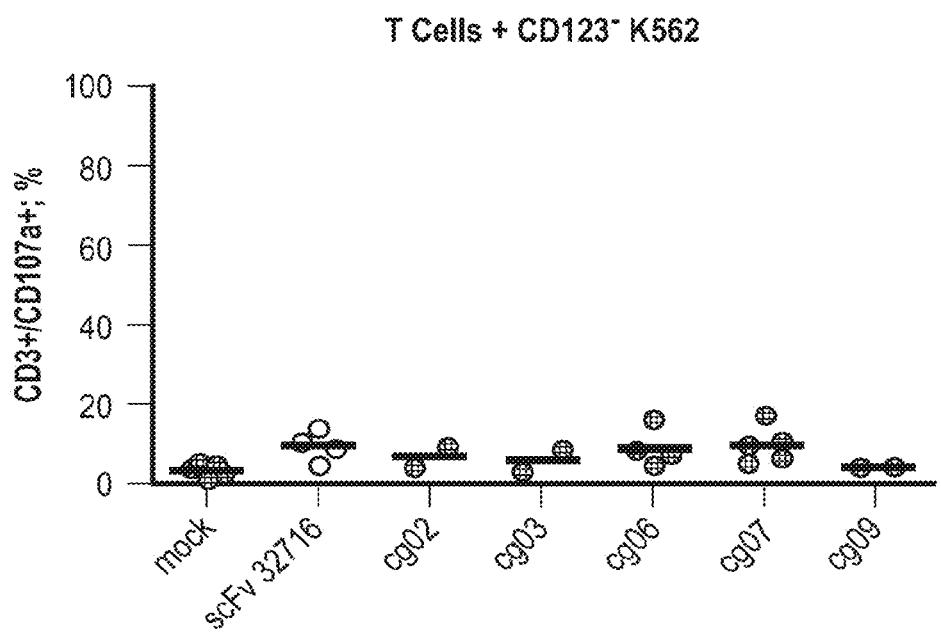
Figure 24C:
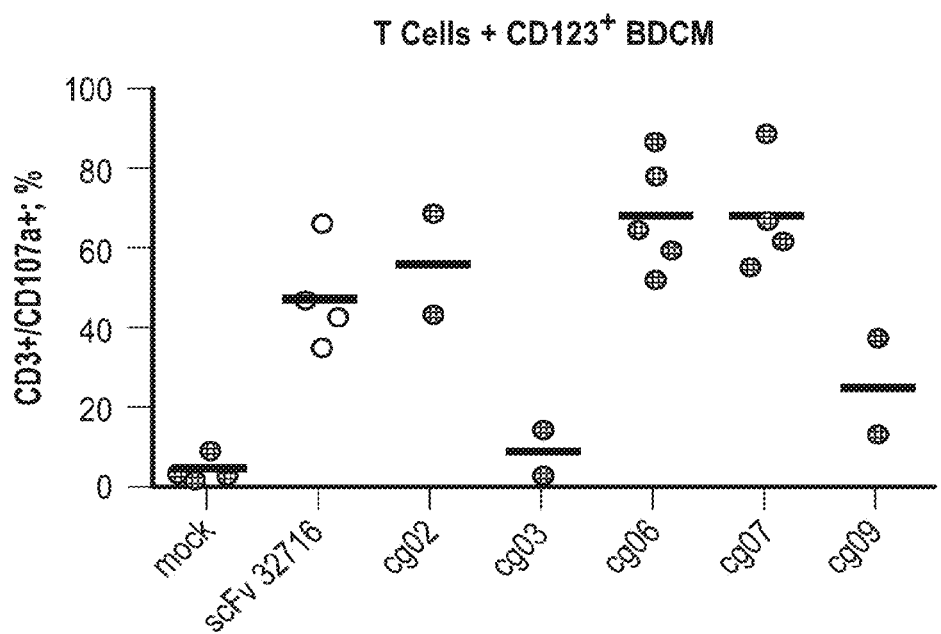
Figure 24D:
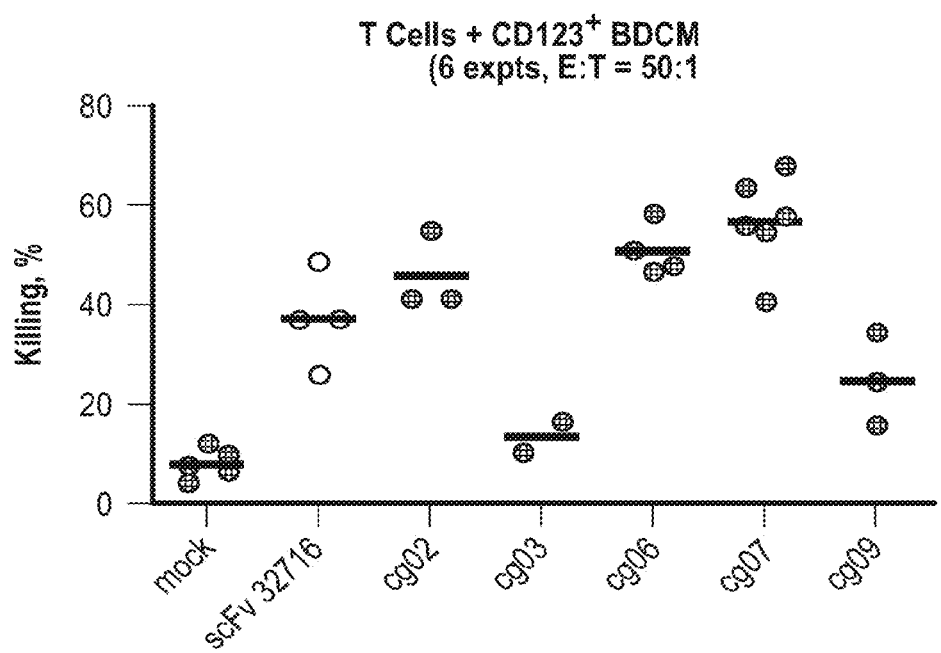
Figure 25A:
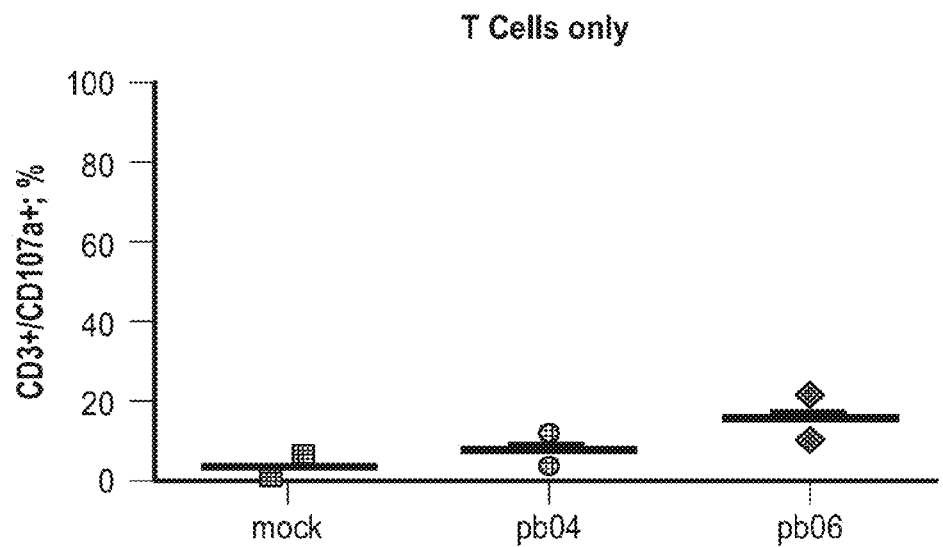
FIGS. 25A-25D. T cells expressing PD-L1-DBDpp-CARs degranulate in response to target binding.
Figure 25B:
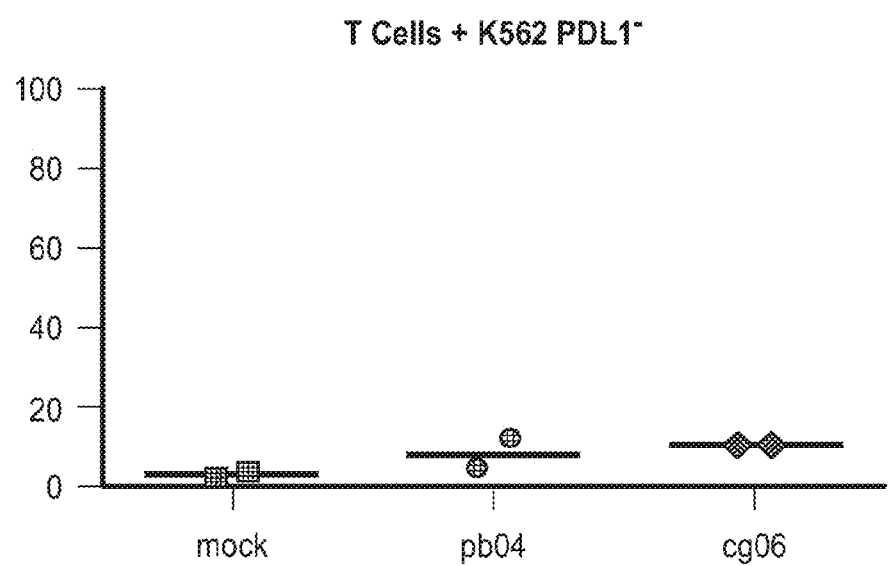
Figure 25C:
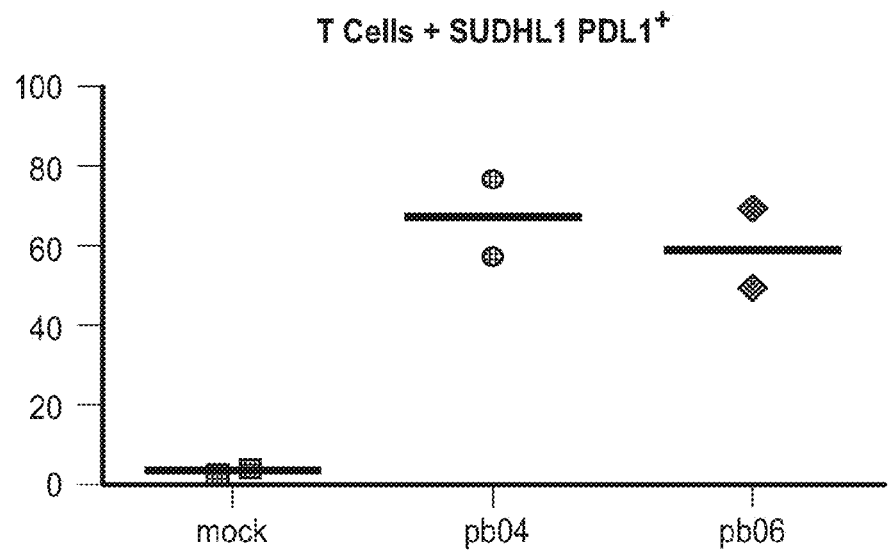
Figure 25D:
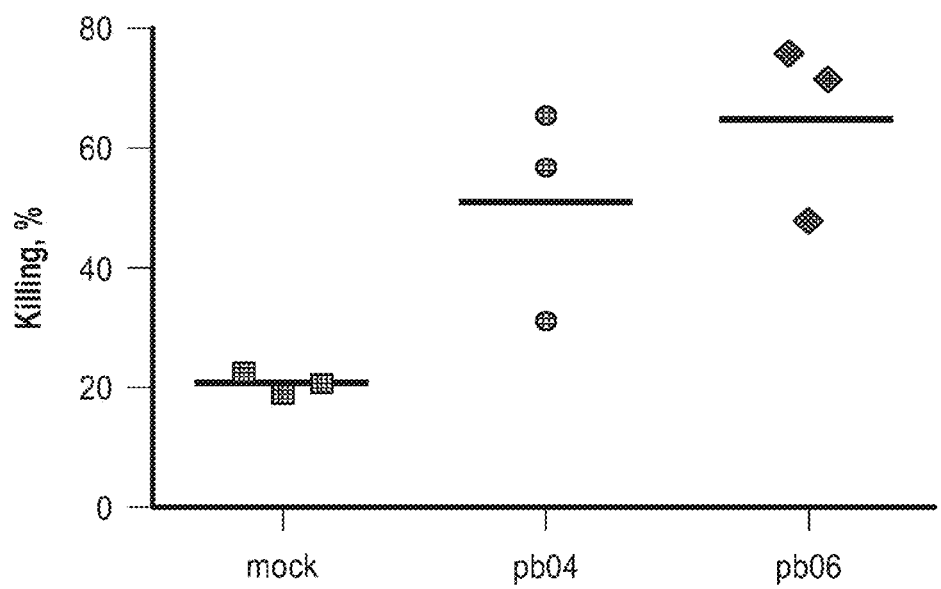

FIGS. 24A-24D summarize these data. FIG. 24A shows production of CD107a (as a marker of degranulation of the DBDpp-CAR T cells) equivalent to negative controls when CD123-targeting DBDpp-CAR T cells are cultured alone. FIG. 24B shows limited CD107a expression when DBDpp-CAR T cells are co-cultured with CD123 negative K562 tumor cells. FIG. 24C shows significant CD107a expression when CD123-targeting DBDpp-CAR T cells are co-cultured with CD123 positive BDCM cells, thus indicating that the T cells are activated, undergoing signaling, and undergoing degranulation will result in tumor eradication. FIG. 24D depicts data from experimental replicates of co-culture of CD123-targeting DBDpp-CAR T with CD123 positive BDCM cells. FIGS. 25A-25D show similar data related to degranulation of T cells expressing PD-L1-DBDpp-CARs. Not only do these data demonstrate that DBDpp-CAR T cells effectively degranulate, these data provide further support for the target-dependent activation of DBDpp-CAR expressing T cells.

Example 13. DBDpp-CAR Mediated Tumor Cytotoxicity is Target Specific

The target-specific function of DBDpp-CAR expressing human T cells was extended to include in vitro tumor cell cytotoxicity as described in FIGS. 26 and 27. These experiments employed CD123+(BDCM, acute myelogenous leukemia) and CD123-(K562, chronic myelogenous leukemia) tumor cells that were pre-loaded with fluorescence enhancing ligand (BATDA). CD123-directed DBDpp-CAR expressing T cells were cultured with tumor cells for 2 hours at various effector to target (E:T) ratios. Mock co-culture and co-culture with CD123-directed scFv-CARs were used as controls. In an additional group of experiments, PD-L1+ (SU-DHL-1, large cell lymphoma) and PD-L1-(K562, chronic myelogenous leukemia) tumor cells were pre-loaded with BATDA. PD-L1-directed DBDpp-CAR expressing T cells were cultured with tumor cells for 2 hours at various E:T ratios. Mock co-cultures were used as controls. BATDA ligand is released as a result of the cytolysis of target cells, and upon addition of Europium solution (Eu), forms a fluorescent and stable chelate, which was measured using a Synergy 2 (Biotek) time-resolved fluorimeter.

Figure 26A:
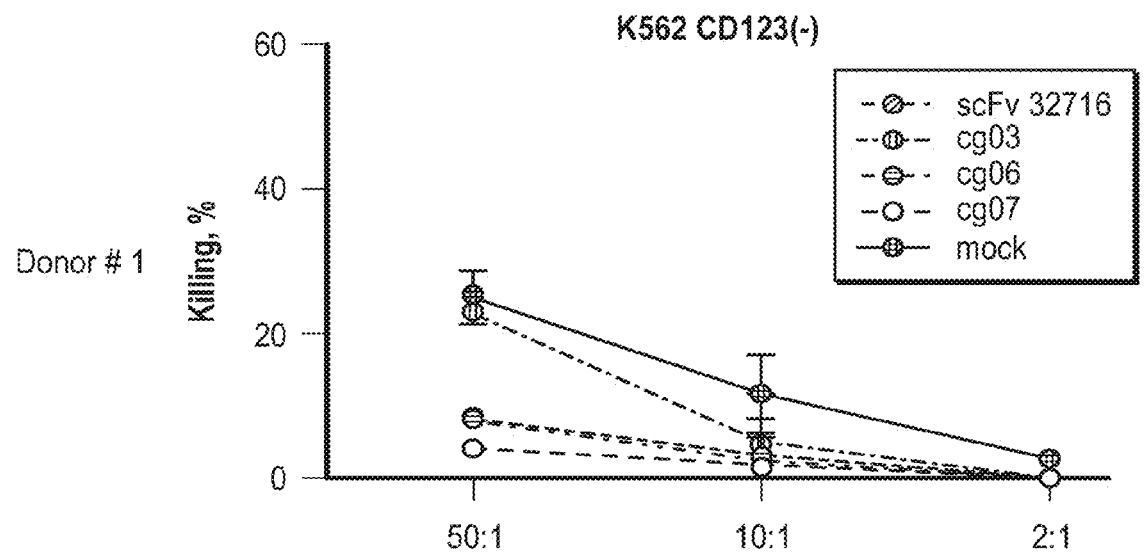
FIGS. 26A-26D. T cells expressing DBDpp-CARs mediate target-specific tumor cytotoxicity.
Figure 26B:
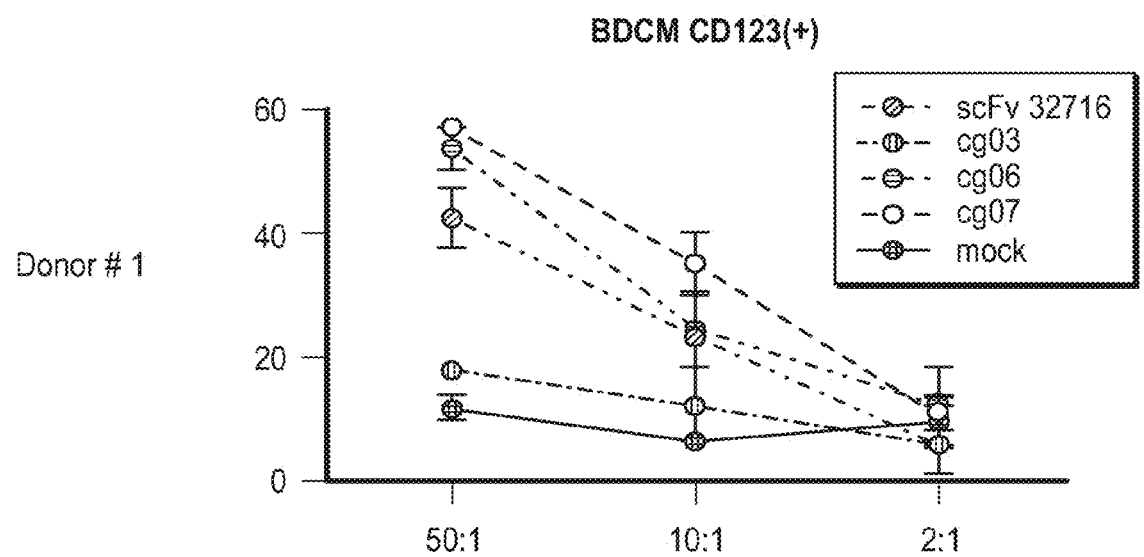
Figure 26C:
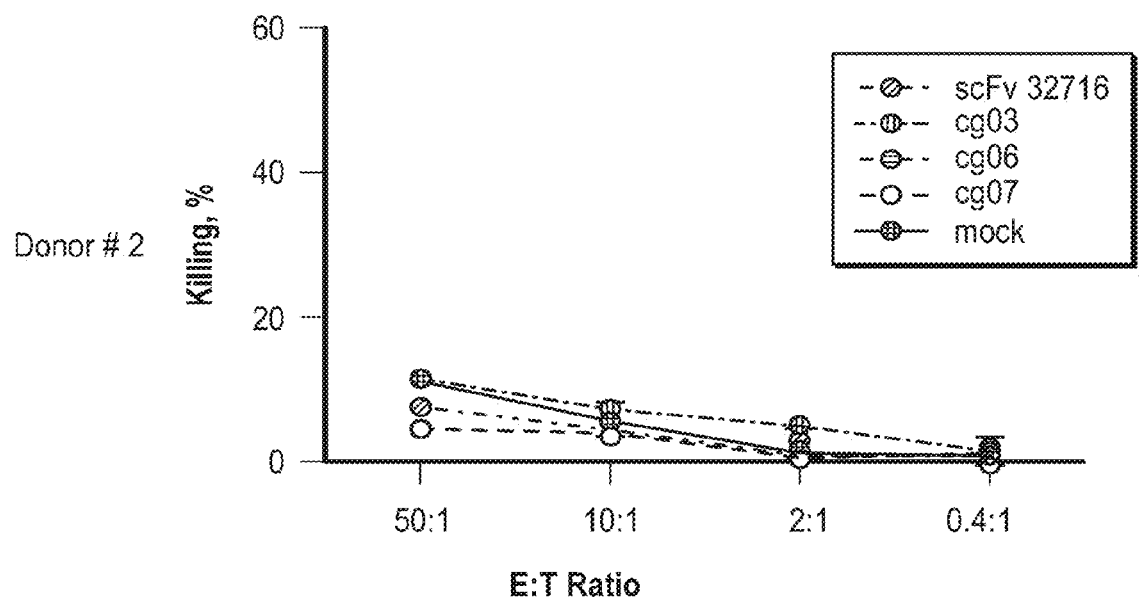
Figure 26D:
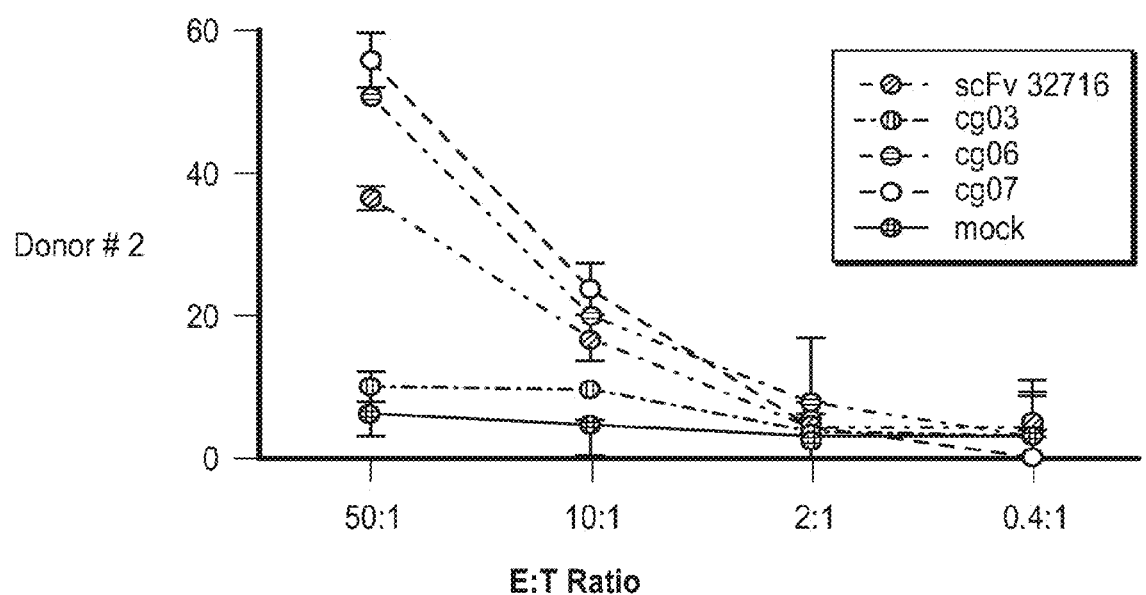
Figure 27A:
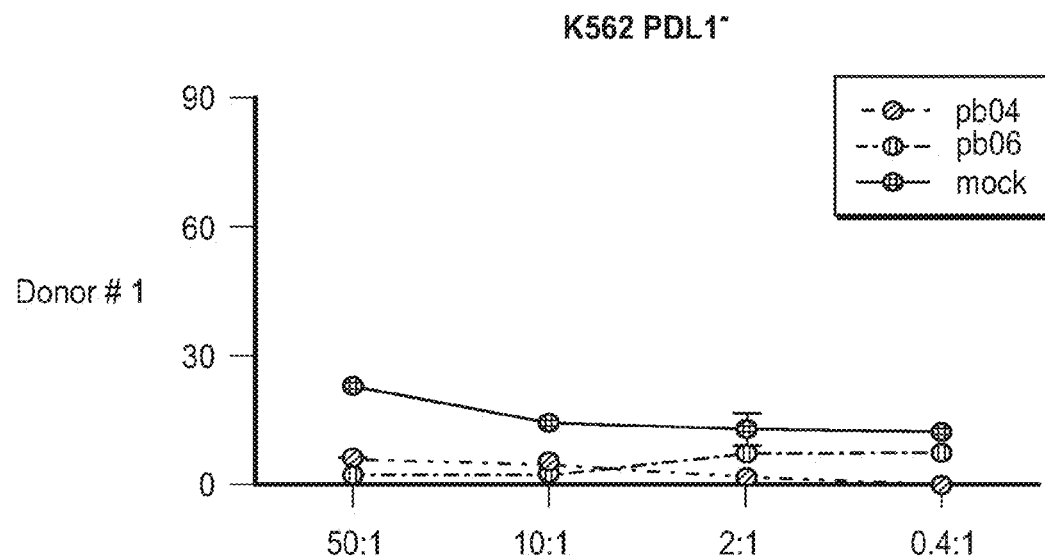
FIGS. 27A-27F. T cells expressing DBDpp-CARs mediate target-specific tumor cytotoxicity.
Figure 27B:
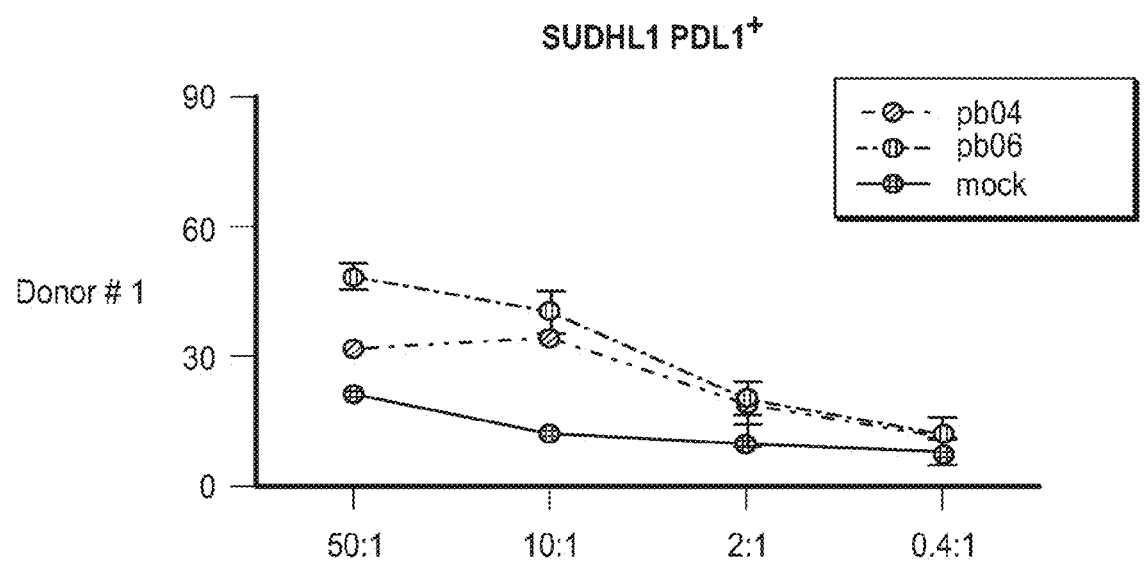
Figure 27C:
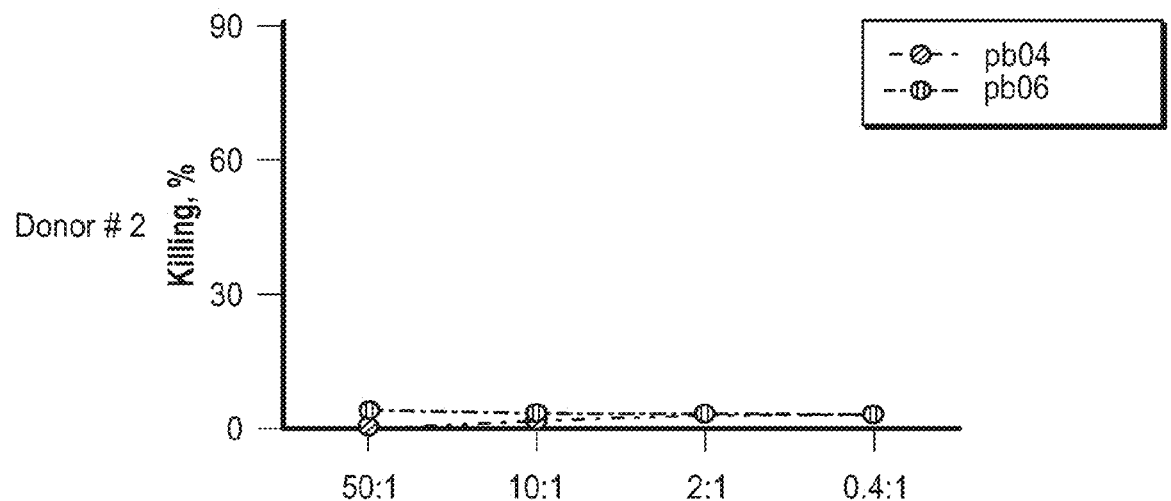
Figure 27D:
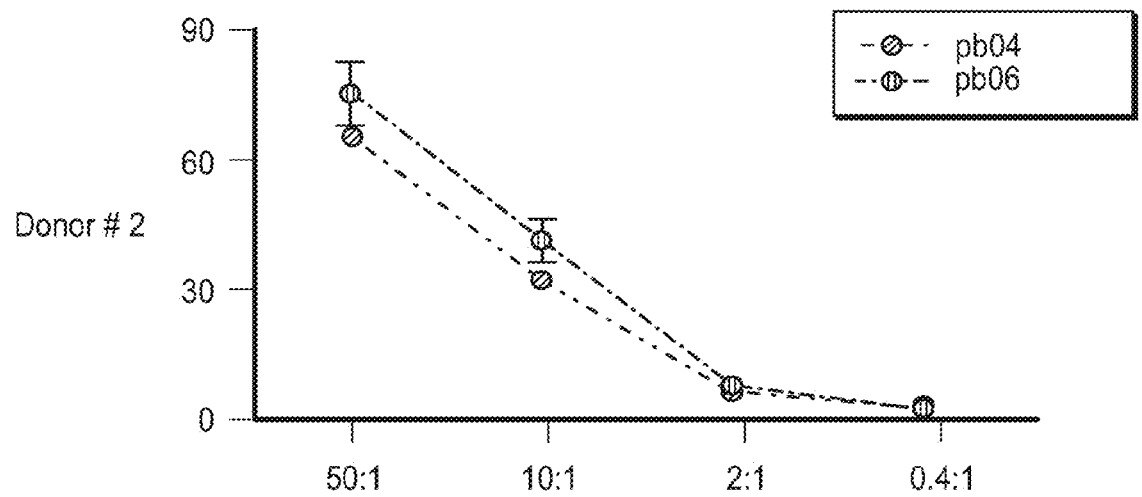
Figure 27E:
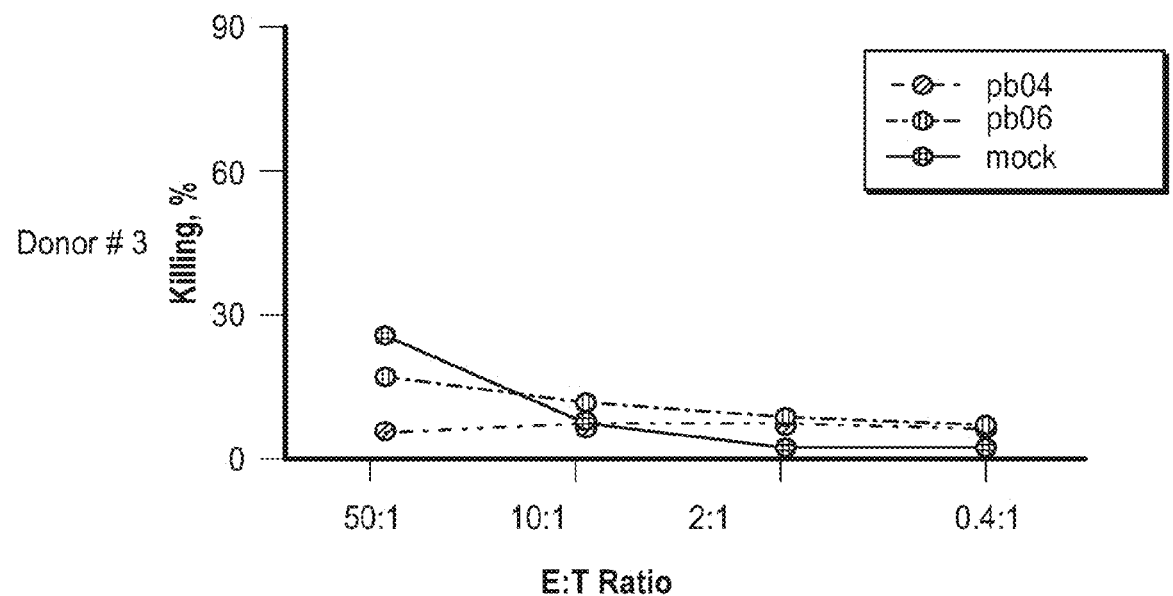
Figure 27F:
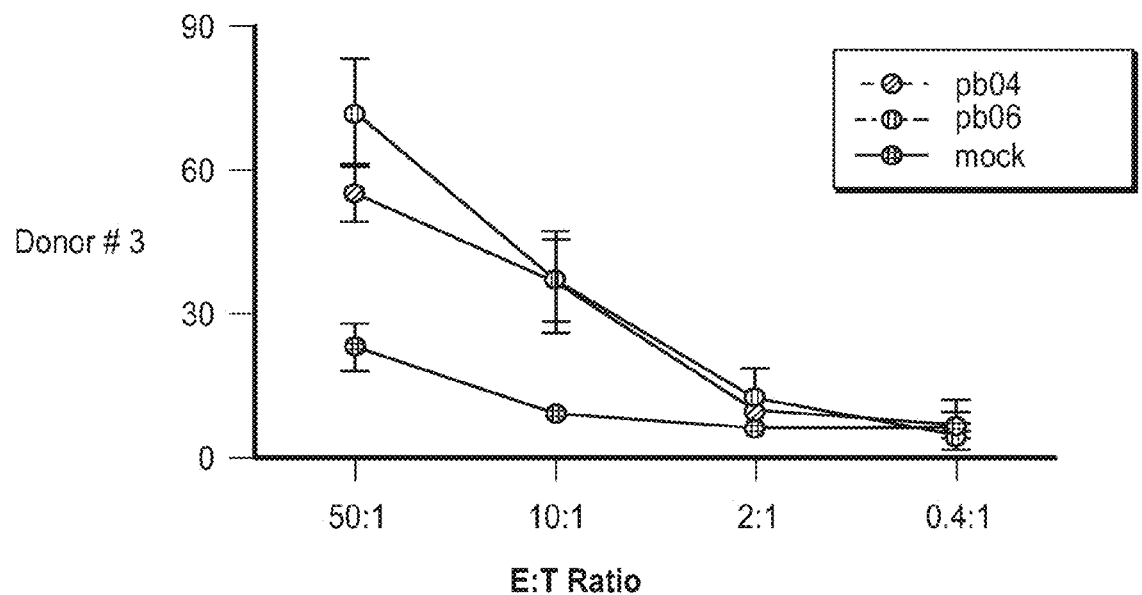

FIGS. 26A-26D and 27A-27F summarize data from these experiments. FIG. 26A shows that co-culture of CD123 targeting DBDpp-CAR T cells with K562 cells (no CD123 expression) yields a kill percentage less than that of mock co-culture controls. In contrast FIG. 26B demonstrates that each of the groups of T cells expressing CD123 targeting DBDpp-CAR kill CD123 positive tumor cells more effectively than mock co-culture controls, and, for some DBDpp, as compared to T cells targeted to CD123 with an scFv. FIGS. 26C and 26D depict similar data with cells from a separate donor.

As a further example, FIGS. 27A-27F show the kill percentage for PD-L1-directed DBDpp-CAR T cells. As discussed above, when co-cultured with cells not expressing PD-L1, there is limited or no cytotoxicity detected (27A, 27C, 27E). However, when co-cultured with cells that do express the target marker PD-L1, there is cytotoxicity that is measured and far exceeds that detected in mock co-culture controls (27B, 27D, 27F). These data extend the functional attributes of DBDpp expressing T cells to include target-specific tumor cell kill.

Example 14. DBDpp Domains Can Be Deimmunized and Retain Function

Many therapeutics have the potential to cause adverse side effects, while providing an effective therapy. In some cases, patients may have an immune reaction to a therapeutic (whether drug or cell based). Because the DBDpp disclosed herein are non-human proteins, in silico analyses were performed to identify potentially immunogenic epitopes and eliminate them without compromising the functional properties of the DBDpp.

In silico analysis of the amino acid sequence of cg06 (SEQ ID NO: 99) identified three 9 amino acid sequences that share characteristics with that of high affinity (binding threshold less than 6%) and promiscuous (present in greater than 50% of relevant alleles) T cell epitopes (Singh, Bioinformatics 17:1236-1237, 2012). Specific amino acid substitutions within cg06 were identified as reducing the number of predicted T cell epitopes. The corresponding point mutations were introduced into cg06, either individually or combination, resulting in a series of 'deimmunized' DBDpp-CARs.

A three-dimensional model of a DBDpp (cg06) is shown in FIG. 28A. FIG. 28B depicts cg06 with one (of three) of the potentially immunogenic epitopes modified to be less potentially immunogenic. FIG. 28C depicts cg06 with two (of three) of the potentially immunogenic epitopes modified. FIG. 28D depicts cg06 with all three of the potentially immunogenic epitopes modified.

Jurkat reporter cells were electroporated with these deimmunized DBDpp-CARs. After 24 hours in culture CAR expression on Jurkat cells was assessed by staining with anti-FLAG monoclonal antibody. The cells were co-cultured for 6 hours with CD123+ target tumor cells (KG1a with low level of CD123 expression and BDCM with high level of CD123 expression). NFAT mediated signaling was measured through the addition to the cells of luciferase assay reagent (Promega) and quantitation of relative luminescence units (RLU).

Figure 29A:
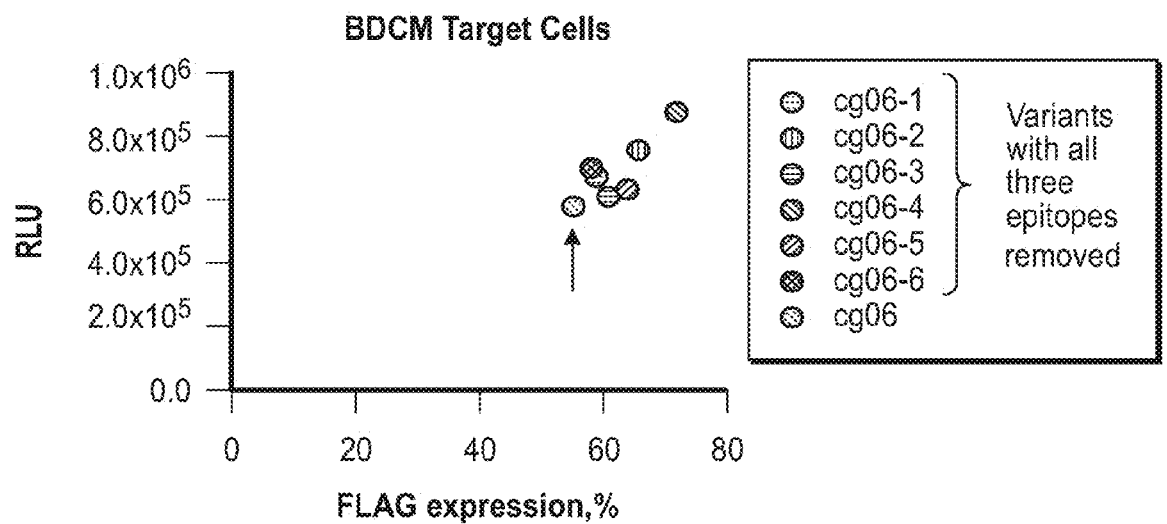
FIGS. 29A-29B. DBDpp with modified epitopes retain functionality.
Figure 29B:
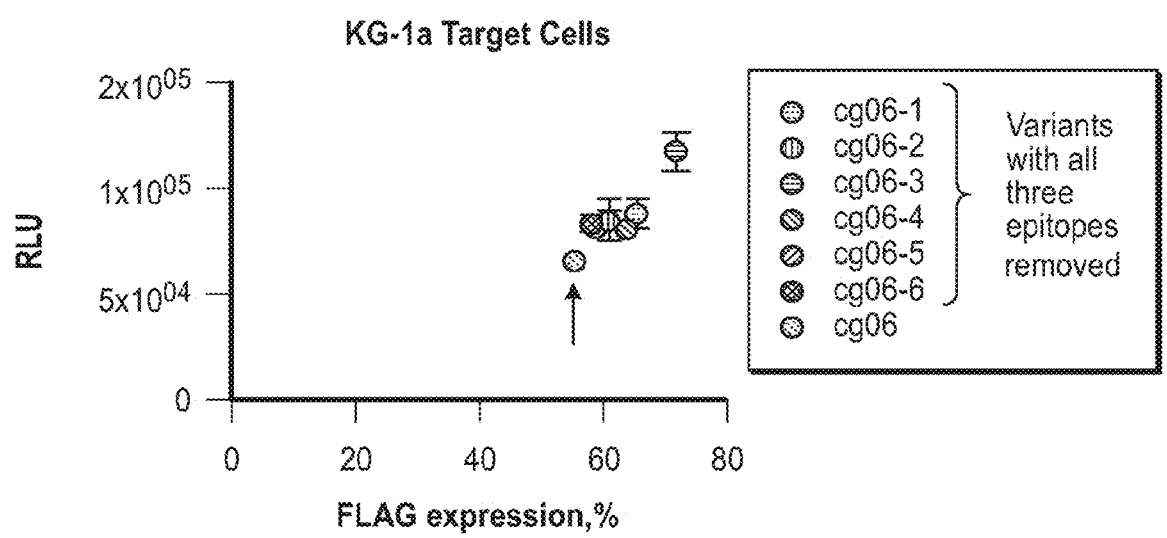

Data from these experiments are shown in FIGS. 29A-29B. FIG. 29A demonstrates that deimmunized CD123-binding DBDpp-CARs (cg06-1 through cg06-6) induce NFAT signaling when co-cultured with CD123-positive BDCM cells. FIG. 29B further demonstrates that CD123-binding DBDpp-CARs also induce NFAT signaling when co-cultured with cells having lower CD123 expression (KG1a)—note the reduced RLU levels compared to FIG. 29A. Taken together, these data demonstrate that the immunogenic potential of a target-binding DBDpp can be decreased by specific amino acid residue substitutions in the DBDpp that do not alter the function of the DBDpp or the target density-dependence of CAR-mediated intracellular signaling—the greater the degree of target present, the greater the degree of response. These data also indicate that DBDpp according to several embodiments disclosed herein can be used as therapeutics and if needed, be modified to reduce the potential for immune responses against the DBDpp-CAR containing cells (e.g., T cells, NK cells, etc.).

Example 15. Bi-Specific DBDpp

In some instances, target cells (e.g., tumor cells) may express more than one marker. In some embodiments, the DBD-CARs target a single marker (e.g., a unique cancer cell marker) on a target cell. In some embodiments, however, certain markers are not unique to cancer cells, but are also expressed on normal cells (although perhaps at different levels). Thus, in several embodiments, targeting two markers presents an opportunity to increase the specificity of an immunotherapeutic agent by engineering a CAR to express a bi-specific DBDpp. In such embodiments the targeted cells most efficiently killed would be those expressing both the markers targeted by the DBDpp (though killing of cells expression one or the other of the markers may still occur). To test this approach, bi-specific DBDpp-CARs were expressed on Jurkat cells and intracellular signaling in response to tumor cells expression one or both targets was measured.

Figures 30A, 30B:
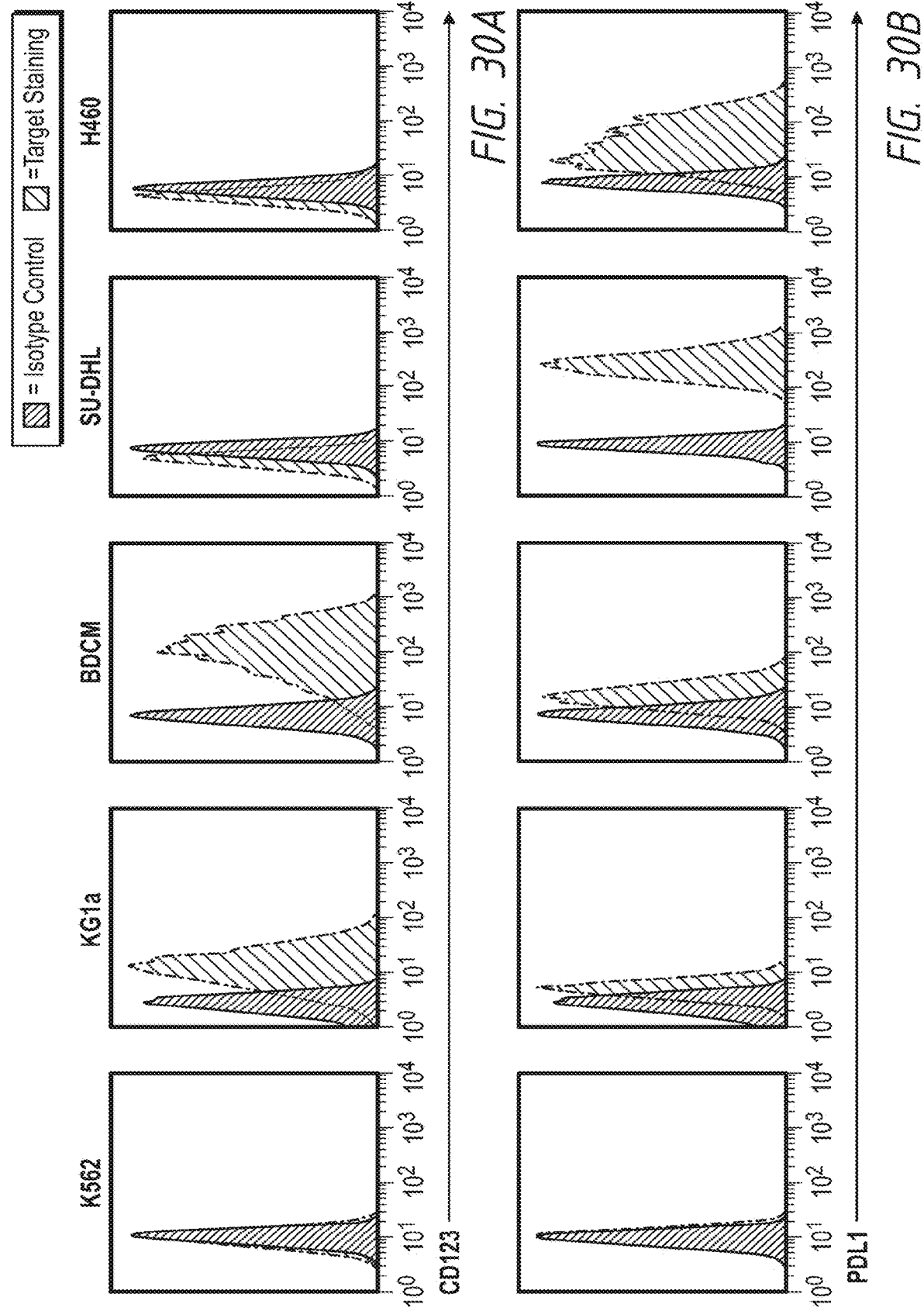
FIGS. 30A-30B. Dual marker expression on tumor cells.
Figures 31A, 31B, 31C, 31D:
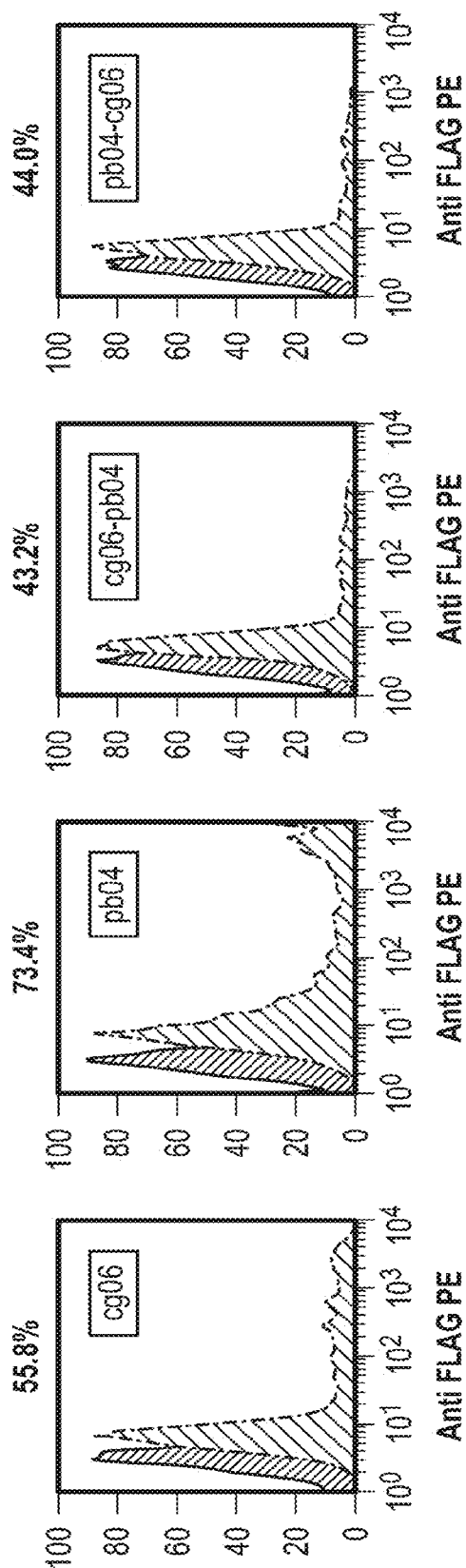
FIGS. 31A-31E. Bi-specific DBDpp-CAR T cells.

FIGS. 30A-30B define the cell surface expression of CD123 and PD-L1 respectively on K562 (CML); KG-1a (AML); BDCM (AML); SU-DHL-1 (LCL) and H460 (Lung carcinoma) cell lines. K562 does not express either target while KG1a and BDCM express CD123 and low levels of PD-L1 relative to the high PD-L1 expression observed on the CD123-negative cells, SU-DHL and H460. These cell lines afford the opportunity to determine if the intracellular signaling of a CD123-binding DBDpp-CAR (cg06) can be enhanced by a bi-specific CAR comprising cg06 (anti-CD123) fused to second DBDpp with specificity for PD-L1 (pb04). FIG. 31A demonstrates that DBDpp-CARs comprising cg06 only, (FIG. 31A), pb04 only (FIG. 31B), cg06 fused to the N-terminus of pb04 (cg06-pb04, FIG. 31C), and pb04 fused to the N-terminus of cg06 9pb-04-cg06, FIG. 31D) can be transduced and expressed in the Jurkat NFAT reporter cell line as assessed by anti-FLAG mAb binding to the CARs. The ability of the mono-specific and bi-specific CARs to activate the NFAT pathway was assessed by co-culturing the various CARs with tumor cells with different level of CD123 and/or PD-L1 expression. Cells were co-cultured with target cells for 6 hours. NFAT mediated signaling was measured through the addition to the cells of luciferase assay reagent (Promega) and quantitation of relative luminescence units (RLU) as a measure of induced intracellular signaling.

Figure 31E:
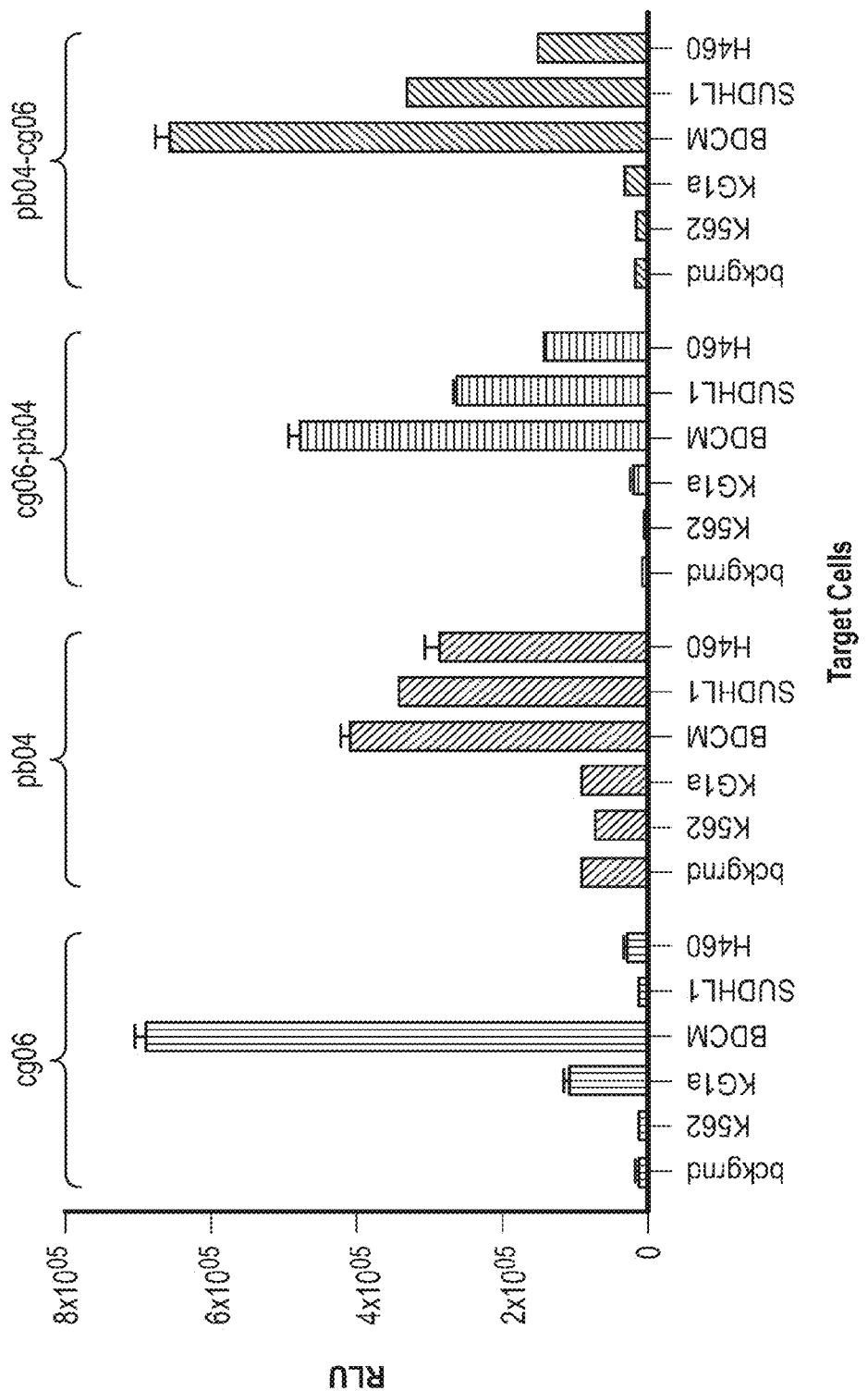

FIG. 31E depicts the results of this experiment. The leftmost group of bars and the histogram show the relative kill effect of the cg06 DBDpp against various cell types. Signaling response after co-culture with highly CD123+ BDCM was the greatest with this DBDpp-CAR. The next group to the right depicts data showing intracellular signaling after co-culture of the pb04 DBDpp against the same cell types. Signaling was highest in BDCM, followed by SUHDL1, and H460 (referring to FIGS. 30A-30B, these are the highest expressing cell lines for CD123 and PD-L1). The next group to the right depicts data showing intracellular signaling of a bi-specific cg06-pb04 DBDpp (cg06 more distal to the T cell membrane as compared to pb04). Finally, the rightmost group shows intracellular signaling from a second bi-specific DBPpp (pb04-cg06 DBDpp, where pb04 is more distal to the T cell membrane as compared to cg06). These two groups indicate that bi-specific DBDpp-CARs do function to promote intracellular signaling. In accordance with several embodiments, bi-specific DBDpp-CARs show enhanced activity (the magnitude of intracellular signaling in the pb04-cg06 group with BDCM cells is greater than can be accounted for by just the pb04 DBDpp alone). Thus in several embodiments, DBDpp-CARs comprising two DBDpps can cooperate to enhance T cell function. In several embodiments, there is a synergy between the various DBDpp used in a bispecific (or other multimeric) DBDpp-CAR.

Example 16. DBDpp-Mediated Tumor Immunotherapy In Vivo

In several embodiments, DBDpp-CAR expressing cells are effective at generating tumor cytotoxicity in vivo. Experiments will be performed in which cancer marker specific DBDpp-CAR are expressed on the surface of T cells (or in other experiments NK cells). A mouse model will be used, in which the mice are genetically engineered to express a solid tumor, or suspension tumor, in which the tumor cells express the cancer marker to which the specific DBDpp-CARs are directed. Control mice with tumor that does not express the targeted marker will be used as a control, as will mice receiving a placebo T-cell therapeutic.

The DBDpp-CAR cells will be administered to the mice and tumor burden will be assessed over time for the mice receiving various DBDpp-CAR. Tumor burden will be assessed by established methods (e.g., in vivo imaging) and mortality will be assessed over time.

As a result of receiving target specific DBD-pp-CAR cells, tumor burden will be reduced in mice expressing the marker specifically targeted by the DBDpp. The reduction will be significant in comparison to those mice receiving a placebo. Likewise, the reduction will be significant in comparison to those mice having tumor cells that do not express the marker specifically targeted by the DBDpp. Further, mortality will be reduced in the mice receiving the target specific DBDpp-CARs as compared to the placebo group and the group of mice with tumors not expressing the specific target marker. The results of this experiment will demonstrate that immune cells expressing DBDpp-CARs are effective therapeutic agents and generate target specific cytotoxicity of tumor cells in vivo.

Example 17. DBDpp-Mediated Tumor Immunotherapy In Vivo

As discussed above, DBDpp-CAR expressing cells are effective at generating tumor cytotoxicity in vivo. Experiments will be performed in which cancer marker specific DBDpp-CAR are expressed on the surface of T cells (or in other experiments NK cells). Clinical trials will demonstrate safety of the DBDpp-CAR cells. Additional trials will be performed to administer DBDpp-CAR cells to humans having a tumor expressing a marker, to which the DBDpp is specifically targeted.

The DBDpp-CAR cells will be administered on a schedule to be determined according to ordinary skill in the art. Tumor progression, tumor burden and mortality will be assessed over time.

As a result of receiving target specific DBDpp-CAR cells, tumor progression will be slowed and overall tumor burden will be reduced. The reduction will be significant in comparison historical data utilizing conventional anti-cancer techniques such as chemotherapy or radiation therapy. Mortality will also decrease in comparison with such therapies. There will be limited off-target cytotoxic effects. The results of this trial will demonstrate that immune cells expressing DBDpp-CARs are effective therapeutic agents and generate target specific cytotoxicity of tumor cells in vivo.

Figure 32:
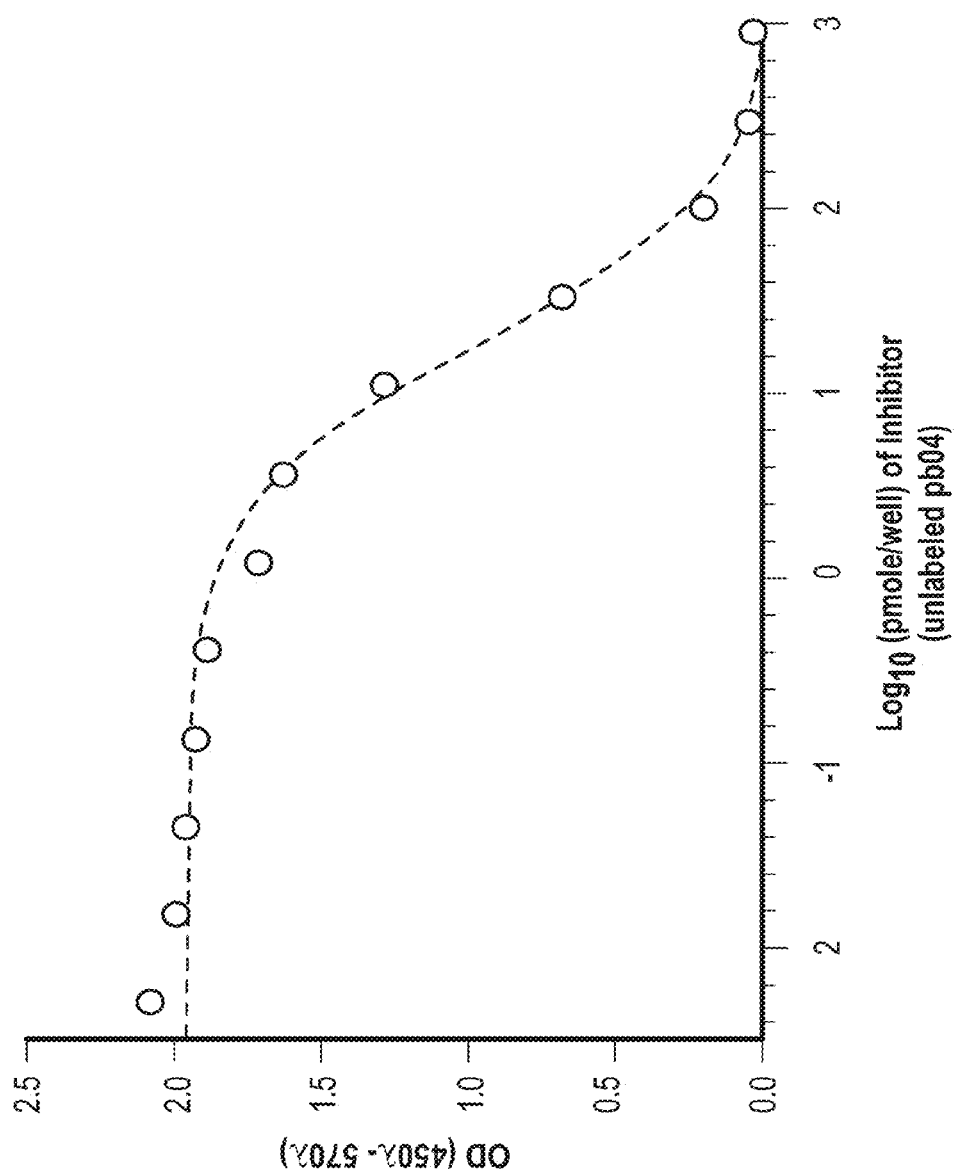
FIG. 32. Competitive DBDpp Binding Assay.

Example 18. Competitive Inhibition Assay to Define Target Epitope Specificity of DBDpp Comprising Distinct Amino Acid Sequences DBDpp can be defined by various structural and functional properties including, but not limited to, primary amino acid sequence, pI, melting point, target-specificity, binding affinity, and target epitope specificity. The target epitope specificity of a first DBDpp can be compared to that of a second DBDpp using a competitive assay format in which the binding of a fixed concentration of the first DBDpp to target is performed in the presence of increasing concentrations of the second DBDpp. If the first and second DBDpp bind to the same epitope, or a partially overlapping epitope, as defined by amino acid sequence or spatially, then the second DBDpp will inhibit (e.g., compete for) binding of the first DBDpp to the target. If, however the second DBDpp does not inhibit the binding of the first DBDpp, then the DBDpp bind to distinct epitopes. This assay format was used to assess the ability of a PD-L1 binding DBDpp, pb04, to inhibit the binding of a fixed concentration (11.1 pmoles/well) of a second PD-L1 binding DBDpp, pb06. FIG. 32 demonstrates a concentration-dependent inhibition of soluble FLAG-tagged pb06 binding to FC-PD-L1 by soluble pb04 with an IC50 concentration of pb04 of 19 pmoles/well. Thus, pb04 and pb06 display shared epitope binding even though their primary amino acid sequences differ (SEQ ID NO:182 and 184). This assay format is readily adapted to characterize the ability of a DBDpp to inhibit ligand binding to the target of the DBDpp.

Example 19. Generation and Selection of CD123-Targeting DBDpp

In accordance with several embodiments of the methods disclosed above, the reference sequence of SEQ ID NO: 1 was modified at a plurality of positions. In one experiment, the modifications resulted in a library of DBDpp corresponding to SEQ ID NO: 6. Non-limiting examples of DBDpp exhibiting specificity for CD123 are represented by the sequences of SEQ ID NOS: 60-69.

in an additional experiment, the modifications resulted in a library of DBDpp corresponding to SEQ ID NO: 2. Non-limiting examples of DBDpp exhibiting specificity for CD123 are represented by the sequences of SEQ ID NOS: 70-91.

In an additional experiment, the modifications resulted in a library of DBDpp corresponding to SEQ ID NO: 4. Non-limiting examples of DBDpp exhibiting specificity for CD123 are represented by the sequences of SEQ ID NOS: 92-127.

Within any of the libraries generated according to the methods disclosed herein, any of the $X_n$ positions in a library sequences can be substituted with a natural or non-natural amino acid, depending on the embodiment. In some embodiments cysteine and/or proline are not used for such substitutions.

Example 20. Generation and Selection of De-Immunized CD123-Targeting DBDpp

In accordance with several embodiments of the methods disclosed above, the reference sequence of SEQ ID NO: 1 was modified at a plurality of positions. In one experiment, the modifications resulted in a library of DBDpp corresponding to SEQ ID NO: 4. According to the methods disclosed herein, select library members were identified and de-immunized by identifying and modifying potentially immunogenic residues. In this experiment, the DBDpp of SEQ ID NO: 99 was modified with an S65E substitution to yield SEQ ID NO: 130, exhibiting reduced immunogenicity.

Example 21. De-Immunization of CD123-Targeting DBDpp

A DBDpp of SEQ ID NO: 99 was generated and identified according to the methods disclosed herein. Further modifications were made to reduce the potential immunogenicity of the DBDpp. In this experiment, a R17Q substitution was made to yield the DBDpp of SEQ ID NO: 128. Additionally, a S24E substitution was made to yield the DBDpp of SEQ ID NO: 129. Also, in accordance with several embodiments, multiple de-immunizing substitutions can be made. For example, SEQ ID NO: 99 was modified with (i) an R17Q, S24E substitution to yield the DBDpp of SEQ ID NO: 131, (ii) an R17Q, S24T substitution to yield the DBDpp of SEQ ID NO: 132, (iii) an R17Q, S24G substitution to yield the DBDpp of SEQ ID NO: 133, (iv) an R17Q, S24E, S65E substitution to yield the DBDpp of SEQ ID NO: 134, (v) an R17Q, S24T, S65E substitution to yield the DBDpp of SEQ ID NO: 135, and an R17Q, S24G, S65E substitution to yield the DBDpp of SEQ ID NO: 136.

Example 22. Generation and Selection of CD19-Targeting DBDpp

In accordance with several embodiments of the methods disclosed above, the reference sequence of SEQ ID NO: 1 was modified at a plurality of positions. In one experiment, the modifications resulted in a library of DBDpp corresponding to SEQ ID NO: 6. Non-limiting examples of DBDpp exhibiting specificity for CD19 are represented by the sequence of SEQ ID NO: 137.

In an additional experiment, the modifications resulted in a library of DBDpp corresponding to SEQ ID NO: 4. Non-limiting examples of DBDpp exhibiting specificity for CD19 are represented by the sequences of SEQ ID NOS: 138-166.

Within any of the libraries generated according to the methods disclosed herein, any of the $X_n$ positions in a library sequences can be substituted with a natural or non-natural amino acid, depending on the embodiment. In some embodiments cysteine and/or proline are not used for such substitutions.

Example 23. Generation and Selection of CD22-Targeting DBDpp

In accordance with several embodiments of the methods disclosed above, the reference sequence of SEQ ID NO: 1 was modified at a plurality of positions. In one experiment, the modifications resulted in a library of DBDpp corresponding to SEQ ID NO: 2. Non-limiting examples of DBDpp exhibiting specificity for CD22 are represented by the sequences of SEQ ID NOS: 167-168.

In an additional experiment, the modifications resulted in a library of DBDpp corresponding to SEQ ID NO: 4. Non-limiting examples of DBDpp exhibiting specificity for CD22 are represented by the sequences of SEQ ID NOS: 169-176.

Within any of the libraries generated according to the methods disclosed herein, any of the $X_n$ positions in a library sequences can be substituted with a natural or non-natural amino acid, depending on the embodiment. In some embodiments cysteine and/or proline are not used for such substitutions.

Example 24. Generation and Selection of DR5-Targeting DBDpp

In accordance with several embodiments of the methods disclosed above, the reference sequence of SEQ ID NO: 1 was modified at a plurality of positions. In one experiment, the modifications resulted in a library of DBDpp corresponding to SEQ ID NO: 6. Non-limiting examples of DBDpp exhibiting specificity for DR5 are represented by the sequences of SEQ ID NOS: 177-178.

In an additional experiment, the modifications resulted in a library of DBDpp corresponding to SEQ ID NO: 2. Non-limiting examples of DBDpp exhibiting specificity for DR5 are represented by the sequence of SEQ ID NO: 179.

In an additional experiment, the modifications resulted in a library of DBDpp corresponding to SEQ ID NO: 4. Non-limiting examples of DBDpp exhibiting specificity for DR5 are represented by the sequence of SEQ ID NO: 180.

Within any of the libraries generated according to the methods disclosed herein, any of the $X_n$ positions in a library sequences can be substituted with a natural or non-natural amino acid, depending on the embodiment. In some embodiments cysteine and/or proline are not used for such substitutions.

Example 25. Generation and Selection of PD-L1-Targeting DBDpp

In accordance with several embodiments of the methods disclosed above, the reference sequence of SEQ ID NO: 1 was modified at a plurality of positions. In one experiment, the modifications resulted in a library of DBDpp corresponding to SEQ ID NO: 4. Non-limiting examples of DBDpp exhibiting specificity for PD-L1 are represented by the sequences of SEQ ID NOS: 181-186.

Within any of the libraries generated according to the methods disclosed herein, any of the $X_n$ positions in a library sequences can be substituted with a natural or non-natural amino acid, depending on the embodiment. In some embodiments cysteine and/or proline are not used for such substitutions.

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a T cell comprising a DBDpp-CAR" include "instructing the administration of a T cell comprising a DBDpp-CAR." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

What is claimed is:

1. A de novo binding domain polypeptide (DBDpp), wherein
   a) the DBDpp comprises three anti-parallel alpha helices joined by linker peptides;
   b) the DBDpp comprises the amino acid sequence of SEQ ID NO:1 comprising 1 to 30 substitutions selected from the group consisting of substitutions of residues 5, 6, 8-10, 12, 13, 15-17, 19-27, 29, 30, 32-34, 36, 37, 39-41, 43-52, 54, 55, 57-59, 61, 62, 64-66, and 68 of SEQ ID NO: 1, substitution of residues 22-24 of SEQ ID NO: 1 with Z1, and substitution of residues 46-49 of SEQ ID NO: 1 with Z2, wherein Z1 and Z2 independently comprise 2 to 30 amino acids;
   c) the DBDpp does not comprise the amino acid sequence of SEQ ID NO:50; and
   d) the DBDpp specifically binds a target of interest.

2. The DBDpp of claim 1, wherein the 1 to 30 substitutions are selected from the group consisting of substitutions at residues 5, 6, 8-10, 12, 13, 15-17, 19-27, 29, 30, 32-34, 36, 37, 39-41, 43-52, 54, 55, 57-59, 61, 62, 64-66, and 68 of SEQ ID NO: 1.

3. The DBDpp of claim 1, wherein the substitutions do not include a substitution with a cysteine or a proline.

4. The DBDpp of claim 1, wherein the target of interest specifically bound by the polypeptide is a cancer antigen.

5. The DBDpp of claim 4, wherein the cancer antigen is PD-L1, CD137, or CD123.

6. The DBDpp of claim 1, wherein the DBD immunospecifically binds to a protein comprising amino acids 19-305 of CD123 (SEQ ID NO: 187).

7. An isolated polypeptide comprising the DBDpp of claim 1.

8. A fusion protein comprising two of more DBDpp according to claim 1, wherein the amino acid sequence of the two of more DBDpp comprise identical or different amino acid sequences.

9. A composition comprising the polypeptide of claim 7 conjugated with a label.

10. The composition of claim 9, wherein the label is a biotin moiety, an enzymatic label, a fluorescent label, a luminescent label, or a bioluminescent label.

11. A composition comprising the polypeptide of claim 7 conjugated to a therapeutic or cytotoxic agent.

12. A composition comprising the polypeptide of claim 7 and a pharmaceutically acceptable carrier.

13. An isolated nucleic acid molecule encoding the polypeptide of claim 7.

14. A host cell comprising the nucleic acid molecule of claim 13.

15. A chimeric antigen receptor (CAR), wherein the CAR comprises a target binding domain, a transmembrane domain, and an intracellular signaling domain, wherein the target binding domain comprises the DBDpp of claim 1.

16. The CAR of claim 15, wherein the intracellular signaling domain is selected from the group consisting of a human CD3 zeta domain, 41BB domain, a CD28 domain, or a combination thereof.

17. The CAR of claim 15, wherein the intracellular signaling domain comprises a costimulatory signaling region.

18. An isolated nucleic acid molecule comprising a sequence encoding the CAR of claim 15.

19. A cell comprising the nucleic acid molecule of claim 18.

20. The cell of claim 19, wherein the DBDpp binds to a tumor antigen associated with a hematologic malignancy or a solid tumor.

21. The cell of claim 20, wherein the tumor antigen is selected from the group consisting of CD137, PD-L1, CD123, CTLA4, CD47, KIR, DR5, TIM3, PD1, EGFR, TCR, CD19, CD20, CD22, ROR 1, mesothelin, CD33/1L3Ra, cMet, PSMA, Glycolipid F77, EGFRvIII, GD2, NY-ESO-1, MAGE A3, or a combination thereof.

22. The cell of claim 19, wherein the cell is a T cell or a natural killer (NK) cell.

23. A method of treating a subject having cancer, the method comprising administering to the subject an immune cell comprising a CAR of claim 15, wherein the target binding domain specifically binds a target of interest expressed by a cancer cell.

24. The method of claim 23, wherein the immune cell is a T cell or a NK cell.

25. The method of claim 23,
  a) wherein the transmembrane domain comprises 41BB or CD28, wherein the cytoplasmic domain comprises an alpha, beta, or zeta chain of the T cell receptor, and wherein the immune cell is a T cell, or
  b) wherein the transmembrane domain comprises CD28, wherein the cytoplasmic domain comprises a zeta chain of the T cell receptor, and wherein the immune cell is a NK cell.

26. The method of claim 23, wherein the target binding domain binds to a tumor antigen associated with a hematologic malignancy or a solid tumor.

27. The method of claim 26, wherein the tumor antigen is selected from the group consisting of CD137, PD-L1, CD123, CTLA4, CD47, KIR, DR5, TIM3, PD1, EGFR, TCR, CD19, CD20, CD22, ROR 1, mesothelin, CD33/1L3Ra, cMet, PSMA, Glycolipid F77, EGFRvIII, GD2, NY-ESO-1, MAGE A3, or a combination thereof.

28. The method of claim 23, wherein the CAR further comprises a second target binding domain having a different target than the target binding domain.

\* \* \* \* \*

SEQUENCE LISTING

```
<160> NUMBER OF SEQ ID NOS: 191

<210> SEQ ID NO 1
<211> LENGTH: 73
<212> TYPE: PRT
<213> ORGANISM: Homo sapiens
```

<400> SEQUENCE: 1

```
Met Gly Ser Trp Ala Glu Phe Lys Gln Arg Leu Ala Ala Ile Lys Thr
1               5                   10                  15

Arg Leu Glu Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70
```

<210> SEQ ID NO 2
<211> LENGTH: 73
<212> TYPE: PRT
<213> ORGANISM: Homo sapiens
<220> FEATURE:
<221> NAME/KEY: VARIANT
<222> LOCATION: (5)..(6)
<223> OTHER INFORMATION: Xaa is any natural or non-natural amino acid residue
<220> FEATURE:
<221> NAME/KEY: VARIANT
<222> LOCATION: (9)..(10)
<223> OTHER INFORMATION: Xaa is any natural or non-natural amino acid residue
<220> FEATURE:
<221> NAME/KEY: VARIANT
<222> LOCATION: (13)..(13)
<223> OTHER INFORMATION: Xaa is any natural or non-natural amino acid residue
<220> FEATURE:
<221> NAME/KEY: VARIANT
<222> LOCATION: (16)..(17)
<223> OTHER INFORMATION: Xaa is any natural or non-natural amino acid residue
<220> FEATURE:
<221> NAME/KEY: VARIANT
<222> LOCATION: (30)..(30)
<223> OTHER INFORMATION: Xaa is any natural or non-natural amino acid residue
<220> FEATURE:
<221> NAME/KEY: VARIANT
<222> LOCATION: (33)..(34)
<223> OTHER INFORMATION: Xaa is any natural or non-natural amino acid residue
<220> FEATURE:
<221> NAME/KEY: VARIANT
<222> LOCATION: (37)..(37)
<223> OTHER INFORMATION: Xaa is any natural or non-natural amino acid residue
<220> FEATURE:
<221> NAME/KEY: VARIANT
<222> LOCATION: (40)..(41)
<223> OTHER INFORMATION: Xaa is any natural or non-natural amino acid residue
<220> FEATURE:
<221> NAME/KEY: VARIANT
<222> LOCATION: (44)..(44)
<223> OTHER INFORMATION: Xaa is any natural or non-natural amino acid residue

<400> SEQUENCE: 2

```
Met Gly Ser Trp Xaa Xaa Phe Lys Xaa Xaa Leu Ala Xaa Ile Lys Xaa
1               5                   10                  15

Xaa Leu Glu Ala Leu Gly Gly Ser Glu Ala Glu Leu Ala Xaa Phe Glu
            20                  25                  30

Xaa Xaa Ile Ala Xaa Phe Glu Xaa Xaa Leu Gln Xaa Tyr Lys Gly Lys
        35                  40                  45
```

-continued

```
Gly Asn Pro Glu Val Glu Ala Leu Arg Lys Glu Ala Ala Ala Ile Arg
        50                  55                  60

Asp Glu Leu Gln Ala Tyr Arg His Asn
 65                  70

<210> SEQ ID NO 3
<211> LENGTH: 73
<212> TYPE: PRT
<213> ORGANISM: Homo sapiens
<220> FEATURE:
<221> NAME/KEY: VARIANT
<222> LOCATION: (32)..(33)
<223> OTHER INFORMATION: Xaa is any natural or non-natural amino acid
      residue
<220> FEATURE:
<221> NAME/KEY: VARIANT
<222> LOCATION: (36)..(36)
<223> OTHER INFORMATION: Xaa is any natural or non-natural amino acid
      residue
<220> FEATURE:
<221> NAME/KEY: VARIANT
<222> LOCATION: (39)..(40)
<223> OTHER INFORMATION: Xaa is any natural or non-natural amino acid
      residue
<220> FEATURE:
<221> NAME/KEY: VARIANT
<222> LOCATION: (43)..(43)
<223> OTHER INFORMATION: Xaa is any natural or non-natural amino acid
      residue
<220> FEATURE:
<221> NAME/KEY: VARIANT
<222> LOCATION: (57)..(58)
<223> OTHER INFORMATION: Xaa is any natural or non-natural amino acid
      residue
<220> FEATURE:
<221> NAME/KEY: VARIANT
<222> LOCATION: (61)..(61)
<223> OTHER INFORMATION: Xaa is any natural or non-natural amino acid
      residue
<220> FEATURE:
<221> NAME/KEY: VARIANT
<222> LOCATION: (64)..(65)
<223> OTHER INFORMATION: Xaa is any natural or non-natural amino acid
      residue
<220> FEATURE:
<221> NAME/KEY: VARIANT
<222> LOCATION: (68)..(68)
<223> OTHER INFORMATION: Xaa is any natural or non-natural amino acid
      residue

<400> SEQUENCE: 3

Met Gly Ser Trp Ala Glu Phe Lys Gln Arg Leu Ala Ala Ile Lys Thr
 1               5                  10                  15

Arg Leu Glu Ala Leu Gly Gly Ser Glu Ala Glu Leu Ala Ala Phe Xaa
                20                  25                  30

Xaa Glu Ile Xaa Ala Phe Xaa Xaa Glu Leu Xaa Ala Tyr Lys Gly Lys
        35                  40                  45

Gly Asn Pro Glu Val Glu Ala Leu Xaa Xaa Glu Ala Xaa Ala Ile Xaa
        50                  55                  60

Xaa Glu Leu Xaa Ala Tyr Arg His Asn
 65                  70

<210> SEQ ID NO 4
<211> LENGTH: 73
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is any natural or non-natural amino acid
```

```
                  residue
<220> FEATURE:
<221> NAME/KEY: VARIANT
<222> LOCATION: (8)..(9)
<223> OTHER INFORMATION: Xaa is any natural or non-natural amino acid
      residue
<220> FEATURE:
<221> NAME/KEY: VARIANT
<222> LOCATION: (12)..(12)
<223> OTHER INFORMATION: Xaa is any natural or non-natural amino acid
      residue
<220> FEATURE:
<221> NAME/KEY: VARIANT
<222> LOCATION: (15)..(16)
<223> OTHER INFORMATION: Xaa is any natural or non-natural amino acid
      residue
<220> FEATURE:
<221> NAME/KEY: VARIANT
<222> LOCATION: (19)..(19)
<223> OTHER INFORMATION: Xaa is any natural or non-natural amino acid
      residue
<220> FEATURE:
<221> NAME/KEY: VARIANT
<222> LOCATION: (55)..(55)
<223> OTHER INFORMATION: Xaa is any natural or non-natural amino acid
      residue
<220> FEATURE:
<221> NAME/KEY: VARIANT
<222> LOCATION: (58)..(59)
<223> OTHER INFORMATION: Xaa is any natural or non-natural amino acid
      residue
<220> FEATURE:
<221> NAME/KEY: VARIANT
<222> LOCATION: (62)..(62)
<223> OTHER INFORMATION: Xaa is any natural or non-natural amino acid
      residue
<220> FEATURE:
<221> NAME/KEY: VARIANT
<222> LOCATION: (65)..(66)
<223> OTHER INFORMATION: Xaa is any natural or non-natural amino acid
      residue

<400> SEQUENCE: 4

Met Gly Ser Trp Xaa Glu Phe Xaa Xaa Arg Leu Xaa Ala Ile Xaa Xaa
1               5                   10                  15

Arg Leu Xaa Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Xaa Leu Arg Xaa Xaa Ala Ala Xaa Ile Arg
    50                  55                  60

Xaa Xaa Leu Gln Ala Tyr Arg His Asn
65                  70

<210> SEQ ID NO 5
<211> LENGTH: 73
<212> TYPE: PRT
<213> ORGANISM: Homo sapiens
<220> FEATURE:
<221> NAME/KEY: VARIANT
<222> LOCATION: (5)..(6)
<223> OTHER INFORMATION: Xaa is any natural or non-natural amino acid
      residue
<220> FEATURE:
<221> NAME/KEY: VARIANT
<222> LOCATION: (9)..(10)
<223> OTHER INFORMATION: Xaa is any natural or non-natural amino acid
      residue
<220> FEATURE:
<221> NAME/KEY: VARIANT
<222> LOCATION: (13)..(13)
<223> OTHER INFORMATION: Xaa is any natural or non-natural amino acid
      residue
```

```
<220> FEATURE:
<221> NAME/KEY: VARIANT
<222> LOCATION: (16)..(17)
<223> OTHER INFORMATION: Xaa is any natural or non-natural amino acid
      residue
<220> FEATURE:
<221> NAME/KEY: VARIANT
<222> LOCATION: (32)..(33)
<223> OTHER INFORMATION: Xaa is any natural or non-natural amino acid
      residue
<220> FEATURE:
<221> NAME/KEY: VARIANT
<222> LOCATION: (36)..(36)
<223> OTHER INFORMATION: Xaa is any natural or non-natural amino acid
      residue
<220> FEATURE:
<221> NAME/KEY: VARIANT
<222> LOCATION: (39)..(40)
<223> OTHER INFORMATION: Xaa is any natural or non-natural amino acid
      residue
<220> FEATURE:
<221> NAME/KEY: VARIANT
<222> LOCATION: (43)..(43)
<223> OTHER INFORMATION: Xaa is any natural or non-natural amino acid
      residue
<220> FEATURE:
<221> NAME/KEY: VARIANT
<222> LOCATION: (55)..(55)
<223> OTHER INFORMATION: Xaa is any natural or non-natural amino acid
      residue
<220> FEATURE:
<221> NAME/KEY: VARIANT
<222> LOCATION: (58)..(59)
<223> OTHER INFORMATION: Xaa is any natural or non-natural amino acid
      residue
<220> FEATURE:
<221> NAME/KEY: VARIANT
<222> LOCATION: (62)..(62)
<223> OTHER INFORMATION: Xaa is any natural or non-natural amino acid
      residue
<220> FEATURE:
<221> NAME/KEY: VARIANT
<222> LOCATION: (65)..(66)
<223> OTHER INFORMATION: Xaa is any natural or non-natural amino acid
      residue

<400> SEQUENCE: 5

Met Gly Ser Trp Xaa Xaa Phe Lys Xaa Xaa Leu Ala Xaa Ile Lys Xaa
1               5                   10                  15

Xaa Leu Glu Ala Leu Gly Gly Ser Glu Ala Glu Leu Ala Ala Phe Xaa
            20                  25                  30

Xaa Glu Ile Xaa Ala Phe Xaa Xaa Glu Leu Xaa Ala Tyr Lys Gly Lys
        35                  40                  45

Gly Asn Pro Glu Val Xaa Leu Arg Xaa Xaa Ala Ala Xaa Ile Arg
    50                  55                  60

Xaa Xaa Leu Gln Ala Tyr Arg His Asn
65                  70

<210> SEQ ID NO 6
<211> LENGTH: 73
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is any natural or non-natural amino acid
      residue
<220> FEATURE:
<221> NAME/KEY: VARIANT
<222> LOCATION: (8)..(9)
<223> OTHER INFORMATION: Xaa is any natural or non-natural amino acid
      residue
<220> FEATURE:
```

<220> FEATURE:
<221> NAME/KEY: VARIANT
<222> LOCATION: (12)..(12)
<223> OTHER INFORMATION: Xaa is any natural or non-natural amino acid residue
<220> FEATURE:
<221> NAME/KEY: VARIANT
<222> LOCATION: (15)..(16)
<223> OTHER INFORMATION: Xaa is any natural or non-natural amino acid residue
<220> FEATURE:
<221> NAME/KEY: VARIANT
<222> LOCATION: (19)..(19)
<223> OTHER INFORMATION: Xaa is any natural or non-natural amino acid residue
<220> FEATURE:
<221> NAME/KEY: VARIANT
<222> LOCATION: (30)..(30)
<223> OTHER INFORMATION: Xaa is any natural or non-natural amino acid residue
<220> FEATURE:
<221> NAME/KEY: VARIANT
<222> LOCATION: (33)..(34)
<223> OTHER INFORMATION: Xaa is any natural or non-natural amino acid residue
<220> FEATURE:
<221> NAME/KEY: VARIANT
<222> LOCATION: (37)..(37)
<223> OTHER INFORMATION: Xaa is any natural or non-natural amino acid residue
<220> FEATURE:
<221> NAME/KEY: VARIANT
<222> LOCATION: (40)..(41)
<223> OTHER INFORMATION: Xaa is any natural or non-natural amino acid residue
<220> FEATURE:
<221> NAME/KEY: VARIANT
<222> LOCATION: (44)..(44)
<223> OTHER INFORMATION: Xaa is any natural or non-natural amino acid residue
<220> FEATURE:
<221> NAME/KEY: VARIANT
<222> LOCATION: (57)..(58)
<223> OTHER INFORMATION: Xaa is any natural or non-natural amino acid residue
<220> FEATURE:
<221> NAME/KEY: VARIANT
<222> LOCATION: (61)..(61)
<223> OTHER INFORMATION: Xaa is any natural or non-natural amino acid residue
<220> FEATURE:
<221> NAME/KEY: VARIANT
<222> LOCATION: (64)..(65)
<223> OTHER INFORMATION: Xaa is any natural or non-natural amino acid residue
<220> FEATURE:
<221> NAME/KEY: VARIANT
<222> LOCATION: (68)..(68)
<223> OTHER INFORMATION: Xaa is any natural or non-natural amino acid residue

<400> SEQUENCE: 6

Met Gly Ser Trp Xaa Glu Phe Xaa Xaa Arg Leu Xaa Ala Ile Xaa Xaa
1               5                   10                  15

Arg Leu Xaa Ala Leu Gly Gly Ser Glu Ala Glu Leu Ala Xaa Phe Glu
            20                  25                  30

Xaa Xaa Ile Ala Xaa Phe Glu Xaa Xaa Leu Gln Xaa Tyr Lys Gly Lys
        35                  40                  45

Gly Asn Pro Glu Val Glu Ala Leu Xaa Xaa Glu Ala Xaa Ala Ile Xaa
    50                  55                  60

Xaa Glu Leu Xaa Ala Tyr Arg His Asn
65                  70

<210> SEQ ID NO 7

```
<211> LENGTH: 126
<212> TYPE: PRT
<213> ORGANISM: HOMO SAPIENS
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: variant
<222> LOCATION: (22)..(51)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: variant
<222> LOCATION: (73)..(102)
<223> OTHER INFORMATION: Xaa is 2-30 natural and/or non-natural amino
      acid residues and up to 28 positions may be absent

<400> SEQUENCE: 7

Met Gly Ser Trp Xaa Xaa Phe Lys Xaa Xaa Leu Ala Xaa Ile Lys Xaa
1               5                   10                  15

Xaa Leu Glu Ala Leu Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Glu Ala Glu Leu Ala Xaa Phe Glu Xaa Xaa Ile Ala Xaa
        50                  55                  60

Phe Glu Xaa Xaa Leu Gln Xaa Tyr Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Asn Pro Glu Val Glu Ala Leu Arg Lys Glu
            100                 105                 110

Ala Ala Ala Ile Arg Asp Glu Leu Gln Ala Tyr Arg His Asn
        115                 120                 125

<210> SEQ ID NO 8
<211> LENGTH: 126
```

```
<212> TYPE: PRT
<213> ORGANISM: homo sapiens
<220> FEATURE:
<221> NAME/KEY: variant
<222> LOCATION: (22)..(51)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: variant
<222> LOCATION: (73)..(102)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (110)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (117)..(118)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid

<400> SEQUENCE: 8

Met Gly Ser Trp Ala Glu Phe Lys Gln Arg Leu Ala Ala Ile Lys Thr
1               5                   10                  15

Arg Leu Glu Ala Leu Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Glu Ala Glu Leu Ala Ala Phe Xaa Xaa Glu Ile Xaa Ala
    50                  55                  60

Phe Xaa Xaa Glu Leu Xaa Ala Tyr Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Asn Pro Glu Val Glu Ala Leu Xaa Xaa Glu
            100                 105                 110

Ala Xaa Ala Ile Xaa Xaa Glu Leu Xaa Ala Tyr Arg His Asn
        115                 120                 125

<210> SEQ ID NO 9
<211> LENGTH: 126
<212> TYPE: PRT
<213> ORGANISM: homo sapines
<220> FEATURE:
<221> NAME/KEY: misc_feature
<222> LOCATION: (5)..(5)
```

```
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: variant
<222> LOCATION: (22)..(51)
<223> OTHER INFORMATION: Xaa is 2-30 natural and/or non-natural amino
      acid residues and up to 28 positions may be absent
<220> FEATURE:
<221> NAME/KEY: variant
<222> LOCATION: (73)..(102)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (118)..(119)
<223> OTHER INFORMATION: Xaa can be any naturally occurring amino acid

<400> SEQUENCE: 9

Met Gly Ser Trp Xaa Glu Phe Xaa Xaa Arg Leu Xaa Ala Ile Xaa Xaa
1               5                   10                  15

Arg Leu Xaa Ala Leu Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Glu Ala Glu Leu Ala Ala Phe Glu Lys Glu Ile Ala Ala
        50                  55                  60

Phe Glu Ser Glu Leu Gln Ala Tyr Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Asn Pro Glu Val Glu Xaa Leu Arg Xaa Xaa
            100                 105                 110

Ala Ala Xaa Ile Arg Xaa Xaa Leu Gln Ala Tyr Arg His Asn
        115                 120                 125

<210> SEQ ID NO 10
<211> LENGTH: 126
<212> TYPE: PRT
<213> ORGANISM: homo sapiens
<220> FEATURE:
<221> NAME/KEY: misc_feature
<222> LOCATION: (5)..(6)
<223> OTHER INFORMATION: Xaa can be any naturally occurring amino acid
```

```
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: variant
<222> LOCATION: (22)..(51)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: variant
<222> LOCATION: (73)..(102)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (118)..(119)
<223> OTHER INFORMATION: Xaa can be any naturally occurring amino acid

<400> SEQUENCE: 10

Met Gly Ser Trp Xaa Xaa Phe Lys Xaa Xaa Leu Ala Xaa Ile Lys Xaa
1               5                   10                  15

Xaa Leu Glu Ala Leu Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Glu Ala Glu Leu Ala Ala Phe Xaa Xaa Glu Ile Xaa Ala
    50                  55                  60

Phe Xaa Xaa Glu Leu Xaa Ala Tyr Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Asn Pro Glu Val Glu Xaa Leu Arg Xaa Xaa
        100                 105                 110

Ala Ala Xaa Ile Arg Xaa Xaa Leu Gln Ala Tyr Arg His Asn
```

```
              115                 120                 125

<210> SEQ ID NO 11
<211> LENGTH: 126
<212> TYPE: PRT
<213> ORGANISM: homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: variant
<222> LOCATION: (22)..(51)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: variant
<222> LOCATION: (73)..(102)
<223> OTHER INFORMATION: Xaa is 2-30 natural and/or non-natural amino
      acid residues and up to 28 positions may be absent
<220> FEATURE:
<221> NAME/KEY: misc_feature
<222> LOCATION: (110)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (117)..(118)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid

<400> SEQUENCE: 11

Met Gly Ser Trp Xaa Glu Phe Xaa Xaa Arg Leu Xaa Ala Ile Xaa Xaa
1               5                   10                  15
```

Arg Leu Xaa Ala Leu Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Glu Ala Glu Leu Ala Xaa Phe Glu Xaa Xaa Ile Ala Xaa
    50                  55                  60

Phe Glu Xaa Xaa Leu Gln Xaa Tyr Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Asn Pro Glu Val Glu Ala Leu Xaa Xaa Glu
            100                 105                 110

Ala Xaa Ala Ile Xaa Xaa Glu Leu Xaa Ala Tyr Arg His Asn
        115                 120                 125

<210> SEQ ID NO 12
<211> LENGTH: 73
<212> TYPE: PRT
<213> ORGANISM: Homo sapiens

<400> SEQUENCE: 12

Met Gly Ser Trp Val Glu Phe Gly His Arg Leu Trp Ala Ile Asp Gln
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Lys Leu Arg Gln Arg Ala Ala Phe Ile Arg
    50                  55                  60

Phe Arg Leu Gln Ala Tyr Arg His Asn
65                  70

<210> SEQ ID NO 13
<211> LENGTH: 73
<212> TYPE: PRT
<213> ORGANISM: Homo sapiens

<400> SEQUENCE: 13

Met Gly Ser Trp Val Glu Phe Ala Asn Arg Leu Trp Ala Ile Asp Gln
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu His Leu Arg Asp Gln Ala Ala Phe Ile Arg
    50                  55                  60

His Lys Leu Gln Ala Tyr Arg His Asn
65                  70

<210> SEQ ID NO 14
<211> LENGTH: 73
<212> TYPE: PRT
<213> ORGANISM: Homo sapiens

<400> SEQUENCE: 14

Met Gly Ser Trp Tyr Glu Phe Arg His Arg Leu Trp Ala Ile Asp Gln
1               5                   10                  15

Arg Leu Tyr Ala Leu Gly Gly Ser Glu Ala Glu Leu Ala Ala Phe Glu

```
                 20                  25                  30

Lys Glu Ile Ala Ala Phe Glu Ser Glu Leu Gln Ala Tyr Lys Gly Lys
             35                  40                  45

Gly Asn Pro Glu Val Glu Gly Leu Arg Glu Ala Ala Phe Ile Arg
         50                  55                  60

Ala Lys Leu Gln Ala Tyr Arg His Asn
65                  70

<210> SEQ ID NO 15
<211> LENGTH: 73
<212> TYPE: PRT
<213> ORGANISM: Homo sapiens

<400> SEQUENCE: 15

Met Gly Ser Trp Tyr Glu Phe Ser Met Arg Leu Trp Ala Ile Asp Gln
1               5                   10                  15

Arg Leu Tyr Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
             35                  40                  45

Gly Asn Pro Glu Val Glu Ala Leu Arg Ala Lys Ala Tyr Ile Arg
         50                  55                  60

Trp Lys Leu Gln Ala Tyr Arg His Asn
65                  70

<210> SEQ ID NO 16
<211> LENGTH: 73
<212> TYPE: PRT
<213> ORGANISM: Homo sapiens

<400> SEQUENCE: 16

Met Gly Ser Trp Phe Glu Phe Asn His Arg Leu Trp Ala Ile Asn Glu
1               5                   10                  15

Arg Leu Tyr Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
             35                  40                  45

Gly Asn Pro Glu Val Glu Arg Leu Arg Ser Met Ala Ala Phe Ile Arg
         50                  55                  60

Tyr Lys Leu Gln Ala Tyr Arg His Asn
65                  70

<210> SEQ ID NO 17
<211> LENGTH: 73
<212> TYPE: PRT
<213> ORGANISM: Homo sapiens

<400> SEQUENCE: 17

Met Gly Ser Trp Tyr Glu Phe Gly His Arg Leu Trp Ala Ile Asp Gln
1               5                   10                  15

Arg Leu Tyr Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
             35                  40                  45

Gly Asn Pro Glu Val Glu Tyr Leu Arg Glu Thr Ala Ala His Ile Arg
         50                  55                  60

Thr Arg Leu Gln Ala Tyr Arg His Asn
65                  70
```

<210> SEQ ID NO 18
<211> LENGTH: 73
<212> TYPE: PRT
<213> ORGANISM: Homo sapiens

<400> SEQUENCE: 18

Met Gly Ser Trp Tyr Glu Phe His Tyr Arg Leu His Ala Ile Asp Gln
1               5                   10                  15

Arg Leu Tyr Ala Leu Gly Gly Ser Glu Ala Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Leu Arg Ile Lys Ala Ala Phe Ile Arg
    50                  55                  60

Asp Arg Leu Gln Ala Tyr Arg His Asn
65                  70

<210> SEQ ID NO 19
<211> LENGTH: 73
<212> TYPE: PRT
<213> ORGANISM: Homo sapiens

<400> SEQUENCE: 19

Met Gly Ser Trp Ala Glu Phe Lys Gln Arg Leu Ala Ala Ile Lys Thr
1               5                   10                  15

Arg Leu Glu Ala Leu Gly Gly Ser Glu Ala Glu Leu Ala Ala Phe Leu
            20                  25                  30

Gly Glu Ile Trp Ala Phe Glu Met Glu Leu Ala Ala Tyr Lys Gly Lys
        35                  40                  45

Gly Asn Pro Glu Val Glu Ala Leu Gly Arg Glu Ala Ala Ile Arg
    50                  55                  60

Met Glu Leu Gln Ala Tyr Arg His Asn
65                  70

<210> SEQ ID NO 20
<211> LENGTH: 73
<212> TYPE: PRT
<213> ORGANISM: Homo sapiens

<400> SEQUENCE: 20

Met Gly Ser Trp Tyr Glu Phe Asp Leu Arg Leu His Ala Ile Tyr Asp
1               5                   10                  15

Arg Leu Val Ala Leu Gly Gly Ser Glu Ala Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ile Leu Arg Asp Asn Ala Ala Tyr Ile Arg
    50                  55                  60

Gln Met Leu Gln Ala Tyr Arg His Asn
65                  70

<210> SEQ ID NO 21
<211> LENGTH: 73
<212> TYPE: PRT
<213> ORGANISM: Homo sapiens

<400> SEQUENCE: 21

Met Gly Ser Trp Thr Glu Phe Thr Tyr Arg Leu Ser Ala Ile Glu Trp

```
            1               5                  10                 15
Arg Leu Trp Ala Leu Gly Gly Ser Glu Ala Glu Leu Ala Trp Phe Glu
            20                 25                 30

Gln Lys Ile Ala Phe Phe Glu Asp Phe Leu Gln Tyr Tyr Lys Gly Lys
        35                 40                 45

Gly Asn Pro Glu Val Glu Ala Leu Lys His Glu Ala Gly Ala Ile Leu
    50                 55                 60

Asn Glu Leu Met Ala Tyr Arg His Asn
65                  70
```

<210> SEQ ID NO 22
<211> LENGTH: 73
<212> TYPE: PRT
<213> ORGANISM: Homo sapiens

<400> SEQUENCE: 22

```
Met Gly Ser Trp Ala Glu Phe Asp His Arg Leu His Ala Ile Arg Glu
1               5                  10                 15

Arg Leu His Ala Leu Gly Gly Ser Glu Ala Glu Leu Ala Ala Phe Glu
            20                 25                 30

Lys Glu Ile Ala Ala Phe Glu Ser Glu Leu Gln Ala Tyr Lys Gly Lys
        35                 40                 45

Gly Asn Pro Glu Val Glu Ile Leu Arg Gly Asn Ala Ala Tyr Ile Arg
    50                 55                 60

Ala Leu Leu Gln Ala Tyr Arg His Asn
65                  70
```

<210> SEQ ID NO 23
<211> LENGTH: 73
<212> TYPE: PRT
<213> ORGANISM: Homo sapiens

<400> SEQUENCE: 23

```
Met Gly Ser Trp Thr Glu Phe Val Gly Arg Leu Ala Ala Ile Glu Phe
1               5                  10                 15

Arg Leu Trp Ala Leu Gly Gly Ser Glu Ala Glu Leu Ala Trp Phe Glu
            20                 25                 30

Ala His Ile Ala Phe Phe Glu Asp Tyr Leu Gln Trp Tyr Lys Gly Lys
        35                 40                 45

Gly Asn Pro Glu Val Glu Ala Leu Arg Glu Glu Ala Gly Ala Ile Met
    50                 55                 60

Glu Glu Leu Lys Ala Tyr Arg His Asn
65                  70
```

<210> SEQ ID NO 24
<211> LENGTH: 73
<212> TYPE: PRT
<213> ORGANISM: Homo sapiens

<400> SEQUENCE: 24

```
Met Gly Ser Trp Thr Glu Phe Tyr Ser Arg Leu Glu Ala Ile Trp Val
1               5                  10                 15

Arg Leu Gln Ala Leu Gly Gly Ser Glu Ala Glu Leu Ala Met Phe Glu
            20                 25                 30

Asp Arg Ile Ala His Phe Glu Trp Phe Leu Gln Gln Tyr Lys Gly Lys
        35                 40                 45

Gly Asn Pro Glu Val Glu Ala Leu His Glu Glu Ala Ile Ala Ile Arg
    50                 55                 60
```

```
Lys Glu Leu Ala Ala Tyr Arg His Asn
 65                  70

<210> SEQ ID NO 25
<211> LENGTH: 73
<212> TYPE: PRT
<213> ORGANISM: Homo sapiens

<400> SEQUENCE: 25

Met Gly Ser Trp His Glu Phe His Asp Arg Leu Gln Ala Ile His Glu
 1               5                  10                  15

Arg Leu Tyr Ala Leu Gly Gly Ser Glu Ala Glu Leu Ala Ala Phe Glu
             20                  25                  30

Lys Glu Ile Ala Ala Phe Glu Ser Glu Leu Gln Ala Tyr Lys Gly Lys
         35                  40                  45

Gly Asn Pro Glu Val Glu Ser Leu Arg Ile Ala Ala His Ile Arg
     50                  55                  60

Gln Val Leu Gln Ala Tyr Arg His Asn
 65                  70

<210> SEQ ID NO 26
<211> LENGTH: 73
<212> TYPE: PRT
<213> ORGANISM: Homo sapiens

<400> SEQUENCE: 26

Met Gly Ser Trp Asn Tyr Phe Lys Asp His Leu Ala Trp Ile Lys Asn
 1               5                  10                  15

Ser Leu Glu Ala Leu Gly Gly Ser Glu Ala Glu Leu Ala His Phe Glu
             20                  25                  30

Thr Ala Ile Ala Ser Phe Glu Arg Gln Leu Gln Glu Tyr Lys Gly Lys
         35                  40                  45

Gly Asn Pro Glu Val Glu Ala Leu Arg Lys Glu Ala Ala Ala Ile Arg
     50                  55                  60

Asp Glu Leu Gln Ala Tyr Arg His Asn
 65                  70

<210> SEQ ID NO 27
<211> LENGTH: 73
<212> TYPE: PRT
<213> ORGANISM: Homo sapiens

<400> SEQUENCE: 27

Met Gly Ser Trp Leu Tyr Phe Lys Glu His Leu Ala His Ile Lys Ala
 1               5                  10                  15

Trp Leu Glu Ala Leu Gly Gly Ser Glu Ala Glu Leu Ala His Phe Glu
             20                  25                  30

Leu Ala Ile Ala Asp Phe Glu Tyr His Leu Gln Glu Tyr Lys Gly Lys
         35                  40                  45

Gly Asn Pro Glu Val Glu Ala Leu Arg Lys Glu Ala Ala Ala Ile Arg
     50                  55                  60

Asp Glu Leu Gln Ala Tyr Arg His Asn
 65                  70

<210> SEQ ID NO 28
<211> LENGTH: 73
<212> TYPE: PRT
<213> ORGANISM: Homo sapiens
```

```
<400> SEQUENCE: 28

Met Gly Ser Trp Val Tyr Phe Lys Glu His Leu Ala Trp Ile Lys Thr
1               5                   10                  15

Glu Leu Glu Ala Leu Gly Gly Ser Glu Ala Glu Leu Ala His Phe Glu
            20                  25                  30

His Ser Ile Ala Asp Phe Glu Met Ser Leu Gln Phe Tyr Lys Gly Lys
        35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 29
<211> LENGTH: 73
<212> TYPE: PRT
<213> ORGANISM: Homo sapiens

<400> SEQUENCE: 29

Met Gly Ser Trp Phe Tyr Phe Lys Gln His Leu Ala Trp Ile Lys Ser
1               5                   10                  15

Tyr Leu Glu Ala Leu Gly Gly Ser Glu Ala Glu Leu Ala His Phe Glu
            20                  25                  30

Arg Ala Ile Ala Ala Phe Glu Gln His Leu Gln Met Tyr Lys Gly Lys
        35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 30
<211> LENGTH: 73
<212> TYPE: PRT
<213> ORGANISM: Homo sapiens

<400> SEQUENCE: 30

Met Gly Ser Trp His Tyr Phe Lys Asp His Leu Ala Glu Ile Lys Gly
1               5                   10                  15

Leu Leu Glu Ala Leu Gly Gly Ser Glu Ala Glu Leu Ala His Phe Glu
            20                  25                  30

Met Ala Ile Ala Asp Phe Glu His Asn Leu Gln Tyr Tyr Lys Gly Lys
        35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 31
<211> LENGTH: 73
<212> TYPE: PRT
<213> ORGANISM: Homo sapiens

<400> SEQUENCE: 31

Met Gly Ser Trp His Tyr Phe Lys Gly His Leu Ala Glu Ile Lys Asn
1               5                   10                  15

His Leu Glu Ala Leu Gly Gly Ser Glu Ala Glu Leu Ala His Phe Glu
            20                  25                  30

Arg Ala Ile Ala Ala Phe Glu Arg Ser Leu Gln Trp Tyr Lys Gly Lys
        35                  40                  45
```

```
Gly Asn Pro Glu Val Glu Ala Leu Arg Lys Glu Ala Ala Ile Arg
        50                  55                  60

Asp Glu Leu Gln Ala Tyr Arg His Asn
 65                  70
```

<210> SEQ ID NO 32
<211> LENGTH: 73
<212> TYPE: PRT
<213> ORGANISM: Homo sapiens

<400> SEQUENCE: 32

```
Met Gly Ser Trp Ile Tyr Phe Lys Glu His Leu Ala Tyr Ile Lys Lys
 1               5                  10                  15

Glu Leu Glu Ala Leu Gly Gly Ser Glu Ala Glu Leu Ala His Phe Glu
                20                  25                  30

Ser Ala Ile Ala Val Phe Glu Ser Thr Leu Gln Tyr Tyr Lys Gly Lys
            35                  40                  45

Gly Asn Pro Glu Val Glu Ala Leu Arg Lys Glu Ala Ala Ile Arg
        50                  55                  60

Asp Glu Leu Gln Ala Tyr Arg His Asn
 65                  70
```

<210> SEQ ID NO 33
<211> LENGTH: 73
<212> TYPE: PRT
<213> ORGANISM: Homo sapiens

<400> SEQUENCE: 33

```
Met Gly Ser Trp Thr Tyr Phe Lys Glu His Leu Ala Glu Ile Lys Tyr
 1               5                  10                  15

Met Leu Glu Ala Leu Gly Gly Ser Glu Ala Glu Leu Ala His Phe Glu
                20                  25                  30

Val Ala Ile Ala Asp Phe Glu Lys Met Leu Gln Tyr Tyr Lys Gly Lys
            35                  40                  45

Gly Asn Pro Glu Val Glu Ala Leu Arg Lys Glu Ala Ala Ile Arg
        50                  55                  60

Asp Glu Leu Gln Ala Tyr Arg His Asn
 65                  70
```

<210> SEQ ID NO 34
<211> LENGTH: 73
<212> TYPE: PRT
<213> ORGANISM: Homo sapiens

<400> SEQUENCE: 34

```
Met Gly Ser Trp Trp Leu Phe Lys Asp His Leu Ala Glu Ile Lys Thr
 1               5                  10                  15

Ala Leu Glu Ala Leu Gly Gly Ser Glu Ala Glu Leu Ala His Phe Glu
                20                  25                  30

Met Ala Ile Ala Ala Phe Glu Lys Gln Leu Gln Tyr Tyr Lys Gly Lys
            35                  40                  45

Gly Asn Pro Glu Val Glu Ala Leu Arg Lys Glu Ala Ala Ile Arg
        50                  55                  60

Asp Glu Leu Gln Ala Tyr Arg His Asn
 65                  70
```

<210> SEQ ID NO 35
<211> LENGTH: 73

```
<212> TYPE: PRT
<213> ORGANISM: Homo sapiens

<400> SEQUENCE: 35

Met Gly Ser Trp Ser Glu Phe Tyr Asn Arg Leu Asp Ala Ile Glu Ser
1               5                   10                  15

Arg Leu Leu Ala Leu Gly Gly Ser Glu Ala Glu Leu Ala Leu Phe Glu
                20                  25                  30

Ile Gln Ile Ala Arg Phe Glu Lys Val Leu Gln Ala Tyr Lys Gly Lys
            35                  40                  45

Gly Asn Pro Glu Val Glu Ala Leu Arg Gly Glu Ala Arg Ala Ile Phe
        50                  55                  60

Ala Glu Leu Tyr Ala Tyr Arg His Asn
65                  70

<210> SEQ ID NO 36
<211> LENGTH: 73
<212> TYPE: PRT
<213> ORGANISM: Homo sapiens

<400> SEQUENCE: 36

Met Gly Ser Trp Tyr Glu Phe Tyr Asn Arg Leu Tyr Ala Ile Glu Ile
1               5                   10                  15

Arg Leu Tyr Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Arg Leu Arg Val Arg Ala Ala Lys Ile Arg
        50                  55                  60

Val Ile Leu Gln Ala Tyr Arg His Asn
65                  70

<210> SEQ ID NO 37
<211> LENGTH: 73
<212> TYPE: PRT
<213> ORGANISM: Homo sapiens

<400> SEQUENCE: 37

Met Gly Ser Trp Leu Trp Phe Lys Ile Phe Leu Ala Glu Ile Lys Tyr
1               5                   10                  15

Phe Leu Glu Ala Leu Gly Gly Ser Glu Ala Glu Leu Ala Ala Phe Asp
                20                  25                  30

Phe Glu Ile His Ala Phe His Val Glu Leu Phe Ala Tyr Lys Gly Lys
            35                  40                  45

Gly Asn Pro Glu Val Glu Val Leu Arg Glu Val Ala Ala Glu Ile Arg
        50                  55                  60

Trp Asp Leu Gln Ala Tyr Arg His Asn
65                  70

<210> SEQ ID NO 38
<211> LENGTH: 73
<212> TYPE: PRT
<213> ORGANISM: Homo sapiens

<400> SEQUENCE: 38

Met Gly Ser Trp Thr Glu Phe Gln Ser Arg Leu Asp Ala Ile His Ser
1               5                   10                  15

Arg Leu Arg Ala Leu Gly Gly Ser Glu Ala Glu Leu Ala Ala Phe Glu
                20                  25                  30
```

```
Lys Glu Ile Ala Ala Phe Glu Ser Glu Leu Gln Ala Tyr Lys Gly Lys
            35                  40                  45

Gly Asn Pro Glu Val Glu Leu Leu Arg Asp Asp Ala Ala Phe Ile Arg
        50                  55                  60

His Phe Leu Gln Ala Tyr Arg His Asn
65                  70

<210> SEQ ID NO 39
<211> LENGTH: 73
<212> TYPE: PRT
<213> ORGANISM: Homo sapiens

<400> SEQUENCE: 39

Met Gly Ser Trp Gln Glu Phe Asp Asp Arg Leu Asn Ala Ile Lys Ala
1               5                   10                  15

Arg Leu Gln Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Asp Leu Arg Asp Asp Ala Ala Phe Ile Arg
        50                  55                  60

Arg Phe Leu Gln Ala Tyr Arg His Asn
65                  70

<210> SEQ ID NO 40
<211> LENGTH: 73
<212> TYPE: PRT
<213> ORGANISM: Homo sapiens

<400> SEQUENCE: 40

Met Gly Ser Trp Tyr Glu Phe Gln Asn Arg Leu His Ala Ile His Glu
1               5                   10                  15

Arg Leu Asn Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Leu Leu Arg Asp Asp Ala Ala Phe Ile Arg
        50                  55                  60

His Phe Leu Gln Ala Tyr Arg His Asn
65                  70

<210> SEQ ID NO 41
<211> LENGTH: 73
<212> TYPE: PRT
<213> ORGANISM: Homo sapiens

<400> SEQUENCE: 41

Met Gly Ser Trp Phe Glu Phe Gln Asp Arg Leu Thr Ala Ile Asn Glu
1               5                   10                  15

Arg Leu Ser Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Thr Leu Arg Ser Asp Ala Ala Phe Ile Arg
        50                  55                  60

Arg Phe Leu Gln Ala Tyr Arg His Asn
65                  70
```

<210> SEQ ID NO 42
<211> LENGTH: 73
<212> TYPE: PRT
<213> ORGANISM: Homo sapiens

<400> SEQUENCE: 42

Met Gly Ser Trp Tyr Glu Phe Glu Ser Arg Leu Asp Ala Ile His Glu
1               5                   10                  15

Arg Leu His Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asn Leu Arg Gly Asp Ala Ala Phe Ile Arg
    50                  55                  60

His Phe Leu Gln Ala Tyr Arg His Asn
65                  70

<210> SEQ ID NO 43
<211> LENGTH: 73
<212> TYPE: PRT
<213> ORGANISM: Homo sapiens

<400> SEQUENCE: 43

Met Gly Ser Trp Tyr Glu Phe Asn His Arg Leu Asp Ala Ile Ser Lys
1               5                   10                  15

Arg Leu Asn Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Glu Leu Arg Gly Asp Ala Ala Phe Ile Arg
    50                  55                  60

His Phe Leu Gln Ala Tyr Arg His Asn
65                  70

<210> SEQ ID NO 44
<211> LENGTH: 73
<212> TYPE: PRT
<213> ORGANISM: Homo sapiens

<400> SEQUENCE: 44

Met Gly Ser Trp Phe Glu Phe Asn Arg Leu His Ala Ile Val His
1               5                   10                  15

Arg Leu Gly Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Thr Leu Arg Ala Asp Ala Ala Phe Ile Arg
    50                  55                  60

His Tyr Leu Gln Ala Tyr Arg His Asn
65                  70

<210> SEQ ID NO 45
<211> LENGTH: 73
<212> TYPE: PRT
<213> ORGANISM: Homo sapiens

<400> SEQUENCE: 45

Met Gly Ser Trp Val Val Phe Lys Val Asp Leu Ala Thr Ile Lys Tyr
1               5                   10                  15

Ile Leu Glu Ala Leu Gly Gly Ser Glu Ala Glu Leu Ala Glu Phe Glu
            20                  25                  30

Gly Glu Ile Ala Gly Phe Glu Tyr Ser Leu Gln Phe Tyr Lys Gly Lys
            35                  40                  45

Gly Asn Pro Glu Val Glu Ala Leu Arg Lys Glu Ala Ala Ala Ile Arg
        50                  55                  60

Asp Glu Leu Gln Ala Tyr Arg His Asn
65                  70

<210> SEQ ID NO 46
<211> LENGTH: 73
<212> TYPE: PRT
<213> ORGANISM: Homo sapiens

<400> SEQUENCE: 46

Met Gly Ser Trp Thr Ile Phe Lys Glu Trp Leu Ala Phe Ile Lys Thr
1               5                   10                  15

Asp Leu Glu Ala Leu Gly Gly Ser Glu Ala Glu Leu Ala Phe Phe Glu
            20                  25                  30

Gly Trp Ile Ala Ser Phe Glu Met Glu Leu Gln Lys Tyr Lys Gly Lys
            35                  40                  45

Gly Asn Pro Glu Val Glu Ala Leu Arg Lys Glu Ala Ala Ala Ile Arg
        50                  55                  60

Asp Glu Leu Gln Ala Tyr Arg His Asn
65                  70

<210> SEQ ID NO 47
<211> LENGTH: 73
<212> TYPE: PRT
<213> ORGANISM: Homo sapiens

<400> SEQUENCE: 47

Met Gly Ser Trp Val Met Phe Lys Trp Leu Leu Ala Asp Ile Lys Ser
1               5                   10                  15

His Leu Glu Ala Leu Gly Gly Ser Glu Ala Glu Leu Ala Phe Phe Glu
            20                  25                  30

Gly Phe Ile Ala Ala Phe Glu Thr His Leu Gln Val Tyr Lys Gly Lys
            35                  40                  45

Gly Asn Pro Glu Val Glu Ala Leu Arg Lys Glu Ala Ala Ala Ile Arg
        50                  55                  60

Asp Glu Leu Gln Ala Tyr Arg His Asn
65                  70

<210> SEQ ID NO 48
<211> LENGTH: 73
<212> TYPE: PRT
<213> ORGANISM: Homo sapiens

<400> SEQUENCE: 48

Met Gly Ser Trp Tyr Ala Phe Lys Asp Tyr Leu Ala Asp Ile Lys Gly
1               5                   10                  15

Trp Leu Glu Ala Leu Gly Gly Ser Glu Ala Glu Leu Ala Phe Phe Glu
            20                  25                  30

Ile Phe Ile Ala Arg Phe Glu Leu Glu Leu Gln Ala Tyr Lys Gly Lys
            35                  40                  45

Gly Asn Pro Glu Val Glu Ala Leu Arg Lys Glu Ala Ala Ala Ile Arg
        50                  55                  60

Asp Glu Leu Gln Ala Tyr Arg His Asn
65                  70

<210> SEQ ID NO 49
<211> LENGTH: 73
<212> TYPE: PRT
<213> ORGANISM: Homo sapiens

<400> SEQUENCE: 49

Met Gly Ser Trp Ala Glu Phe Lys Gln Arg Leu Ala Ala Ile Lys Thr
1               5                   10                  15

Arg Leu Gln Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 50
<211> LENGTH: 9
<212> TYPE: PRT
<213> ORGANISM: Homo sapiens

<400> SEQUENCE: 50

Leu Ala Ala Ile Lys Thr Arg Leu Gln
1               5

<210> SEQ ID NO 51
<211> LENGTH: 84
<212> TYPE: PRT
<213> ORGANISM: Homo sapiens

<400> SEQUENCE: 51

Met Gly Ser Trp Val Glu Phe Gly His Arg Leu Trp Ala Ile Asp Gln
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Lys Leu Arg Gln Arg Ala Ala Phe Ile Arg
    50                  55                  60

Phe Arg Leu Gln Ala Tyr Arg His Asn Gly Gly Gly Ser His His
65                  70                  75                  80

His His His His

<210> SEQ ID NO 52
<211> LENGTH: 84
<212> TYPE: PRT
<213> ORGANISM: Homo sapiens

<400> SEQUENCE: 52

Met Gly Ser Trp Val Glu Phe Ala Asn Arg Leu Trp Ala Ile Asp Gln
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

-continued

Gly Asn Pro Glu Val Glu His Leu Arg Asp Gln Ala Ala Phe Ile Arg
            50                  55                  60

His Lys Leu Gln Ala Tyr Arg His Asn Gly Gly Gly Ser His His
 65                  70                  75                  80

His His His His

<210> SEQ ID NO 53
<211> LENGTH: 84
<212> TYPE: PRT
<213> ORGANISM: Homo sapiens

<400> SEQUENCE: 53

Met Gly Ser Trp Tyr Glu Phe Arg His Arg Leu Trp Ala Ile Asp Gln
 1               5                  10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Gly Leu Arg Glu Ala Ala Ala Phe Ile Arg
            50                  55                  60

Ala Lys Leu Gln Ala Tyr Arg His Asn Gly Gly Gly Ser His His
 65                  70                  75                  80

His His His His

<210> SEQ ID NO 54
<211> LENGTH: 84
<212> TYPE: PRT
<213> ORGANISM: Homo sapiens

<400> SEQUENCE: 54

Met Gly Ser Trp Tyr Glu Phe Ser Met Arg Leu Trp Ala Ile Asp Gln
 1               5                  10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Ala Lys Ala Ala Tyr Ile Arg
            50                  55                  60

Trp Lys Leu Gln Ala Tyr Arg His Asn Gly Gly Gly Ser His His
 65                  70                  75                  80

His His His His

<210> SEQ ID NO 55
<211> LENGTH: 84
<212> TYPE: PRT
<213> ORGANISM: Homo sapiens

<400> SEQUENCE: 55

Met Gly Ser Trp Phe Glu Phe Asn His Arg Leu Trp Ala Ile Asn Glu
 1               5                  10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Arg Leu Arg Ser Met Ala Ala Phe Ile Arg
            50                  55                  60

Tyr Lys Leu Gln Ala Tyr Arg His Asn Gly Gly Gly Ser His His 65 70 75 80

His His His His

<210> SEQ ID NO 56
<211> LENGTH: 84
<212> TYPE: PRT
<213> ORGANISM: Homo sapiens

<400> SEQUENCE: 56

Met Gly Ser Trp Tyr Glu Phe Gly His Arg Leu Trp Ala Ile Asp Gln
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg Glu Thr Ala Ala His Ile Arg
    50                  55                  60

Thr Arg Leu Gln Ala Tyr Arg His Asn Gly Gly Gly Ser His His
65                  70                  75                  80

His His His His

<210> SEQ ID NO 57
<211> LENGTH: 84
<212> TYPE: PRT
<213> ORGANISM: Homo sapiens

<400> SEQUENCE: 57

Met Gly Ser Trp Tyr Glu Phe His Tyr Arg Leu His Ala Ile Asp Gln
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Glu Leu Arg Ile Lys Ala Ala Phe Ile Arg
    50                  55                  60

Asp Arg Leu Gln Ala Tyr Arg His Asn Gly Gly Gly Ser His His
65                  70                  75                  80

His His His His

<210> SEQ ID NO 58
<211> LENGTH: 84
<212> TYPE: PRT
<213> ORGANISM: Homo sapiens

<400> SEQUENCE: 58

Met Gly Ser Trp Ala Glu Phe Lys Gln Arg Leu Ala Ala Ile Lys Thr
1               5                   10                  15

Arg Leu Glu Ala Leu Gly Gly Ser Glu Ala Glu Leu Ala Ala Phe Leu
            20                  25                  30

Gly Glu Ile Trp Ala Phe Glu Met Glu Leu Ala Ala Tyr Lys Gly Lys
        35                  40                  45

Gly Asn Pro Glu Val Glu Ala Leu Gly Arg Glu Ala Ala Ala Ile Arg
    50                  55                  60

Met Glu Leu Gln Ala Tyr Arg His Asn Gly Gly Gly Ser His His
65                  70                  75                  80

His His His His

<210> SEQ ID NO 59
<211> LENGTH: 406
<212> TYPE: PRT
<213> ORGANISM: Homo sapiens

<400> SEQUENCE: 59

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln Asp Ile Glu Gly Arg Met Asp Lys Ser Cys Asp Lys Thr
                165                 170                 175

His Thr Cys Pro Pro Cys Pro Ala Pro Glu Leu Leu Gly Gly Pro Ser
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
        275                 280                 285

Ile Ser Lys Ala Lys Gly Gln Pro Arg Glu Pro Gln Val Tyr Thr Leu
290                 295                 300

Pro Pro Ser Arg Asp Glu Leu Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
370                 375                 380
```

Leu His Asn His Tyr Thr Gln Lys Ser Leu Ser Leu Ser Pro Gly Lys
385                 390                 395                 400

His His His His His His
            405

<210> SEQ ID NO 60
<211> LENGTH: 73
<212> TYPE: PRT
<213> ORGANISM: Homo sapiens

<400> SEQUENCE: 60

Met Gly Ser Trp Ile Glu Phe Glu Asp Arg Leu Asp Ala Ile Thr Asp
1               5                   10                  15

Arg Leu Trp Ala Leu Gly Gly Ser Glu Ala Glu Leu Ala Glu Phe Glu
            20                  25                  30

His Gln Ile Ala Phe Phe Glu Glu Asp Leu Gln Trp Tyr Lys Gly Lys
        35                  40                  45

Gly Asn Pro Glu Val Glu Ala Leu His Met Glu Ala Glu Ala Ile Met
    50                  55                  60

Glu Glu Leu Gly Ala Tyr Arg His Asn
65                  70

<210> SEQ ID NO 61
<211> LENGTH: 73
<212> TYPE: PRT
<213> ORGANISM: Homo sapiens

<400> SEQUENCE: 61

Met Gly Ser Trp Val Glu Phe Glu Tyr Arg Leu Asp Ala Ile Ser Asp
1               5                   10                  15

Arg Leu Trp Ala Leu Gly Gly Ser Glu Ala Glu Leu Ala Phe Phe Glu
            20                  25                  30

Asn Glu Ile Ala Ser Phe Glu Ser Asp Leu Gln Phe Tyr Lys Gly Lys
        35                  40                  45

Gly Asn Pro Glu Val Glu Ala Leu Met Phe Glu Ala Glu Ala Ile Asp
    50                  55                  60

Asp Glu Leu His Ala Tyr Arg His Asn
65                  70

<210> SEQ ID NO 62
<211> LENGTH: 73
<212> TYPE: PRT
<213> ORGANISM: Homo sapiens

<400> SEQUENCE: 62

Met Gly Ser Trp Tyr Glu Phe Glu Asp Arg Leu Ala Ala Ile Glu Ala
1               5                   10                  15

Arg Leu Trp Ala Leu Gly Gly Ser Glu Ala Glu Leu Ala Asp Phe Glu
            20                  25                  30

Glu Glu Ile Ala Tyr Phe Glu His Gly Leu Gln Trp Tyr Lys Gly Lys
        35                  40                  45

Gly Asn Pro Glu Val Glu Ala Leu Glu Ser Gly Ala Met Ala Ile Ile
    50                  55                  60

Asp Glu Leu His Ala Tyr Arg His Asn
65                  70

<210> SEQ ID NO 63
<211> LENGTH: 73

<212> TYPE: PRT
<213> ORGANISM: Homo sapiens

<400> SEQUENCE: 63

Met Gly Ser Trp Tyr Glu Phe Glu Glu Arg Leu Asp Ala Ile Glu Asp
1               5                   10                  15

Arg Leu Ile Ala Leu Gly Gly Ser Glu Ala Glu Leu Ala Ile Phe Glu
            20                  25                  30

Asp Ile Ile Ala Phe Phe Glu Gln Asp Leu Gln Tyr Tyr Lys Gly Lys
        35                  40                  45

Gly Asn Pro Glu Val Glu Ala Leu Glu Met Glu Ala Glu Ala Ile Ser
    50                  55                  60

Ile Glu Leu Asp Ala Tyr Arg His Asn
65                  70

<210> SEQ ID NO 64
<211> LENGTH: 73
<212> TYPE: PRT
<213> ORGANISM: Homo sapiens

<400> SEQUENCE: 64

Met Gly Ser Trp Trp Glu Phe Glu Asp Arg Leu Trp Ala Ile Asp Arg
1               5                   10                  15

Arg Leu Met Ala Leu Gly Gly Ser Glu Ala Glu Leu Ala Val Phe Glu
            20                  25                  30

Gln Met Ile Ala His Phe Glu Gln Ile Leu Gln Val Tyr Lys Gly Lys
        35                  40                  45

Gly Asn Pro Glu Val Glu Ala Leu His Phe Glu Ala His Ala Ile Gly
    50                  55                  60

Met Glu Leu Ala Ala Tyr Arg His Asn
65                  70

<210> SEQ ID NO 65
<211> LENGTH: 73
<212> TYPE: PRT
<213> ORGANISM: Homo sapiens

<400> SEQUENCE: 65

Met Gly Ser Trp Glu Glu Phe His Glu Arg Leu Asp Ala Ile Asp Glu
1               5                   10                  15

Arg Leu Glu Ala Leu Gly Gly Ser Glu Ala Glu Leu Ala Phe Phe Glu
            20                  25                  30

Asp Asp Ile Ala Ser Phe Glu Asp Trp Leu Gln Trp Tyr Lys Gly Lys
        35                  40                  45

Gly Asn Pro Glu Val Glu Ala Leu Ser Arg Glu Ala Asp Ala Ile Asn
    50                  55                  60

Phe Glu Leu Glu Ala Tyr Arg His Asn
65                  70

<210> SEQ ID NO 66
<211> LENGTH: 73
<212> TYPE: PRT
<213> ORGANISM: Homo sapiens

<400> SEQUENCE: 66

Met Gly Ser Trp Glu Glu Phe Asp Lys Arg Leu Asp Ala Ile Thr Arg
1               5                   10                  15

Arg Leu Met Ala Leu Gly Gly Ser Glu Ala Glu Leu Ala Glu Phe Glu
            20                  25                  30

Ser Thr Ile Ala Trp Phe Glu Trp Asp Leu Gln Glu Tyr Lys Gly Lys
        35                  40                  45

Gly Asn Pro Glu Val Glu Ala Leu Asp Trp Glu Ala Tyr Ala Ile Asp
    50                  55                  60

Tyr Glu Leu Gly Ala Tyr Arg His Asn
65                  70

<210> SEQ ID NO 67
<211> LENGTH: 73
<212> TYPE: PRT
<213> ORGANISM: Homo sapiens

<400> SEQUENCE: 67

Met Gly Ser Trp Ser Glu Phe Val Asp Arg Leu Asp Ala Ile Phe Asp
1               5                   10                  15

Arg Leu Trp Ala Leu Gly Gly Ser Glu Ala Glu Leu Ala Trp Phe Glu
                20                  25                  30

Asp Thr Ile Ala His Phe Glu Trp Asn Leu Gln Glu Tyr Lys Gly Lys
        35                  40                  45

Gly Asn Pro Glu Val Glu Ala Leu Asn Gly Glu Ala Asp Ala Ile Thr
    50                  55                  60

Asp Glu Leu His Ala Tyr Arg His Asn
65                  70

<210> SEQ ID NO 68
<211> LENGTH: 73
<212> TYPE: PRT
<213> ORGANISM: Homo sapiens

<400> SEQUENCE: 68

Met Gly Ser Trp Trp Glu Phe Thr Asp Arg Leu Asp Ala Ile Phe Asp
1               5                   10                  15

Arg Leu Trp Ala Leu Gly Gly Ser Glu Ala Glu Leu Ala Ala Phe Glu
                20                  25                  30

Glu Ser Ile Ala Ile Phe Glu Gln Asp Leu Gln Tyr Tyr Lys Gly Lys
        35                  40                  45

Gly Asn Pro Glu Val Glu Ala Leu Glu Glu Ala Asn Ala Ile Gln
    50                  55                  60

Tyr Glu Leu Glu Ala Tyr Arg His Asn
65                  70

<210> SEQ ID NO 69
<211> LENGTH: 73
<212> TYPE: PRT
<213> ORGANISM: Homo sapiens

<400> SEQUENCE: 69

Met Gly Ser Trp Trp Glu Phe Thr Asp Arg Leu Glu Ala Ile Glu Asp
1               5                   10                  15

Arg Leu Trp Ala Leu Gly Gly Ser Glu Ala Glu Leu Ala His Phe Glu
                20                  25                  30

Asp Ser Ile Ala Gln Phe Glu Gln Glu Leu Gln Trp Tyr Lys Gly Lys
        35                  40                  45

Gly Asn Pro Glu Val Glu Ala Leu Ala Asp Glu Ala Asp Ala Ile Glu
    50                  55                  60

Ser Glu Leu His Ala Tyr Arg His Asn
65                  70

<210> SEQ ID NO 70
<211> LENGTH: 73
<212> TYPE: PRT
<213> ORGANISM: Homo sapiens

<400> SEQUENCE: 70

Met Gly Ser Trp Glu Trp Phe Lys Ser Asp Leu Ala Ser Ile Lys Trp
1               5                   10                  15

Glu Leu Glu Ala Leu Gly Gly Ser Glu Ala Glu Leu Ala Trp Phe Glu
            20                  25                  30

His Asp Ile Ala Glu Phe Glu Glu Asp Leu Gln Trp Tyr Lys Gly Lys
        35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 71
<211> LENGTH: 73
<212> TYPE: PRT
<213> ORGANISM: Homo sapiens

<400> SEQUENCE: 71

Met Gly Ser Trp Asp His Phe Lys Asn Asp Leu Ala Trp Ile Lys Lys
1               5                   10                  15

His Leu Glu Ala Leu Gly Gly Ser Glu Ala Glu Leu Ala Glu Phe Glu
            20                  25                  30

Ala Val Ile Ala Tyr Phe Glu Leu Tyr Leu Gln Gly Tyr Lys Gly Lys
        35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 72
<211> LENGTH: 73
<212> TYPE: PRT
<213> ORGANISM: Homo sapiens

<400> SEQUENCE: 72

Met Gly Ser Trp Glu Phe Phe Lys Glu Val Leu Ala Glu Ile Lys Tyr
1               5                   10                  15

Asp Leu Glu Ala Leu Gly Gly Ser Glu Ala Glu Leu Ala Trp Phe Glu
            20                  25                  30

Thr Asp Ile Ala Gly Phe Glu Ile Asp Leu Gln Val Tyr Lys Gly Lys
        35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 73
<211> LENGTH: 73
<212> TYPE: PRT
<213> ORGANISM: Homo sapiens

<400> SEQUENCE: 73

Met Gly Ser Trp Tyr Asp Phe Lys Glu Asp Leu Ala Asp Ile Lys Trp
1               5                   10                  15

Met Leu Glu Ala Leu Gly Gly Ser Glu Ala Glu Leu Ala Glu Phe Glu
            20                  25                  30

Asn Val Ile Ala Tyr Phe Glu Asn Asp Leu Gln Glu Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 74
<211> LENGTH: 73
<212> TYPE: PRT
<213> ORGANISM: Homo sapiens

<400> SEQUENCE: 74

Met Gly Ser Trp Ser Phe Phe Lys Asp Asp Leu Ala Glu Ile Lys Tyr
1               5                   10                  15

Phe Leu Glu Ala Leu Gly Gly Ser Glu Ala Glu Leu Ala Met Phe Glu
            20                  25                  30

Gln Thr Ile Ala Glu Phe Glu Tyr Asp Leu Gln Asp Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 75
<211> LENGTH: 73
<212> TYPE: PRT
<213> ORGANISM: Homo sapiens

<400> SEQUENCE: 75

Met Gly Ser Trp Val Thr Phe Lys Asp Glu Leu Ala Asp Ile Lys Asp
1               5                   10                  15

Phe Leu Glu Ala Leu Gly Gly Ser Glu Ala Glu Leu Ala Phe Phe Glu
            20                  25                  30

Val Asp Ile Ala Glu Phe Glu Ala Glu Leu Gln Phe Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 76
<211> LENGTH: 73
<212> TYPE: PRT
<213> ORGANISM: Homo sapiens

<400> SEQUENCE: 76

Met Gly Ser Trp Ser Trp Phe Lys Glu Asp Leu Ala Asp Ile Lys Phe
1               5                   10                  15

Glu Leu Glu Ala Leu Gly Gly Ser Glu Ala Glu Leu Ala Trp Phe Glu
            20                  25                  30

Leu Asp Ile Ala Asp Phe Glu Gln Ala Leu Gln Gln Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 77
<211> LENGTH: 73
<212> TYPE: PRT
<213> ORGANISM: Homo sapiens

<400> SEQUENCE: 77

Met Gly Ser Trp Trp Glu Phe Lys Glu Asp Leu Ala Glu Ile Lys Trp
1               5                   10                  15

Phe Leu Glu Ala Leu Gly Gly Ser Glu Ala Glu Leu Ala Trp Phe Glu
                20                  25                  30

His Asp Ile Ala Lys Phe Glu Phe Glu Leu Gln Tyr Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 78
<211> LENGTH: 73
<212> TYPE: PRT
<213> ORGANISM: Homo sapiens

<400> SEQUENCE: 78

Met Gly Ser Trp Asp Glu Phe Lys Glu Asp Leu Ala His Ile Lys Thr
1               5                   10                  15

Asp Leu Glu Ala Leu Gly Gly Ser Glu Ala Glu Leu Ala Leu Phe Glu
                20                  25                  30

Asp Glu Ile Ala Asp Phe Glu Met Tyr Leu Gln His Tyr Lys Gly Lys
            35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 79
<211> LENGTH: 73
<212> TYPE: PRT
<213> ORGANISM: Homo sapiens

<400> SEQUENCE: 79

Met Gly Ser Trp Phe Met Phe Lys Glu Glu Leu Ala Asp Ile Lys Asp
1               5                   10                  15

Trp Leu Glu Ala Leu Gly Gly Ser Glu Ala Glu Leu Ala Ser Phe Glu
                20                  25                  30

Ser Tyr Ile Ala Trp Phe Glu Gln Asp Leu Gln Trp Tyr Lys Gly Lys
            35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 80
<211> LENGTH: 73
<212> TYPE: PRT
<213> ORGANISM: Homo sapiens

<400> SEQUENCE: 80

Met Gly Ser Trp Gln Ile Phe Lys Gly Glu Leu Ala Tyr Ile Lys Gln
1               5                   10                  15

Tyr Leu Glu Ala Leu Gly Gly Ser Glu Ala Leu Ala Phe Phe Glu
                20                  25                  30

Phe Asp Ile Ala Glu Phe Glu Asp Leu Gln Tyr Tyr Lys Gly Lys
            35                  40                  45

Gly Asn Pro Glu Val Glu Ala Leu Arg Lys Glu Ala Ala Ile Arg
        50                  55                  60

Asp Glu Leu Gln Ala Tyr Arg His Asn
65                  70

<210> SEQ ID NO 81
<211> LENGTH: 73
<212> TYPE: PRT
<213> ORGANISM: Homo sapiens

<400> SEQUENCE: 81

Met Gly Ser Trp Tyr Ile Phe Lys Glu Asp Leu Ala Glu Ile Lys Glu
1               5                   10                  15

Glu Leu Glu Ala Leu Gly Gly Ser Glu Ala Glu Leu Ala Tyr Phe Glu
                20                  25                  30

Glu Glu Ile Ala Leu Phe Glu Met Glu Leu Gln Trp Tyr Lys Gly Lys
            35                  40                  45

Gly Asn Pro Glu Val Glu Ala Leu Arg Lys Glu Ala Ala Ile Arg
        50                  55                  60

Asp Glu Leu Gln Ala Tyr Arg His Asn
65                  70

<210> SEQ ID NO 82
<211> LENGTH: 73
<212> TYPE: PRT
<213> ORGANISM: Homo sapiens

<400> SEQUENCE: 82

Met Gly Ser Trp Tyr Tyr Phe Lys Asp Glu Leu Ala Asp Ile Lys Trp
1               5                   10                  15

Asp Leu Glu Ala Leu Gly Gly Ser Glu Ala Glu Leu Ala Trp Phe Glu
                20                  25                  30

Met Leu Ile Ala Gln Phe Glu Leu Asp Leu Gln Trp Tyr Lys Gly Lys
            35                  40                  45

Gly Asn Pro Glu Val Glu Ala Leu Arg Lys Glu Ala Ala Ile Arg
        50                  55                  60

Asp Glu Leu Gln Ala Tyr Arg His Asn
65                  70

<210> SEQ ID NO 83
<211> LENGTH: 73
<212> TYPE: PRT
<213> ORGANISM: Homo sapiens

<400> SEQUENCE: 83

Met Gly Ser Trp Phe Asn Phe Lys Glu Glu Leu Ala Val Ile Lys Phe
1               5                   10                  15

Gln Leu Glu Ala Leu Gly Gly Ser Glu Ala Glu Leu Ala Phe Phe Glu
                20                  25                  30

Trp Val Ile Ala Asp Phe Glu Asp Asp Leu Gln Glu Tyr Lys Gly Lys
            35                  40                  45

Gly Asn Pro Glu Val Glu Ala Leu Arg Lys Glu Ala Ala Ile Arg
                50                  55                  60

Asp Glu Leu Gln Ala Tyr Arg His Asn
 65                  70

<210> SEQ ID NO 84
<211> LENGTH: 73
<212> TYPE: PRT
<213> ORGANISM: Homo sapiens

<400> SEQUENCE: 84

Met Gly Ser Trp Tyr Met Phe Lys Glu Glu Leu Ala Asp Ile Lys Trp
 1               5                  10                  15

Tyr Leu Glu Ala Leu Gly Gly Ser Glu Ala Glu Leu Ala Trp Phe Glu
                20                  25                  30

Asp Asp Ile Ala Gly Phe Glu Trp Asp Leu Gln Ala Tyr Lys Gly Lys
                35                  40                  45

Gly Asn Pro Glu Val Glu Ala Leu Arg Lys Glu Ala Ala Ile Arg
                50                  55                  60

Asp Glu Leu Gln Ala Tyr Arg His Asn
 65                  70

<210> SEQ ID NO 85
<211> LENGTH: 73
<212> TYPE: PRT
<213> ORGANISM: Homo sapiens

<400> SEQUENCE: 85

Met Gly Ser Trp His Val Phe Lys Thr Glu Leu Ala Asp Ile Lys Phe
 1               5                  10                  15

Tyr Leu Glu Ala Leu Gly Gly Ser Glu Ala Glu Leu Ala Met Phe Glu
                20                  25                  30

Leu Trp Ile Ala Glu Phe Glu His Gly Leu Gln Asp Tyr Lys Gly Lys
                35                  40                  45

Gly Asn Pro Glu Val Glu Ala Leu Arg Lys Glu Ala Ala Ile Arg
                50                  55                  60

Asp Glu Leu Gln Ala Tyr Arg His Asn
 65                  70

<210> SEQ ID NO 86
<211> LENGTH: 73
<212> TYPE: PRT
<213> ORGANISM: Homo sapiens

<400> SEQUENCE: 86

Met Gly Ser Trp Tyr Val Phe Lys Asp Glu Leu Ala Glu Ile Lys Gln
 1               5                  10                  15

Phe Leu Glu Ala Leu Gly Gly Ser Glu Ala Glu Leu Ala Trp Phe Glu
                20                  25                  30

Asp Asp Ile Ala Glu Phe Glu Thr Gln Leu Gln His Tyr Lys Gly Lys
                35                  40                  45

Gly Asn Pro Glu Val Glu Ala Leu Arg Lys Glu Ala Ala Ile Arg
                50                  55                  60

Asp Glu Leu Gln Ala Tyr Arg His Asn
 65                  70

<210> SEQ ID NO 87
<211> LENGTH: 73
<212> TYPE: PRT

<213> ORGANISM: Homo sapiens

<400> SEQUENCE: 87

Met Gly Ser Trp Thr Glu Phe Lys Gly Glu Leu Ala Glu Ile Lys Trp
1               5                   10                  15

Ile Leu Glu Ala Leu Gly Gly Ser Glu Ala Glu Leu Ala Phe Phe Glu
                20                  25                  30

Asp Glu Ile Ala Ala Phe Glu Trp Asp Leu Gln Lys Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 88
<211> LENGTH: 73
<212> TYPE: PRT
<213> ORGANISM: Homo sapiens

<400> SEQUENCE: 88

Met Gly Ser Trp Phe Trp Phe Lys Glu Asp Leu Ala Phe Ile Lys Glu
1               5                   10                  15

Asp Leu Glu Ala Leu Gly Gly Ser Glu Ala Glu Leu Ala Trp Phe Glu
                20                  25                  30

Asp Gly Ile Ala Phe Phe Glu Trp Asp Leu Gln Asp Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 89
<211> LENGTH: 73
<212> TYPE: PRT
<213> ORGANISM: Homo sapiens

<400> SEQUENCE: 89

Met Gly Ser Trp Ser Trp Phe Lys Glu Asp Leu Ala Ser Ile Lys Ala
1               5                   10                  15

Val Leu Glu Ala Leu Gly Gly Ser Glu Ala Glu Leu Ala Phe Phe Glu
                20                  25                  30

Ser Asp Ile Ala Glu Phe Glu Gln Glu Leu Gln Tyr Tyr Lys Gly Lys
            35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70

<210> SEQ ID NO 90
<211> LENGTH: 73
<212> TYPE: PRT
<213> ORGANISM: Homo sapiens

<400> SEQUENCE: 90

Met Gly Ser Trp Ile Leu Phe Lys Asp Asp Leu Ala Trp Ile Lys Glu
1               5                   10                  15

Thr Leu Glu Ala Leu Gly Gly Ser Glu Ala Glu Leu Ala Phe Phe Glu
                20                  25                  30

Asp Asn Ile Ala Asp Phe Glu Glu Gln Leu Gln Gly Tyr Lys Gly Lys
            35                  40                  45

Gly Asn Pro Glu Val Glu Ala Leu Arg Lys Gly Ala Ala Ile Arg
 50                  55                  60

Asp Glu Leu Gln Ala Tyr Arg His Asn
 65                  70

<210> SEQ ID NO 91
<211> LENGTH: 73
<212> TYPE: PRT
<213> ORGANISM: Homo sapiens

<400> SEQUENCE: 91

Met Gly Ser Trp Gln Trp Phe Lys Asp Asp Leu Ala Tyr Ile Lys Glu
 1               5                  10                  15

Thr Leu Glu Ala Leu Gly Gly Ser Glu Ala Glu Leu Ala Leu Phe Glu
            20                  25                  30

Asp Met Ile Ala Asp Phe Glu Phe Glu Leu Gln Trp Tyr Lys Gly Lys
            35                  40                  45

Gly Asn Pro Glu Val Glu Ala Leu Arg Lys Gly Ala Ala Ile Arg
 50                  55                  60

Asp Glu Leu Gln Ala Tyr Arg His Asn
 65                  70

<210> SEQ ID NO 92
<211> LENGTH: 73
<212> TYPE: PRT
<213> ORGANISM: Homo sapiens

<400> SEQUENCE: 92

Met Gly Ser Trp Glu Glu Phe His Ser Arg Leu Asp Ala Ile Asp Asp
 1               5                  10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Trp Leu Arg Trp Glu Ala Ala Thr Ile Arg
 50                  55                  60

Glu Thr Leu Gln Ala Tyr Arg His Asn
 65                  70

<210> SEQ ID NO 93
<211> LENGTH: 73
<212> TYPE: PRT
<213> ORGANISM: Homo sapiens

<400> SEQUENCE: 93

Met Gly Ser Trp Ser Glu Phe Trp Gln Arg Leu Glu Ala Ile Glu Asp
 1               5                  10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Trp Leu Arg Glu Asn Ala Ala Met Ile Arg
 50                  55                  60

Asp Glu Leu Gln Ala Tyr Arg His Asn
 65                  70

<210> SEQ ID NO 94
<211> LENGTH: 73
<212> TYPE: PRT
<213> ORGANISM: Homo sapiens

<400> SEQUENCE: 94

Met Gly Ser Trp Thr Glu Phe Ala Trp Arg Leu Asp Ala Ile Tyr Asp
1               5                   10                  15

Arg Leu Leu Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg His Val Ala Ala Asn Ile Arg
    50                  55                  60

Arg Glu Leu Gln Ala Tyr Arg His Asn
65                  70

<210> SEQ ID NO 95
<211> LENGTH: 73
<212> TYPE: PRT
<213> ORGANISM: Homo sapiens

<400> SEQUENCE: 95

Met Gly Ser Trp Asp Glu Phe Tyr Tyr Arg Leu Glu Ala Ile Glu Met
1               5                   10                  15

Arg Leu Gly Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Leu Arg His Tyr Ala Ala Gln Ile Arg
    50                  55                  60

His Met Leu Gln Ala Tyr Arg His Asn
65                  70

<210> SEQ ID NO 96
<211> LENGTH: 73
<212> TYPE: PRT
<213> ORGANISM: Homo sapiens

<400> SEQUENCE: 96

Met Gly Ser Trp Ile Glu Phe Asn Met Arg Leu Asp Ala Ile Tyr Glu
1               5                   10                  15

Arg Leu Val Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Lys Val Ala Ala Asn Ile Arg
    50                  55                  60

Leu Glu Leu Gln Ala Tyr Arg His Asn
65                  70

<210> SEQ ID NO 97
<211> LENGTH: 73
<212> TYPE: PRT
<213> ORGANISM: Homo sapiens

<400> SEQUENCE: 97

Met Gly Ser Trp Ser Glu Phe Asn Met Arg Leu Asp Ala Ile Tyr Glu
1               5                   10                  15

Arg Leu Thr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Trp Leu Arg His Ser Ala Ala Arg Ile Arg
 50                  55                  60

Leu Glu Leu Gln Ala Tyr Arg His Asn
 65                  70

<210> SEQ ID NO 98
<211> LENGTH: 73
<212> TYPE: PRT
<213> ORGANISM: Homo sapiens

<400> SEQUENCE: 98

Met Gly Ser Trp Val Glu Phe Asn Ile Arg Leu Asp Ala Ile Tyr Glu
 1               5                  10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Lys Leu Arg His Trp Ala Ala Ser Ile Arg
 50                  55                  60

Arg Glu Leu Gln Ala Tyr Arg His Asn
 65                  70

<210> SEQ ID NO 99
<211> LENGTH: 73
<212> TYPE: PRT
<213> ORGANISM: Homo sapiens

<400> SEQUENCE: 99

Met Gly Ser Trp Asp Glu Phe Gly Arg Arg Leu Tyr Ala Ile Glu Trp
 1               5                  10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Lys Leu Arg Glu Ile Ala Ala Val Ile Arg
 50                  55                  60

Ser Asn Leu Gln Ala Tyr Arg His Asn
 65                  70

<210> SEQ ID NO 100
<211> LENGTH: 73
<212> TYPE: PRT
<213> ORGANISM: Homo sapiens

<400> SEQUENCE: 100

Met Gly Ser Trp Ile Glu Phe Tyr Asp Arg Leu Glu Ala Ile Tyr Asp
 1               5                  10                  15

Arg Leu Asp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Trp Leu Arg Glu Asp Ala Ala Phe Ile Arg
 50                  55                  60

Ser Trp Leu Gln Ala Tyr Arg His Asn 65                  70

<210> SEQ ID NO 101
<211> LENGTH: 73
<212> TYPE: PRT
<213> ORGANISM: Homo sapiens

<400> SEQUENCE: 101

Met Gly Ser Trp Thr Glu Phe Asp Arg Arg Leu Asp Ala Ile Trp Asp
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Glu Glu Ala Ala Asp Ile Arg
    50                  55                  60

Asp Tyr Leu Gln Ala Tyr Arg His Asn
65                  70

<210> SEQ ID NO 102
<211> LENGTH: 73
<212> TYPE: PRT
<213> ORGANISM: Homo sapiens

<400> SEQUENCE: 102

Met Gly Ser Trp Thr Glu Phe Asp Arg Arg Leu Asp Ala Ile Trp Asp
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Glu Glu Ala Ala Asp Ile Arg
    50                  55                  60

Asp Tyr Leu Gln Ala Tyr Arg His Asn
65                  70

<210> SEQ ID NO 103
<211> LENGTH: 73
<212> TYPE: PRT
<213> ORGANISM: Homo sapiens

<400> SEQUENCE: 103

Met Gly Ser Trp Ile Glu Phe Glu Val Arg Leu Asp Ala Ile Tyr Asn
1               5                   10                  15

Arg Leu Ala Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Arg Leu Arg Arg Tyr Ala Ala Asn Ile Arg
    50                  55                  60

His Glu Leu Gln Ala Tyr Arg His Asn
65                  70

<210> SEQ ID NO 104
<211> LENGTH: 73
<212> TYPE: PRT
<213> ORGANISM: Homo sapiens

<400> SEQUENCE: 104

```
Met Gly Ser Trp Thr Glu Phe His Asp Arg Leu Glu Ala Ile Asp Asp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Tyr Leu Arg Glu Ala Ala Gln Ile Arg
        50                  55                  60

Trp Glu Leu Gln Ala Tyr Arg His Asn
65                  70
```

<210> SEQ ID NO 105
<211> LENGTH: 73
<212> TYPE: PRT
<213> ORGANISM: Homo sapiens

<400> SEQUENCE: 105

```
Met Gly Ser Trp Tyr Glu Phe His His Arg Leu Asp Ala Ile Tyr Glu
1               5                   10                  15

Arg Leu Leu Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Trp Leu Arg Ser Ser Ala Ala Asn Ile Arg
        50                  55                  60

Lys Glu Leu Gln Ala Tyr Arg His Asn
65                  70
```

<210> SEQ ID NO 106
<211> LENGTH: 73
<212> TYPE: PRT
<213> ORGANISM: Homo sapiens

<400> SEQUENCE: 106

```
Met Gly Ser Trp His Glu Phe Asp Gln Arg Leu Trp Ala Ile Glu Glu
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Thr Leu Arg Leu Tyr Ala Ala Leu Ile Arg
        50                  55                  60

His Asp Leu Gln Ala Tyr Arg His Asn
65                  70
```

<210> SEQ ID NO 107
<211> LENGTH: 73
<212> TYPE: PRT
<213> ORGANISM: Homo sapiens

<400> SEQUENCE: 107

```
Met Gly Ser Trp Ile Glu Phe Glu Ser Arg Leu Trp Ala Ile Glu Asp
1               5                   10                  15

Arg Leu Leu Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
                35                  40                  45

Gly Asn Pro Glu Val Glu Phe Leu Arg Leu Glu Ala Ala Asp Ile Arg
```

<210> SEQ ID NO 108
<211> LENGTH: 73
<212> TYPE: PRT
<213> ORGANISM: Homo sapiens

<400> SEQUENCE: 108

Met Gly Ser Trp Tyr Glu Phe Glu Asn Arg Leu Gly Ala Ile Gly Asp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Asp Glu Ala Ala Tyr Ile Arg
    50                  55                  60

Ala Val Leu Gln Ala Tyr Arg His Asn
65                  70

<210> SEQ ID NO 109
<211> LENGTH: 73
<212> TYPE: PRT
<213> ORGANISM: Homo sapiens

<400> SEQUENCE: 109

Met Gly Ser Trp Asn Glu Phe Tyr Asp Arg Leu Ser Ala Ile Tyr Phe
1               5                   10                  15

Arg Leu Gln Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu His Leu Arg Trp Tyr Ala Ala Asp Ile Arg
    50                  55                  60

Met Ile Leu Gln Ala Tyr Arg His Asn
65                  70

<210> SEQ ID NO 110
<211> LENGTH: 73
<212> TYPE: PRT
<213> ORGANISM: Homo sapiens

<400> SEQUENCE: 110

Met Gly Ser Trp Tyr Glu Phe Glu Tyr Arg Leu Glu Ala Ile Glu Asp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg Glu Glu Ala Ala Trp Ile Arg
    50                  55                  60

Val Trp Leu Gln Ala Tyr Arg His Asn
65                  70

<210> SEQ ID NO 111
<211> LENGTH: 73
<212> TYPE: PRT
<213> ORGANISM: Homo sapiens

<400> SEQUENCE: 111

Met Gly Ser Trp Val Glu Phe Glu Asn Arg Leu Glu Ala Ile Glu Asn
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Glu Asp Ala Ala Gln Ile Arg
    50                  55                  60

Met Met Leu Gln Ala Tyr Arg His Asn
65                  70

<210> SEQ ID NO 112
<211> LENGTH: 73
<212> TYPE: PRT
<213> ORGANISM: Homo sapiens

<400> SEQUENCE: 112

Met Gly Ser Trp Tyr Glu Phe Trp Asp Arg Leu Glu Ala Ile Asp Asp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Gln Glu Ala Ala Trp Ile Arg
    50                  55                  60

Glu Glu Leu Gln Ala Tyr Arg His Asn
65                  70

<210> SEQ ID NO 113
<211> LENGTH: 73
<212> TYPE: PRT
<213> ORGANISM: Homo sapiens

<400> SEQUENCE: 113

Met Gly Ser Trp Phe Glu Phe Trp Asp Arg Leu Asp Ala Ile Glu Asp
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Glu Leu Arg Asp Glu Ala Ala Trp Ile Arg
    50                  55                  60

Gly Thr Leu Gln Ala Tyr Arg His Asn
65                  70

<210> SEQ ID NO 114
<211> LENGTH: 73
<212> TYPE: PRT
<213> ORGANISM: Homo sapiens

<400> SEQUENCE: 114

Met Gly Ser Trp Thr Glu Phe Asp Arg Leu Asp Ala Ile Trp Asp
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys 35                  40                  45

Gly Asn Pro Glu Val Glu Trp Leu Arg Glu Glu Ala Ala Asp Ile Arg
        50                  55                  60

Asp Tyr Leu Gln Ala Tyr Arg His Asn
 65                  70

<210> SEQ ID NO 115
<211> LENGTH: 73
<212> TYPE: PRT
<213> ORGANISM: Homo sapiens

<400> SEQUENCE: 115

Met Gly Ser Trp Trp Glu Phe Glu Met Arg Leu Glu Ala Ile Glu Asp
  1               5                  10                  15

Arg Leu Phe Ala Leu Gly Gly Ser Glu Ala Glu Leu Ala Ala Phe Glu
                 20                  25                  30

Lys Glu Ile Ala Ala Phe Glu Ser Glu Leu Gln Ala Tyr Lys Gly Lys
             35                  40                  45

Gly Asn Pro Glu Val Glu Ser Leu Arg Trp Glu Ala Ala Phe Ile Arg
        50                  55                  60

Asp Ile Leu Gln Ala Tyr Arg His Asn
 65                  70

<210> SEQ ID NO 116
<211> LENGTH: 73
<212> TYPE: PRT
<213> ORGANISM: Homo sapiens

<400> SEQUENCE: 116

Met Gly Ser Trp Val Glu Phe Tyr Asp Arg Leu His Ala Ile Tyr Phe
  1               5                  10                  15

Arg Leu Leu Ala Leu Gly Gly Ser Glu Ala Glu Leu Ala Ala Phe Glu
                 20                  25                  30

Lys Glu Ile Ala Ala Phe Glu Ser Glu Leu Gln Ala Tyr Lys Gly Lys
             35                  40                  45

Gly Asn Pro Glu Val Glu Asp Leu Arg Trp Tyr Ala Ala Asp Ile Arg
        50                  55                  60

Leu Val Leu Gln Ala Tyr Arg His Asn
 65                  70

<210> SEQ ID NO 117
<211> LENGTH: 73
<212> TYPE: PRT
<213> ORGANISM: Homo sapiens

<400> SEQUENCE: 117

Met Gly Ser Trp Tyr Glu Phe Tyr Asn Arg Leu Ser Ala Ile Tyr Ala
  1               5                  10                  15

Arg Leu Gln Ala Leu Gly Gly Ser Glu Ala Glu Leu Ala Ala Phe Glu
                 20                  25                  30

Lys Glu Ile Ala Ala Phe Glu Ser Glu Leu Gln Ala Tyr Lys Gly Lys
             35                  40                  45

Gly Asn Pro Glu Val Glu Asp Leu Arg Trp Tyr Ala Ala Asp Ile Arg
        50                  55                  60

Tyr Met Leu Gln Ala Tyr Arg His Asn
 65                  70

<210> SEQ ID NO 118

```
<211> LENGTH: 73
<212> TYPE: PRT
<213> ORGANISM: Homo sapiens

<400> SEQUENCE: 118

Met Gly Ser Trp Phe Glu Phe Trp Gly Arg Leu Glu Ala Ile Glu Ser
1               5                   10                  15

Arg Leu Lys Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Glu Leu Arg Glu His Ala Ala Trp Ile Arg
    50                  55                  60

Ala Tyr Leu Gln Ala Tyr Arg His Asn
65                  70

<210> SEQ ID NO 119
<211> LENGTH: 73
<212> TYPE: PRT
<213> ORGANISM: Homo sapiens

<400> SEQUENCE: 119

Met Gly Ser Trp Thr Glu Phe Ser Ile Arg Leu Glu Ala Ile Tyr Asp
1               5                   10                  15

Arg Leu Val Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Val Leu Arg Thr Tyr Ala Ala Asn Ile Arg
    50                  55                  60

His Glu Leu Gln Ala Tyr Arg His Asn
65                  70

<210> SEQ ID NO 120
<211> LENGTH: 73
<212> TYPE: PRT
<213> ORGANISM: Homo sapiens

<400> SEQUENCE: 120

Met Gly Ser Trp Tyr Glu Phe Glu Asn Arg Leu Glu Ala Ile Glu Glu
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Met Leu Arg Glu Glu Ala Ala Phe Ile Arg
    50                  55                  60

Asp Trp Leu Gln Ala Tyr Arg His Asn
65                  70

<210> SEQ ID NO 121
<211> LENGTH: 73
<212> TYPE: PRT
<213> ORGANISM: Homo sapiens

<400> SEQUENCE: 121

Met Gly Ser Trp Tyr Glu Phe Val Ile Arg Leu Glu Ala Ile Glu Asp
1               5                   10                  15

Arg Leu Trp Ala Leu Gly Gly Ser Glu Ala Glu Leu Ala Ala Phe Glu
```

```
                    20                  25                  30

Lys Glu Ile Ala Ala Phe Glu Ser Glu Leu Gln Ala Tyr Lys Gly Lys
        35                  40                  45

Gly Asn Pro Glu Val Glu Val Leu Arg Trp Tyr Ala Ala Asp Ile Arg
    50                  55                  60

His Glu Leu Gln Ala Tyr Arg His Asn
65                  70

<210> SEQ ID NO 122
<211> LENGTH: 73
<212> TYPE: PRT
<213> ORGANISM: Homo sapiens

<400> SEQUENCE: 122

Met Gly Ser Trp Ile Glu Phe Glu Asp Arg Leu Glu Ala Ile Glu Asp
1               5                   10                  15

Arg Leu Phe Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Gln Glu Ala Ala Glu Ile Arg
    50                  55                  60

Leu Met Leu Gln Ala Tyr Arg His Asn
65                  70

<210> SEQ ID NO 123
<211> LENGTH: 73
<212> TYPE: PRT
<213> ORGANISM: Homo sapiens

<400> SEQUENCE: 123

Met Gly Ser Trp Thr Glu Phe Asn Leu Arg Leu Asp Ala Ile Tyr Asp
1               5                   10                  15

Arg Leu Met Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Ala Ser Ala Ala Ala Ile Arg
    50                  55                  60

Val Glu Leu Gln Ala Tyr Arg His Asn
65                  70

<210> SEQ ID NO 124
<211> LENGTH: 73
<212> TYPE: PRT
<213> ORGANISM: Homo sapiens

<400> SEQUENCE: 124

Met Gly Ser Trp Ser Glu Phe Tyr Leu Arg Leu Asp Ala Ile Tyr Asp
1               5                   10                  15

Arg Leu Asp Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Lys Thr Ala Ala Asn Ile Arg
    50                  55                  60

Glu Glu Leu Gln Ala Tyr Arg His Asn
65                  70
```

<210> SEQ ID NO 125
<211> LENGTH: 73
<212> TYPE: PRT
<213> ORGANISM: Homo sapiens

<400> SEQUENCE: 125

Met Gly Ser Trp Ser Glu Phe His Val Arg Leu Asp Ala Ile Tyr Ala
1               5                   10                  15

Arg Leu Asp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Arg Leu Arg Glu Trp Ala Ala Asn Ile Arg
    50                  55                  60

Arg Glu Leu Gln Ala Tyr Arg His Asn
65                  70

<210> SEQ ID NO 126
<211> LENGTH: 73
<212> TYPE: PRT
<213> ORGANISM: Homo sapiens

<400> SEQUENCE: 126

Met Gly Ser Trp His Glu Phe Gly Val Arg Leu Asp Ala Ile Tyr Asp
1               5                   10                  15

Arg Leu Met Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Phe Leu Arg Gln Ala Ala Asn Ile Arg
    50                  55                  60

Ser Glu Leu Gln Ala Tyr Arg His Asn
65                  70

<210> SEQ ID NO 127
<211> LENGTH: 73
<212> TYPE: PRT
<213> ORGANISM: Homo sapiens

<400> SEQUENCE: 127

Met Gly Ser Trp Tyr Glu Phe Ser Met Arg Leu Asp Ala Ile Tyr Asp
1               5                   10                  15

Arg Leu Met Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Gln Leu Arg Gly Tyr Ala Ala Asn Ile Arg
    50                  55                  60

Asn Glu Leu Gln Ala Tyr Arg His Asn
65                  70

<210> SEQ ID NO 128
<211> LENGTH: 73
<212> TYPE: PRT
<213> ORGANISM: Homo sapiens

<400> SEQUENCE: 128

Met Gly Ser Trp Asp Glu Phe Gly Arg Arg Leu Tyr Ala Ile Glu Trp

```
                1               5                   10                  15
Gln Leu Tyr Ala Leu Gly Gly Ser Glu Ala Glu Leu Ala Ala Phe Glu
                        20                  25                  30

Lys Glu Ile Ala Ala Phe Glu Ser Glu Leu Gln Ala Tyr Lys Gly Lys
            35                  40                  45

Gly Asn Pro Glu Val Glu Lys Leu Arg Glu Ile Ala Ala Val Ile Arg
        50                  55                  60

Ser Asn Leu Gln Ala Tyr Arg His Asn
65                  70
```

<210> SEQ ID NO 129
<211> LENGTH: 73
<212> TYPE: PRT
<213> ORGANISM: Homo sapiens

<400> SEQUENCE: 129

```
Met Gly Ser Trp Asp Glu Phe Gly Arg Arg Leu Tyr Ala Ile Glu Trp
1               5                   10                  15

Arg Leu Tyr Ala Leu Gly Gly Glu Ala Glu Leu Ala Ala Phe Glu
                        20                  25                  30

Lys Glu Ile Ala Ala Phe Glu Ser Glu Leu Gln Ala Tyr Lys Gly Lys
            35                  40                  45

Gly Asn Pro Glu Val Glu Lys Leu Arg Glu Ile Ala Ala Val Ile Arg
        50                  55                  60

Ser Asn Leu Gln Ala Tyr Arg His Asn
65                  70
```

<210> SEQ ID NO 130
<211> LENGTH: 73
<212> TYPE: PRT
<213> ORGANISM: Homo sapiens

<400> SEQUENCE: 130

```
Met Gly Ser Trp Asp Glu Phe Gly Arg Arg Leu Tyr Ala Ile Glu Trp
1               5                   10                  15

Arg Leu Tyr Ala Leu Gly Gly Ser Glu Ala Glu Leu Ala Ala Phe Glu
                        20                  25                  30

Lys Glu Ile Ala Ala Phe Glu Ser Glu Leu Gln Ala Tyr Lys Gly Lys
            35                  40                  45

Gly Asn Pro Glu Val Glu Lys Leu Arg Glu Ile Ala Ala Val Ile Arg
        50                  55                  60

Glu Asn Leu Gln Ala Tyr Arg His Asn
65                  70
```

<210> SEQ ID NO 131
<211> LENGTH: 73
<212> TYPE: PRT
<213> ORGANISM: Homo sapiens

<400> SEQUENCE: 131

```
Met Gly Ser Trp Asp Glu Phe Gly Arg Arg Leu Tyr Ala Ile Glu Trp
1               5                   10                  15

Gln Leu Tyr Ala Leu Gly Gly Glu Glu Ala Glu Leu Ala Ala Phe Glu
                        20                  25                  30

Lys Glu Ile Ala Ala Phe Glu Ser Glu Leu Gln Ala Tyr Lys Gly Lys
            35                  40                  45

Gly Asn Pro Glu Val Glu Lys Leu Arg Glu Ile Ala Ala Val Ile Arg
        50                  55                  60
```

Ser Asn Leu Gln Ala Tyr Arg His Asn
65                  70

<210> SEQ ID NO 132
<211> LENGTH: 73
<212> TYPE: PRT
<213> ORGANISM: Homo sapiens

<400> SEQUENCE: 132

Met Gly Ser Trp Asp Glu Phe Gly Arg Arg Leu Tyr Ala Ile Glu Trp
1               5                   10                  15

Gln Leu Tyr Ala Leu Gly Gly Thr Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Lys Leu Arg Glu Ile Ala Ala Val Ile Arg
    50                  55                  60

Ser Asn Leu Gln Ala Tyr Arg His Asn
65                  70

<210> SEQ ID NO 133
<211> LENGTH: 73
<212> TYPE: PRT
<213> ORGANISM: Homo sapiens

<400> SEQUENCE: 133

Met Gly Ser Trp Asp Glu Phe Gly Arg Arg Leu Tyr Ala Ile Glu Trp
1               5                   10                  15

Gln Leu Tyr Ala Leu Gly Gly Gly Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Lys Leu Arg Glu Ile Ala Ala Val Ile Arg
    50                  55                  60

Ser Asn Leu Gln Ala Tyr Arg His Asn
65                  70

<210> SEQ ID NO 134
<211> LENGTH: 73
<212> TYPE: PRT
<213> ORGANISM: Homo sapiens

<400> SEQUENCE: 134

Met Gly Ser Trp Asp Glu Phe Gly Arg Arg Leu Tyr Ala Ile Glu Trp
1               5                   10                  15

Gln Leu Tyr Ala Leu Gly Gly Glu Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Lys Leu Arg Glu Ile Ala Ala Val Ile Arg
    50                  55                  60

Glu Asn Leu Gln Ala Tyr Arg His Asn
65                  70

<210> SEQ ID NO 135
<211> LENGTH: 73
<212> TYPE: PRT
<213> ORGANISM: Homo sapiens -continued

```
<400> SEQUENCE: 135

Met Gly Ser Trp Asp Glu Phe Gly Arg Arg Leu Tyr Ala Ile Glu Trp
1               5                   10                  15

Gln Leu Tyr Ala Leu Gly Gly Thr Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Lys Leu Arg Glu Ile Ala Ala Val Ile Arg
    50                  55                  60

Glu Asn Leu Gln Ala Tyr Arg His Asn
65                  70

<210> SEQ ID NO 136
<211> LENGTH: 73
<212> TYPE: PRT
<213> ORGANISM: Homo sapiens

<400> SEQUENCE: 136

Met Gly Ser Trp Asp Glu Phe Gly Arg Arg Leu Tyr Ala Ile Glu Trp
1               5                   10                  15

Gln Leu Tyr Ala Leu Gly Gly Gly Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Lys Leu Arg Glu Ile Ala Ala Val Ile Arg
    50                  55                  60

Glu Asn Leu Gln Ala Tyr Arg His Asn
65                  70

<210> SEQ ID NO 137
<211> LENGTH: 73
<212> TYPE: PRT
<213> ORGANISM: Homo sapiens

<400> SEQUENCE: 137

Met Gly Ser Trp Glu Glu Phe Glu Leu Arg Leu Asn Ala Ile Glu Glu
1               5                   10                  15

Arg Leu Tyr Ala Leu Gly Gly Ser Glu Ala Glu Leu Ala Tyr Phe Glu
            20                  25                  30

Tyr Val Ile Ala Asp Phe Glu Gly Asn Leu Gln Arg Tyr Lys Gly Lys
        35                  40                  45

Gly Asn Pro Glu Val Glu Ala Leu Tyr Phe Glu Ala Asp Ala Ile Phe
    50                  55                  60

Glu Glu Leu Val Ala Tyr Arg His Asn
65                  70

<210> SEQ ID NO 138
<211> LENGTH: 73
<212> TYPE: PRT
<213> ORGANISM: Homo sapiens

<400> SEQUENCE: 138

Met Gly Ser Trp Phe Glu Phe Asn His Arg Leu Trp Ala Ile Phe Glu
1               5                   10                  15

Arg Leu Met Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45
```

-continued

Gly Asn Pro Glu Val Glu Tyr Leu Arg Ala Met Ala Ala Val Ile Arg
    50                  55                  60

Tyr His Leu Gln Ala Tyr Arg His Asn
65                  70

<210> SEQ ID NO 139
<211> LENGTH: 73
<212> TYPE: PRT
<213> ORGANISM: Homo sapiens

<400> SEQUENCE: 139

Met Gly Ser Trp Glu Glu Phe Asp Gly Arg Leu Phe Ala Ile Glu Gln
1               5                   10                  15

Arg Leu Gln Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Val Leu Arg Trp Phe Ala Ala Gly Ile Arg
    50                  55                  60

Asp Phe Leu Gln Ala Tyr Arg His Asn
65                  70

<210> SEQ ID NO 140
<211> LENGTH: 73
<212> TYPE: PRT
<213> ORGANISM: Homo sapiens

<400> SEQUENCE: 140

Met Gly Ser Trp Ala Glu Phe Tyr His Arg Leu Tyr Ala Ile Glu Thr
1               5                   10                  15

Arg Leu Ser Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg His Trp Ala Ala Trp Ile Arg
    50                  55                  60

Thr Tyr Leu Gln Ala Tyr Arg His Asn
65                  70

<210> SEQ ID NO 141
<211> LENGTH: 73
<212> TYPE: PRT
<213> ORGANISM: Homo sapiens

<400> SEQUENCE: 141

Met Gly Ser Trp Val Glu Phe Ser Asp Arg Leu Tyr Ala Ile Glu Glu
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Glu Leu Arg Glu Leu Ala Ala Ile Ile Arg
    50                  55                  60

His Ser Leu Gln Ala Tyr Arg His Asn
65                  70

<210> SEQ ID NO 142
<211> LENGTH: 73

```
<212> TYPE: PRT
<213> ORGANISM: Homo sapiens

<400> SEQUENCE: 142

Met Gly Ser Trp Trp Glu Phe Glu Gly Arg Leu Tyr Ala Ile Glu Glu
1               5                   10                  15

Arg Leu Thr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg Glu Trp Ala Ala Trp Ile Arg
    50                  55                  60

Gln Met Leu Gln Ala Tyr Arg His Asn
65                  70

<210> SEQ ID NO 143
<211> LENGTH: 73
<212> TYPE: PRT
<213> ORGANISM: Homo sapiens

<400> SEQUENCE: 143

Met Gly Ser Trp Trp Glu Phe Glu His Arg Leu Tyr Ala Ile Glu Glu
1               5                   10                  15

Arg Leu Val Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg Asn Trp Ala Ala Tyr Ile Arg
    50                  55                  60

Met Ala Leu Gln Ala Tyr Arg His Asn
65                  70

<210> SEQ ID NO 144
<211> LENGTH: 73
<212> TYPE: PRT
<213> ORGANISM: Homo sapiens

<400> SEQUENCE: 144

Met Gly Ser Trp Trp Glu Phe Glu Ala Arg Leu Tyr Ala Ile Glu Phe
1               5                   10                  15

Arg Leu Ser Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg Ser Trp Ala Ala Tyr Ile Arg
    50                  55                  60

Thr Ser Leu Gln Ala Tyr Arg His Asn
65                  70

<210> SEQ ID NO 145
<211> LENGTH: 73
<212> TYPE: PRT
<213> ORGANISM: Homo sapiens

<400> SEQUENCE: 145

Met Gly Ser Trp Trp Glu Phe Glu Ala Arg Leu Trp Ala Ile Glu Ser
1               5                   10                  15

Arg Leu Lys Ala Leu Gly Gly Ser Glu Ala Glu Leu Ala Ala Phe Glu
            20                  25                  30
```

Lys Glu Ile Ala Ala Phe Glu Ser Glu Leu Gln Ala Tyr Lys Gly Lys
            35                  40                  45

Gly Asn Pro Glu Val Glu Tyr Leu Arg His Trp Ala Ala Tyr Ile Arg
        50                  55                  60

Val Ile Leu Gln Ala Tyr Arg His Asn
65                  70

<210> SEQ ID NO 146
<211> LENGTH: 73
<212> TYPE: PRT
<213> ORGANISM: Homo sapiens

<400> SEQUENCE: 146

Met Gly Ser Trp Trp Glu Phe Glu Ala Arg Leu Tyr Ala Ile Glu Phe
1               5                   10                  15

Arg Leu Ser Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Tyr Leu Arg Ser Trp Ala Ala Tyr Ile Arg
        50                  55                  60

Thr Ser Leu Gln Ala Tyr Arg His Asn
65                  70

<210> SEQ ID NO 147
<211> LENGTH: 73
<212> TYPE: PRT
<213> ORGANISM: Homo sapiens

<400> SEQUENCE: 147

Met Gly Ser Trp Glu Glu Phe Tyr His Arg Leu Asp Ala Ile Glu Leu
1               5                   10                  15

Arg Leu Tyr Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Tyr Leu Arg Trp Tyr Ala Ala Glu Ile Arg
        50                  55                  60

Glu Ile Leu Gln Ala Tyr Arg His Asn
65                  70

<210> SEQ ID NO 148
<211> LENGTH: 73
<212> TYPE: PRT
<213> ORGANISM: Homo sapiens

<400> SEQUENCE: 148

Met Gly Ser Trp Tyr Glu Phe Tyr Glu Arg Leu Asp Ala Ile Asp Thr
1               5                   10                  15

Arg Leu Trp Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Phe Leu Arg Glu Tyr Ala Ala Glu Ile Arg
        50                  55                  60

His Phe Leu Gln Ala Tyr Arg His Asn
65                  70

<210> SEQ ID NO 149
<211> LENGTH: 73
<212> TYPE: PRT
<213> ORGANISM: Homo sapiens

<400> SEQUENCE: 149

Met Gly Ser Trp Asn Glu Phe Phe Asp Arg Leu Asp Ala Ile Leu Tyr
1               5                   10                  15

Arg Leu Asp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg Phe Val Ala Ala Asp Ile Arg
    50                  55                  60

Ser Trp Leu Gln Ala Tyr Arg His Asn
65                  70

<210> SEQ ID NO 150
<211> LENGTH: 73
<212> TYPE: PRT
<213> ORGANISM: Homo sapiens

<400> SEQUENCE: 150

Met Gly Ser Trp Ile Glu Phe Asp Asp Arg Leu Leu Ala Ile Met Asp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Asp Leu Arg Asp Val Ala Ala Asp Ile Arg
    50                  55                  60

His Tyr Leu Gln Ala Tyr Arg His Asn
65                  70

<210> SEQ ID NO 151
<211> LENGTH: 73
<212> TYPE: PRT
<213> ORGANISM: Homo sapiens

<400> SEQUENCE: 151

Met Gly Ser Trp Tyr Glu Phe Trp Glu Arg Leu Asp Ala Ile Thr Phe
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Thr Trp Ala Ala Asp Ile Arg
    50                  55                  60

Ala Ile Leu Gln Ala Tyr Arg His Asn
65                  70

<210> SEQ ID NO 152
<211> LENGTH: 73
<212> TYPE: PRT
<213> ORGANISM: Homo sapiens

<400> SEQUENCE: 152

Met Gly Ser Trp Glu Glu Phe Tyr Ile Arg Leu Asp Ala Ile Met Glu
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Tyr Ala Ala Asp Ile Arg
    50                  55                  60

His Phe Leu Gln Ala Tyr Arg His Asn
65                  70

<210> SEQ ID NO 153
<211> LENGTH: 73
<212> TYPE: PRT
<213> ORGANISM: Homo sapiens

<400> SEQUENCE: 153

Met Gly Ser Trp Ile Glu Phe Glu Glu Arg Leu Tyr Ala Ile Glu Thr
1               5                   10                  15

Arg Leu Leu Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Phe Leu Arg Val Val Ala Ala Asp Ile Arg
    50                  55                  60

Glu Trp Leu Gln Ala Tyr Arg His Asn
65                  70

<210> SEQ ID NO 154
<211> LENGTH: 73
<212> TYPE: PRT
<213> ORGANISM: Homo sapiens

<400> SEQUENCE: 154

Met Gly Ser Trp Ile Glu Phe Glu His Arg Leu Ser Ala Ile Asn Asp
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Glu Trp Ala Ala Asp Ile Arg
    50                  55                  60

Ser Leu Leu Gln Ala Tyr Arg His Asn
65                  70

<210> SEQ ID NO 155
<211> LENGTH: 73
<212> TYPE: PRT
<213> ORGANISM: Homo sapiens

<400> SEQUENCE: 155

Met Gly Ser Trp Phe Glu Phe Glu Met Arg Leu Asp Ala Ile Met Ala
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Tyr Ala Ala Asp Ile Arg
    50                  55                  60

-continued

Asp Tyr Leu Gln Ala Tyr Arg His Asn
65                  70

<210> SEQ ID NO 156
<211> LENGTH: 73
<212> TYPE: PRT
<213> ORGANISM: Homo sapiens

<400> SEQUENCE: 156

Met Gly Ser Trp Tyr Glu Phe Val Tyr Arg Leu Asp Ala Ile Tyr Asp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Tyr Ala Ala Asp Ile Arg
    50                  55                  60

Asp Phe Leu Gln Ala Tyr Arg His Asn
65                  70

<210> SEQ ID NO 157
<211> LENGTH: 73
<212> TYPE: PRT
<213> ORGANISM: Homo sapiens

<400> SEQUENCE: 157

Met Gly Ser Trp Val Glu Phe Glu Asp Arg Leu Asp Ala Ile Leu Glu
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Glu Leu Ala Ala Asp Ile Arg
    50                  55                  60

Asp Phe Leu Gln Ala Tyr Arg His Asn
65                  70

<210> SEQ ID NO 158
<211> LENGTH: 73
<212> TYPE: PRT
<213> ORGANISM: Homo sapiens

<400> SEQUENCE: 158

Met Gly Ser Trp Phe Glu Phe Glu Glu Arg Leu Ile Ala Ile Glu Glu
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Tyr Leu Arg Trp Ile Ala Ala Asp Ile Arg
    50                  55                  60

Asp Val Leu Gln Ala Tyr Arg His Asn
65                  70

<210> SEQ ID NO 159
<211> LENGTH: 73
<212> TYPE: PRT
<213> ORGANISM: Homo sapiens

<400> SEQUENCE: 159

```
Met Gly Ser Trp Ile Glu Phe Ala Asp Arg Leu Asp Ala Ile Leu Asp
1               5                   10                  15

Arg Leu Asp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Glu Ile Ala Ala Asp Ile Arg
    50                  55                  60

Ala Tyr Leu Gln Ala Tyr Arg His Asn
65                  70
```

<210> SEQ ID NO 160
<211> LENGTH: 73
<212> TYPE: PRT
<213> ORGANISM: Homo sapiens

<400> SEQUENCE: 160

```
Met Gly Ser Trp Leu Glu Phe Glu Tyr Arg Leu Asp Ala Ile Leu Asp
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Glu Val Ala Ala Asp Ile Arg
    50                  55                  60

Met Leu Leu Gln Ala Tyr Arg His Asn
65                  70
```

<210> SEQ ID NO 161
<211> LENGTH: 73
<212> TYPE: PRT
<213> ORGANISM: Homo sapiens

<400> SEQUENCE: 161

```
Met Gly Ser Trp Tyr Glu Phe His Asp Arg Leu Asp Ala Ile Thr Asn
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Asp Trp Ala Ala Asp Ile Arg
    50                  55                  60

Val Trp Leu Gln Ala Tyr Arg His Asn
65                  70
```

<210> SEQ ID NO 162
<211> LENGTH: 73
<212> TYPE: PRT
<213> ORGANISM: Homo sapiens

<400> SEQUENCE: 162

```
Met Gly Ser Trp Gln Glu Phe Glu Gln Arg Leu Asp Ala Ile Asn Trp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45
```

```
Gly Asn Pro Glu Val Glu Glu Leu Arg Glu Trp Ala Ala Asp Ile Arg
        50                  55                  60

Ile Phe Leu Gln Ala Tyr Arg His Asn
65                  70

<210> SEQ ID NO 163
<211> LENGTH: 73
<212> TYPE: PRT
<213> ORGANISM: Homo sapiens

<400> SEQUENCE: 163

Met Gly Ser Trp Tyr Glu Phe Tyr Ser Arg Leu Asp Ala Ile Asp Ser
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Phe Leu Arg Asp Tyr Ala Ala Glu Ile Arg
        50                  55                  60

Arg Tyr Leu Gln Ala Tyr Arg His Asn
65                  70

<210> SEQ ID NO 164
<211> LENGTH: 73
<212> TYPE: PRT
<213> ORGANISM: Homo sapiens

<400> SEQUENCE: 164

Met Gly Ser Trp Glu Phe His Asp Arg Leu Glu Ala Ile Ser Asp
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asp Leu Arg Asp Trp Ala Ala Asp Ile Arg
        50                  55                  60

Phe Tyr Leu Gln Ala Tyr Arg His Asn
65                  70

<210> SEQ ID NO 165
<211> LENGTH: 73
<212> TYPE: PRT
<213> ORGANISM: Homo sapiens

<400> SEQUENCE: 165

Met Gly Ser Trp Trp Glu Phe Asp Glu Arg Leu Tyr Ala Ile Glu Asp
1               5                   10                  15

Arg Leu Phe Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Trp Leu Arg Ile Val Ala Ala Asp Ile Arg
        50                  55                  60

Glu Ile Leu Gln Ala Tyr Arg His Asn
65                  70

<210> SEQ ID NO 166
<211> LENGTH: 73
<212> TYPE: PRT
```

<213> ORGANISM: Homo sapiens

<400> SEQUENCE: 166

Met Gly Ser Trp Glu Phe Glu Tyr Arg Leu Met Ala Ile Glu Val
1               5                   10                  15

Arg Leu Trp Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Val Leu Arg Glu Ile Ala Ala Asp Ile Arg
    50                  55                  60

Gln Ile Leu Gln Ala Tyr Arg His Asn
65                  70

<210> SEQ ID NO 167
<211> LENGTH: 73
<212> TYPE: PRT
<213> ORGANISM: Homo sapiens

<400> SEQUENCE: 167

Met Gly Ser Trp Val Val Phe Lys Gln Arg Leu Ala Tyr Ile Lys Asp
1               5                   10                  15

Leu Leu Glu Ala Leu Gly Gly Ser Glu Ala Glu Leu Ala Tyr Phe Glu
            20                  25                  30

Met Ser Ile Ala Phe Phe Glu Asp Leu Gln Val Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 168
<211> LENGTH: 73
<212> TYPE: PRT
<213> ORGANISM: Homo sapiens

<400> SEQUENCE: 168

Met Gly Ser Trp Tyr Glu Phe Lys Asn Asp Leu Ala Trp Ile Lys Val
1               5                   10                  15

His Leu Glu Ala Leu Gly Gly Ser Glu Ala Glu Leu Ala Tyr Phe Glu
            20                  25                  30

Phe Arg Ile Ala His Phe Glu Asn Ala Leu Gln Tyr Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 169
<211> LENGTH: 73
<212> TYPE: PRT
<213> ORGANISM: Homo sapiens

<400> SEQUENCE: 169

Met Gly Ser Trp Val Glu Phe Tyr Asn Arg Leu Trp Ala Ile Asp His
1               5                   10                  15

Arg Leu His Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Val Leu Arg Tyr His Ala Ala Ser Ile Arg
        50                  55                  60

Val Thr Leu Gln Ala Tyr Arg His Asn
65                  70

<210> SEQ ID NO 170
<211> LENGTH: 73
<212> TYPE: PRT
<213> ORGANISM: Homo sapiens

<400> SEQUENCE: 170

Met Gly Ser Trp Ser Glu Phe Tyr Asp Arg Leu His Ala Ile His His
1               5                  10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Ala Leu Arg Asp Thr Ala Ala Phe Ile Arg
        50                  55                  60

Thr Arg Leu Gln Ala Tyr Arg His Asn
65                  70

<210> SEQ ID NO 171
<211> LENGTH: 73
<212> TYPE: PRT
<213> ORGANISM: Homo sapiens

<400> SEQUENCE: 171

Met Gly Ser Trp Lys Glu Phe His Phe Arg Leu His Ala Ile Glu His
1               5                  10                  15

Arg Leu Ile Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu Phe Leu Arg Ala Lys Ala Ala Asn Ile Arg
        50                  55                  60

Thr His Leu Gln Ala Tyr Arg His Asn
65                  70

<210> SEQ ID NO 172
<211> LENGTH: 73
<212> TYPE: PRT
<213> ORGANISM: Homo sapiens

<400> SEQUENCE: 172

Met Gly Ser Trp Phe Glu Phe His Gly Arg Leu His Ala Ile Tyr Gly
1               5                  10                  15

Arg Leu Ser Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
            35                  40                  45

Gly Asn Pro Glu Val Glu His Leu Arg Ala His Ala Ala His Ile Arg
        50                  55                  60

Asp His Leu Gln Ala Tyr Arg His Asn
65                  70

```
<210> SEQ ID NO 173
<211> LENGTH: 73
<212> TYPE: PRT
<213> ORGANISM: Homo sapiens

<400> SEQUENCE: 173

Met Gly Ser Trp Tyr Glu Phe Ala Asp Arg Leu His Ala Ile His Gln
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Met Thr Ala Ala Phe Ile Arg
    50                  55                  60

Ser Arg Leu Gln Ala Tyr Arg His Asn
65                  70

<210> SEQ ID NO 174
<211> LENGTH: 73
<212> TYPE: PRT
<213> ORGANISM: Homo sapiens

<400> SEQUENCE: 174

Met Gly Ser Trp Asn Glu Phe Tyr Asn Arg Leu His Ala Ile His Gln
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ser Leu Arg Gln Thr Ala Ala Tyr Ile Arg
    50                  55                  60

Asp Arg Leu Gln Ala Tyr Arg His Asn
65                  70

<210> SEQ ID NO 175
<211> LENGTH: 73
<212> TYPE: PRT
<213> ORGANISM: Homo sapiens

<400> SEQUENCE: 175

Met Gly Ser Trp Asn Glu Phe Ala Asp Arg Leu His Ala Ile His Gln
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ser Leu Arg Met Thr Ala Ala Phe Ile Arg
    50                  55                  60

Ser Arg Leu Gln Ala Tyr Arg His Asn
65                  70

<210> SEQ ID NO 176
<211> LENGTH: 73
<212> TYPE: PRT
<213> ORGANISM: Homo sapiens

<400> SEQUENCE: 176

Met Gly Ser Trp Thr Glu Phe Ser Tyr Arg Leu Gly Ala Ile Gln Ser
1               5                   10                  15
```

Arg Leu His Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu His Leu Arg Tyr Asn Ala Ala Lys Ile Arg
    50                  55                  60

His Phe Leu Gln Ala Tyr Arg His Asn
65                  70

<210> SEQ ID NO 177
<211> LENGTH: 73
<212> TYPE: PRT
<213> ORGANISM: Homo sapiens

<400> SEQUENCE: 177

Met Gly Ser Trp Gln Glu Phe Thr Thr Arg Leu Glu Ala Ile Tyr His
1               5                   10                  15

Arg Leu Arg Ala Leu Gly Gly Ser Glu Ala Glu Leu Ala Asn Phe Glu
            20                  25                  30

Gly Phe Ile Ala Glu Phe Glu Gly Asn Leu Gln Met Tyr Lys Gly Lys
        35                  40                  45

Gly Asn Pro Glu Val Glu Ala Leu Val His Glu Ala Tyr Ala Ile Met
    50                  55                  60

Glu Glu Leu His Ala Tyr Arg His Asn
65                  70

<210> SEQ ID NO 178
<211> LENGTH: 73
<212> TYPE: PRT
<213> ORGANISM: Homo sapiens

<400> SEQUENCE: 178

Met Gly Ser Trp Val Glu Phe Phe Asp Arg Leu Lys Ala Ile His Asp
1               5                   10                  15

Arg Leu Glu Ala Leu Gly Gly Ser Glu Ala Glu Leu Ala His Phe Glu
            20                  25                  30

Lys Leu Ile Ala His Phe Glu His Arg Leu Gln Asn Tyr Lys Gly Lys
        35                  40                  45

Gly Asn Pro Glu Val Glu Ala Leu Glu Lys Glu Ala Asp Ala Ile Leu
    50                  55                  60

Tyr Glu Leu Ala Ala Tyr Arg His Asn
65                  70

<210> SEQ ID NO 179
<211> LENGTH: 73
<212> TYPE: PRT
<213> ORGANISM: Homo sapiens

<400> SEQUENCE: 179

Met Gly Ser Trp Tyr Tyr Phe Lys His His Leu Ala Trp Ile Lys Met
1               5                   10                  15

Glu Leu Glu Ala Leu Gly Gly Ser Glu Ala Glu Leu Ala His Phe Glu
            20                  25                  30

Ser Ser Ile Ala Ser Phe Glu Arg Asp Leu Gln Gln Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn

<210> SEQ ID NO 180
<211> LENGTH: 73
<212> TYPE: PRT
<213> ORGANISM: Homo sapiens

<400> SEQUENCE: 180

Met Gly Ser Trp Val Glu Phe His Ile Arg Leu His Ala Ile Gln Tyr
1               5                   10                  15

Arg Leu Tyr Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Glu Leu Arg His Trp Ala Ala Phe Ile Arg
    50                  55                  60

Leu Gln Leu Gln Ala Tyr Arg His Asn
65                  70

<210> SEQ ID NO 181
<211> LENGTH: 73
<212> TYPE: PRT
<213> ORGANISM: Homo sapiens

<400> SEQUENCE: 181

Met Gly Ser Trp Asn Glu Phe His Asp Arg Leu Asn Ala Ile His Ala
1               5                   10                  15

Arg Leu His Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Asn Leu Arg Asp Asp Ala Ala Phe Ile Arg
    50                  55                  60

Arg Phe Leu Gln Ala Tyr Arg His Asn
65                  70

<210> SEQ ID NO 182
<211> LENGTH: 73
<212> TYPE: PRT
<213> ORGANISM: Homo sapiens

<400> SEQUENCE: 182

Met Gly Ser Trp Tyr Glu Phe Thr Val Arg Leu Glu Ala Ile His Glu
1               5                   10                  15

Arg Leu Lys Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ile Leu Arg Asp Asp Ala Ala Phe Ile Arg
    50                  55                  60

Arg Phe Leu Gln Ala Tyr Arg His Asn
65                  70

<210> SEQ ID NO 183
<211> LENGTH: 73
<212> TYPE: PRT
<213> ORGANISM: Homo sapiens

<400> SEQUENCE: 183

Met Gly Ser Trp Lys Glu Phe Asp Asp Arg Leu Asn Ala Ile Lys Ala
1               5                   10                  15

Arg Leu Gln Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Asp Leu Arg Asp Asp Ala Ala Phe Ile Arg
        50                  55                  60

Arg Phe Leu Gln Ala Tyr Arg His Asn
65                  70

<210> SEQ ID NO 184
<211> LENGTH: 73
<212> TYPE: PRT
<213> ORGANISM: Homo sapiens

<400> SEQUENCE: 184

Met Gly Ser Trp Tyr Glu Phe Asp Asp Arg Leu Asn Ala Ile His Asp
1               5                   10                  15

Arg Leu Gln Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Asp Leu Arg Asp Asp Ala Ala Phe Ile Arg
        50                  55                  60

Arg Phe Leu Gln Ala Tyr Arg His Asn
65                  70

<210> SEQ ID NO 185
<211> LENGTH: 73
<212> TYPE: PRT
<213> ORGANISM: Homo sapiens

<400> SEQUENCE: 185

Met Gly Ser Trp Asn Glu Phe Lys Asn Arg Leu Asp Ala Ile His Lys
1               5                   10                  15

Arg Leu Asn Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Asn Leu Arg Asp Asp Ala Ala Phe Ile Arg
        50                  55                  60

His Phe Leu Gln Ala Tyr Arg His Asn
65                  70

<210> SEQ ID NO 186
<211> LENGTH: 73
<212> TYPE: PRT
<213> ORGANISM: Homo sapiens

<400> SEQUENCE: 186

Met Gly Ser Trp Thr Glu Phe Glu Gln Arg Leu Glu Ala Ile His Asn
1               5                   10                  15

Arg Leu Gln Ala Leu Gly Gly Ser Glu Ala Glu Leu Ala Ala Phe Glu
                20                  25                  30

Lys Glu Ile Ala Ala Phe Glu Ser Glu Leu Gln Ala Tyr Lys Gly Lys
            35                  40                  45

Gly Asn Pro Glu Val Glu Glu Leu Arg Asn Asp Ala Ala Phe Ile Arg

```
                50                  55                  60
His Phe Leu Gln Ala Tyr Arg His Asn
 65                  70
```

<210> SEQ ID NO 187
<211> LENGTH: 378
<212> TYPE: PRT
<213> ORGANISM: Homo sapiens
<220> FEATURE:
<221> NAME/KEY: misc_feature
<223> OTHER INFORMATION: CD123 (interleukin-3 receptor-alpha)

<400> SEQUENCE: 187

```
Met Val Leu Leu Trp Leu Thr Leu Leu Leu Ile Ala Leu Pro Cys Leu
 1               5                  10                  15

Leu Gln Thr Lys Glu Asp Pro Asn Pro Pro Ile Thr Asn Leu Arg Met
                20                  25                  30

Lys Ala Lys Ala Gln Gln Leu Thr Trp Asp Leu Asn Arg Asn Val Thr
            35                  40                  45

Asp Ile Glu Cys Val Lys Asp Ala Asp Tyr Ser Met Pro Ala Val Asn
        50                  55                  60

Asn Ser Tyr Cys Gln Phe Gly Ala Ile Ser Leu Cys Glu Val Thr Asn
 65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Glu Gly Ala Asn Thr Arg Ala Trp
290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335
```

```
Arg Ile Pro His Met Lys Asp Pro Ile Gly Asp Ser Phe Gln Asn Asp
                340                 345                 350

Lys Leu Val Val Trp Glu Ala Gly Lys Ala Gly Leu Glu Glu Cys Leu
        355                 360                 365

Val Thr Glu Val Gln Val Gln Lys Thr
    370                 375

<210> SEQ ID NO 188
<211> LENGTH: 5
<212> TYPE: PRT
<213> ORGANISM: Artificial Sequence
<220> FEATURE:
<223> OTHER INFORMATION: Peptide linker

<400> SEQUENCE: 188

Gly Gly Gly Gly Gly
1               5

<210> SEQ ID NO 189
<211> LENGTH: 8
<212> TYPE: PRT
<213> ORGANISM: Artificial Sequence
<220> FEATURE:
<223> OTHER INFORMATION: Peptide linker

<400> SEQUENCE: 189

Gly Gly Gly Gly Gly Gly Gly Gly
1               5

<210> SEQ ID NO 190
<211> LENGTH: 10
<212> TYPE: PRT
<213> ORGANISM: Artificial Sequence
<220> FEATURE:
<223> OTHER INFORMATION: Peptide linker

<400> SEQUENCE: 190

Gly Gly Gly Gly Thr Gly Gly Gly Gly Ser
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Peptide linker

<400> SEQUENCE: 191

Gly Gly Gly Gly Asp Gly Gly Gly Gly Ser
1               5                   10
```